US012661436B2

(12) United States Patent
Edick et al.

(10) Patent No.: US 12,661,436 B2
(45) Date of Patent: Jun. 23, 2026

(54) BIOABSORBABLE MAGNESIUM ALLOY WITH CONTROLLED MULTI-PHASE ABSORPTION

(71) Applicant: Magsorbeo Biomedical Corp., Detroit, MI (US)

(72) Inventors: Jacob Edick, Detroit, MI (US); Carolyn Woldring, East Lansing, MI (US)

(73) Assignee: Magsorbeo Biomedical Corp., East Lansing, MI (US)

( * ) Notice: Subject to any disclaimer, the term of this patent is extended or adjusted under 35 U.S.C. 154(b) by 0 days.

(21) Appl. No.: 19/177,238

(22) Filed: Apr. 11, 2025

(65) Prior Publication Data

US 2025/0319237 A1      Oct. 16, 2025

Related U.S. Application Data

(60) Provisional application No. 63/632,593, filed on Apr. 11, 2024.

(51) Int. Cl.
| | |
|---|---|
| *C22C 23/04* | (2006.01) |
| *A61L 31/02* | (2006.01) |
| *A61L 31/14* | (2006.01) |

(52) U.S. Cl.
CPC ........... *A61L 31/022* (2013.01); *A61L 31/148* (2013.01); *C22C 23/04* (2013.01)

(58) Field of Classification Search
CPC ......... C22C 23/04; C22C 23/00; C22C 23/02; C22C 23/06; A61L 31/022; A61L 31/148; C22F 1/06
See application file for complete search history.

(56) References Cited

U.S. PATENT DOCUMENTS

| | | | |
|---|---|---|---|
| 2020/0123636 A1* | 4/2020 | Eliezer | A61L 31/026 |
| 2021/0137709 A1 | 5/2021 | Stinson et al. | |

FOREIGN PATENT DOCUMENTS

| | | | | |
|---|---|---|---|---|
| WO | WO-2014001321 A1 * | 1/2014 | | C22C 23/04 |
| WO | WO-2017035072 A1 * | 3/2017 | | A61L 31/022 |

OTHER PUBLICATIONS

Bakhsheshi-Rad, H. R., et al. "Mechanical and bio-corrosion properties of quaternary Mg—Ca—Mn—Zn alloys compared with binary Mg—Ca alloys." Materials & Design 53 (2014): 283-292.*
Zhao, Ying, et al. "Improved surface corrosion resistance of WE43 magnesium alloy by dual titanium and oxygen ion implantation." Thin Solid Films 529 (2013): 407-411.*
Bazhenov, et al., Microstructure and mechanical and corrosion properties of hot-extruded Mg—Zn—Ca—(Mn) biodegradable alloys, Journal of Magnesium and Alloys, 2021, pp. 1428-1442, vol. 9, Issue 4.
Alam, et al., Rare-earth- and aluminum-free, high strength dilute magnesium alloy for Biomedical Applications, Scientific Reports, 2020, 15 pages, vol. 10:15839.
Han, et al., Effect of Mn Element Addition on the Microstructure, Mechanical Properties, and Corrosion Properties of Mg-3Zn-0.2Ca Alloy, Frontiers in Materials, 2019, 10 pages, vol. 6:324.
Bamberger, et al., Precipitation hardening in Mg—Ca—Zn alloys, Metallurgical and Materials Transactions A, 2006, pp. 481-487, vol. 37.
Nie, et al., The effect of Zn/Ca ratio on the microstructure, texture and mechanical properties of dilute Mg—Zn—Ca—Mn alloys that exhibit superior strength, Journal of Materials Science, 2020, pp. 3588-3604, vol. 55.
Herzog, et al., Titanium versus plasma electrolytic oxidation surface—modified magnesium miniplates in a forehead secondary fracture healing model in sheep, Acta Biomaterialia, 2024, pp. 98-110, vol. 185.
Suuronen, et al., Comparison of absorbable self-reinforced multilayer poly-1-lactide and metallic plates for the fixation of mandibular body osteotomies: an experimental study in sheep, Journal of Oral Maxillofacial Surgery, 1992, pp. 255-262, vol. 50, Issue 3.
Turostowski, et al., Titanium vs PEO Surface-Modified Magnesium Plate Fixation in a Mandible Bone Healing Model in Sheep, ACS Biomaterials Science & Engineering, 2024, pp. 4901-4915, vol. 10, Issue 8.
Marek, et al., Degradation behavior and osseointegration of Mg—Zn—Ca screws in different bone regions of growing sheep: a pilot study, Regenerative Biomaterials, 2022, 14 pages, vol. 10, rbac077.
Imwinkelried, et al., Pre-clinical testing of human size magnesium implants in miniature pigs: Implant degradation and bone fracture healing at multiple implantation sites, Materials Science & Engineering C, 2020, 10 pages, vol. 108:110389.
Kopp, et al., Long-term in vivo observations show biocompatibility and performance of ZX00 magnesium screws surface-modified by plasma-electrolytic oxidation in Göttingen miniature pigs, Acta Biomaterialia, 2023, pp. 720-733, vol. 157.
Naujokat, et al., Osteosynthesis of a cranio-osteoplasty with a biodegradable magnesium plate system in miniature pigs, Acta Biomaterialia, 2017, pp. 434-445, vol. 62.
Naujokat, et al., Influence of surface modifications on the degradation of standard- sized magnesium plates and healing of mandibular osteotomies in miniature pigs, International Journal of Oral and Maxillofacial Surgery, 2020, pp. 272-283, vol. 49, Issue 2.

(Continued)

*Primary Examiner* — Jessee R Roe
(74) *Attorney, Agent, or Firm* — Christensen, Fonder, Dardi & Busse PLLC; Timothy J. Busse

(57) ABSTRACT

A bioabsorbable magnesium alloy for use in an orthopedic implant comprises magnesium, zinc in an amount of 0.5-4 weight percent, calcium in an amount of 0.1-1.5 weight percent, and manganese in an amount of up to 1.5 weight percent. The alloy exhibits a controlled, multi-phase absorption profile when exposed to physiological conditions, including an initial period of minimal degradation, followed by a steady-state phase, and concluding with an accelerated absorption phase. A method of manufacturing the alloy includes casting, solution treating, and extruding. An orthopedic implant device formed from the alloy comprises a body that exhibits the controlled, multi-phase absorption profile when implanted.

18 Claims, 86 Drawing Sheets

(56)　　　　　　References Cited

OTHER PUBLICATIONS

Schaller, et al., Fracture healing and bone remodeling with human standard-sized magnesium versus polylactide-co-lycolide plate and screw systems using a mini-swine craniomaxillofacial osteotomy fixation model, Journal of Craniomaxillofacial Trauma, 2018, pp. 2138-2150, vol. 76, Issue 10.

Grïn, et al., Comparison of a resorbable magnesium implant in small and large growing-animal models, Acta Biomaterialia, 2018, pp. 378-386, vol. 78.

Torroni, et al., Histo-morphologic characteristics of intra-osseous implants of WE43 Mg alloys with and without heat treatment in an in vivo cranial bone sheep model, Journal of Cranio-Maxillofacial Surgery, 2018, pp. 473-478, vol. 46, Issue 3.

Klíma, et al., A Complex Evaluation of the In-Vivo Biocompatibility and Degradation of an Extruded ZnMgSr Absorbable Alloy Implanted into Rabbit Bones for 360 Days, International Journal of Molecular Sciences, 2021, 24 pages, vol. 22, Issue 24, 13444.

Imwinkelried, et al., Effect of a plasmaelectrolytic coating on the strength retention of in vivo and in vitro degraded magnesium implants, Acta Biomaterialia, 2013, pp. 8643-8649, vol. 9, Issue 10.

Holweg, et al., A lean magnesium-zinc-calcium alloy ZX00 used for bone fracture stabilization in a large growing-animal model, Acta Biomaterialia, 2022, pp. 646-659, vol. 113.

Schäublin, et al., Precipitation in lean Mg—Zn—Ca alloys, Acta Materialia, 2022, 19 pages, vol. 239:118223.

Zhao, et al., Development of weak-textured and high-performance Mg—Zn—Ca alloy sheets based on Zn content optimization, Journal of Alloys and Compounds, 2020, 28 pages, vol. 849: 156640.

* cited by examiner

—■— Curasorb – PD C         —●—MAGNEZIX

Mg-2Zn-0.4Ca

Mg-2Zn-0.4Ca-0.8Mn

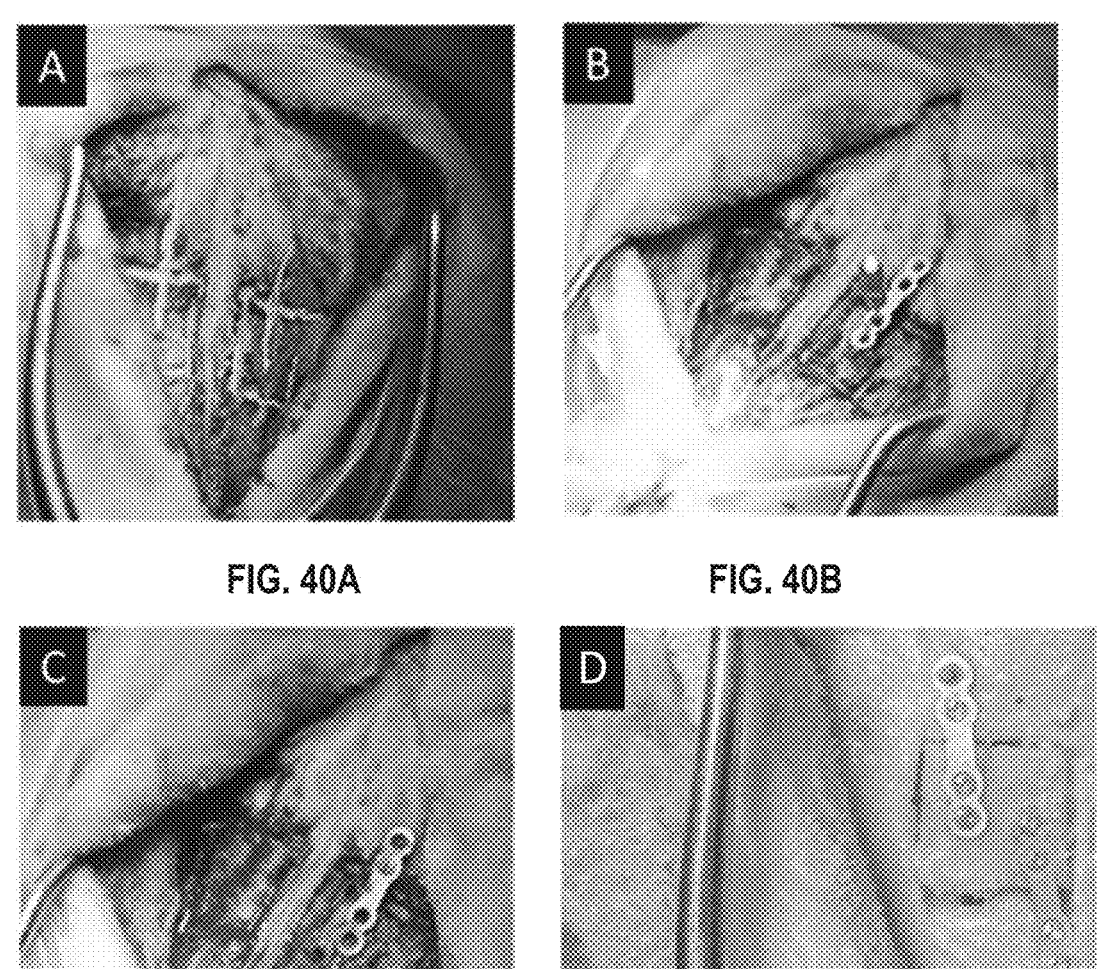
FIG. 40A                    FIG. 40B
FIG. 40C                    FIG. 40D
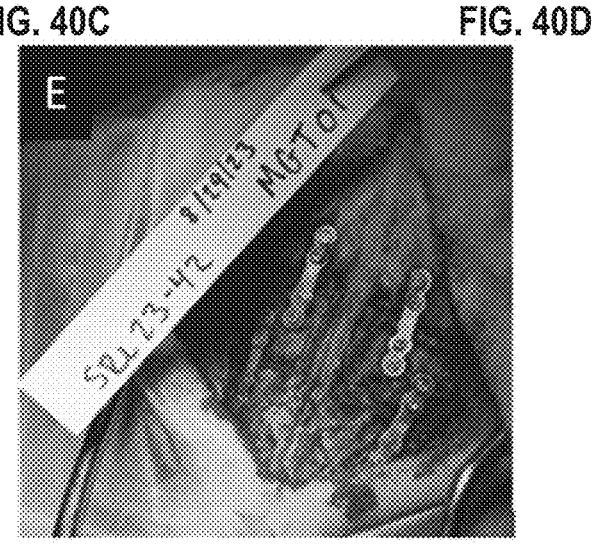
FIG. 40E

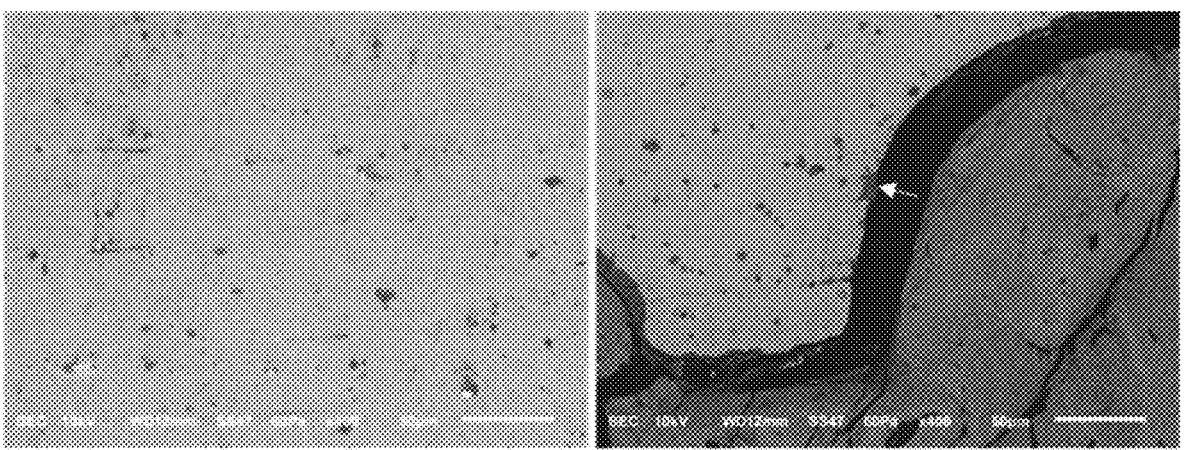
FIG. 41A                                    FIG. 41B

☆Curasorb Alloy B
  Ovine Frontal Bone Ostectomy
×ZX00MEO
  Porcine Frontal Bone (No Osteotomy)
○ZX00
  Sheep Metaphysis (No Osteotomy)
▪ZX00
  Ovine Tibial Shaft Osteotomy
◇MgYREZr
  Porcine Mandibular Osteotomy
◆MgYREZr
  Porcine Nasal Bone (No Osteotomy)
▫BioMg250
  Canine Mandibular Osteotomy

Preclinical Material
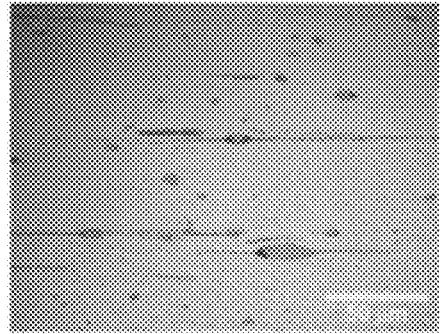
C08-02, Ext. + 430oC/24h/FAC + Ext.
2ⁿᵈ Ext.: ER: 30; Temp: ~290°C
Group 1 Extrusion Billet
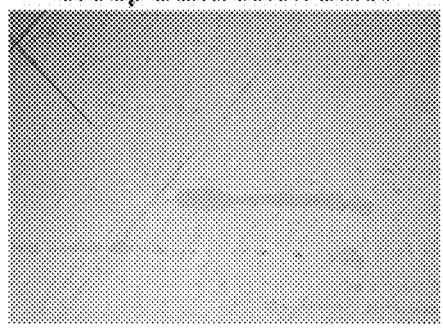
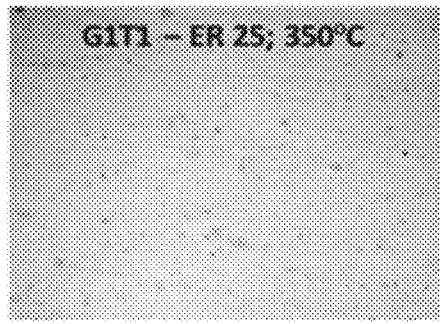
G1T1 – ER 25; 350°C
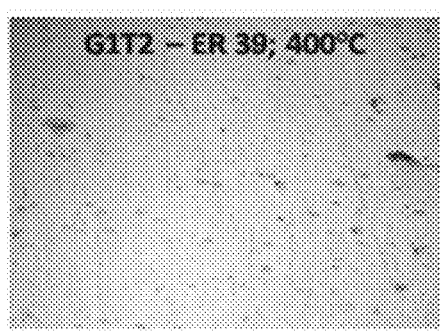
G1T2 – ER 30; 400°C
FIG. 51

Preclinical Material
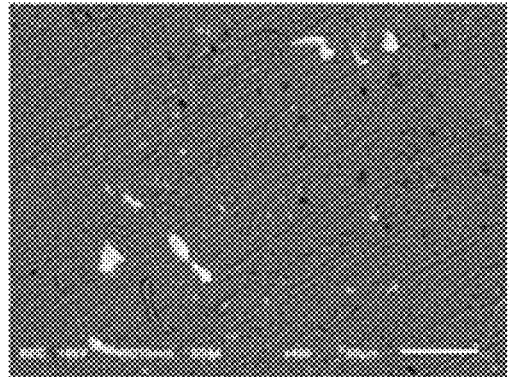
C08-02, Ext. + 430oC/24h/FAC + Ext.
2$^{nd}$ Ext.: ER: 30; Temp: ~290°C
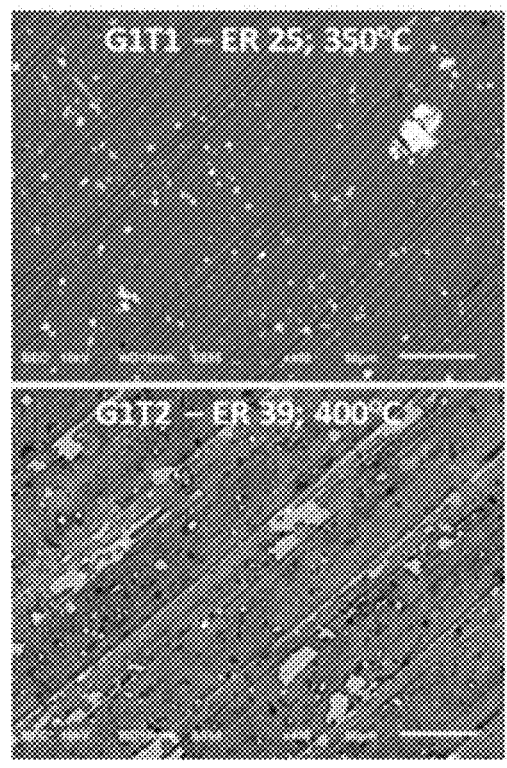
FIG. 52

Preclinical Material
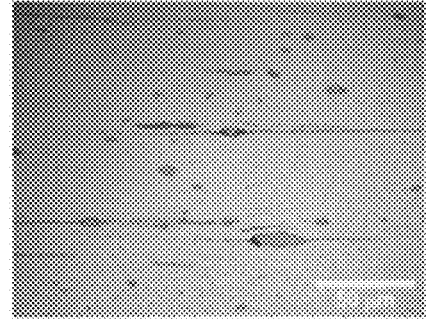
C08-02, Ext. + 430oC/24h/FAC + Ext.
2ⁿᵈ Ext.: ER: 30; Temp: ~290°C
Group 2 Extrusion Billet
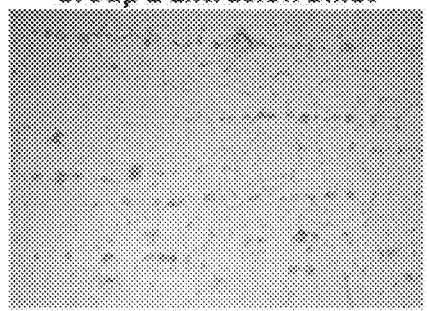
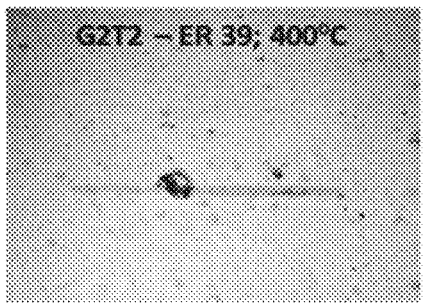
FIG. 53

—◇— B21 – Ext: ER 14 @ 350C – ST: 410C/24hr/FAC – Ext: ER 25 @ 350C
—✕— B21 – Ext: ER 14 @ 350C – ST: 410C/24hr/FAC – Ext: ER 39 @ 400C
—○— B24 – Ext: ER 14 @ 350C – ST: 430C/24hr/FAC – Ext: ER 25 @ 350C
—●— B24 – Ext: ER 14 @ 350C – ST: 430C/24hr/FAC – Ext: ER 39 @ 400C
—■— Preclinical Plates
—☆— Preclinical Screws

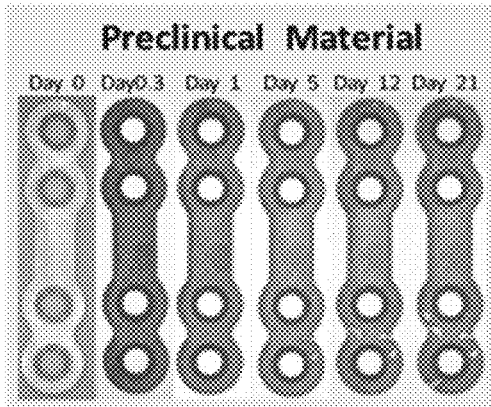
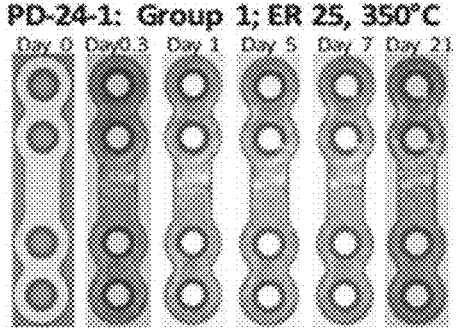
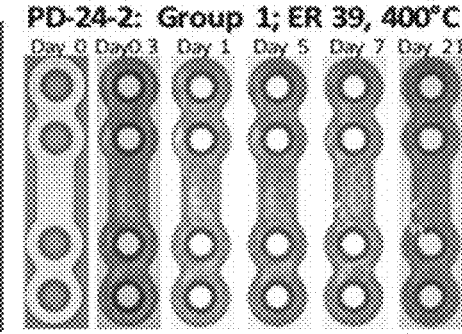
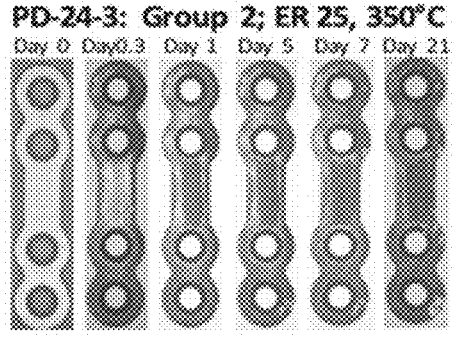
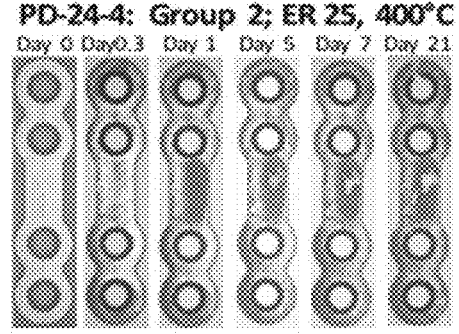
FIG. 55

800

701

First Extrusion 802

703

Second Extrusion 806

705

Solution Treatment 804

707

Third Extrusion 808

709

400C 4H

Area %: .603

Mean Area: 2.179 micron^2

Max Area: 4.918 micron^2

400C 4H/ 200C 2H

Area%: .729

Mean Area:2.795 micron^2

Max Area: 6.115 micron^2

400C 4H/ 250C 2H
Area%: 2.688
Mean Area: 1.862 micron^2
Max Area: 6.659 micron^2

400C 4H/ 300C 2H
Area%: 9.303
Mean Area: 7.914 micron^2
Max Area: 40.718 micron^2

400C 4H
Area %: 3.4
Mean Area: 3.993 micron^2
Max Area: 10.655 micron^2

400C 4H / 200C 2H
Area %: 24.37
Mean Area: 57.17 micron^2
Max Area: 111.936 micron^2

400C 4H / 250C 2H
Area %: 27.23
Mean Area: 42.949 micron^2
Max Area: 209.383 micron^2

400C 4H / 300C 2H
Area %: 7.742
Mean Area: 19.279 micron^2
Max Area: 37.407 micron^2

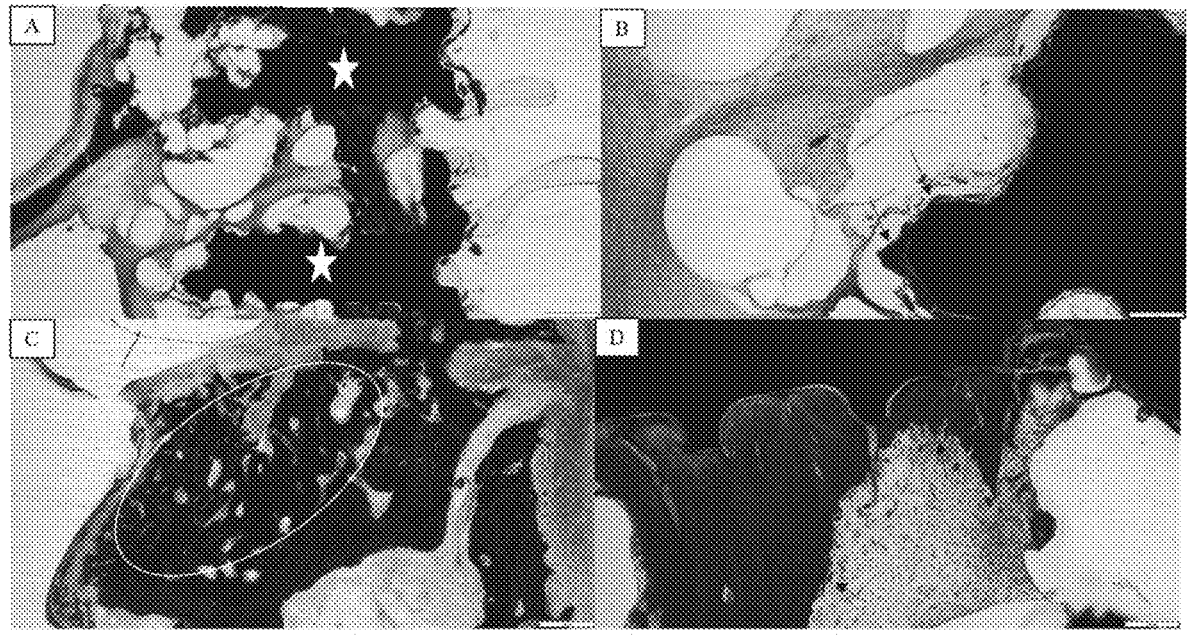
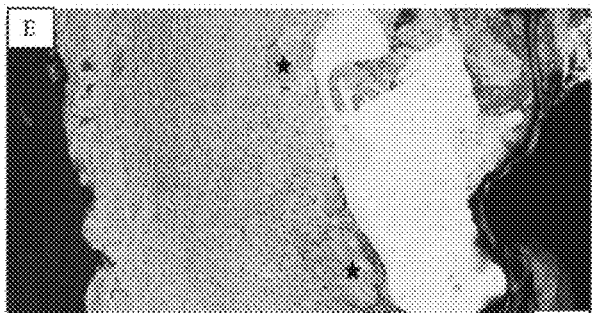
FIG. 78

BIOABSORBABLE MAGNESIUM ALLOY WITH CONTROLLED MULTI-PHASE ABSORPTION

CROSS-REFERENCE TO RELATED APPLICATIONS

This application claims priority to U.S. Provisional Application No. 63/632,593, titled ADJUSTABLE MAGNESIUM ALLOY AND METHOD OF MAKING THE SAME, filed Apr. 11, 2024, which is hereby incorporated by reference in its entirety.

TECHNICAL FIELD

The present disclosure relates to bioabsorbable magnesium alloys for medical implants, and more particularly to a bioabsorbable magnesium alloy with a controlled multi-phase absorption profile for use in orthopedic implant devices.

BACKGROUND

Magnesium and its alloys have garnered significant interest in the field of biomedical implants due to their biocompatibility, biodegradability, and mechanical properties similar to natural bone. These materials offer potential advantages over traditional metallic implants, such as eliminating the need for secondary surgeries to remove non-degradable implants and reducing stress shielding effects.

However, the development of magnesium-based implants faces challenges related to controlling their degradation rate in physiological environments. Rapid corrosion of magnesium alloys can lead to premature loss of mechanical integrity and the generation of hydrogen gas and poor osseointegration of the implant, which may interfere with the healing process. Conversely, excessively slow degradation can result in prolonged presence of the implant beyond the necessary healing period.

Efforts to address these challenges have focused on alloying magnesium with other elements to modify its corrosion behavior and mechanical properties. Zinc, calcium, and manganese are among the alloying elements that have been explored for their potential to enhance the performance of magnesium-based implants. These elements can influence factors such as grain refinement, precipitation strengthening, and the formation of protective surface layers.

The bioabsorption profile of magnesium alloys is a complex interplay of various factors, including alloy composition, microstructure, and processing methods. Achieving a controlled degradation rate that matches the healing process of bone or other tissues remains an area of active research.

The potential applications of bioabsorbable magnesium alloys extend across various fields of orthopedics and maxillofacial surgery. These materials could be used in devices such as bone plates, screws, and pins for fracture fixation, as well as in scaffolds for tissue engineering. However, each application may present unique requirements in terms of mechanical properties, degradation kinetics, and biocompatibility.

Furthermore, the long-term biological effects of magnesium alloy implants and their degradation products require careful consideration. While magnesium is generally well-tolerated by the body, the release of alloying elements and the local changes in pH associated with magnesium corrosion may have implications for tissue response and healing.

Advancements in the field of bioabsorbable magnesium alloys have the potential to revolutionize the treatment of orthopedic and maxillofacial conditions. However, realizing this potential requires overcoming challenges related to alloy design, processing, and in vivo performance. Accordingly, there is a need for new magnesium compositions, processing techniques, and implant designs that offer improved outcomes for patients and expand the possibilities of regenerative medicine.

SUMMARY

According to an aspect of the present disclosure, a bioabsorbable magnesium alloy for use in an orthopedic implant is provided. The alloy includes magnesium, zinc in an amount of 0.5-4 weight percent, calcium in an amount of 0.2-1.0 weight percent, and a third alloying element in an amount of up to 1.0 weight percent. The alloy comprises a microstructure having a lower amount of $Mg_2Ca$ phase relative to ternary intermetallic phases. The alloy forms a protective oxide layer when exposed to physiological conditions. The alloy exhibits a controlled, multi-phase absorption profile when exposed to physiological conditions, the profile comprising an initial period of minimal degradation, followed by a steady-state phase, and concluding with an accelerated absorption phase.

According to other aspects of the present disclosure, the bioabsorbable magnesium alloy may include one or more of the following features. The zinc may be present in an amount of 2-1.5 weight percent. The calcium may be present in an amount of 0.3-0.8 weight percent. The manganese may be present in an amount of 0.6-1.0 weight percent. The initial period of minimal degradation may last for 7-14 days, the steady-state phase may extend from approximately 2 to 8 weeks post-implantation, and the accelerated absorption phase may begin after 8-12 weeks. The alloy may be substantially free of $Mg_2Ca$ phase. The alloy may have an anode to a cathode ratio of at least 20:1.

According to another aspect of the present disclosure, a bioabsorbable magnesium alloy for use in an orthopedic implant is provided. The alloy includes magnesium, zinc in an amount of 0.5-4 weight percent, calcium in an amount of 0.2-1.0 weight percent, and a third alloying element in an amount of up to 1.0 weight percent. The alloy comprises a microstructure having a ternary intermetallic phase with a volume fraction between 0.5% and 5%, the ternary intermetallic phase having an average particle size between 50 nm and 500 nm, and $Mg_2Ca$ phase present in a volume fraction of less than 1% with an average particle diameter of less than 200 nm. The alloy exhibits a controlled, multi-phase absorption profile when exposed to physiological conditions, the profile comprising an initial period of minimal degradation, followed by a steady-state phase, and concluding with an accelerated absorption phase.

According to other aspects of the present disclosure, the bioabsorbable magnesium alloy may include one or more of the following features. The ternary intermetallic phase may comprise $Ca_2Mg_6Zn_3$. The ternary intermetallic phase may have a volume fraction between 1% and 3%. The ternary intermetallic phase may have an average particle size between 100 nm and 300 nm. The $Mg_2Ca$ phase may be present in a volume fraction of less than 0.5%. The $Mg_2Ca$ phase may have an average particle diameter of less than 100 nm. The alloy may form a protective oxide layer when exposed to physiological conditions, the oxide layer having a thickness between 10 nm and 500 nm.

According to another aspect of the present disclosure, an orthopedic implant device is provided. The device includes a body formed from a bioabsorbable magnesium alloy, the alloy comprising magnesium, 1-4 weight percent zinc, 0.2-1.0 weight percent calcium, and 0.3-1.0 weight percent manganese. The alloy comprises a microstructure having a lower amount of $Mg_2Ca$ phase relative to ternary intermetallic phases. The alloy forms a protective oxide layer when exposed to physiological conditions. The alloy exhibits a controlled, multi-phase absorption profile when exposed to physiological conditions, the profile comprising an initial period of minimal degradation, followed by a steady-state phase, and concluding with an accelerated absorption phase.

According to other aspects of the present disclosure, the orthopedic implant device may include one or more of the following features. The zinc may be present in an amount of 2-2.5 weight percent, the calcium may be present in an amount of 0.8-1.0 weight percent, and the manganese may be present in an amount of 0.6-1.0 weight percent. The alloy may form a protective oxide layer when exposed to physiological conditions, the oxide layer having a thickness between 10 nm and 500 nm. The ternary intermetallic phases may comprise $Ca_2Mg_6Zn_3$ and may have a volume fraction between 0.5% and 5%, with an average particle size between 50 nm and 500 nm. The $Mg_2Ca$ phase may be present in a volume fraction of less than 0.5% with an average particle diameter of less than 100 nm. The device may be configured for use in maxillofacial trauma and reconstruction applications.

According to an aspect of the present disclosure, a bioabsorbable magnesium alloy for use in an orthopedic implant is provided. The alloy includes magnesium, zinc in an amount of 1-4 weight percent, calcium in an amount of 0.2-1.0 weight percent, and manganese in an amount of 0.3 to 1.0 weight percent. In some cases, the alloy includes 0.2-1.0 weight percent of calcium. In some cases, the alloy includes 0.3 to 1.0 weight percent of manganese. The alloy includes a microstructure having no or minimal amount of $Mg_2Ca$ phase relative to ternary intermetallic phases. In some cases, the alloy includes a microstructure that is substantially free of $Mg_2Ca$ phase. As used herein, the term "substantially free of" refers to a composition, material, or system in which the specified component is either absent or present only in a trace amount that does not materially affect the structure, function, or performance of the overall system. In some embodiments, "substantially free of" means that the component is present in an amount of less than about 1.0 wt %, less than about 0.5 wt %, less than about 0.1 wt %, or below the detectable limit of standard analytical methods used to detect such a component. In some cases, $Mg_2Ca$ may be present in a volume fraction of less than 1% with the average diameter of the $Mg_2Ca$ phase precipitates being less than 200 nm. In some cases, the alloy includes a microstructure that is completely free of $Mg_2Ca$ phase. The alloy exhibits a controlled, multi-phase absorption profile when exposed to physiological conditions, the profile comprising an initial period of minimal degradation, followed by a steady-state phase, and concluding with an accelerated absorption phase.

According to other aspects of the present disclosure, the bioabsorbable magnesium alloy may include one or more of the following features. The zinc may be present in an amount of 2-2.5 weight percent. The calcium may be present in an amount of 0.3-1.0 weight percent. The manganese may be present in an amount of 0.6-1.0 weight percent. In some aspects of the disclosure, the alloy may consist of magnesium, 2-2.5 weight percent zinc, 0.8-1.2 weight percent calcium, 0.6-1.0 weight percent manganese, and less than 1 weight percent of trace elements. The initial period of minimal degradation may last for 7-14 days. The steady-state phase may extend from approximately 2 to 8 weeks post-implantation. The accelerated absorption phase may begin after 8-12 weeks.

According to another aspect of the present disclosure, a method of manufacturing a bioabsorbable magnesium alloy for use in an orthopedic implant is provided. The method includes casting an alloy comprising magnesium, 1-4 weight percent zinc, 0.6-1.5 weight percent calcium, and 0.6-1.5 weight percent manganese, solution treating the cast alloy, and extruding the solution treated alloy to form an extruded alloy. The extruded alloy exhibits a controlled, multi-phase absorption profile when exposed to physiological conditions.

According to other aspects of the present disclosure, the method may include one or more of the following features. Solution treating the cast alloy may comprise heating the cast alloy to a temperature between 400° C. and 525° C. for 1 to 24 hours. Extruding the solution treated alloy may comprise extruding at a temperature between 325° C. and 350° C. Extruding the solution treated alloy may comprise using an extrusion ratio between 15 and 39. The method may further comprise performing a second extrusion on the extruded alloy. The second extrusion may be performed at a temperature lower than the first extrusion and complemented with further heat treating between 400° C. and 525° C. and aging between 200° C. and 325° C. The controlled, multi-phase absorption profile in an in vivo environment (e.g., implanted in a mammal) may comprise an initial period of minimal degradation lasting 7-14 days, followed by a steady-state phase extending from 2 to 8 weeks, and concluding with an accelerated absorption phase beginning after 8-12 weeks.

According to another aspect of the present disclosure, an orthopedic implant device is provided. The device includes a body formed from a bioabsorbable magnesium alloy, the alloy comprising magnesium, 1-4 weight percent zinc, 0.3-1.5 weight percent calcium, and 0.4-1.0 weight percent manganese. The device exhibits a controlled, multi-phase absorption profile when implanted, the profile comprising an initial period of minimal degradation lasting 7-14 days, followed by a steady-state phase lasting 2-8 weeks, and concluding with an accelerated absorption phase. In some embodiments, the orthopedic implant device may be one or more of the following: compression screws, pins, staples, and any device that can be implanted in a body.

According to other aspects of the present disclosure, the orthopedic implant device may include one or more of the following features. The zinc may be present in an amount of 2-2.5 weight percent, the calcium may be present in an amount of 0.8-1.2 weight percent, and the manganese may be present in an amount of 0.4-1.0 weight percent. The body may comprise a plate having a thickness of 0.6 mm, a width of 5.0 mm, and a length of 23 mm. The device may further comprise a plurality of screws configured to secure the plate to bone, each screw having a shaft diameter of 1.7 mm and a head diameter of 2.65 mm. The plate may include four holes arranged in pairs, with two holes positioned near each end of the plate. The device may be configured for use in maxillofacial trauma and reconstruction applications.

According to an aspect of the present disclosure, a bioabsorbable magnesium alloy for use in an orthopedic implant is provided. The alloy includes magnesium, zinc in an amount of 0.5-4 weight percent, calcium in an amount of 0.3-1.5 weight percent, and manganese in an amount of 0-1.5 weight percent. The alloy exhibits a controlled, multi-phase absorption profile when exposed to physiological conditions, the profile comprising an initial period of minimal degradation, followed by a steady-state phase, and concluding with an accelerated absorption phase.

According to other aspects of the present disclosure, the bioabsorbable magnesium alloy may include one or more of the following features. The zinc may be present in an amount of 2-2.5 weight percent. The calcium may be present in an amount of 0.8-1.2 weight percent. The manganese may be present in an amount of 0.4-1.0 weight percent. The initial period of minimal degradation may last for 7-14 days. The steady-state phase may extend from approximately 2 to 8 weeks post-implantation. The accelerated absorption phase may begin after 8-12 weeks.

According to another aspect of the present disclosure, a method of manufacturing a bioabsorbable magnesium alloy for use in an orthopedic implant is provided. The method includes casting an alloy comprising magnesium, 0.5-4 weight percent zinc, 0.3-1.5 weight percent calcium, and 0-1.0 weight percent manganese, solution treating the cast alloy, and extruding the solution treated alloy to form an extruded alloy. The extruded alloy exhibits a controlled, multi-phase absorption profile when exposed to physiological conditions.

According to other aspects of the present disclosure, the method may include one or more of the following features. Solution treating the cast alloy may comprise heating the cast alloy to a temperature between 400° C. to 600° C., for example, 500° C. and 550° C. for 1 to 24 hours (e.g., 6 hours). Extruding the solution treated alloy may comprise extruding at a temperature between 300° C. and 350° C. Extruding the solution treated alloy may comprise using an extrusion ratio greater than 20 (e.g., 25, 39, etc.). The method may further comprise performing a second extrusion on the extruded alloy. The second extrusion may be performed at a temperature lower than the first extrusion. The controlled, multi-phase absorption profile may comprise an initial period of minimal degradation lasting 7-14 days, followed by a steady-state phase extending from 2 to 8 weeks, and concluding with an accelerated absorption phase beginning after 8-12 weeks.

According to another aspect of the present disclosure, an orthopedic implant device is provided. The device includes a body formed from a bioabsorbable magnesium alloy, the alloy comprising magnesium, 0.5-4 weight percent zinc, 0.5-1.5 weight percent calcium, and 0-1.5 weight percent manganese. The device exhibits a controlled, multi-phase absorption profile when implanted, the profile comprising an initial period of minimal degradation lasting 7-14 days, followed by a steady-state phase lasting 2-8 weeks, and concluding with an accelerated absorption phase.

According to other aspects of the present disclosure, the orthopedic implant device may include one or more of the following features. The zinc may be present in an amount of 2-2.5 weight percent, the calcium may be present in an amount of 0.8-1.2 weight percent, and the manganese may be present in an amount of 0.4-1.0 weight percent. The body may comprise a plate having a thickness of 0.6 mm, a width of 5.0 mm, and a length of 23 mm. The device may further comprise a plurality of screws configured to secure the plate to bone, each screw having a shaft diameter of 1.7 mm and a head diameter of 2.65 mm. The plate may include four holes arranged in pairs, with two holes positioned near each end of the plate. The device may be configured for use in maxillofacial trauma and reconstruction applications.

According to an aspect of the present disclosure, a bioabsorbable magnesium alloy for use in an orthopedic implant is provided. The alloy includes magnesium, zinc in an amount of 1-3 weight percent, calcium in an amount of 0.5-1.5 weight percent, and manganese in an amount of 0-1.0 weight percent. The alloy exhibits a controlled, multi-phase absorption profile when exposed to physiological conditions, the profile comprising an initial period of minimal degradation, followed by a steady-state phase, and concluding with an accelerated absorption phase.

According to other aspects of the present disclosure, the bioabsorbable magnesium alloy may include one or more of the following features. The zinc may be present in an amount of 2-2.5 weight percent. The calcium may be present in an amount of 0.8-1.2 weight percent. The manganese may be present in an amount of 0.4-0.8 weight percent. The initial period of minimal degradation may last for 7-14 days. The steady-state phase may extend from approximately 2 to 8 weeks post-implantation. The accelerated absorption phase may begin after 8-12 weeks.

According to another aspect of the present disclosure, a method of manufacturing a bioabsorbable magnesium alloy for use in an orthopedic implant is provided. The method includes casting an alloy comprising magnesium, 1-3 weight percent zinc, 0.5-1.5 weight percent calcium, and 0-1.0 weight percent manganese, solution treating the cast alloy, and extruding the solution treated alloy to form an extruded alloy. The extruded alloy exhibits a controlled, multi-phase absorption profile when exposed to physiological conditions.

According to other aspects of the present disclosure, the method may include one or more of the following features. Solution treating the cast alloy may comprise heating the cast alloy to a temperature between 400° C. and 450° C. for 6 to 24 hours. Extruding the solution treated alloy may comprise extruding at a temperature between 325° C. and 350° C. Extruding the solution treated alloy may comprise using an extrusion ratio between 25 and 39. The method may further comprise performing a second extrusion on the extruded alloy. The second extrusion may be performed at a temperature lower than the first extrusion. The controlled, multi-phase absorption profile may comprise an initial period of minimal degradation lasting 7-14 days, followed by a steady-state phase extending from 2 to 8 weeks, and concluding with an accelerated absorption phase beginning after 8-12 weeks.

According to another aspect of the present disclosure, an orthopedic implant device is provided. The device includes a body formed from a bioabsorbable magnesium alloy, the alloy comprising magnesium, 1-3 weight percent zinc, 0.5-1.5 weight percent calcium, and 0-1.0 weight percent manganese. The device exhibits a controlled, multi-phase absorption profile when implanted, the profile comprising an initial period of minimal degradation lasting 7-14 days, followed by a steady-state phase lasting 2-8 weeks, and concluding with an accelerated absorption phase.

According to other aspects of the present disclosure, the orthopedic implant device may include one or more of the following features. The zinc may be present in an amount of 2-2.5 weight percent, the calcium may be present in an amount of 0.8-1.2 weight percent, and the manganese may be present in an amount of 0.4-0.8 weight percent. The body may comprise a plate having a thickness of 0.6 mm, a width of 5.0 mm, and a length of 23 mm. The device may further comprise a plurality of screws configured to secure the plate to bone, each screw having a shaft diameter of 1.7 mm and a head diameter of 2.65 mm. The plate may include four holes arranged in pairs, with two holes positioned near each end of the plate. The device may be configured for use in maxillofacial trauma and reconstruction applications.

BRIEF DESCRIPTION OF THE DRAWINGS

The disclosure can be understood in consideration of the following detailed description of various embodiments in connection with the accompanying drawings.

FIG. 40A-40E depict a series of surgical photographs documenting implantation of a plate device, according to an embodiment.

FIG. 41A and FIG. 41B illustrates a scanning electron microscope micrograph of a microstructure sample, according to an embodiment.

FIG. 51 shows metallographic micrographs comparing longitudinal microstructures of three magnesium alloy samples, according to an embodiment.

FIG. 52 illustrates scanning electron microscope micrographs comparing microstructural features of different magnesium alloy samples, according to aspects of the present disclosure.

FIG. 53 depicts metallographic micrographs comparing microstructural features of magnesium alloy samples under different extrusion conditions, according to an embodiment.

FIG. 55 shows a series of images arranged in multiple groups under various test conditions, according to aspects of the present disclosure.

FIGS. 77-84 show images of an animal(s) post-implantation.

DETAILED DESCRIPTION

Figure 1:
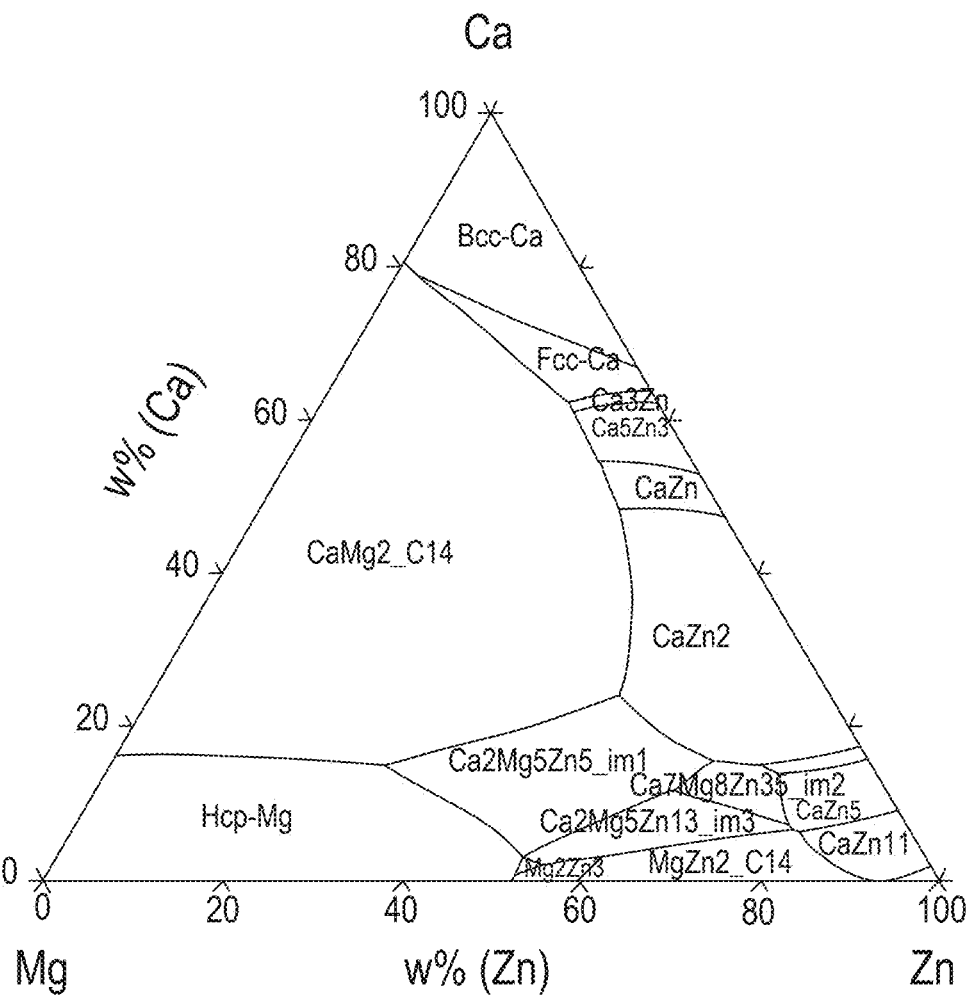
FIG. 1 depicts a ternary phase diagram showing composition relationships between magnesium, calcium, and zinc, according to aspects of the present disclosure.

For purposes of promoting an understanding of the principles of the disclosure, reference will now be made to the embodiments illustrated in the drawings, and specific language will be used to describe the same. It will nonetheless be understood that no limitation of the scope of the disclosure is intended by the illustration and description of certain embodiments of the disclosure. In addition, any alterations and/or modifications of the illustrated and/or described embodiment(s) are contemplated as being within the scope of the present disclosure. Further, any other applications of the principles of the disclosure, as illustrated and/or described herein, as would normally occur to one skilled in the art to which the disclosure pertains, are contemplated as being within the scope of the present disclosure.

The present disclosure relates to bioabsorbable magnesium alloys for use in orthopedic implants and fixation devices. These alloys may provide controlled absorption profiles tailored for specific clinical applications while maintaining sufficient mechanical properties during critical healing phases. In some cases, the magnesium alloys may exhibit improved performance characteristics compared to existing bioabsorbable materials.

The present disclosure relates to a bioabsorbable magnesium alloy for orthopedic implants that offers superior absorption characteristics and controlled degradation behavior. This alloy aims to address several key challenges in the field of bioabsorbable implants, including achieving a controlled, multi-phase absorption profile that matches bone healing rates, avoiding initial burst absorption commonly seen in other magnesium alloys, maintaining bone density adjacent to implants during healing, providing sufficient mechanical strength during critical healing phases, and enabling complete implant absorption within clinically optimal timeframes. The bioabsorbable magnesium alloy system can maintain its mechanical integrity for approximately 13 weeks post-implantation, extending beyond the typical bone healing period. Following this initial phase of sustained strength, the implant may undergo a controlled degradation process. As the absorption progresses, the mechanical properties of the implant gradually diminish, allowing for a smooth transfer of load-bearing function to the healed tissue. During this absorption phase, the constituent elements of the alloy—magnesium (Mg), zinc (Zn), manganese (Mn), and calcium (Ca)—may be released into the surrounding physiological environment. These released minerals may be metabolized by the body, potentially contributing to local tissue health and regeneration processes.

A unique advantage of the alloy and implant systems being developed for the intended use and future uses such as mandible fixation, is the minimized absorption upon implantation and through healing which allows for design of more complex implants to serve a broader patient population. The unique absorption characteristics not only allow for implant designs that may optimize biological response but also allow for design of locking plate and screw systems which require slow initial absorption to maintain the plate/screw mechanical locking features. The aim is to achieve a level of performance beyond the current state of the art to lower complication rates, such as infections, while addressing a larger patient population compared to existing resorbable polymer and bioabsorbable magnesium technologies. This will be achieved by launching systems indicated for use in load-bearing anatomies such as mandible where high hardware infection and removal rates persist with no available options for absorbable hardware.

The implant (e.g., maxillofacial fixation system devices, plates and screws) can be used for osteotomy, stabilization, and fixation in fracture repair and reconstructive procedures for trauma and orthognathic procedures involving the maxilla, zygoma, orbital rim, and frontal bone in adult patients. Plates can be in various shapes and sizes and may be bent or cut to accommodate target anatomy. The implant system can be bioabsorbable and may bioabsorb within 1.5 years following implantation. The system can act as compensation for broken bones (injury) and as a modification of anatomy for reconstruction procedures in the maxillofacial skeleton. Typical users of the system may be oral and maxillofacial surgeons, plastic and reconstructive surgeons, and periodontal surgeons. The implant can be implanted in the maxillofacial skeleton (maxilla and zygoma), orbital rim and frontal bone for adult and pediatric patients requiring temporary fixation; bioabsorption can occur as bone strength is gained and the lifetime of the device's functional use has been reached.

An advantage of the disclosed alloy and implant systems, including future applications such as mandibular fixation, is their controlled absorption profile upon implantation and during healing. This enables the design of more complex implant geometries suitable for a broader patient population. The controlled resorption characteristics not only support implant designs that optimize biological response but also enable development of locking plate and screw systems that require delayed initial absorption to preserve mechanical interlock. The systems aim to exceed current state-of-the-art performance by reducing complication rates, such as infection, while serving a wider patient demographic than existing resorbable polymer or bioabsorbable magnesium technologies. In particular, the systems are intended for use in load-bearing anatomical sites, such as the mandible, where high infection and hardware removal rates persist and absorbable hardware solutions are currently unavailable.

The present disclosure provides a bioabsorbable magnesium alloy for orthopedic implants that offer superior absorption characteristics and controlled degradation behavior. Unlike conventional approaches that may rely on the formation of $Mg_2Ca$ phases, the alloy composition and processing methods described herein are designed to promote the formation of ternary intermetallic phases while minimizing $Mg_2Ca$ phases. This approach allows for precise control over the alloy's microstructure, resulting in a multi-phase absorption profile that can be tailored to match bone healing rates. The alloy composition and processing methods described herein may provide improved corrosion resistance, more uniform degradation, and better mechanical properties compared to traditional magnesium alloys used in bioabsorbable implants.

The bioabsorbable magnesium alloy described herein may include specific contents of zinc and calcium that are carefully selected to minimize or avoid the precipitation of $Mg_2Ca$ phases. In some aspects, the zinc content may range from 0.5-4 weight percent, while the calcium content may range from 0.5-1.5 weight percent. These composition ranges, combined with carefully selected processing techniques, may allow for the promotion of ternary intermetallic phases while reducing or eliminating the formation of $Mg_2Ca$ phases.

The processing techniques may include specific casting, solution treatment, and extrusion parameters. For example, the solution treatment temperature may be maintained below the $Mg_2Ca$ formation temperature, which may be determined through thermal analysis techniques such as differential scanning calorimetry (DSC). In some cases, the solution treatment may be performed at temperatures between 400° C. and 450° C. for 6 to 24 hours. The extrusion process may be carried out at temperatures between 325° C. and 350° C., with extrusion ratios between 25 and 39.

By controlling both the alloy composition and processing parameters, the microstructure of the magnesium alloy may be tailored to achieve the desired balance of mechanical properties and controlled degradation behavior, while minimizing the presence of $Mg_2Ca$ phases that could lead to non-uniform corrosion.

To accomplish these goals, the invention utilizes a specific alloy composition comprising magnesium with controlled amounts of zinc (0.5-4 wt %), calcium (0.5-1.5 wt %), and one or more additional alloying elements, such as a third alloying element (e.g., manganese (Mn), strontium (Sr), aluminum (Al), yttrium (Y), cerium (Ce), gadolinium (Gd), neodymium (Nd), etc.). In some cases, the third alloying element may be manganese (up to 1.5 wt %). The alloy's microstructure is optimized by reducing or eliminating $Mg_2Ca$ phases relative to ternary intermetallic phases, which helps control corrosion rate and uniformity Additionally, the third alloying element (e.g., manganese) may contribute to the formation of a robust surface oxide layer that aids in controlling initial degradation. The alloy is processed using tailored methods, including specific casting, solution treatment, and extrusion parameters, to achieve the desired microstructure and properties.

$Mg_2Ca$ phase may have detrimental effects on the implant. Since they tend to form in stringers and can be difficult to manipulate with heat treatments, their morphology and anodic properties can cause aggressive localized attack of the implant. On the other hand, ternary phases can be manipulated to increase the corrosion rate with a uniform distribution to encourage uniform corrosion. Higher process temperatures cause increased ternary volume fraction and phase size increase corrosion rate. This is in contrast to the $Mg_2Ca$ phases which tend to form in long stringers, can be difficult to manipulate through heat treatment, and are anodic causing localized attack.

Increasing alloy processing temperatures may transition GP zones into ternary phases. Solute elements (Zn and Ca) may segregate to grain boundaries as a layer of fine precipitates, which means more grain refinement will lead to more grain boundary area for those elements to segregate to at the expense of the ternary phases. In some embodiments, when Zn is at least 2.0% by weight, fine dispersions of precipitates may be found along grain boundaries, which may be beneficial. Heating to gradually higher temperatures may first cause GP zones, then at increasingly higher temperatures causes GP zone consolidation into $Mg_2Ca$ and ternary phases. Processing can be used to first suppress formation of the larger ternary phases in favor of GP zones and fine distributions at the grain boundaries, and heat treatments can precipitate larger ternary phases to alter absorption rate. Dynamic recrystallization processing can be used to produce ternary phases at grain boundaries. Static heat treatments can be used to produce GP zones and ternary precipitates within the grains. By increasing Zn/Ca ratio, ternary phases can be exclusively obtained, and temperatures can be varied (e.g., increased) to change the precipitate volume fraction and morphology to control the corrosion rate.

The resulting bioabsorbable magnesium alloy exhibits a multi-phase absorption profile, engineered to have an initial period of minimal degradation, followed by a steady-state phase, and concluding with an accelerated absorption phase. This profile, combined with carefully balanced mechanical properties and degradation rates, ensures that the implant maintains structural integrity during critical healing periods while allowing for gradual absorption. This approach results in a bioabsorbable magnesium alloy that offers improved performance over existing technologies, particularly in terms of controlled degradation, bone density maintenance, and osseointegration. While the invention is particularly targeted for use in maxillofacial trauma and reconstruction applications, it also shows potential for broader orthopedic use.

In use, temporary implants need to maintain mechanical support and integrity until healing within an implant recipient is achieved and a temporary implant is no longer needed. In general, a relatively slower absorption rate during healing may accelerate to a higher absorption rate after healing such that the entire implant may be gone after one to two years. Such an absorption profile may be achieved by using larger volume fractions of zinc (Zn) and calcium (Ca) (1% by weight or higher) and by adjusting the Zn to Ca ratio in a magnesium-calcium-zinc (Mg—Ca—Zn) based alloy system. The disclosed magnesium alloy may reduce biocompatibility issues associated with rare-earth metal alloying by limiting alloying elements to Ca, Zn, and in some embodiments Mn.

The absorption profile may be further modified by using a third alloying element, such as manganese (Mn). Increasing Mn content may increase the formation of a more stable surface oxide which slows corrosion and prolongs the life of an implant to fit the exact needs of the implant's functional life. The third alloying element may also be aluminum (Al) or strontium (Sr). The absorption profile of the bioabsorbable magnesium alloy may be further modified by incorporating additional alloying elements beyond zinc and calcium. While manganese (Mn) is a suitable choice for its ability to enhance the formation of a stable surface oxide layer, other elements may also be used to tailor the alloy's properties and degradation behavior.

In some aspects, aluminum (Al) may be used as a third alloying element. Aluminum can contribute to solid solution strengthening and may help refine the grain structure of the alloy. The addition of aluminum may also influence the corrosion behavior of the alloy, potentially slowing the overall degradation rate.

Alternatively, strontium (Sr) may be incorporated as a third alloying element. Strontium has been shown to have beneficial effects on bone formation and may enhance the bioactivity of the implant. In some cases, strontium may also contribute to grain refinement and may influence the formation and distribution of intermetallic phases within the alloy.

The choice of the third alloying element may depend on the specific requirements of the implant application. For instance, aluminum may be preferred in cases where additional strength is required, while strontium might be chosen for applications where enhanced bone growth stimulation is desired. The concentration of these elements may be carefully controlled to achieve the desired balance of properties and degradation behavior.

In some embodiments, combinations of these elements (Mn, Al, Sr) may be used to further fine-tune the alloy's properties. The specific composition may be optimized based on factors such as the intended anatomical location of the implant, expected load-bearing requirements, and desired absorption timeline.

According to embodiments, the disclosed alloy may include Zn and Ca alloying at relatively higher levels (area fraction of at least 0.1%, 0.25%, 0.5%, or 1.0% ternary phase as observed in a 2-dimensional micrograph) to encourage faster absorption in the later stages of implant life and to ensure full absorption is reached within the target time. The disclosed alloy may also include Zn and Ca alloying at relatively higher levels along with the average diameter and maximum phase size of the ternary phase which alters the electrochemical properties (electrochemical potential) of the alloy. The phase fraction of the ternary phase must be low enough to encourage a slow and uniform absorption profile in the early stage of implant life for the intended implant application, but high enough to encourage implant strength and faster absorption in the later post-healing stage of the implant life. In embodiments, the phase fraction of the ternary phase may be approximately 0% to 15% and may include a maximum phase length ranging from approximately 50 to approximately 200 microns, where a phase may form as a stringer or a string of closely spaced ternary phase precipitates. In embodiments, the phase fraction of the ternary phase may be approximately 0.25% to 15% and may include a maximum precipitate length of approximately 200 microns. In embodiments, the phase fraction of the ternary phase may be approximately 0.25% to 5% and may include a maximum precipitate length of approximately 100 microns. In embodiments, the phase fraction of the ternary phase may be approximately 0.1% to 3.5% and may include a maximum precipitate length of approximately 50 microns. As absorption progresses, the resistivity of an oxide layer decreases as ternary phases and remaining zinc from the ternary phases and solid solution accumulates in the oxide layer, thus facilitating electron exchange across the layer and causing the absorption rate to accelerate. To obtain low absorption rates in the early stages of implant life, uniform absorption, and control the time at which the acceleration of absorption occurs, the ternary phase sizes must be reduced through an engineered thermomechanical processing recipe. Process parameters and/or a final aging treatment can be utilized to manipulate the average diameter of the ternary phases to adjust the absorption profile of the alloy for the intended implant application.

According to embodiments, a method to reduce the ternary phase sizes may utilize a series of hot working and solution annealing steps. This may include, for example, extruding a cast billet, solution-treating the billet above the equilibrium solidus temperature, and extruding the billet again. In some embodiments, solution treating is effective at reducing the sizes of, or eliminating, ternary phases when performed after a working step.

In embodiments, plastic deformation techniques may be used to increase size and volume fraction of ternary phases in elongated concentrations within the disclosed alloy. Elongated phases and elongated concentrations of phases, or stringers (due to working direction through thermomechanical processing) may increase corrosion rate and decrease uniformity of corrosion through localized corrosion i.e., pitting as compared to spherical phases. Elongated phases typically form along the principal working direction when a mechanical process is applied to an as-cast billet. Large, elongated phases may then be reduced and broken up by applying a solution heat treatment after a thermomechanical process to make absorption more uniform.

In some embodiments, plastic deformation techniques such as equal channel angular processing (ECAP) may be used to refine microstructure further, thereby increasing strength, ductility, and other material properties. In some embodiments, plastic deformation techniques may include heating the disclosed alloy to a suitable temperature to facilitate plastic deformation without inducing cracking or fractures. The heated alloy may be subjected to multiple high-strain, or high-pressure, passes through a die to increase deformation and refine grain structure. In this way, plastic deformation may create a homogenous microstructure of fine grains.

Further manipulation of the absorption profile can be achieved by solution treating and annealing after working to further manipulate ternary phase. Guiner-Preston (GP) zones may form from solute Zn and Ca atoms during hot deformation processing and/or an aging treatment. Creating GP zones through aging can be used to increase the strength of the alloy/implant with no or minimal change to the absorption rate. The process may include solution treating at or above 400° C., then following with an aging treatment between 150° C. and 350° C. In this way, solution heat treatment preferentially sacrifices the larger ternary phases by allowing those alloying elements to diffuse into solution, which are then depleted by formation of GP zones and smaller ternary phases through aging heat treatments.

Solute elements (Zn and Ca) preferentially segregate to grain boundaries during precipitation reactions that occur during thermomechanical processing and aging heat treatments, resulting in more grain refinement leading to more grain boundary area for those elements to segregate to. During thermomechanical processing, smaller size ternary phases and GP zones form at the expense of the larger ternary phases, reducing the average size of ternary phases. Large ternary phases are further reduced through solution heat treatments where the volume fraction of ternary phase is reduced for a given alloy composition, thus decreasing the electrochemical potential of the alloy while reducing the microgalvanic effects through a reduction in cathodic phases and an increase in the anode to cathode ratio, thus slowing the absorption rate. Through subsequent thermomechanical processing after a solution heat treatment, these solute elements may be re-precipitated into smaller diameter phases.

According to embodiments, alloying elements that may also accomplish grain refinement as mentioned above may include strontium (Sr), aluminum (Al), tin (Sn), silver (Ag), and copper (Cu). In embodiments. Alloying may include introducing a third phase, such as $\alpha$-Mn and other alloying elements/phases, to reduce grain sizes and increase the number of precipitates at grain boundaries, thus reducing precipitate size.

According to embodiments, a method may include solution treating and thermomechanical processing to increase the number fraction of ternary precipitates, which will cause a decrease in average size for a given alloy composition. Solution treating reduces the size of the largest precipitates and breaks up large strings of precipitates that exist after extrusion and mechanically working the material breaks up the precipitates into smaller sizes. Hot working, such as extrusion, creates dislocations for GP zones and subsequent ternary precipitates to nucleate, increasing the number of precipitates and reducing the size. Further, GP zones and their subsequent precipitates generally form and reside at or near grain boundaries, thus increasing the grain boundary area by reducing grain size via thermomechanical processing which provides more nucleation sites for GP zones and ternary phase precipitation, increasing the number density of phases and thus reducing ternary phase diameters to lower absorption rate.

To increase the absorption rate, an aging heat treatment at higher temperatures can be applied to increase the size of the ternary precipitates by eliminating the GP zones and solute atoms. Breaking up the ternary phases into smaller sizes, then heat treating to increase the size is advantageous because this leads to a more uniform statistical distribution of phase sizes which results in more uniform implant absorption. Alternatively, the same result may be achieved by increasing the extrusion temperature.

The magnesium alloys described herein may comprise zinc, calcium, and manganese as alloying elements. The alloy may comprise up to 5 weight percent zinc, up to 2 weight percent calcium, and up to 2 weight percent of an additional alloying element, such as manganese. In some cases, the zinc content may be 0.45%, 0.5%, 1.2%, 1.5%, 2%, 2.5%, 3%, or 3.5% by weight. In some cases, the calcium content may be 0.3%, 0.4%, 0.45%, 0.5%, 0.8%, 1%, 1.2%, or 1.5% by weight. In some cases, the manganese content may be 0.2%, 0.4%, 0.5%, 0.6%, 0.7%, or 1% by weight. In some embodiments, the alloy composition may include 1-3% zinc, 0.5-1.5% calcium, and 0-1.0% manganese by weight, with the balance being magnesium and incidental impurities. In some cases, the calcium content may be 0.2-1.0% by weight. In some cases, the content may be 0.3-0.8% by weight. In some cases, the manganese content may be 0.3-1.0% by weight. The specific concentrations of alloying elements may be adjusted to achieve desired absorption rates and mechanical properties for particular orthopedic applications.

A key feature of these magnesium alloys may be their ability to provide a controlled, multi-phase absorption profile. This absorption behavior may be characterized by an initial period of minimal degradation, followed by a steady-state phase, and concluding with an accelerated absorption phase. By tailoring this profile, the alloys may maintain structural integrity during critical healing periods while subsequently degrading in a predictable manner.

The magnesium alloys disclosed herein may offer potential advantages over existing bioabsorbable materials in terms of absorption kinetics, mechanical strength retention, and biocompatibility. These alloys may be processed using various techniques to further optimize their properties for specific orthopedic applications.

The bioabsorbable magnesium alloy may comprise zinc, calcium, and manganese as alloying elements. In some cases, the alloy composition may include 1-3% zinc, 0.5-1.5% calcium, and 0-1.0% manganese by weight, with the balance being magnesium and incidental impurities. The specific concentrations of alloying elements may be adjusted to achieve desired absorption rates and mechanical properties for particular orthopedic applications.

In some embodiments, the magnesium alloy may have a composition of approximately 2% zinc, 1% calcium, and 1% manganese by weight. This composition may be suitable for preclinical studies and may provide a balance of corrosion resistance, mechanical strength, and biocompatibility.

The inclusion of zinc in the alloy may contribute to improved corrosion resistance and mechanical properties. Zinc may also play a role in refining the grain structure of the alloy. The calcium content may help to control the corrosion rate and may contribute to the formation of beneficial precipitates within the alloy microstructure. Manganese may act as a grain refiner and may improve the alloy's resistance to corrosion.

The ratios between these alloying elements may be adjusted to fine-tune the alloy's properties. For example, increasing the zinc to calcium ratio may alter the formation of intermetallic phases, potentially affecting the alloy's degradation behavior. The manganese content may be varied to optimize grain refinement and corrosion resistance.

The alloy may have a Zn/Ca ratio between 0-6. In some cases, the Zn/Ca ratio may be 1.01. In some cases, the Zn/Ca ratio may be 1.30. In some cases, the Zn/Ca ratio may be 1.34. In some cases, the Zn/Ca ratio may be 1.41. In some cases, the Zn/Ca ratio may be 1.75. In some cases, the Zn/Ca ratio may be 1.78. In some cases, the Zn/Ca ratio may be 1.90. In some cases, the Zn/Ca ratio may be 1.97. In some cases, the Zn/Ca ratio may be 2.05. In some cases, the Zn/Ca ratio may be 2.08. In some cases, the Zn/Ca ratio may be 2.11. In some cases, the Zn/Ca ratio may be 2.14. In some cases, the Zn/Ca ratio may be 2.15. In some cases, the Zn/Ca ratio may be 2.24. In some cases, the Zn/Ca ratio may be 2.36. In some cases, the Zn/Ca ratio may be 2.37. In some cases, the Zn/Ca ratio may be 2.39. In some cases, the Zn/Ca ratio may be 2.50. In some cases, the Zn/Ca ratio may be 2.52. In some cases, the Zn/Ca ratio may be 2.56. In some cases, the Zn/Ca ratio may be 2.64. In some cases, the Zn/Ca ratio may be 2.76. In some cases, the Zn/Ca ratio may be 2.77. In some cases, the Zn/Ca ratio may be 2.79. In some cases, the Zn/Ca ratio may be 2.82. In some cases, the Zn/Ca ratio may be 2.83. In some cases, the Zn/Ca ratio may be 2.84. In some cases, the Zn/Ca ratio may be 2.88. In some cases, the Zn/Ca ratio may be 2.89. In some cases, the Zn/Ca ratio may be 2.90. In some cases, the Zn/Ca ratio may be 2.94. In some cases, the Zn/Ca ratio may be 2.99. In some cases, the Zn/Ca ratio may be 3.01. In some cases, the Zn/Ca ratio may be 3.05. In some cases, the Zn/Ca ratio may be 3.09. In some cases, the Zn/Ca ratio may be 3.10. In some cases, the Zn/Ca ratio may be 3.19. In some cases, the Zn/Ca ratio may be 3.27. In some cases, the Zn/Ca ratio may be 3.29. In some cases, the Zn/Ca ratio may be 3.59. In some cases, the Zn/Ca ratio may be 3.60. In some cases, the Zn/Ca ratio may be 3.69. In some cases, the Zn/Ca ratio may be 3.79. In some cases, the Zn/Ca ratio may be 3.81. In some cases, the Zn/Ca ratio may be 3.84. In some cases, the Zn/Ca ratio may be 3.85. In some cases, the Zn/Ca ratio may be 3.86. In some cases, the Zn/Ca ratio may be 3.87. In some cases, the Zn/Ca ratio may be 4.02. In some cases, the Zn/Ca ratio may be 4.07. In some cases, the Zn/Ca ratio may be 4.11. In some cases, the Zn/Ca ratio may be 4.14. In some cases, the Zn/Ca ratio may be 4.27. In some cases, the Zn/Ca ratio may be 4.28. In some cases, the Zn/Ca ratio may be 4.48. In some cases, the Zn/Ca ratio may be 4.55. In some cases, the Zn/Ca ratio may be 4.85. In some cases, the Zn/Ca ratio may be 4.90. In some cases, the Zn/Ca ratio may be 5.37.

In some cases, trace amounts of other elements may be present in the alloy. These trace elements may include, but are not limited to, iron, nickel, copper, and aluminum. The concentrations of these trace elements may be controlled to minimize their impact on the alloy's performance.

The alloy may have a sum of trace elements between 0-1 weight percent. In some cases, the sum of trace elements may be 0.034%. In some cases, the sum of trace elements may be 0.037%. In some cases, the sum of trace elements may be 0.038%. In some cases, the sum of trace elements may be 0.040%. In some cases, the sum of trace elements may be 0.042%. In some cases, the sum of trace elements may be 0.043%. In some cases, the sum of trace elements may be 0.047%. In some cases, the sum of trace elements may be 0.051%. In some cases, the sum of trace elements may be 0.052%. In some cases, the sum of trace elements may be 0.053%. In some cases, the sum of trace elements may be 0.054%. In some cases, the sum of trace elements may be 0.056%. In some cases, the sum of trace elements may be 0.057%. In some cases, the sum of trace elements may be 0.059%. In some cases, the sum of trace elements may be 0.060%. In some cases, the sum of trace elements may be 0.070%. In some cases, the sum of trace elements may be 0.080%. In some cases, the sum of trace elements may be 0.100%.

The composition of the magnesium alloy may be tailored to achieve specific absorption profiles and mechanical properties. By adjusting the concentrations of zinc, calcium, and manganese, the alloy's behavior may be optimized for different orthopedic applications, such as maxillofacial reconstruction or extremity fixation.

The magnesium alloy may be processed using various techniques to optimize its properties for specific orthopedic applications. In some cases, the processing methods may include casting, solution treatment, and extrusion steps.

The alloy may have a liquidus temperature between 600-650° C. In some cases, the liquidus temperature may be 641° C. In some cases, the liquidus temperature may be 642° C. In some cases, the liquidus temperature may be 644° C.

The alloy may have a solidus temperature between 300-410° C. In some cases, the solidus temperature may be 335° C. In some cases, the solidus temperature may be 400° C. In some cases, the solidus temperature may be 404° C. In some cases, the solidus temperature may be 407° C.

FIG. 55 depicts a flowchart including a method 600 of preparing the disclosed alloy. In step 602, the method may include extruding a magnesium alloy a first time (e.g., the magnesium alloy including about 1-3% by weight zinc, about 0.5-1.5% by weight calcium, about 0-1.0% by weight of an alloying element), and a balance of magnesium. Step 604 may include solution treating the magnesium alloy. Step 606 may include extruding the magnesium alloy a second time.

Figure 56:
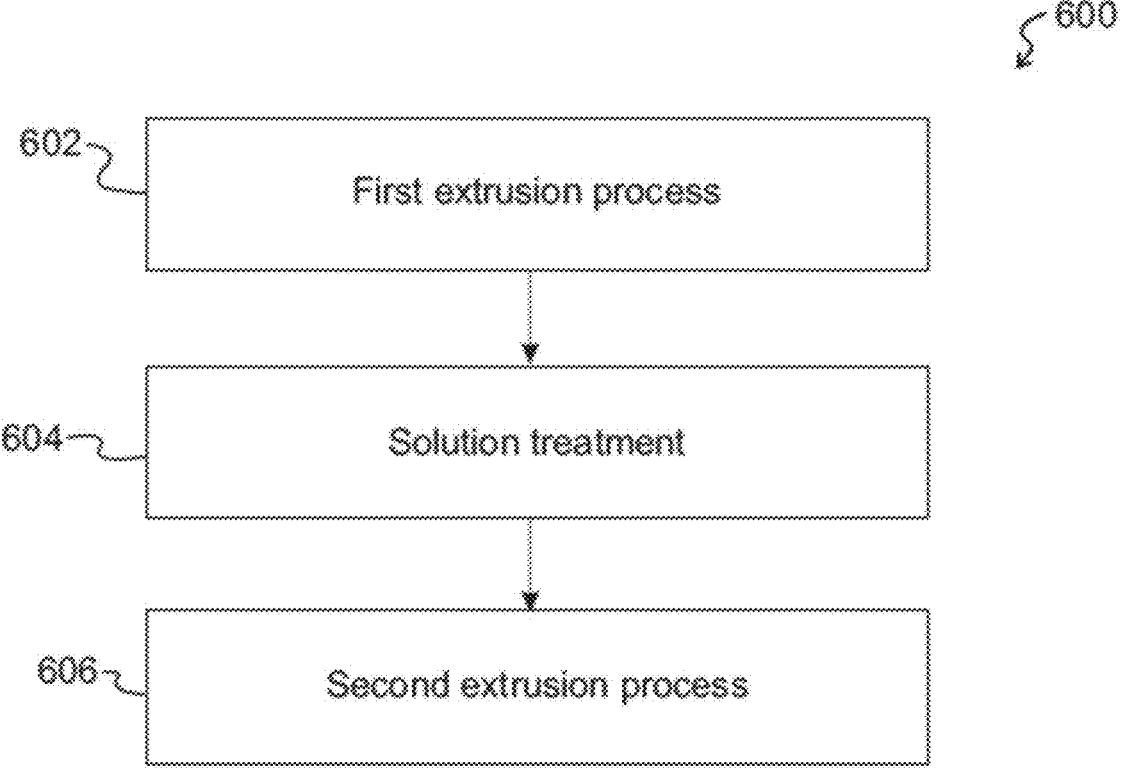
FIG. 56 depicts a flowchart including a method of preparing the disclosed alloy according to an embodiment.

FIG. 56 depicts a flowchart 700 including a method of preparing the disclosed alloy. A first microstructure 701 of the alloy is shown as cast. The method may include a first extrusion 702 step resulting in a second microstructure 703. The method may include a solution treatment 704 step resulting in a third microstructure 705. The method may include a second extrusion 706 step resulting in a fourth microstructure 707.

Figure 57:
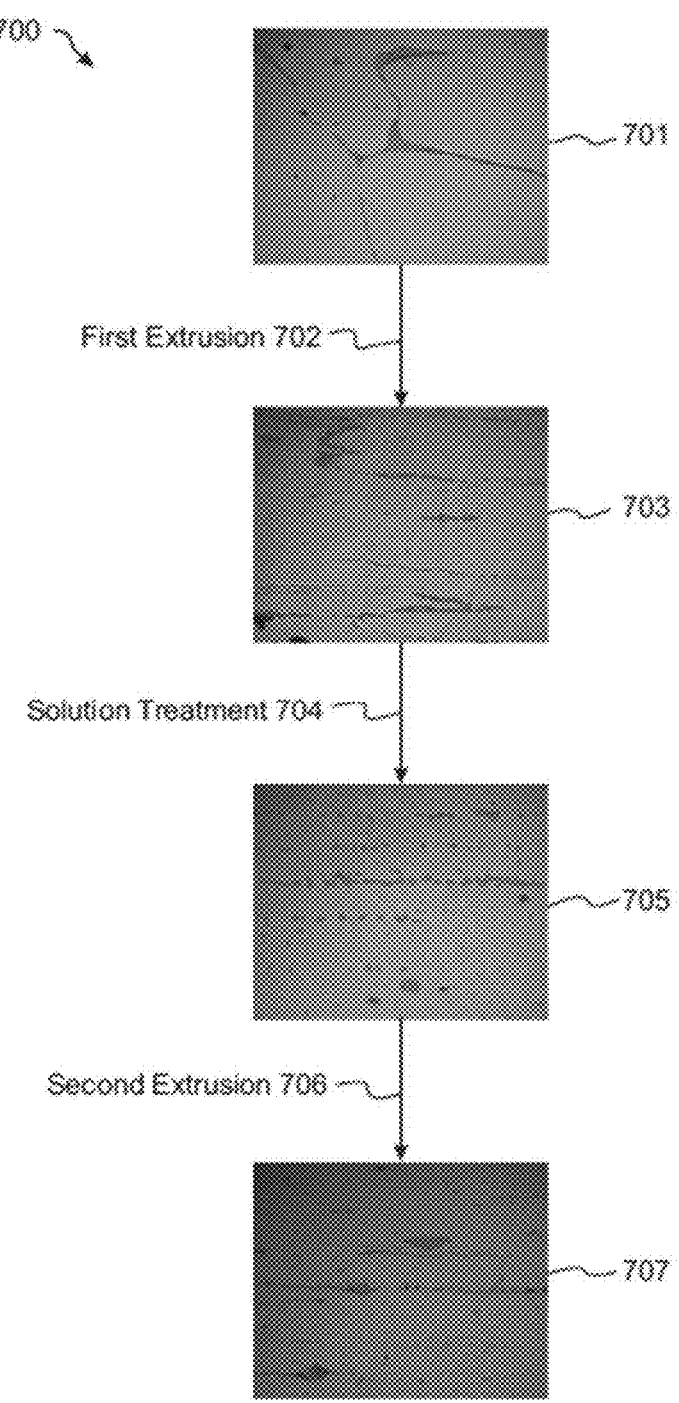
FIG. 57 depicts a flowchart including a method of preparing the disclosed alloy according to an embodiment.
Figure 58:
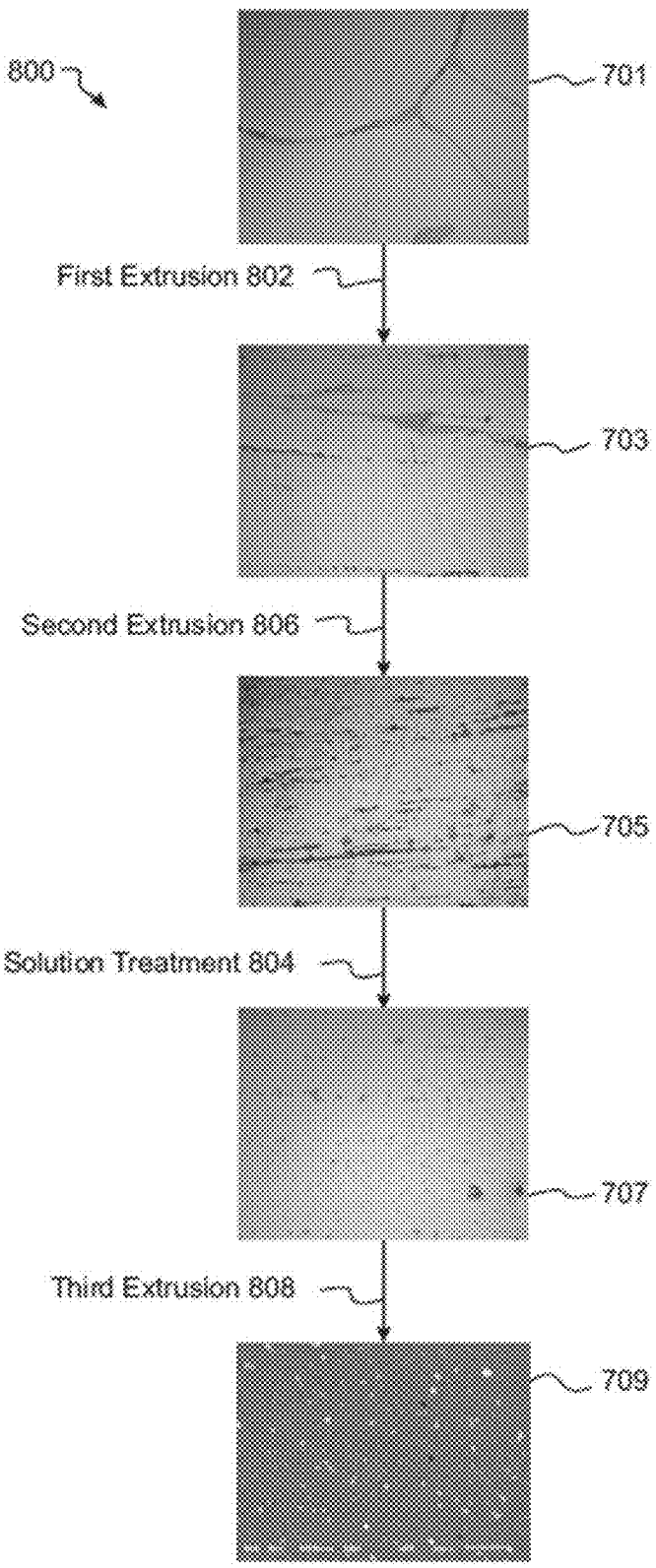
FIG. 58 depicts a flowchart including a method of preparing the disclosed alloy according to an embodiment.
Figure 59:
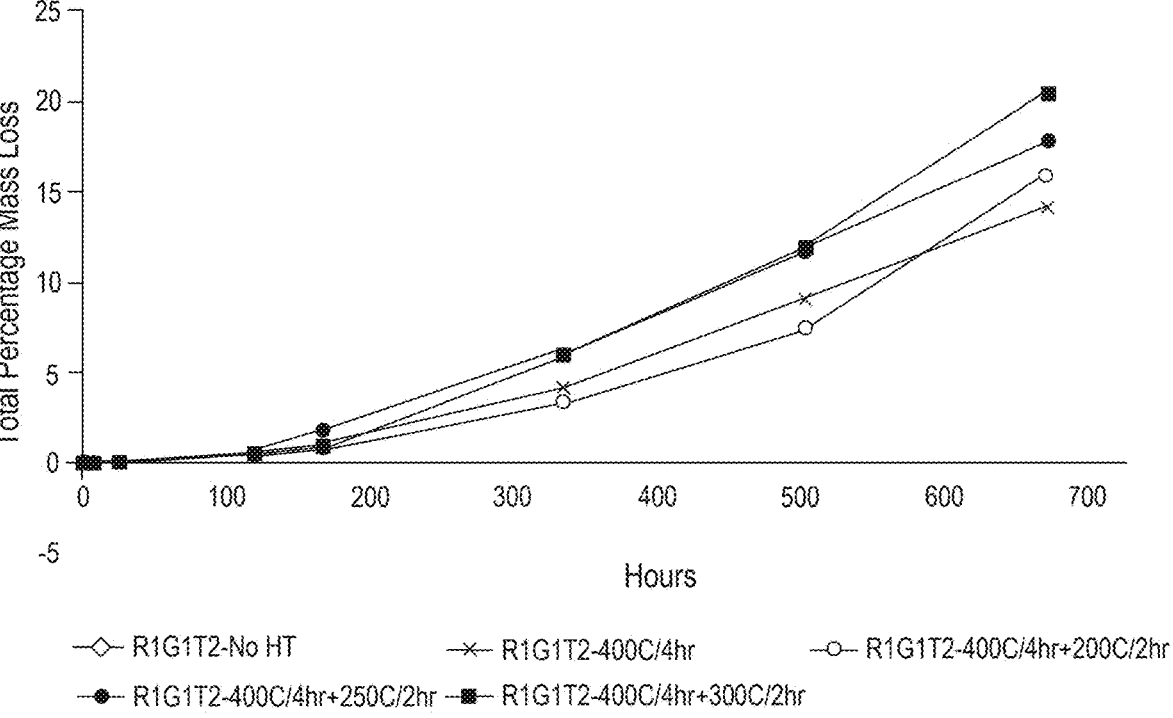
FIG. 59 depicts a graph showing total percentage mass loss over time for multiple magnesium alloy samples under different heat treatment conditions.
Figure 60:
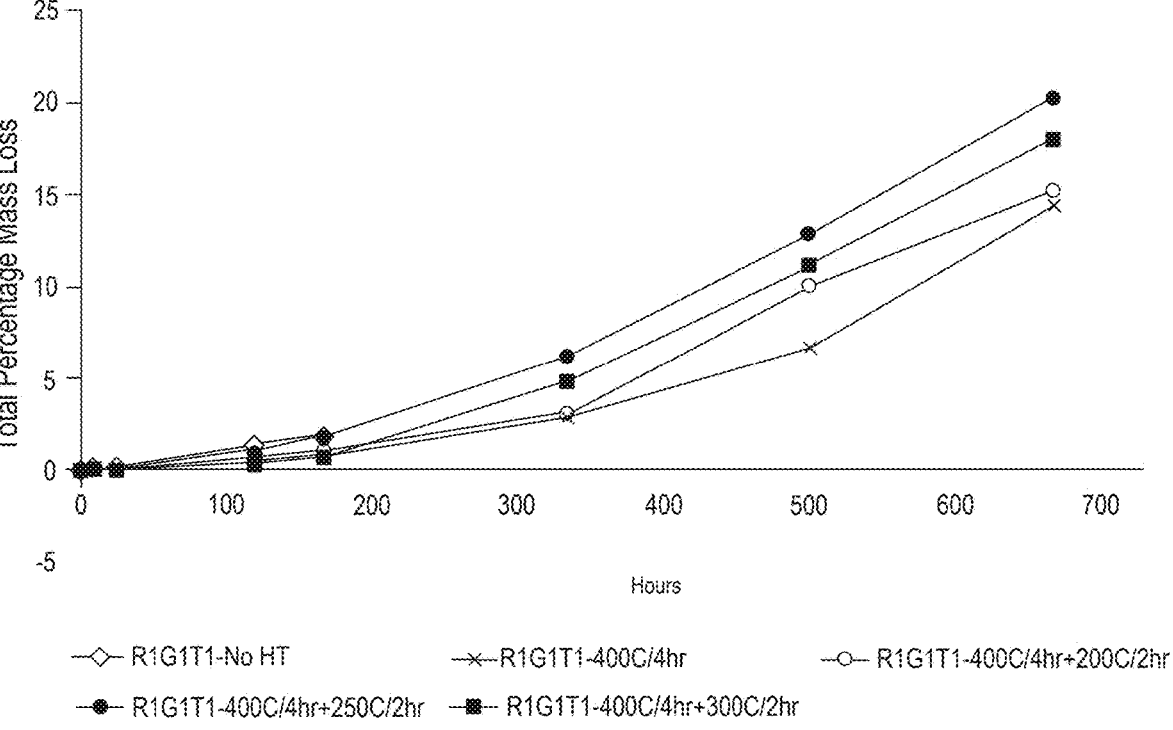
FIG. 60 depicts a graph showing total percentage mass loss over time for multiple magnesium alloy samples under different heat treatment conditions.
Figure 61:
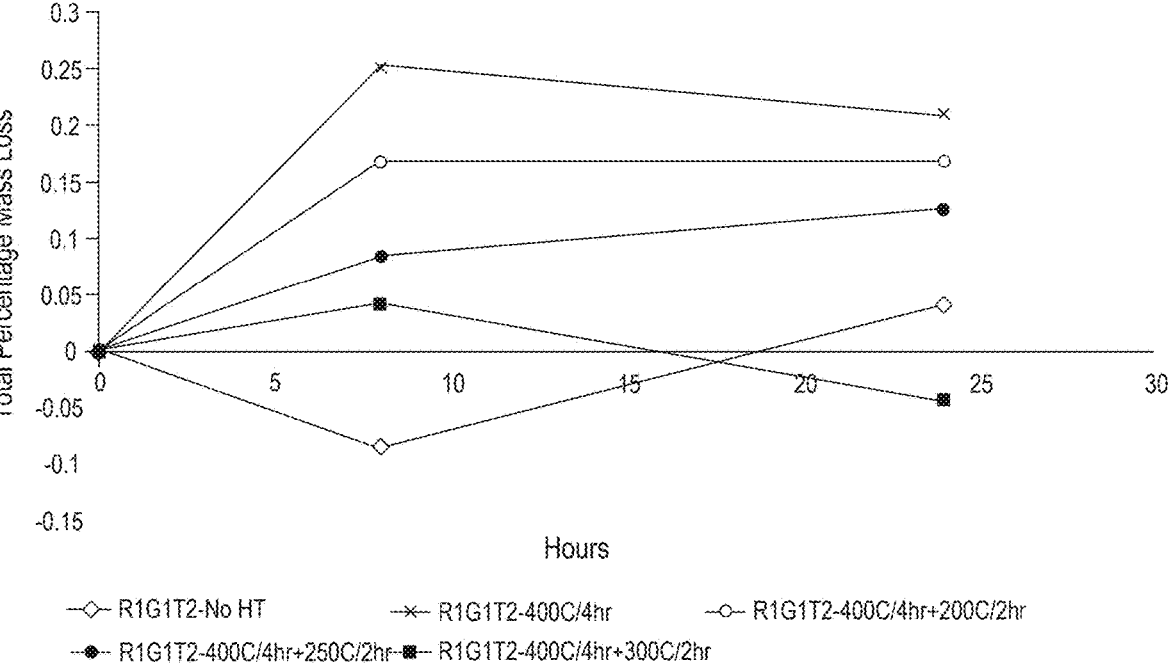
FIG. 61 depicts a graph showing total percentage mass loss over time for multiple magnesium alloy samples under different heat treatment conditions.
Figure 62:
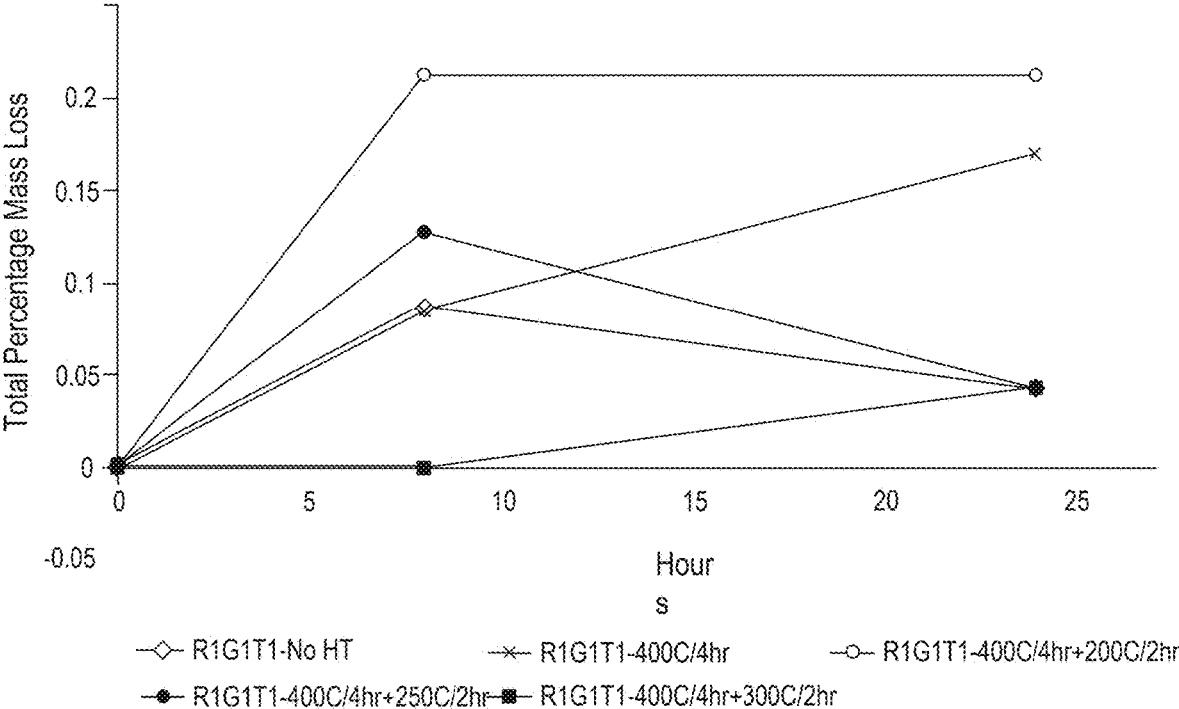
FIG. 62 depicts a graph showing total percentage mass loss over time for multiple magnesium alloy samples under different heat treatment conditions.
Figure 63:
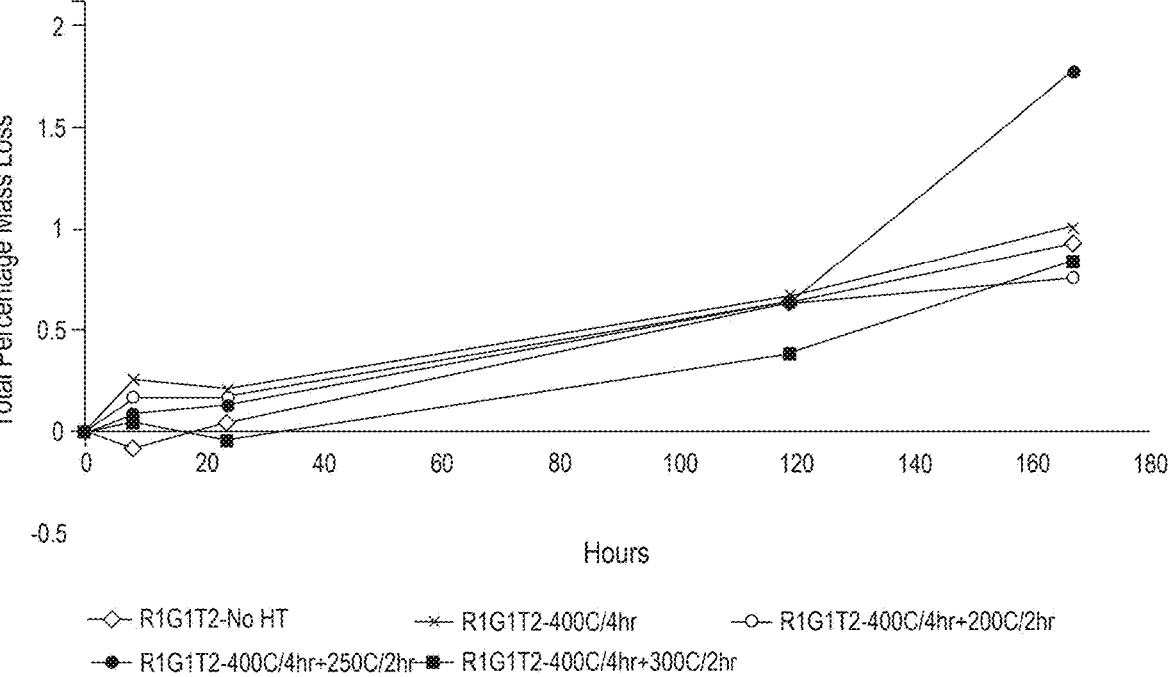
FIG. 63 depicts a graph showing total percentage mass loss over time for multiple magnesium alloy samples under different heat treatment conditions.
Figure 64:
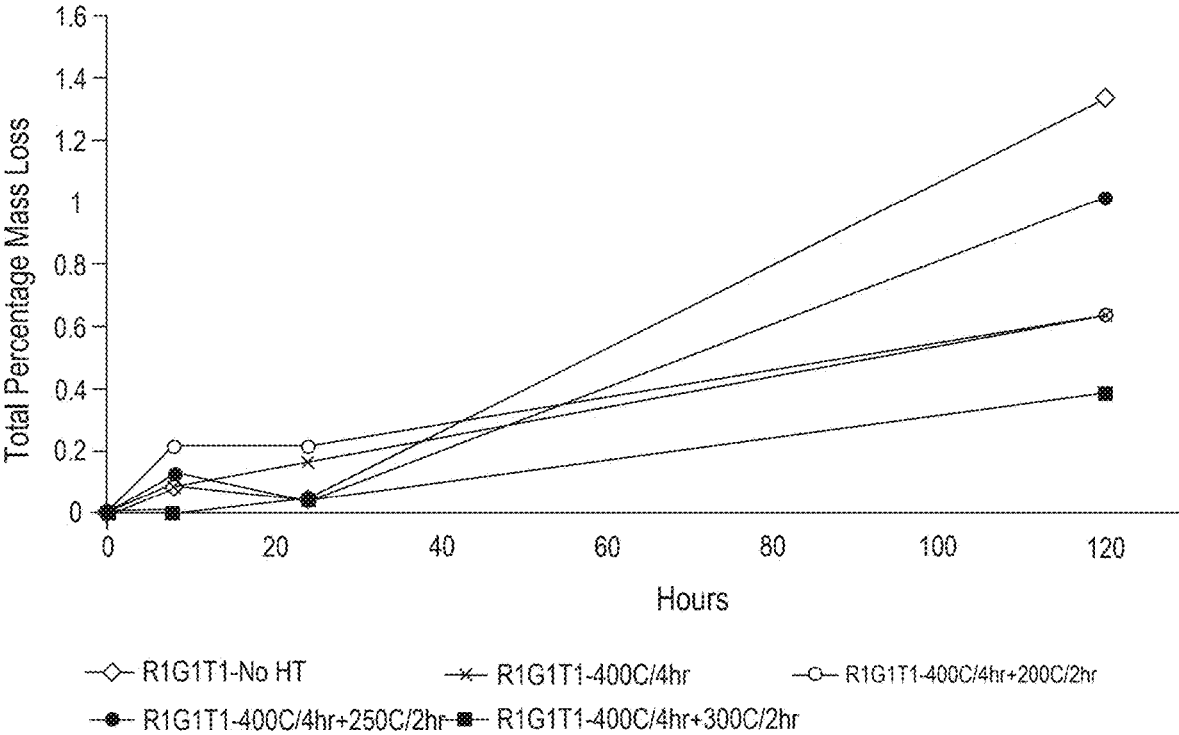
FIG. 64 depicts a graph showing total percentage mass loss over time for multiple magnesium alloy samples under different heat treatment conditions.
Figure 65:
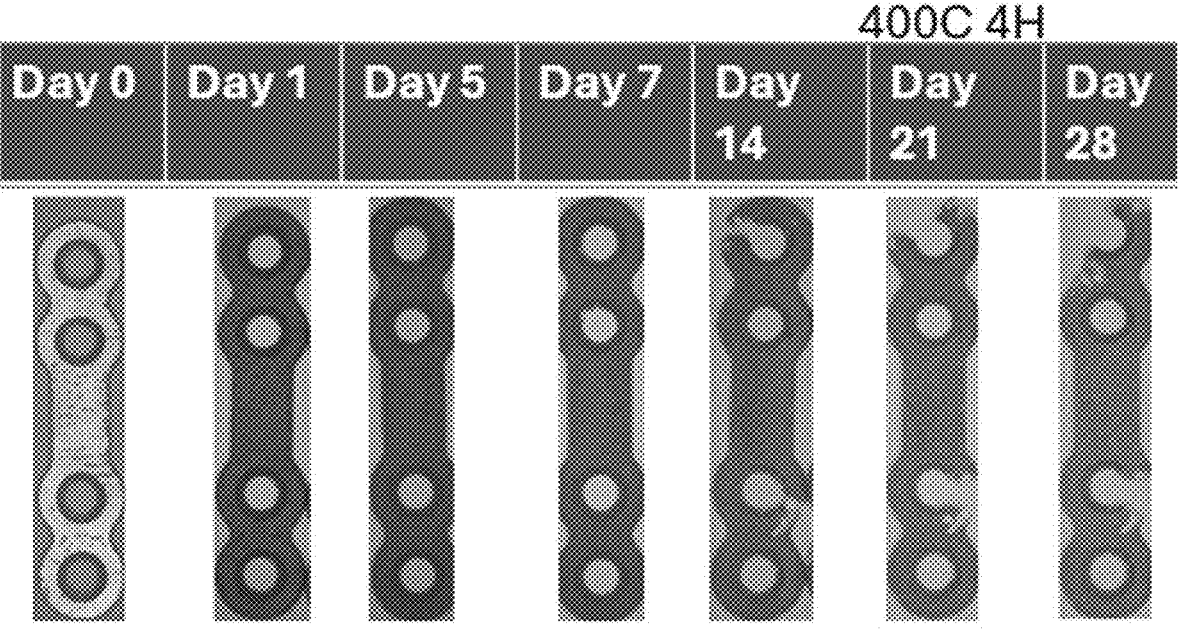
FIG. 65 shows a series of images documenting the progressive degradation of magnesium alloy plate samples over time.
Figure 66:
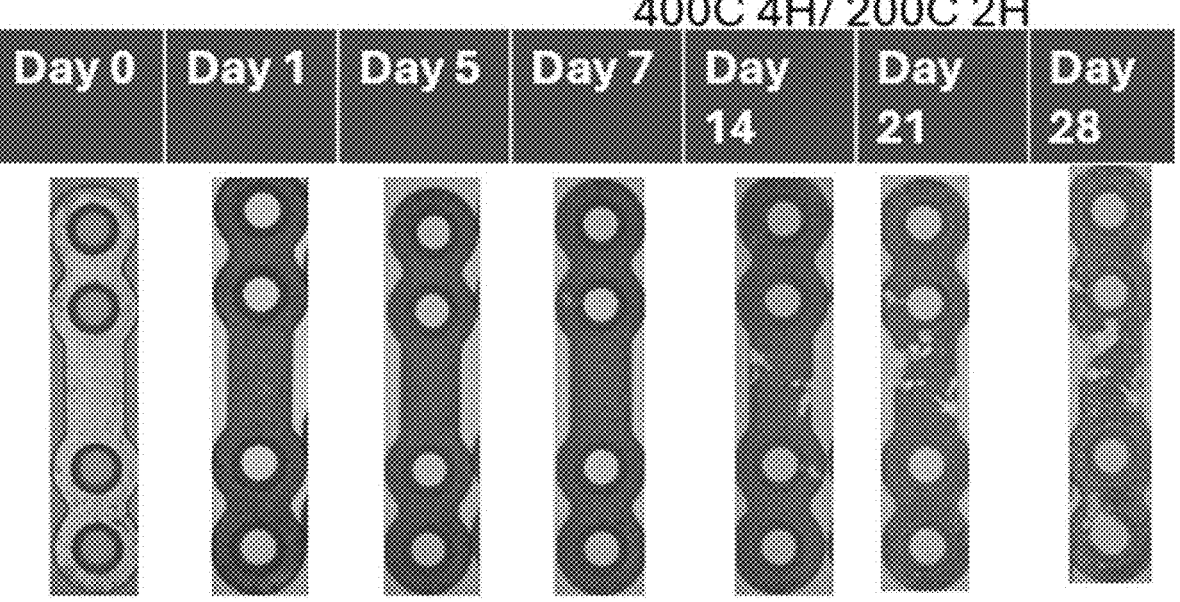
FIG. 66 shows a series of images documenting the progressive degradation of magnesium alloy plate samples over time.
Figure 67:
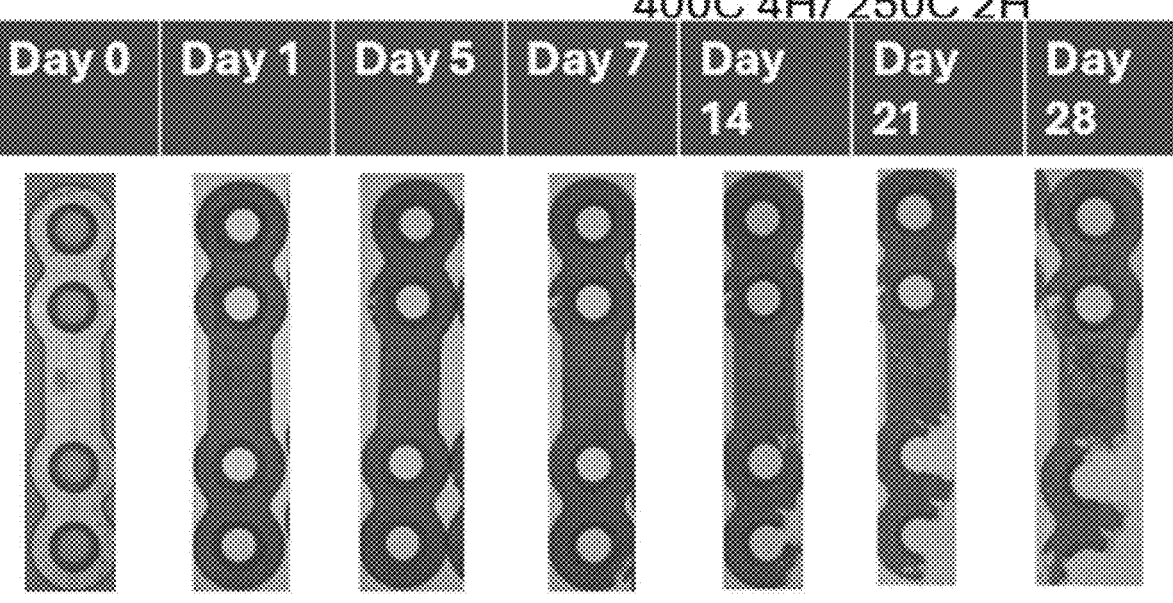
FIG. 67 shows a series of images documenting the progressive degradation of magnesium alloy plate samples over time.
Figure 68:
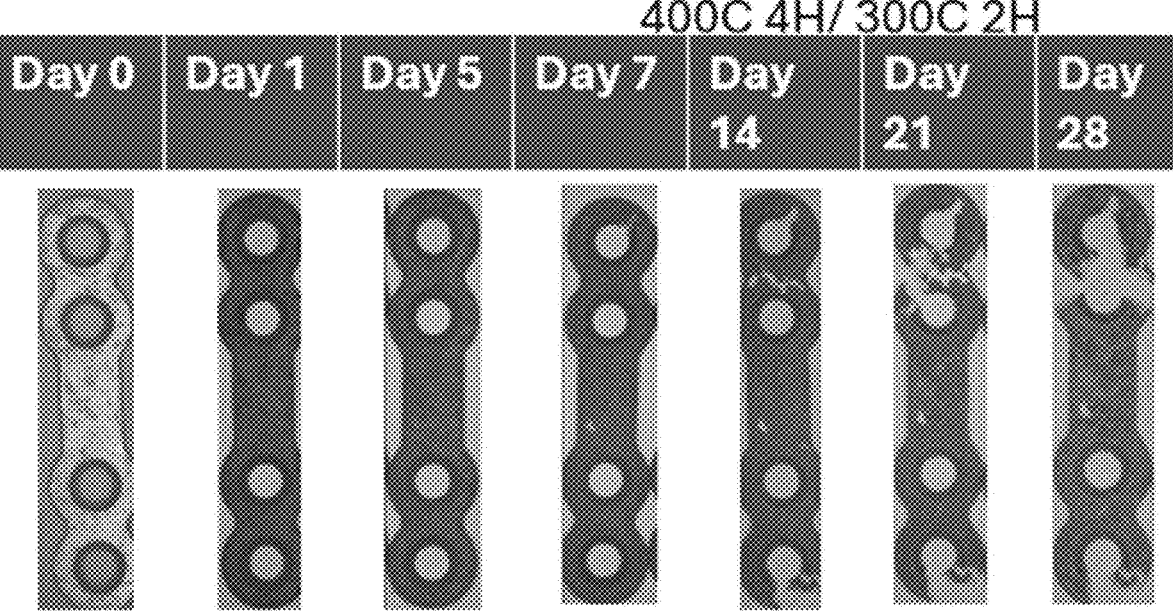
FIG. 68 shows a series of images documenting the progressive degradation of magnesium alloy plate samples over time.
Figure 69:
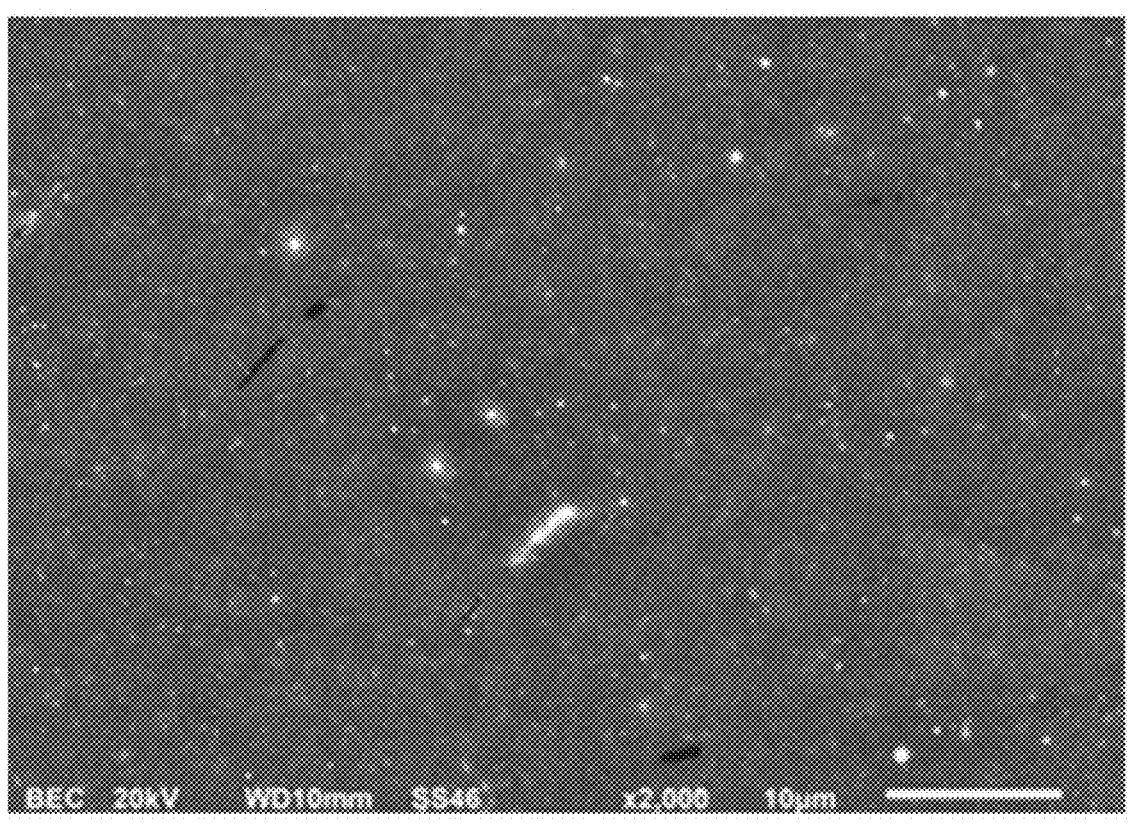
FIG. 69 shows a scanning electron microscope (SEM) micrograph displaying a microstructural view of a magnesium alloy sample.
Figure 70:
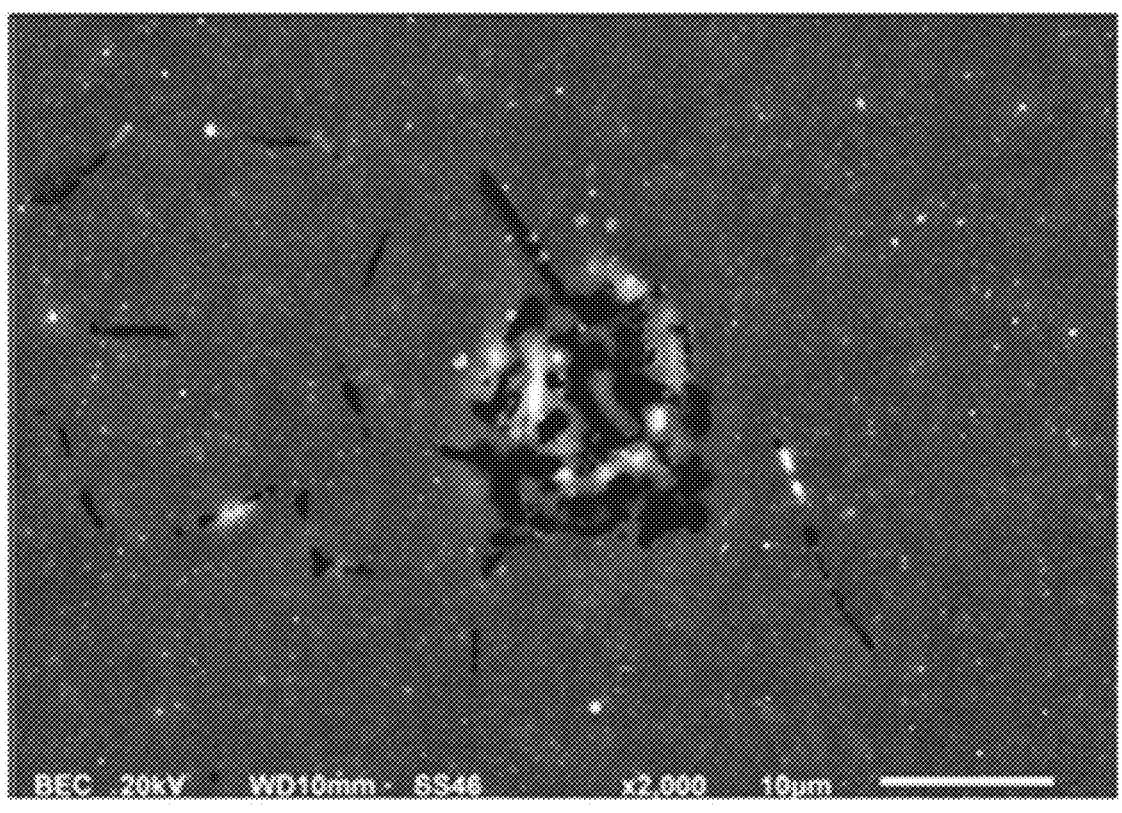
FIG. 70 shows a SEM micrograph displaying a microstructural view of a magnesium alloy sample.
Figure 71:
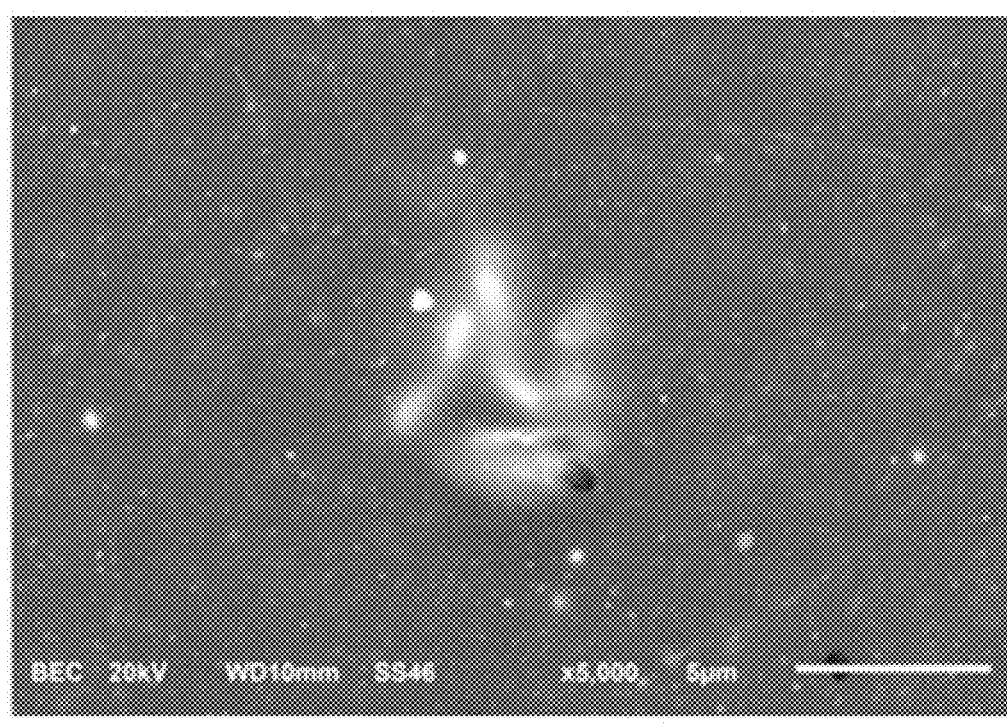
FIG. 71 shows a SEM micrograph displaying a microstructural view of a magnesium alloy sample.
Figure 72:
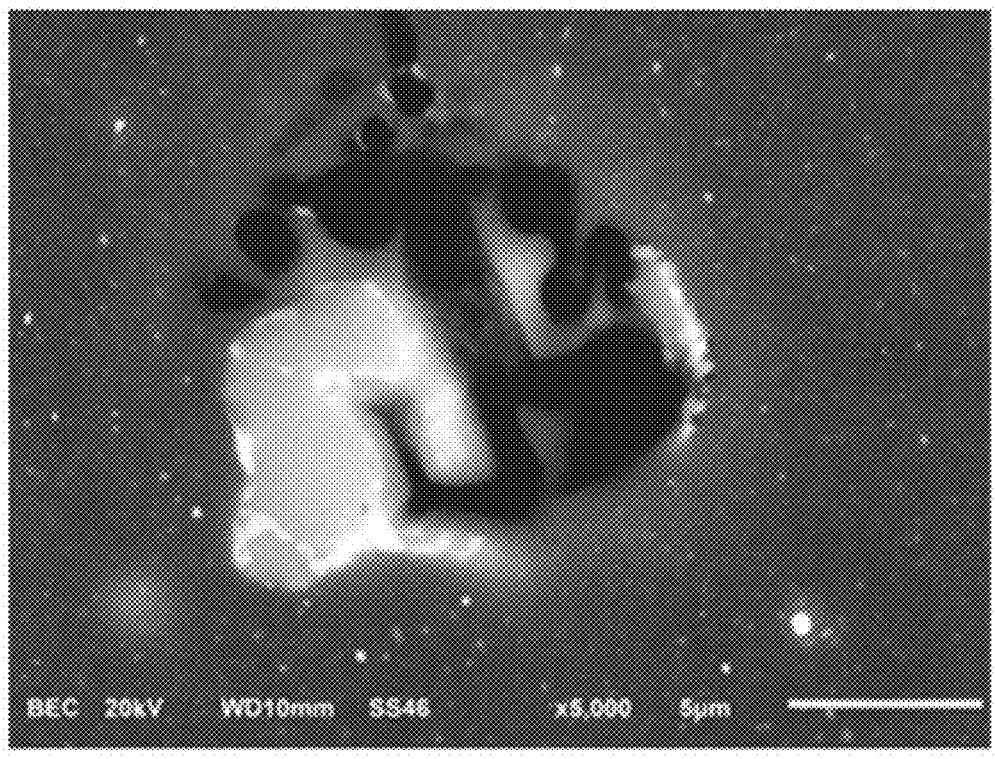
FIG. 72 shows a SEM micrograph displaying a microstructural view of a magnesium alloy sample.
Figure 73:
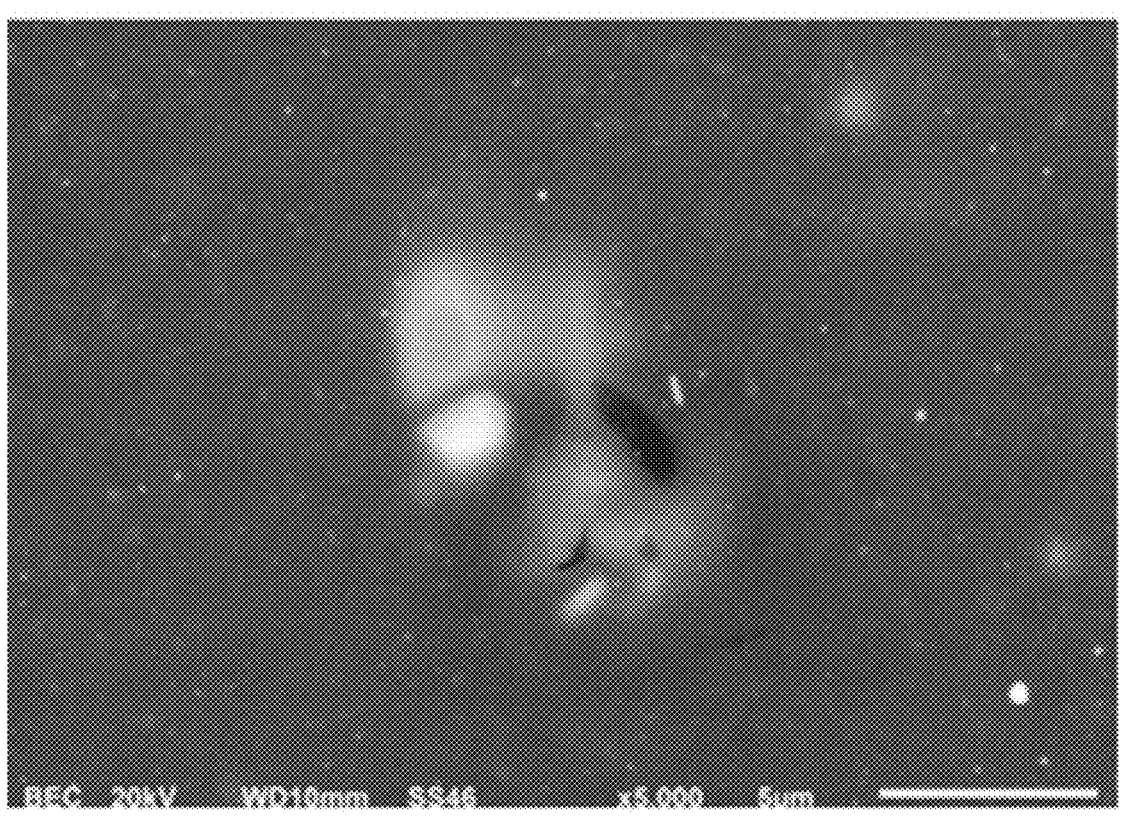
FIG. 73 shows a SEM micrograph displaying a microstructural view of a magnesium alloy sample.
Figure 74:
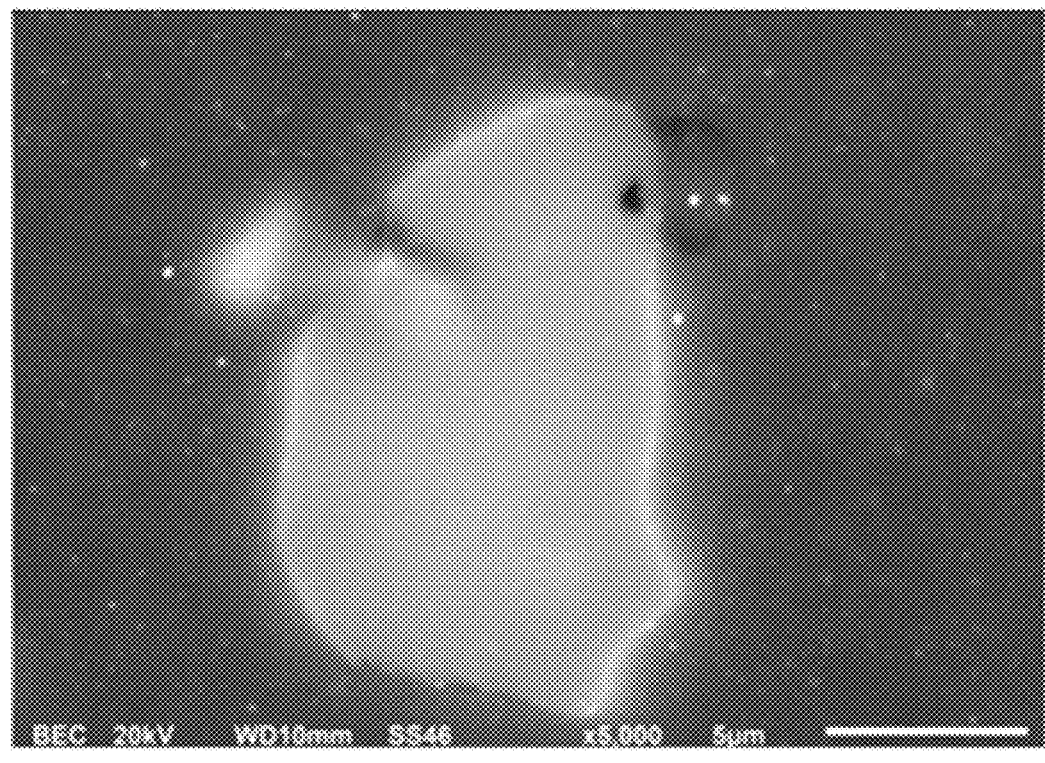
FIG. 74 shows a SEM micrograph displaying a microstructural view of a magnesium alloy sample.
Figure 75:
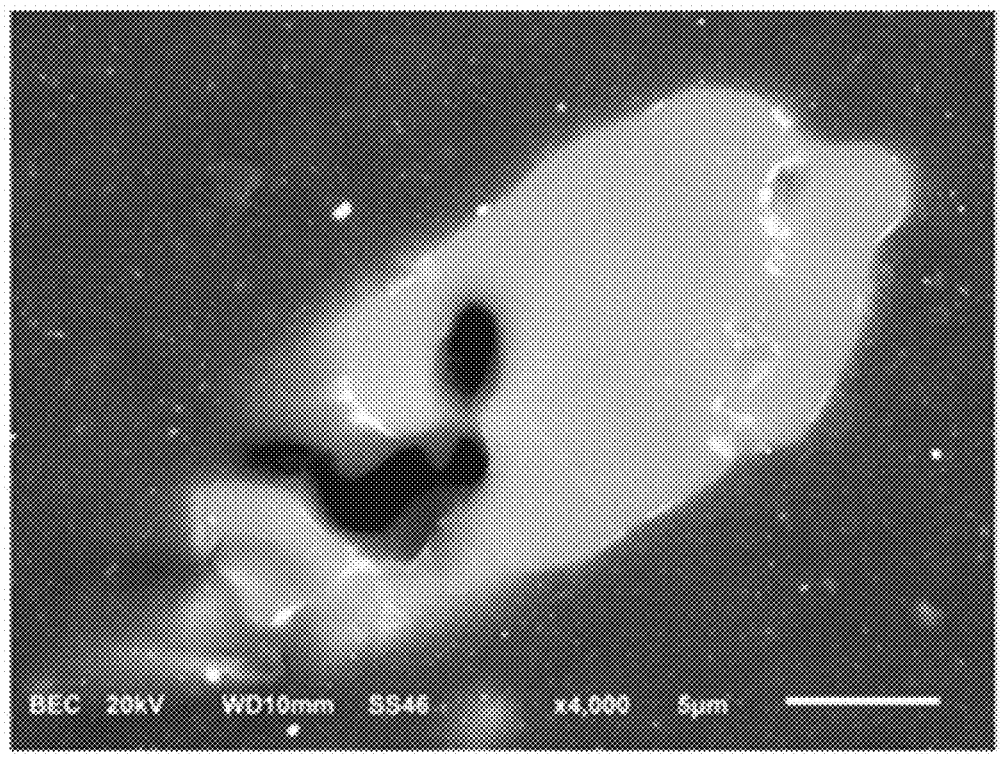
FIG. 75 shows a SEM micrograph displaying a microstructural view of a magnesium alloy sample.
Figure 76:
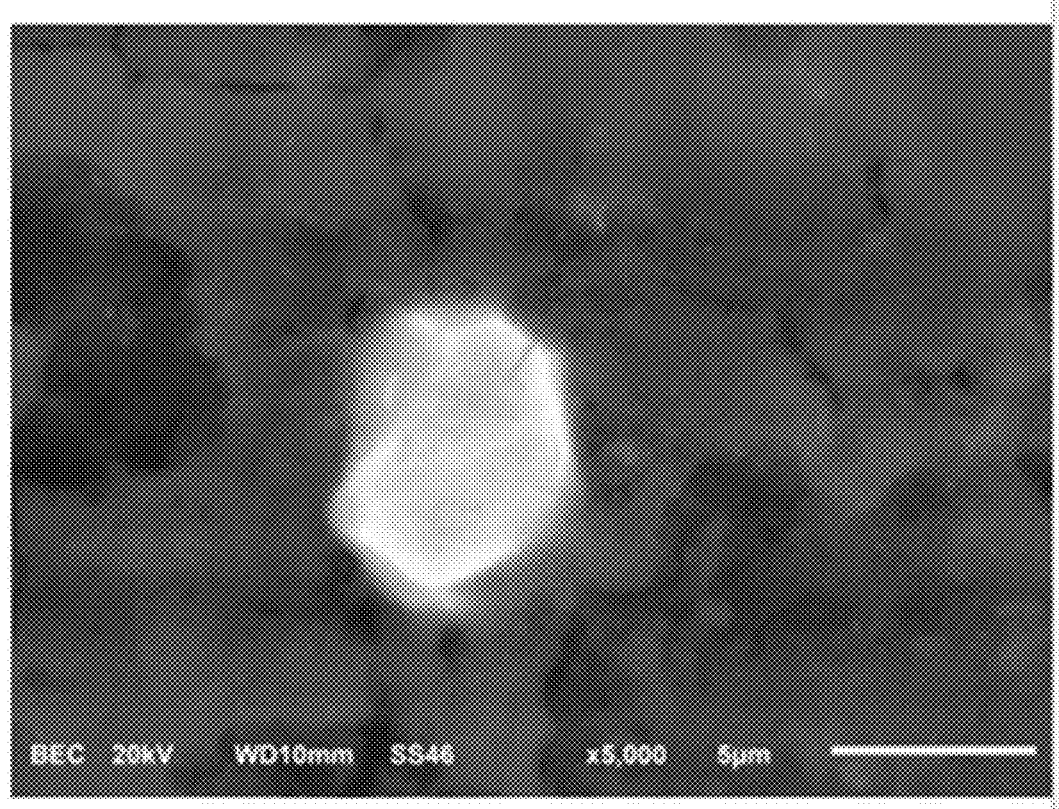
FIG. 76 shows a SEM micrograph displaying a microstructural view of a magnesium alloy sample.

FIG. 57 depicts a flowchart 800 including a method of preparing the disclosed alloy. A first microstructure 701 of the alloy is shown as cast. The method may include a first extrusion 802 step resulting in a second microstructure 703. The method may include a second extrusion 806 step resulting in a third microstructure 705. The first and second extrusion steps may be performed in the same or separate steps. The method may include a solution treatment 804 step resulting in a fourth microstructure 707. The method may include a third extrusion 708 step resulting in a fifth microstructure 709.

The alloy may be initially cast into a billet form. In some cases, the first extrusion billet may have a diameter of 9.5 inches and a length of 30 inches. These dimensions may allow for efficient processing in subsequent steps.

The alloy may have a first extrusion billet diameter between 0-10 inches. In some cases, the first extrusion billet diameter may be 9.5 inches. The alloy may have a first extrusion billet length between 0-50 inches. In some cases, the first extrusion billet length may be 30 inches.

After casting, the billet may undergo solution treatment to homogenize the microstructure and dissolve any secondary phases. In some cases, the solution treatment may be performed at 410° C. for 24 hours. This heat treatment process may help to improve the alloy's mechanical properties and corrosion resistance.

The alloy may undergo solution treatment at temperatures between 300-550° C. In some cases, the solution treatment temperature may be 320° C. In some cases, the solution treatment temperature may be 350° C. In some cases, the solution treatment temperature may be 410° C. In some cases, the solution treatment temperature may be 430° C. In some cases, the solution treatment temperature may be 450° C. In some cases, the solution treatment temperature may be 460° C. In some cases, the solution treatment temperature may be 500° C. In some cases, the solution treatment temperature may be 530° C.

The alloy may undergo solution treatment for durations between 0-30 hours. In some cases, the solution treatment duration may be 6.5 hours. In some cases, the solution treatment duration may be 8 hours. In some cases, the solution treatment duration may be 12 hours. In some cases, the solution treatment duration may be 16 hours. In some cases, the solution treatment duration may be 24 hours.

In embodiments, processing may include solution treating the magnesium alloy including solution heat treating the magnesium alloy at about 450° C. for about 6.5 hours with forced air cooling.

In embodiments, processing may include solution treating the magnesium alloy, including solution heat treating the magnesium alloy at about 500° C. for about 6.5 hours with forced air cooling and at about 450° C. for about 6.5 hours with forced air cooling.

In embodiments, processing may include solution treating the magnesium alloy including solution heat treating the magnesium alloy at about 350° C. for about 12 hours with forced air cooling and at about 450° C. for about 8 hours with forced air cooling, wherein the method further includes aging the magnesium alloy at about 250° C. for about 0.5 hours with forced air cooling.

In embodiments, processing may include solution treating the magnesium alloy including solution heat treating the magnesium alloy at about 400° C. for about 4 hours with forced air cooling and at about 200° C. for about 2 hours with forced air cooling.

In embodiments, processing may include solution treating the magnesium alloy including solution heat treating the magnesium alloy at about 320° C. for about 8 hours with water quench cooling and at about 430° C. for about 16 hours with water quench cooling.

In embodiments, processing may include solution treating the magnesium alloy, including solution heat treating the magnesium alloy at about 430° C. for about 24 hours with forced air cooling.

Following solution treatment, the billet may be subjected to a series of extrusion processes. In some cases, a first extrusion may be performed with an extrusion ratio of 7. The extrusion temperature may be maintained at 350° C., and the ram speed may be set to 0.375 inches per minute (ipm). These parameters may help to achieve the desired microstructure and mechanical properties in the extruded material.

As used herein, the term "extrusion ratio" refers to the ratio of the cross-sectional area of the initial billet to the cross-sectional area of the extruded product. For example, an extrusion ratio of 25 means the cross-sectional area of the initial billet is 25 times larger than the cross-sectional area of the extruded product. Higher extrusion ratios generally result in greater deformation and refinement of the alloy microstructure during the extrusion process. The alloy may have an extrusion ratio between 0-50. In some cases, the extrusion ratio may be 7, 9, 9.2, 14, 25, 30, or 39.

In some cases, a second extrusion may be performed with an extrusion ratio of 14. This additional extrusion step may further refine the grain structure and improve the alloy's overall performance characteristics.

A third extrusion may also be conducted in some cases. The extrusion ratio for this step may range from 25 to 39, depending on the specific requirements of the final product. This final extrusion process may help to achieve the desired shape and properties for the orthopedic implant or fixation device.

The extrusion speed may range from 0 to 4 m/min. In some cases, the extrusion speed may be 0.21 m/min. In some cases, the extrusion speed may be 0.22 m/min. In some cases, the extrusion speed may be 0.27 m/min. In some cases, the extrusion speed may be 0.29 m/min. In some cases, the extrusion speed may be 0.30 m/min. In some cases, the extrusion speed may be 0.32 m/min. In some cases, the extrusion speed may be 0.36 m/min. In some cases, the extrusion speed may be 0.37 m/min. In some cases, the extrusion speed may be 0.40 m/min. In some cases, the extrusion speed may be 0.42 m/min. In some cases, the extrusion speed may be 0.58 m/min. In some cases, the extrusion speed may be 0.66 m/min. In some cases, the extrusion speed may be 0.71 m/min. In some cases, the extrusion speed may be 0.75 m/min. In some cases, the extrusion speed may be 0.96 m/min. In some cases, the extrusion speed may be 1.08 m/min. In some cases, the extrusion speed may be 1.55 m/min. In some cases, the extrusion speed may be 2.11 m/min. In some cases, the extrusion speed may be 3.02 m/min.

The breakthrough pressure for extrusion may range from 500 to 1000 psi. In some cases, the breakthrough pressure may be 569.1 psi. In some cases, the breakthrough pressure may be 605.9 psi. In some cases, the breakthrough pressure may be 715.8 psi. In some cases, the breakthrough pressure may be 729.2 psi. In some cases, the breakthrough pressure may be 752.2 psi. In some cases, the breakthrough pressure may be 764.5 psi. In some cases, the breakthrough pressure may be 764.9 psi. In some cases, the breakthrough pressure may be 778.6 psi. In some cases, the breakthrough pressure may be 779.5 psi. In some cases, the breakthrough pressure may be 780.4 psi. In some cases, the breakthrough pressure may be 783.6 psi. In some cases, the breakthrough pressure may be 796.9 psi. In some cases, the breakthrough pressure may be 807.0 psi. In some cases, the breakthrough pressure may be 814.3 psi. In some cases, the breakthrough pressure may be 828.3 psi. In some cases, the breakthrough pressure may be 830.8 psi. In some cases, the breakthrough pressure may be 874.5 psi. In some cases, the breakthrough pressure may be 919.9 psi. In some cases, the breakthrough pressure may be 964.3 psi.

In embodiments, processing may include extruding the magnesium alloy the first time includes heat treating the magnesium alloy at about 350° C. for about 8 hours; and extruding the magnesium alloy at about 350° C. at a ram speed of about 0.375 ipm.

In embodiments, processing may include extruding the magnesium alloy at about 350° C. at a ram speed of about 0.375 ipm is performed including a 1-port 3.5-inch diameter die.

In embodiments, processing may include extruding the magnesium alloy the second time includes preheating the magnesium alloy at about 350° C.; and extruding the magnesium alloy at about 340° C. at a ram speed ranging from about 0.3 ipm to about 0.5 ipm.

In embodiments, processing may include extruding the magnesium alloy at about 340° C. at a ram speed ranging from about 0.3 ipm to about 0.5 ipm is performed including a 4-port 0.27-inch diameter die.

In embodiments, processing may include extruding the magnesium alloy at about 340° C. at a ram speed ranging from about 0.3 ipm to about 0.5 ipm is performed including a 1-port 1.58-inch by 0.155-inch die.

In embodiments, processing may include increasing extrusion temperature to increase the formation of GP zones and ternary phases as well as increasing absorption rate by allowing GP zones to further consolidate into ternary phase, allowing modification of ternary phase size and volume fraction. Intentional modification to increase ternary phase size and volume fraction results in adjustment of the absorption profile of the alloy by increasing the absorption rate, to meet the needs of the implant application being designed for. Alternatively, processing conditions can be chosen to maximize GP zone formation and limit consolidation of ternary phases, minimizing the absorption rate of the alloy, providing further means of adjusting an implant's absorption profile.

In embodiments, processing may include plastic deformation techniques such as ECAP, equal channel angular extrusion (ECAE), high pressure torsion (HPT) processing, rolling, hot or cold drawing, extrusion, forging, swaging, or the like to refine microstructure and reduce average ternary phase diameter further, thereby increasing strength, ductility, and other material properties. In embodiments, processing may include grain size reduction via severe plastic deformation, alloying or milling, thermomechanical processing, and the like to modify or control absorption profiles of the disclosed alloy.

The specific processing parameters, such as temperatures, durations, and extrusion ratios, may be adjusted to tailor the alloy's properties for particular applications. By carefully controlling these processing steps, the magnesium alloy may be optimized to provide the desired combination of mechanical strength, corrosion resistance, and absorption profile for orthopedic use.

The alloy may be processed at temperatures between 0-700° C. In some cases, the processing temperatures may be 290° C., 315° C., 320° C., 325° C., 335° C., 340° C., 345° C., 350° C., 375° C., 400° C., 407° C., 410° C., 430° C., 450° C., 460° C., 500° C., or 530° C.

The alloy may undergo aging treatment at temperatures between 200-300° C. In some cases, the aging treatment temperature may be 200° C. In some cases, the aging treatment temperature may be 250° C.

The alloy may undergo aging treatment for durations between 0-5 hours. In some cases, the aging treatment duration may be 30 minutes. In some cases, the aging treatment duration may be 2 hours.

The microstructure of the bioabsorbable magnesium alloy may play a significant role in determining its properties and performance characteristics. In some cases, the alloy may exhibit a grain structure with precipitate phases distributed throughout the matrix.

The grain structure of the magnesium alloy may be influenced by the processing methods and alloying elements. In some cases, the grains may be equiaxed or elongated, depending on the specific processing conditions. The grain size and morphology may affect the mechanical properties and corrosion behavior of the alloy. The alloy may have an average grain size of 0 to 50 m after extrusion. In some cases, the average grain size may be 5 m.

Precipitate phases may form within the magnesium matrix during solidification and subsequent processing steps. These precipitates may include binary and ternary intermetallic compounds. The alloy may have a maximum intermetallic precipitate length between 0-200 microns. In some cases, the maximum intermetallic phase precipitate length may be 14 microns. In some cases, the maximum intermetallic phase precipitate length may be 19 microns. In some cases, the maximum intermetallic phase precipitate length may be 140 microns. In some cases, the maximum intermetallic phase precipitate length may be 172 microns. In some cases, the ternary precipitate may have a maximum length ranging from 50 to 200 microns. In some cases, the maximum length may be 50 microns. In some cases, the maximum length may be 200 microns. The size and distribution of these precipitates may influence the alloy's strength, ductility, and corrosion resistance.

The bioabsorbable magnesium alloy may contain binary and ternary intermetallic compounds within its microstructure. Binary intermetallic compounds may be formed between two metallic elements, such as $Mg_2Ca$ or $MgZn$. These compounds can influence the alloy's mechanical properties and corrosion behavior.

Ternary intermetallic compounds involve three metallic elements, such as $Ca_2Mg_5Zn_5$, $Ca_7Mg_8Zn_{35}$, $Ca_2Mg_5Zn_{13}$, $Ca_2Mg_6Zn_3$, and other possible combinations of the constituent elements in the alloy. The presence and distribution of these intermetallic compounds play a crucial role in determining the alloy's overall performance characteristics. For example, finely dispersed ternary phases can contribute to strengthening the alloy through precipitation hardening, while their size and morphology can affect the corrosion rate and uniformity. The formation of these intermetallic compounds is influenced by the alloy composition and processing parameters, allowing for tailoring of the alloy's properties to suit specific orthopedic applications. In some cases, the alloy comprises $Ca_2Mg_5Zn_5$ as the primary intermetallic phase. In some cases, the alloy comprises less than 0.5% by volume of $Mg_2Ca$ phase.

The presence and distribution of these intermetallic compounds play a crucial role in determining the alloy's overall performance characteristics. For example, finely dispersed ternary phases can contribute to strengthening the alloy through precipitation hardening, while their size and morphology can affect the corrosion rate and uniformity. The formation of these intermetallic compounds is influenced by the alloy composition and processing parameters, allowing for tailoring of the alloy's properties to suit specific orthopedic applications.

The volume fraction (as measured by area fraction in a 2D plane viewed by metallography or electron microscope at different magnifications, e.g., 100×-500×, such as 400×-500×, to achieve a field of view that allows measurement of a large populations of particles) of the ternary phase in the alloy may range from 0 to 15%. In some cases, the volume fraction may be 0.6%. In some cases, the volume fraction may be 0.9%. In some cases, the volume fraction may be 1.1%. In some cases, the volume fraction may be 1.4%. In some cases, the volume fraction may be 1.7%. In some cases, the volume fraction may be 1.9%. This range allows for tailoring of the alloy's properties to suit specific orthopedic applications. A lower volume fraction of ternary phase may result in improved ductility, while a higher volume fraction may contribute to increased strength and corrosion resistance. The ternary phase, typically composed of intermetallic compounds such as $Ca_2Mg_5Zn_5$ or $Ca_2Mg_6Zn_3$, plays a crucial role in determining the alloy's mechanical properties and degradation behavior. By carefully controlling the volume fraction of these phases through composition and processing parameters, the absorption profile and mechanical integrity of the implant can be optimized for different clinical applications, such as maxillofacial reconstruction or small bone fixation. The ability to adjust this volume fraction provides a key mechanism for balancing the competing requirements of initial strength, controlled degradation, and long-term bioabsorption in orthopedic implants.

The alloy may contain 0-2 mole fraction of $Ca_2Mg_5Zn_5$. In some cases, the mole fraction of $Ca_2Mg_5Zn_5$ may be 0.6%. In some cases, the mole fraction of $Ca_2Mg_5Zn_5$ may be 0.9%. In some cases, the mole fraction of $Ca_2Mg_5Zn_5$ may be 1.1%. In some cases, the mole fraction of $Ca_2Mg_5Zn_5$ may be 1.4%. In some cases, the mole fraction of $Ca_2Mg_5Zn_5$ may be 1.7%. In some cases, the mole fraction of $Ca_2Mg_5Zn_5$ may be 1.9%.

The alloy may contain 0-1 mole fraction of α-Mn. In some cases, the mole fraction of α-Mn may be 0.1%. In some cases, the mole fraction of α-Mn may be 0.2%.

The alloy may contain intermetallic phase precipitates with an average size between 0-200 μm². In some cases, the average phase precipitate size may be 5.9 μm², 6.8 μm², or 10.7 μm².

The alloy may contain intermetallic phases occupying 0-10% of the alloy area. In some cases, the area percentage may be 0.3%, 0.9%, 1.2%, 1.4%, 1.7%, 1.9%, 2.9%, 3%, or 4.2%.

The distribution of precipitate phases within the alloy matrix may be influenced by processing parameters such as solution treatment temperature and duration, as well as extrusion conditions. In some cases, a uniform distribution of fine precipitates may be desirable for optimizing the alloy's mechanical and corrosion properties.

Precipitate phases refer to secondary solid phases that form within the primary magnesium matrix of the alloy during solidification or subsequent heat treatment processes. These phases, typically intermetallic compounds, play a crucial role in determining the alloy's mechanical properties and corrosion behavior. In the context of bioabsorbable magnesium alloys, precipitate phases can include binary compounds such as $Mg_2Ca$ or $MgZn$, as well as ternary compounds like $Ca_2Mg_6Zn_3$. The size, distribution, and volume fraction of these precipitate phases significantly influence the alloy's strength, ductility, and absorption profile. By carefully controlling the alloy composition and processing parameters, the characteristics of these precipitate phases can be tailored to achieve the desired balance between mechanical integrity and controlled degradation for specific orthopedic applications.

The alloy may exhibit a corrosion potential difference of 0 to 100 mV between the α-Mg matrix and intermetallic phase precipitates.

The presence and characteristics of these microstructural features may contribute to the alloy's overall performance. For example, finely dispersed precipitates may act as obstacles to dislocation motion, potentially enhancing the alloy's strength. Additionally, the nature and distribution of these phases may influence the alloy's corrosion behavior by affecting the formation and stability of protective surface layers.

The microstructure of the magnesium alloy may evolve over time as the material degrades in the physiological environment. This evolution may contribute to the alloy's controlled absorption profile, with changes in the precipitate phases and grain structure potentially influencing the rate and uniformity of degradation.

By carefully controlling the alloy composition and processing parameters, the microstructural features may be optimized to achieve the desired combination of mechanical properties, corrosion resistance, and absorption characteristics for specific orthopedic applications.

The bioabsorbable magnesium alloy may exhibit mechanical properties suitable for orthopedic implant applications. In some cases, the alloy may demonstrate a combination of strength and ductility that allows for effective load-bearing while maintaining formability.

The alloy may exhibit an ultimate tensile strength between 0-500 MPa. In some cases, the ultimate tensile strength may be 238 MPa, 240 MPa, 245 MPa, 262 MPa, 272 MPa, 298 MPa, 299 MPa, 301 MPa, 305 MPa, 308 MPa, 309 MPa, 310 MPa, 311 MPa, 313 MPa, 315 MPa, 317 MPa, 319 MPa, 321 MPa, or 345 MPa. The ultimate tensile strength of the magnesium alloy may range from 200 to 300 MPa. This strength range may provide sufficient mechanical integrity for many orthopedic applications. The alloy may exhibit a yield strength between 0-500 MPa. In some cases, the yield strength may be 97 MPa, 130 MPa, 132 MPa, 159 MPa, 231 MPa, 259 MPa, 261 MPa, 265 MPa, 275 MPa, 279 MPa, 281 MPa, 282 MPa, 286 MPa, 287 MPa, 288 MPa, 292 MPa, or 293 MPa. In some cases, the yield strength of the alloy may be between 150 and 250 MPa, allowing for controlled deformation under load.

The alloy may have a torque strength between 0-10 in-lbs. In some cases, the torque strength may be 5.42 in-lbs. In some cases, the torque strength may be 5.43 in-lbs. In some cases, the torque strength may be 5.44 in-lbs. In some cases, the torque strength may be 5.60 in-lbs. In some cases, the torque strength may be 5.77 in-lbs. In some cases, the torque strength may be 5.78 in-lbs. In some cases, the torque strength may be 5.92 in-lbs.

The alloy may exhibit an elongation to failure between 0-30%. In some cases, the elongation to failure may be 7.2%, 7.7%, 8.5%, 8.7%, 9%, 9.7%, 9.8%, 11%, 11.3%, 11.5%, 12%, 13%, 13.7%, 13.8%, 14%, 15.7%, 19.7%, 20%, 23%, or 24.3%. The elongation to failure of the magnesium alloy may range from 10% to 20%. This level of ductility may allow for some plastic deformation before fracture, potentially improving the alloy's resistance to brittle failure modes.

In some cases, the magnesium alloy may exhibit a Young's modulus between 40 and 45 GPa. This elastic modulus may be closer to that of natural bone compared to traditional metallic implant materials, potentially reducing stress shielding effects.

The fatigue strength of the magnesium alloy may be in the range of 100 to 150 MPa at 107 cycles. This fatigue resistance may be sufficient for many orthopedic applications where cyclic loading occurs.

The mechanical properties of the magnesium alloy may be influenced by the specific composition and processing conditions. In some cases, adjusting the zinc, calcium, and manganese content may allow for tailoring of the alloy's strength and ductility to suit particular orthopedic applications.

Compared to pure magnesium, which typically has an ultimate tensile strength around 90 MPa and elongation of 2-6%, the alloyed material may offer significantly improved mechanical performance. The addition of alloying elements and careful processing may contribute to grain refinement and precipitation strengthening, enhancing the overall mechanical properties.

When compared to other magnesium alloys used in orthopedic applications, such as AZ91 or WE43, the bioabsorbable magnesium alloy may offer comparable or superior strength while potentially providing improved corrosion resistance and biocompatibility. In some cases, the alloy may exhibit a more favorable balance of strength and ductility compared to these existing magnesium alloys.

The mechanical properties of the bioabsorbable magnesium alloy may also be compared to traditional orthopedic implant materials. While the magnesium alloy may not match the absolute strength of materials like stainless steel or titanium alloys, the combination of adequate mechanical properties and bioabsorbability may offer unique advantages for certain orthopedic applications.

In some cases, the mechanical properties of the magnesium alloy may evolve over time as the material degrades in the physiological environment. The initial strength and ductility may be maintained for a period sufficient to support bone healing, followed by a gradual reduction in mechanical properties as the implant is absorbed.

The magnesium alloy may also exhibit favorable fatigue and wear resistance characteristics. In some cases, the alloy may demonstrate improved resistance to stress corrosion cracking compared to other magnesium alloys, potentially enhancing its reliability in orthopedic applications.

The hardness of the magnesium alloy may range from 50 to 70 on the Vickers hardness scale. This hardness range may provide adequate wear resistance for many orthopedic applications while still allowing for machining and forming processes during implant manufacturing.

In some cases, the magnesium alloy may demonstrate anisotropic mechanical properties due to the extrusion and processing methods used in its production. The strength and ductility may vary depending on the loading direction relative to the material's processing history. This anisotropy may be considered when designing and implementing orthopedic implants using this alloy.

The fracture toughness of the magnesium alloy may be in the range of 15 to 20 MPa·m$^{1/2}$. This level of fracture toughness may provide resistance to crack propagation, potentially improving the overall reliability and safety of orthopedic implants made from this material.

The specific mechanical properties of the magnesium alloy may be tailored through adjustments in composition and processing parameters to meet the requirements of different orthopedic applications, such as maxillofacial reconstruction, small bone fixation, or larger load-bearing implants.

The bioabsorbable magnesium alloy may exhibit a controlled, multi-phase absorption profile when exposed to physiological conditions. This absorption behavior may be characterized by distinct phases, including an initial period of minimal degradation, followed by a steady-state phase, and concluding with an accelerated absorption phase.

The alloy may exhibit a mass loss percentage between 0-100% during corrosion testing. In some cases, the mass loss percentage may be 20% at 6000 hours. In some cases, the mass loss percentage may be 32% at 6 weeks. In some cases, the mass loss percentage may be 35% at 6 weeks. In some cases, the mass loss percentage may be 55% at 12 weeks. In some cases, the mass loss percentage may be 60% at 3000 hours. In some cases, the mass loss percentage may be 65% at 12 weeks.

The alloy may exhibit a corrosion rate between 0-2 mm/year. In some cases, the corrosion rate may be 0.05 mm/year, 0.08 mm/year, 0.09 mm/year, 0.11 mm/year, 0.14 mm/year, 0.16 mm/year, 0.21 mm/year, 0.24 mm/year, 0.3 mm/year, 0.54 mm/year, 0.62 mm/year, 0.63 mm/year, 0.64 mm/year, 0.69 mm/year, 0.73 mm/year, or 1.1 mm/year.

In some cases, the initial phase of minimal degradation may last for 7-14 days. During this period, the corrosion rate may be relatively low, typically below 0.1 mm/year. This initial stability may allow for proper implant integration and initiation of the healing process.

The steady-state phase may extend from approximately 2 to 8 weeks post-implantation. During this period, the corrosion rate may increase slightly but remain controlled, typically ranging from 0.1 to 0.5 mm/year. This phase may provide mechanical support during critical stages of bone healing.

The accelerated absorption phase may begin after 8-12 weeks, with corrosion rates potentially increasing to 0.5-1.0 mm/year. This final phase may facilitate complete absorption of the implant as the healed tissue assumes full load-bearing capacity.

The magnesium alloy may demonstrate different mass loss profiles depending on the specific composition and processing conditions. In some cases, the total mass loss after 6 months may range from 30% to 70%, with the rate of mass loss increasing over time.

Corrosion behavior may be influenced by the alloy's microstructure and composition. The presence and distribution of intermetallic phases may affect the uniformity of corrosion. In some cases, a more homogeneous microstructure may lead to more uniform corrosion and absorption.

The magnesium alloy may exhibit different corrosion rates in various physiological environments. In some cases, the corrosion rate in simulated body fluid may be 20-30% higher than in phosphate-buffered saline, due to the presence of additional ionic species.

The alloy may form a surface oxide layer with a thickness of 0 to 500 nm when exposed to physiological conditions. In some cases, the thickness may be 50 nm.

The thickness of implant corrosion layer may range from 0 to 340 microns. In some cases, the thickness may be 42 microns. In some cases, the thickness may be 94 microns. In some cases, the thickness may be 118 microns. In some cases, the thickness may be 340 microns.

Compared to other bioabsorbable materials, the magnesium alloy may offer more predictable and controllable absorption kinetics. For example, the alloy may maintain its structural integrity for a longer period compared to some polymeric bioabsorbable materials, which may undergo more rapid initial degradation.

In some cases, the magnesium alloy may demonstrate improved corrosion resistance compared to pure magnesium or binary magnesium alloys. The addition of zinc, calcium, and manganese may contribute to the formation of more stable protective surface layers, potentially slowing the overall corrosion rate.

The absorption behavior of the magnesium alloy may be further tailored through surface treatments or coatings. In some cases, anodization or the application of biodegradable polymer coatings may be used to modify the initial corrosion rate and absorption profile.

The pH of the local environment may influence the corrosion behavior of the magnesium alloy. In some cases, the alloy may exhibit increased corrosion rates in more acidic environments, while showing improved stability in neutral or slightly alkaline conditions.

The mechanical loading conditions may also affect the corrosion and absorption behavior of the magnesium alloy. In some cases, areas of high stress concentration may experience accelerated corrosion due to stress corrosion cracking or fatigue-corrosion interactions.

The absorption of the magnesium alloy may lead to the release of magnesium, zinc, calcium, and manganese ions into the surrounding tissue. In some cases, these released ions may have beneficial effects on bone healing and tissue regeneration, potentially contributing to the bioactivity of the implant material.

The corrosion products formed during the absorption process may include magnesium hydroxide, magnesium carbonate, and various calcium phosphate compounds. In some cases, these corrosion products may form a protective layer on the implant surface, temporarily slowing the corrosion rate.

The absorption behavior of the magnesium alloy may be monitored in vivo using various imaging techniques. In some cases, micro-computed tomography or magnetic resonance imaging may be used to track changes in implant volume and density over time, providing insights into the absorption kinetics in different anatomical locations.

The bioabsorbable magnesium alloy may be used to create various implant designs for orthopedic applications. In some cases, these implants may include plates and screws for bone fixation.

The implant may have a plate length between 0-50 mm. A plate design may have a length of 23 mm. This length may be suitable for certain maxillofacial or small bone fixation applications. The implant may have a plate width between 0-10 mm. The width of the plate may be 5 mm, providing sufficient surface area for attachment to bone while minimizing the overall implant footprint. The implant may have a plate thickness between 0-5 mm. The plate thickness may be 0.6 mm, balancing the need for mechanical strength with a low profile design.

In some cases, the plate may include multiple holes for screw fixation. These holes may be arranged in a linear pattern along the length of the plate. The number and spacing of holes may be optimized for specific anatomical locations and fixation requirements.

A screw design for use with the plate may have a thread length of 5 mm. This thread length may provide adequate purchase in bone for secure fixation. The implant may have a screw shaft diameter between 0-5 mm. The shaft diameter of the screw may be 1.7 mm, allowing for a balance between strength and minimal bone disruption during insertion.

The screw head may be designed to sit flush with the plate surface when fully inserted. In some cases, the screw head may have a low-profile design to minimize soft tissue irritation. The screw may also feature a self-tapping design to facilitate insertion. The implant may have a screw head diameter between 0-10 mm. In some cases, the screw head diameter may be 2.65 mm.

The plate and screw designs may be tailored for specific anatomical locations and clinical indications. For example, plates for mandibular fracture fixation may have different dimensions and contours compared to those designed for metacarpal fractures.

In some cases, the implant designs may incorporate features to enhance their bioabsorbable properties. These features may include controlled variations in thickness or surface treatments to modulate the absorption rate in different regions of the implant.

The magnesium alloy implants may be manufactured using various techniques, such as machining, forging, or 3D printing. The specific manufacturing method may be selected based on the implant design complexity and desired material properties.

Surface treatments or coatings may be applied to the implants to further control their absorption behavior or enhance their biocompatibility. These treatments may include anodization, plasma electrolytic oxidation, or the application of biodegradable polymer coatings.

The implant designs may undergo rigorous mechanical testing to ensure they meet the required performance standards for their intended applications. This testing may include static and dynamic loading scenarios to simulate physiological conditions.

In some cases, the implant designs may be optimized using finite element analysis to identify areas of high stress concentration and refine the geometry for improved mechanical performance.

The bioabsorbable magnesium alloy implants may be designed to maintain their mechanical integrity for a specific duration before gradual absorption. This absorption profile may be tailored to match the expected healing time for different orthopedic applications.

The bioabsorbable magnesium alloy may demonstrate favorable in vivo performance characteristics when used in orthopedic implant applications. Animal studies may provide insights into the alloy's osseointegration, healing response, and absorption profile under physiological conditions.

In some cases, the magnesium alloy implants may exhibit good osseointegration properties. The implant surface may allow for direct bone apposition and ingrowth. This osseointegration process may begin within the first few weeks after implantation and continue over several months.

The healing response to the magnesium alloy implants may be characterized by minimal inflammatory reaction. In some cases, the presence of the implant may stimulate increased osteoblast activity in the surrounding bone tissue. This osteogenic effect may contribute to enhanced bone formation and accelerated healing compared to traditional non-absorbable implants.

The absorption profile of the magnesium alloy in vivo may closely match the controlled, multi-phase behavior observed in vitro. In some cases, the initial period of minimal degradation may last for 2-4 weeks post-implantation. This period may allow for proper implant integration and initiation of the healing process.

The in vivo to in vitro absorption rate ratio may range from 0-15. In some cases, the in vivo to in vitro ratio may be 2x. In some cases, the ratio may be 3x. In some cases, the ratio may be 6x. In some cases, the ratio may be 9x. In some cases, the ratio may be 12x. In some cases, the in vivo tests were conducted in an animal, such as sheep. In some cases, in vitro tests were performed on screw, plates, and other objects made from the test composition.

Following the initial phase, the implant may enter a steady-state absorption period lasting 8-12 weeks. During this time, the corrosion rate may remain relatively constant, providing continued mechanical support while allowing for gradual tissue ingrowth.

The final accelerated absorption phase may begin after 12-16 weeks, with complete implant resorption typically occurring within 6-12 months. The specific absorption time-line may vary depending on factors such as implant size, location, and local physiological conditions.

In some cases, the degradation products of the magnesium alloy may have beneficial effects on the surrounding tissue through a controlled and stable alloy absorption rate. The stable release of magnesium ions may promote osteoblast proliferation and differentiation. Alternatively, a burst release of magnesium ions promotes osteoclast proliferation and differentiation resulting in poor osseointegration of the implant which may also be attributed to hydrogen gas accumulation. The presence of zinc and calcium in the alloy may also contribute to positive effects on bone metabolism.

The mechanical properties of the magnesium alloy implants may evolve during the in vivo absorption process. In some cases, the implants may maintain sufficient strength to support physiological loads for 12-16 weeks post-implantation. This period may allow for adequate bone healing in many orthopedic applications.

Histological analysis of tissue samples from animal studies may reveal the formation of a fibrous capsule around the implant during the early stages of healing. This capsule may gradually be replaced by new bone tissue as the implant degrades and is resorbed.

In some cases, the magnesium alloy implants may demonstrate a more favorable foreign body response compared to traditional metallic implants. The gradual absorption of the implant material may reduce the long-term presence of a foreign body, potentially decreasing the risk of chronic inflammation or implant-related complications.

The absorption of the magnesium alloy implants may be monitored in vivo using various imaging techniques. In some cases, radiographic analysis may show a gradual decrease in implant density over time, correlating with the progression of implant degradation and bone formation.

Micro-computed tomography (micro-CT) analysis may provide detailed information on the spatial and temporal patterns of implant degradation and new bone formation. In some cases, micro-CT data may reveal a gradual transition from implant material to newly formed bone tissue over the course of several months.

The magnesium alloy implants may demonstrate biocompatibility in various anatomical locations. In some cases, studies may be conducted using implants in long bones, cranial defects, and maxillofacial applications. The alloy's performance may be evaluated in both load-bearing and non-load-bearing situations.

In some cases, the magnesium alloy implants may show favorable performance in infection-prone environments. The gradual release of metal ions during the degradation process may contribute to a local antibacterial effect, potentially reducing the risk of implant-associated infections.

The in vivo performance of the magnesium alloy implants may be compared to that of traditional bioabsorbable materials, such as poly-lactic acid (PLA) or poly-glycolic acid (PGA) implants. In some cases, the magnesium alloy may demonstrate improved mechanical properties and a more controlled absorption profile compared to these polymeric materials.

Animal studies may also evaluate the systemic effects of the degrading magnesium alloy implants. In some cases, serum magnesium levels may show a slight increase during the implant absorption process, but may remain within physiological ranges. The released alloying elements may be metabolized and excreted without causing adverse systemic effects.

The in vivo performance of the magnesium alloy may be influenced by the specific implant design and surface characteristics. In some cases, implants with optimized surface topography may demonstrate enhanced osseointegration and more uniform degradation compared to implants with smooth surfaces.

Long-term follow-up in animal studies may provide insights into the complete remodeling of the implant site. In some cases, the area of implantation may be fully replaced by native bone tissue within 12-18 months, with no residual implant material detectable.

The magnesium alloy implants may demonstrate different in vivo performance characteristics depending on the age and health status of the animal subjects. In some cases, younger animals may show more rapid implant integration and bone formation compared to older subjects.

The in vivo absorption profile of the magnesium alloy may be influenced by mechanical loading conditions. In some cases, implants in load-bearing locations may show slightly accelerated degradation rates compared to those in non-load-bearing sites.

Animal studies may also evaluate the performance of the magnesium alloy implants in revision scenarios. In some cases, the gradual absorption of the implant material may facilitate easier removal or replacement if necessary, potentially reducing tissue damage compared to the removal of permanent metallic implants.

The bioabsorbable nature of the magnesium alloy implants may offer advantages in growing subjects. In some cases, the gradual absorption of the implant may allow for unimpeded bone growth and remodeling, potentially reducing the need for implant removal or revision surgeries in pediatric applications.

In vivo studies may also assess the potential for stress shielding effects with the magnesium alloy implants. In some cases, the gradual reduction in implant stiffness during the absorption process may help to mitigate stress shielding, potentially leading to improved long-term bone quality compared to permanent metallic implants.

The bioabsorbable magnesium alloy may exhibit functional performance characteristics that arise from the interplay between its composition, processing methods, microstructure, and implant designs. This synergistic relationship may allow for tailored properties suitable for orthopedic applications.

The alloy composition, including zinc, calcium, and manganese, may influence both the mechanical properties and corrosion behavior. In some cases, zinc may contribute to solid solution strengthening and grain refinement, potentially enhancing the alloy's strength and corrosion resistance. Calcium may form intermetallic phases that may affect the alloy's degradation rate, while manganese may improve corrosion resistance through the formation of more stable surface films.

Processing methods, such as solution treatment and multi-stage extrusion, may further modify the alloy's microstructure and properties. In some cases, solution treatment may homogenize the microstructure and dissolve secondary phases, potentially improving corrosion resistance. The extrusion process may refine the grain structure and align precipitates, which may enhance mechanical strength and influence the degradation behavior.

The resulting microstructure, characterized by grain size, precipitate distribution, and phase composition, may directly impact the alloy's functional performance. In some cases, a fine grain structure may contribute to improved strength and more uniform corrosion. The distribution and morphology of precipitate phases may affect both mechanical properties and degradation kinetics.

Implant designs leveraging this bioabsorbable magnesium alloy may be tailored to specific orthopedic applications. In some cases, the dimensions and geometry of plates and screws may be optimized to provide adequate mechanical support while facilitating controlled degradation. The implant design may also influence the local stress distribution and fluid dynamics, potentially affecting the in vivo degradation profile.

The interaction of these factors may result in a bioabsorbable implant with a controlled, multi-phase absorption profile. In some cases, the initial stability provided by the alloy composition and microstructure may allow for proper implant integration. The subsequent steady-state degradation phase may be influenced by the precipitate distribution and implant geometry, potentially providing sustained mechanical support during critical healing periods.

The gradual evolution of mechanical properties during degradation may be a result of the interplay between microstructural changes and the implant's design features. In some cases, the loss of strength may be partially offset by tissue ingrowth, facilitated by the implant's geometry and surface characteristics.

The biocompatibility and osteogenic potential of the magnesium alloy may be influenced by the combined effects of composition, microstructure, and degradation products. In some cases, the controlled release of magnesium, zinc, and calcium ions may stimulate local bone formation, while the evolving implant surface may promote cell adhesion and tissue integration.

The corrosion behavior of the alloy may be modulated by the interaction of composition, microstructure, and implant design. In some cases, the formation of protective surface layers may be influenced by the alloy's phase composition and the local physiological environment created by the implant geometry.

The overall functional performance of the bioabsorbable magnesium alloy in orthopedic applications may thus be a result of the complex interplay between its fundamental material characteristics and the specific implant design. This integrated approach may allow for the development of implants with tailored absorption profiles, mechanical properties, and biological responses suitable for various orthopedic indications.

In the development of a bioabsorbable magnesium alloy (e.g., Curasorb) for use in biodegradable implants (e.g., orthopedic implants, maxillofacial trauma and reconstruction), extensive research and experimentation with magnesium alloys were undertaken. The research and experimentation included a thorough examination of the microstructural, mechanical, and corrosion properties of hot-extruded Mg—Zn—Ca—(Mn) biodegradable alloys.

Detailed phase diagrams and optimal extrusion conditions for compositions like the bioabsorbable magnesium alloy were identified. See, e.g., Bazhenov V E, Li A V, Komissarov A A, Koltygin A V, Tavolzhanskii S A, Bautin V A, Voropaeva O O, Mukhametshina A M, Tokar A A (2021), Microstructure and mechanical and corrosion properties of hot-extruded Mg—Zn—Ca—(Mn) biodegradable alloys. Journal of Magnesium and Alloys 9(4):1428-1442, which is hereby incorporated by reference in its entirety herein. The literature may also be found in https://doi.org/10.1016/j.jma.2020.11.008.

The conditions for processing a comparative alloy (e.g., Bioretec ZX00) were identified and guided the selection of an extrusion temperature of 345° C. See, e.g., Alam M E, Pal S, Decker R, Ferreri N C, Knezevic M, Beyerlein I J (2020) Rare-earth- and aluminum-free, high strength dilute magnesium alloy for Biomedical Applications. Scientific Reports 10:15839, which is hereby incorporated by reference in its entirety herein. The literature may also be found in https://doi.org/10.1038/s41598-020-72374-z. Complementary studies showed promising results at a lower extrusion temperature of 315° C. See, e.g., Han Y Y, You C, Zhao Y, Chen M F, Wang L (2019) Effect of Mn Element Addition on the Microstructure, Mechanical Properties, and Corrosion Properties of Mg-3Zn-0.2Ca Alloy. Frontiers in Materials 6:324, which is hereby incorporated by reference in its entirety herein. The literature may also be found in https://doi.org/10.3389/fmats.2019.00324. The research helped establish an effective temperature range of 325-350° C. for processing bioabsorbable magnesium alloy.

The efficacy of a two-stage heat treatment on Mg—Ca—Zn alloys without low melting temperature phases formed under Scheil conditions can be achieved. The Scheil condition refers to a theoretical solidification model used in metallurgy to predict microsegregation and solidification behavior during the cooling of alloys. See, e.g., Bamberger M, Levi G, Vander Sande J B (2006) Precipitation hardening in Mg—Ca—Zn alloys. Metallurgical and Materials Transactions A 37:481-487, which is hereby incorporated by reference in its entirety herein. The literature may also be found in https://doi.org/10.1007/s11661-006-0019-9.

The size of ternary precipitates (intermetallic phases) can be reduced when annealing is followed by hot working/aging. Annealing at 400° C. for one hour can effectively dissolve GP zones, leading to smaller (and maybe more uniform) ternary phases. See, e.g., Alam et al. as cited above.

The two-step heat treatment process on Mg—Ca—Zn alloys can produce optimal morphological traits. Optical and scanning electron microscopy may reveal decreased volume fraction of precipitation phases, which may predominantly comprise small spherical forms. See, e.g., Nie K, Zhu Z, Munroe P, Deng K, Han J (2020) The effect of Zn/Ca ratio on the microstructure, texture and mechanical properties of dilute Mg— Zn—Ca—Mn alloys that exhibit superior strength. Journal of Materials Science 55:3588-3604, which is hereby incorporated by reference in its entirety herein. The literature may also be found in https://doi.org/10.1007/s10853-019-04174-4. Such precipitate phases may ensure more uniform corrosion, particularly beneficial for enhancing the stability and longevity of cathodic phases like the ternary Mg—Zn—Ca phase, while potentially being less effective for anodic phases such as Mg2Ca. These characteristics may help achieve the desired performance in bioabsorbable magnesium alloys used in medical applications.

Building on these foundational insights, the development of the new bioabsorbable magnesium alloy has been initiated to harness the unique benefits of magnesium in creating a superior, bioabsorbable implant material.

EXAMPLES

The present studies have been conducted to develop and validate a new bioabsorbable magnesium alloy (e.g., Curasorb™), designed to outperform existing technologies. These studies have demonstrated that the alloy's absorption profile can be precisely controlled, ensuring predictable performance across three phases: a gradual start, a steady plateau, and an accelerating absorption phase. This tailored approach enables customization of the magnesium alloy to meet the specific requirements of orthopedic implants for various clinical indications.

The first prototypes (e.g., Curasorb alpha prototypes) exhibited a slower initial absorption rate than comparative alloys (e.g., Bioretec's REMEOS/ZX00 and nanoMAG's BioMg 250), addressing a critical clinical challenge-rapid absorption or "burst effect" seen in other alloys, which can lead to bone density loss resulting in instability and implant failure. In addition to tailored absorption, the alloys demonstrated mechanical properties comparable to or exceeding those of comparative alloys, ensuring sufficient strength during the critical phases of implant integration and degradation. Advanced processing techniques were also shown to enhance both corrosion profiles and absorption uniformity, providing further differentiation from competing technologies.

The first prototypes (e.g., Curasorb alpha prototypes) matched the mechanical performance of comparative products (e.g., Syntellix's MAGNEZIX compression screws) while also providing baseline data to correlate the published in vivo absorption performance of the comparative products (e.g., MAGNEZIX) with its in vitro corrosion behavior in simulated body conditions. These results established the minimum viable product (MVP) specifications, which will guide further development through extensive preclinical studies, design freeze, and commercialization.

Currently in development, the second prototypes (e.g., Curasorb beta prototypes) will build on these successes and learnings with refined compositions and optimized processing methods. The development of a bioabsorbable magnesium alloy for biodegradable orthopedic implants is underway, with the first iteration targeted for use in maxillofacial trauma and reconstruction. These advancements aim to precisely tune absorption behavior for maxillofacial and extremities applications, enhance mechanical properties, and enhance the performance of absorbable magnesium implants.

The goal is to develop a next-generation bioabsorbable magnesium alloy with superior absorption characteristics tailored to orthopedic applications.

Unlike other approaches that rely on minimal alloying elements, the present disclosure employs higher levels of zinc (Zn) and manganese (Mn) in the alloy to achieve:

Controlled Absorption Profiles: Faster absorption at later stages for complete implant absorption within clinically optimal timeframes.

Strong Osseointegration: A slower initial absorption rate to avoid the "burst effect" seen in other alloys, ensuring bone/implant stability and better patient outcomes.

Predictable and Customizable Performance: Optimized absorption process (e.g., minimal absorption through healing with gradually accelerating absorption rate) tailored for clinical needs.

Achieving these objectives will position the alloy as a transformative solution in the bioabsorbable magnesium alloy market, addressing unmet clinical needs and unlocking significant commercial opportunities.

The materials from alloying study I and alloying study II were evaluated to confirm that composition targets were met and determine material properties. A summary of the testing is presented in Tables 15 and 17 for alloying study I, Table 18 for alloying study II, and Table 23 for alloying study III.

Example 0: CALPHAD Modeling of Mg—Zn—Ca—Mn alloys

Panda software with PanMg 2023 database was used in this project. The Schiel model (assuming no diffusion in solid but complete mixing/diffusion in liquid) provides a reasonable prediction of as-cast microstructure in most casting processes. The equilibrium model (assuming complete diffusion/mixing in solid and liquid phases) provides a good prediction of fully annealed microstructure or extremely slow-cooled solidification microstructure. There are three Mg—Zn—Ca ternary phases in the database, with $Ca_2Mg_5Zn_5$ ($Ca_2Mg_6Zn_3$ reported in ThermoCalc) as the major ternary phase as shown in FIG. 1.

Figure 2:
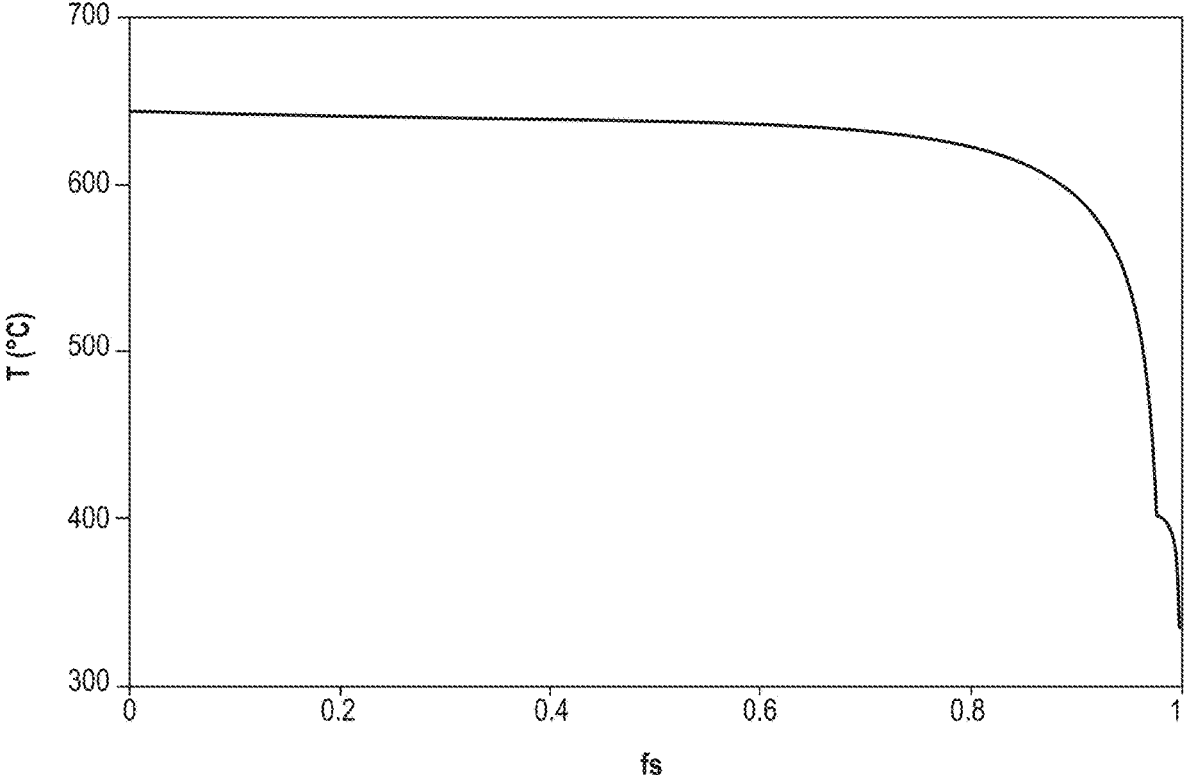
FIG. 2 shows a temperature versus fraction solid graph for alloy solidification analysis, according to an embodiment.

FIG. 2 shows a temperature vs. fraction solid (fs) graph showing the liquidus, $Ca_2Mg_5Zn_5$ formation, and solidus temperatures of Alloy 1-1.5Zn-0.4Ca-0.7Mn (wt. %) based on the Scheil modeling. The liquidus ($\alpha$-Mg) temperature appears to be about 644° C. The $Ca_2Mg_5Zn_5$ formation temperature appears to be about 402° C. The solidus temperature appears to be about 335° C. The final solidification microstructure contains 1.4% mole fraction of $Ca_2Mg_5Zn_5$, 0.1% mole fraction of $\alpha$-Mn, and a balance of $\alpha$-Mg.

Figure 3:
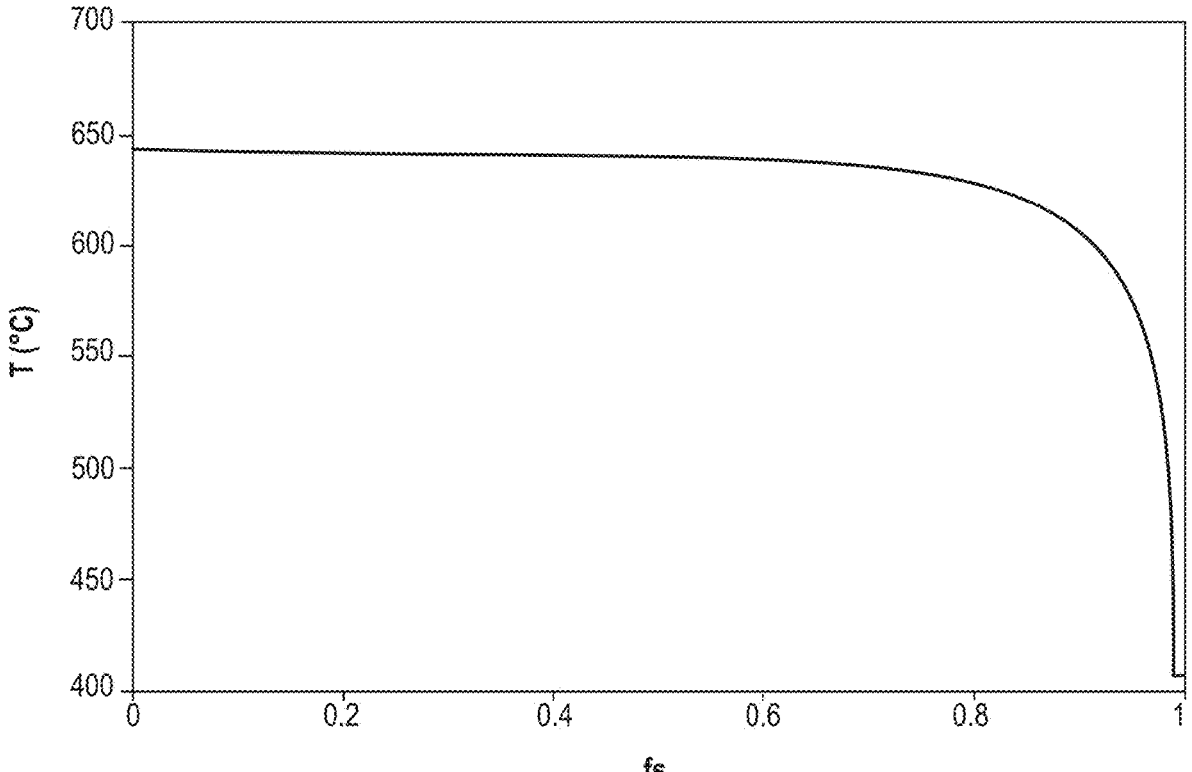
FIG. 3 illustrates a temperature versus fraction solid curve representing a solidification profile, according to aspects of the present disclosure.

FIG. 3 shows a temperature vs. fraction solid (fs) graph showing the liquidus, $Ca_2Mg_5Zn_5$ formation, and solidus temperatures of Alloy 1-1.5Zn-0.4Ca-0.7Mn (wt. %) based on the equilibrium modeling. The liquidus ($\alpha$-Mg) temperature appears to be about 644° C. The $Ca_2Mg_5Zn_5$ formation temperature appears to be about 408° C. The solidus temperature appears to be about 407° C. The final solidification microstructure contains 0.6% mole fraction of $Ca_2Mg_5Zn_5$, 0.2% mole fraction of $\alpha$-Mn, and a balance of $\alpha$-Mg.

Figure 4:
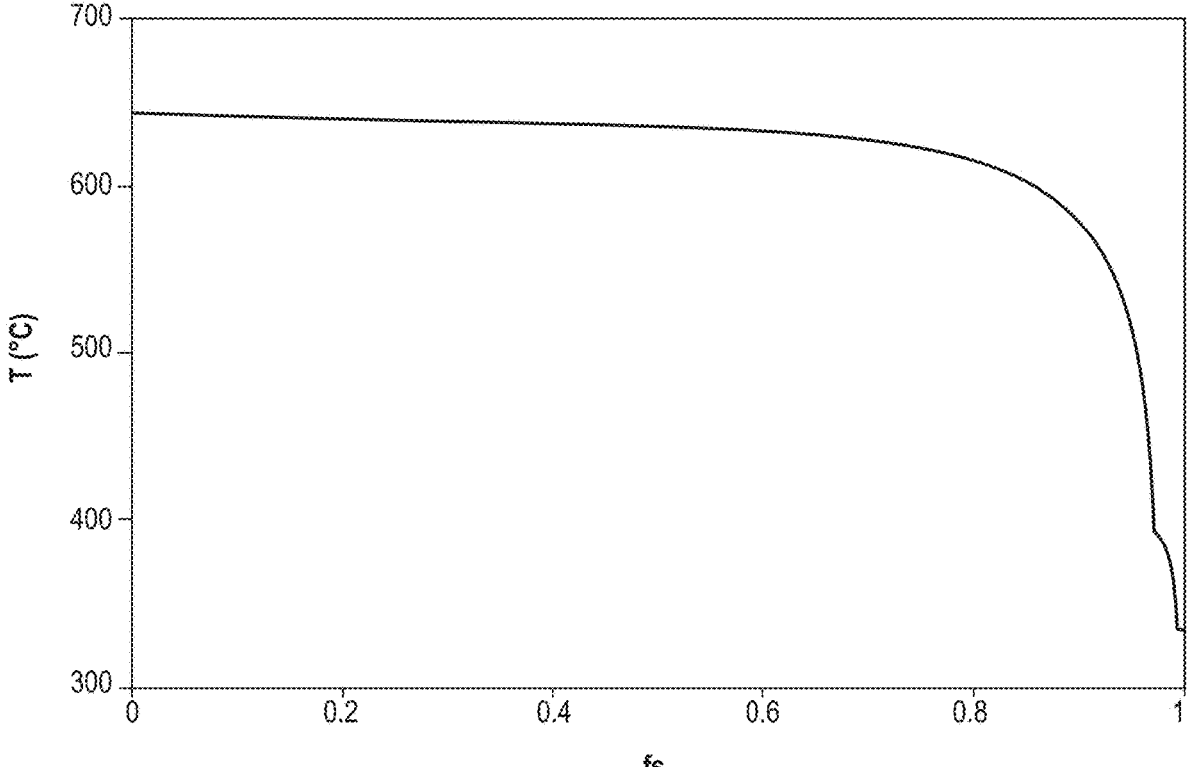
FIG. 4 depicts a temperature versus fraction solid curve showing a cooling/solidification profile, according to an embodiment.

FIG. 4 shows a temperature vs. fraction solid (fs) graph showing the liquidus, $Ca_2Mg_5Zn_5$ formation, and solidus temperatures of Alloy 2-2.0Zn-0.4Ca-0.7Mn (wt. %) based on the Scheil modeling. The liquidus ($\alpha$-Mg) temperature appears to be about 642° C. The $Ca_2Mg_5Zn_5$ formation temperature appears to be about 394° C. The solidus temperature appears to be about 335° C. The final solidification ture appears to be about 641° C. The $Ca_2Mg_5Zn_5$ formation temperature appears to be about 402° C. The solidus temperature appears to be about 400° C. The final solidification microstructure contains 1.1% mole fraction of $Ca_2Mg_5Zn_5$, 0.2% mole fraction of $\alpha$-Mn, and a balance of $\alpha$-Mg.

All three alloys show similar microstructure, consisting of mostly Mg—Zn—Ca ternary phases (approximately $Ca_2Mg_5Zn_5$) and a small amount of $\alpha$-Mn phases. Increasing Zn content can increase the fraction of Mg—Zn—Ca ternary phases in as-cast microstructure. A heat treatment below the solidus temperature can dissolve about half of the ternary phases if needed. Most of Mn is in solid solution of $\alpha$-Mg, with about 0.1% mole fraction $\alpha$-Mn phase in as-cast and 0.2% mole fraction $\alpha$-Mn precipitate in equilibrium microstructure. Table 1 summarizes the mole fractions of $Ca_2Mg_5Zn_5$ and $\alpha$-Mn of Alloys 1-3 based on Scheil and equilibrium modelling. Table 2 summarizes the solidus and liquidus temperatures of Alloys 1-3 based on Scheil and equilibrium modelling.

Table 1 shows the mole fractions of $Ca_2Mg_5Zn_5$ and $\alpha$-Mn of Alloys 1-3 based on Scheil and equilibrium modelling

| Alloy | Scheil (mole fraction) | | Equilibrium (mole fraction) | |
|---|---|---|---|---|
| (composition in wt. %) | $Ca_2Mg_5Zn_5$ | $\alpha$-Mn | $Ca_2Mg_5Zn_5$ | $\alpha$-Mn |
| Alloy 1 - 1.5Zn—0.4Ca—0.7Mn | 1.4 | 0.1 | 0.6 | 0.2 |
| Alloy 2 - 2.0Zn—0.4Ca—0.7Mn | 1.7 | 0.1 | 0.9 | 0.2 |
| Alloy 3 - 2.5Zn—0.4Ca—0.7Mn | 1.9 | 0.1 | 1.1 | 0.2 | microstructure contains 1.7% mole fraction of $Ca_2Mg_5Zn_5$, 0.1% mole fraction of $\alpha$-Mn, and a balance of $\alpha$-Mg.

Figure 5:
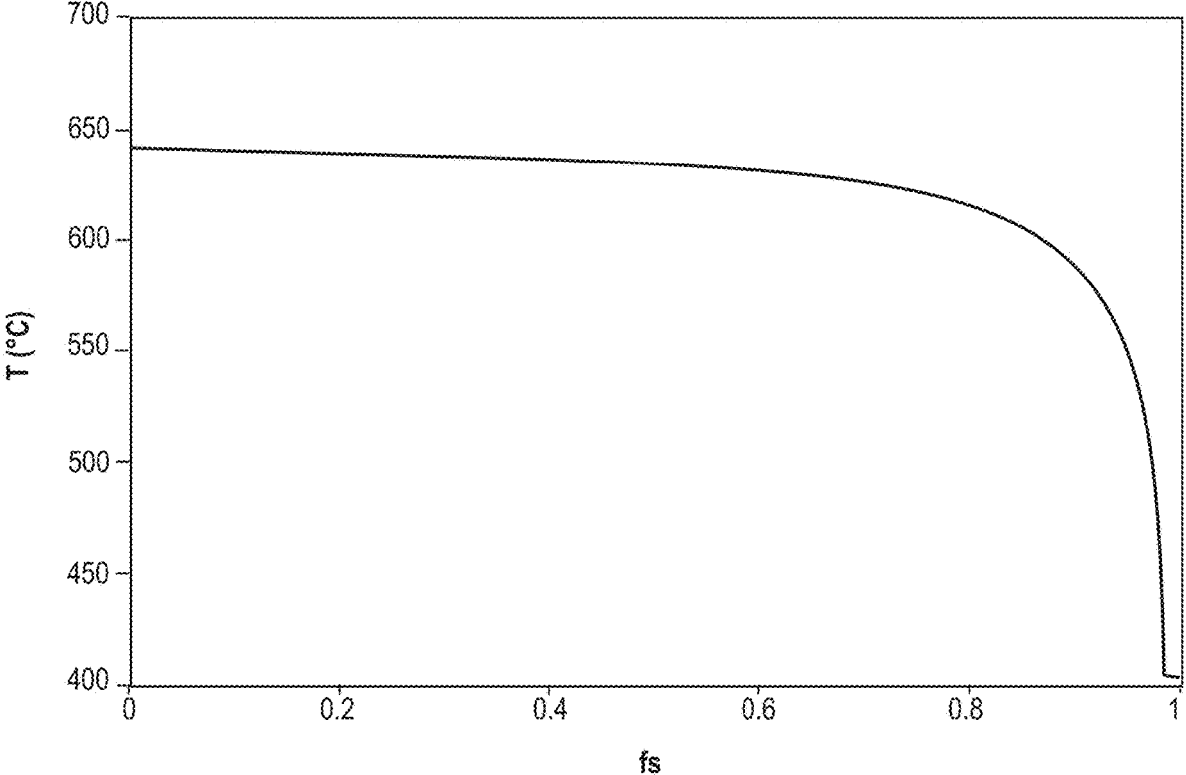
FIG. 5 shows a temperature versus fraction solid graph of a cooling curve analysis, according to aspects of the present disclosure.

FIG. 5 shows a temperature vs. fraction solid (fs) graph showing the liquidus, $Ca_2Mg_5Zn_5$ formation, and solidus temperatures of Alloy 2-2.0Zn-0.4Ca-0.7Mn (wt. %) based on the equilibrium modeling. The liquidus ($\alpha$-Mg) temperature appears to be about 642° C. The $Ca_2Mg_5Zn_5$ formation temperature appears to be about 405° C. The solidus temperature appears to be about 404° C. The final solidification microstructure contains 0.9% mole fraction of $Ca_2Mg_5Zn_5$, 0.2% mole fraction of $\alpha$-Mn, and a balance of $\alpha$-Mg.

Figure 6:
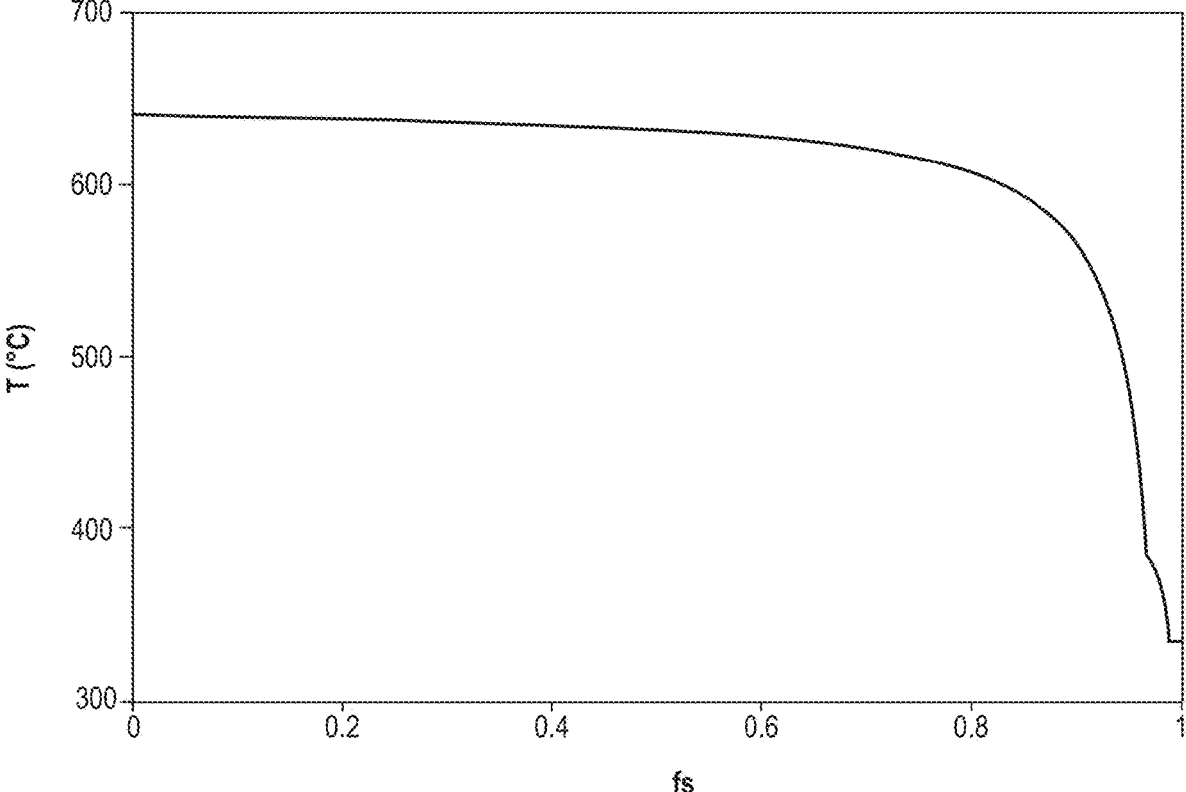
FIG. 6 illustrates a temperature versus fraction solid graph of a cooling curve analysis, according to an embodiment.

FIG. 6 shows a temperature vs. fraction solid (fs) graph showing the liquidus, $Ca_2Mg_5Zn_5$ formation, and solidus temperatures of Alloy 3-2.5Zn-0.4Ca-0.7Mn (wt. %) based on the Scheil modeling. The liquidus ($\alpha$-Mg) temperature appears to be about 641° C. The $Ca_2Mg_5Zn_5$ formation temperature appears to be about 386° C. The solidus temperature appears to be about 335° C. The final solidification microstructure contains 1.9% mole fraction of $Ca_2Mg_5Zn_5$, 0.1% mole fraction of $\alpha$-Mn, and a balance of $\alpha$-Mg.

Figure 7:
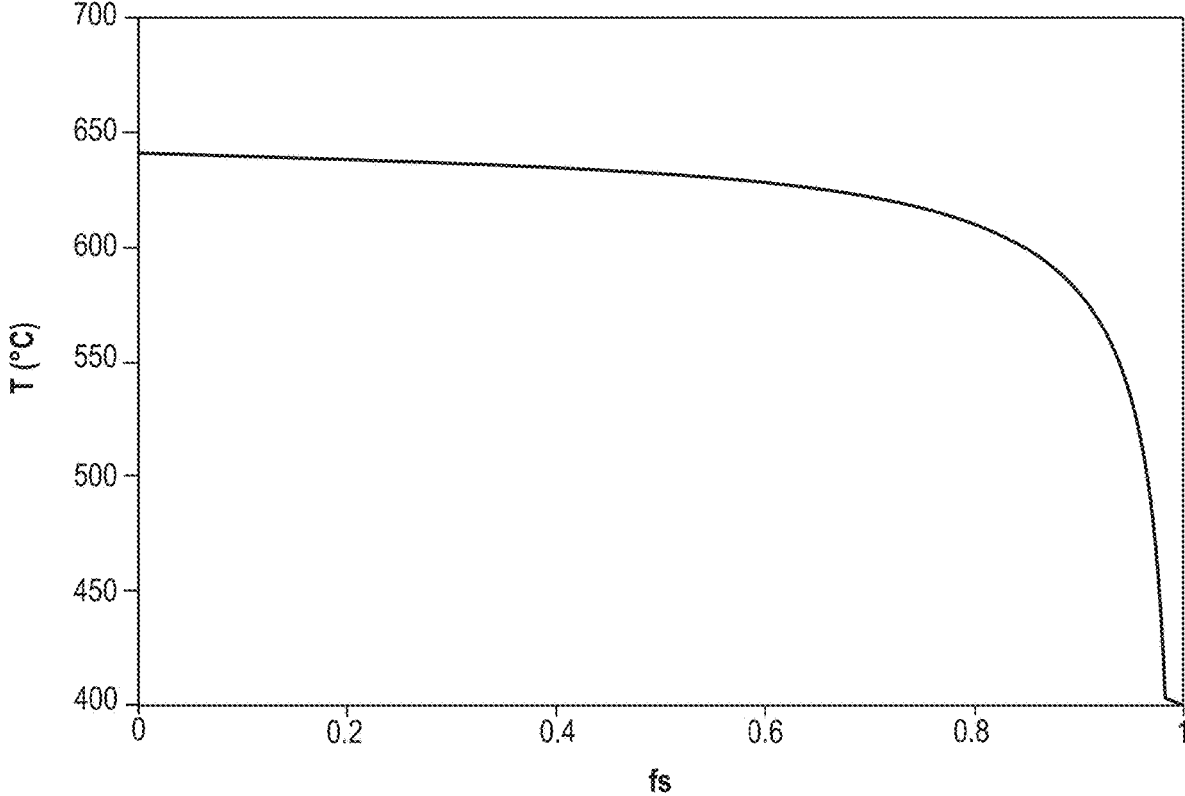
FIG. 7 depicts a temperature versus fraction solid plot representing a cooling/solidification curve, according to aspects of the present disclosure.

FIG. 7 shows a temperature vs. fraction solid (fs) graph showing the liquidus, $Ca_2Mg_5Zn_5$ formation, and solidus temperatures of Alloy 3-2.5Zn-0.4Ca-0.7Mn (wt. %) based on the equilibrium modeling. The liquidus ($\alpha$-Mg) tempera- Table 2 shows solidus and liquidus temperatures of Alloys 1-3 based on Scheil and equilibrium modelling

| Alloy | Scheil (° C.) | | Equilibrium (° C.) | |
|---|---|---|---|---|
| (composition in wt. %) | Liquidus | Solidus | Liquidus | Solidus |
| Alloy 1 - 1.5Zn—0.4Ca—0.7Mn | 644 | 335 | 644 | 407 |
| Alloy 2 - 2.0Zn—0.4Ca—0.7Mn | 642 | 335 | 642 | 404 |
| Alloy 3 - 2.5Zn—0.4Ca—0.7Mn | 641 | 335 | 641 | 400 |

Example 1: Compositional Analysis

Alloying Study I—Target Compositions

A matrix of eight alloy compositions (e.g., RD alloys) was designed to demonstrate technical feasibility of a bioabsorbable magnesium alloy (e.g., Curasorb Alloy). The target compositions included variations in zinc (Zn), calcium (Ca), and manganese (Mn) content, with magnesium (Mg) as the balance. The alloys were designated A1 through A8, with Zn content ranging from 2.0% to 3.5%, Ca content at 1.0%, and Mn content varying between 0.2% and 0.6% by weight. Two control alloys were selected for comparative testing against the RD alloys, specifically focusing on immersion corrosion performance. The targeted compositions are summarized in Table 3.

TABLE 3

Target Composition Ranges for Alloying Study I:
RD alloys A1-A8 and comparative alloys C1 & C2.

| | | Target Compositions | | | | | | | |
| | | Alloying Elements | | | Trace Elements | | | | |
| Alloy | Mg | Zn | Ca | Mn | Fe | Ni | Cu | Al | Si |
| --- | --- | --- | --- | --- | --- | --- | --- | --- | --- |
| A1 | Balance | 2.0 ± 0.2 | 1.0 ± 0.2 | 0.6 ± 0.2 | <0.010 | <0.010 | <0.010 | <0.010 | <0.010 |
| A2 | Balance | 2.0 ± 0.2 | 1.0 ± 0.2 | 0.4 ± 0.2 | <0.010 | <0.010 | <0.010 | <0.010 | <0.010 |
| A3 | Balance | 2.5 ± 0.2 | 1.0 ± 0.2 | 0.6 ± 0.2 | <0.010 | <0.010 | <0.010 | <0.010 | <0.010 |
| A4 | Balance | 2.5 ± 0.2 | 1.0 ± 0.2 | 0.4 ± 0.2 | <0.010 | <0.010 | <0.010 | <0.010 | <0.010 |
| A5 | Balance | 2.5 ± 0.2 | 1.0 ± 0.2 | 0.2 ± 0.2 | <0.010 | <0.010 | <0.010 | <0.010 | <0.010 |
| A6 | Balance | 3.0 ± 0.2 | 1.0 ± 0.2 | 0.4 ± 0.2 | <0.010 | <0.010 | <0.010 | <0.010 | <0.010 |
| A7 | Balance | 3.0 ± 0.2 | 1.0 ± 0.2 | 0.2 ± 0.2 | <0.010 | <0.010 | <0.010 | <0.010 | <0.010 |
| A8 | Balance | 3.5 ± 0.2 | 1.0 ± 0.2 | 0.2 ± 0.2 | <0.010 | <0.010 | <0.010 | <0.010 | <0.010 |
| C1 | Balance | 0.45 ± 0.2 | 0.45 ± 0.2 | — | <0.010 | <0.010 | <0.010 | <0.010 | <0.010 |
| C2 | Balance | 1.2 ± 0.2 | 0.5 ± 0.2 | 0.5 ± 0.2 | <0.010 | <0.010 | <0.010 | <0.010 | <0.010 |

Alloying Study II—Process Development Run

Leveraging the results of the first study (Alloying Study I), a second alloying study was executed using production-grade equipment (e.g., Terves). Three alloys, as shown in Table 4, were produced, aiming to further decelerate the corrosion rate. This study targeted Zn:Ca ratios of 1.3 and 2, Mn content between 0.4-1.0 wt %, and trace elements summing up to 0.1%

TABLE 4

Target composition ranges for Alloying Study II (PD A-C).

| | | Target Compositions | | | | | | | |
| | | Alloying Elements | | | Trace Elements | | | | |
| Alloy | Mg | Zn | Ca | Mn | Fe | Ni | Cu | Al | Si |
| --- | --- | --- | --- | --- | --- | --- | --- | --- | --- |
| PD A | balance | 2.0 ± 0.2 | 1.5 ± 0.2 | 0.4 ± 0.2 | <0.010 | <0.010 | <0.010 | <0.010 | <0.010 |
| PD B | balance | 2.0 ± 0.2 | 1.0 ± 0.2 | 1.0 ± 0.2 | <0.010 | <0.010 | <0.010 | <0.010 | <0.010 |
| PD C | balance | 2.0 ± 0.2 | 1.0 ± 0.2 | 0.4 ± 0.2 | <0.010 | <0.010 | <0.010 | <0.010 | <0.010 |

Alloying Study III—Process Development Run

Leveraging the results of previous studies, a third alloying study was executed using production-grade equipment (e.g., Terves). The same equipment and material that were used in Alloying Study II were used in this study. Four alloys, as shown in Table 5, were produced, aiming to reduce $Mg_2Ca$ formation and increase ductility.

TABLE 5

Target composition ranges for Alloying Study III

| | | Target Compositions | | | | | | | |
| | | Alloying Elements | | | Trace Elements | | | | |
| Alloy | Mg | Zn | Ca | Mn | Fe | Ni | Cu | Al | Si |
| --- | --- | --- | --- | --- | --- | --- | --- | --- | --- |
| 165-2 | Balance | 2.5 ± 0.2 | 0.4 ± 0.1 | 0.8 ± 0.1 | <0.010 | <0.010 | <0.010 | <0.010 | <0.010 |
| 310-1 | Balance | 2 ± 0.2 | 0.4 ± 0.1 | 0.8 ± 0.1 | <0.010 | <0.010 | <0.010 | <0.010 | <0.010 |
| 310-2 | Balance | 2.5 ± 0.2 | 0.4 ± 0.1 | 0.8 ± 0.1 | <0.010 | <0.010 | <0.010 | <0.010 | <0.010 |
| 029-1 | Balance | 2.0 ± 0.2 | 0.4 ± 0.1 | 0.8 ± 0.1 | <0.010 | <0.010 | <0.010 | <0.010 | <0.010 |

Alloying Study I Material Processing—Casting, Solution Treatment, Extrusion 24 permanent mold castings with 1.25" diameter were produced over two casting days using either 60 lb. gas-fired furnace (e.g., manufactured by L. Haberny Co. Inc.) with ladle pour into the mold or the 10 lb. electric furnace with direct pour into the mold. The molds were filtered with a wire mesh suspended in the sprue/riser.

The raw materials used to produce the castings and melt disks and their compositions are presented in Tables 6A and 6B.

TABLE 6A

Alloying Study I Raw Materials and Suppliers

| Material | Form | Supplier |
|---|---|---|
| Mg | UHP Mg Ingot, Grade 1 | US Mag |
| Ca | Wire (Scrap) | Hickman, Williams & Company |
| Zn | High Grade 2-14 Mesh Shot | Amalgamet Canada LP |
| Mn | LH Flake | N.T. Ruddock Co (Manganese Metal Co) |

TABLE 6B

Alloying Study I Composition of Raw Materials

| Material | Mg | Ca | Zn | Mn | Al | Si | Fe | Ni | Cu |
|---|---|---|---|---|---|---|---|---|---|
| Mg | REM | 0.001 | 0.001 | 0.005 | 0.006 | 0.005 | 0.007 | 0.001 | 0.001 |
| Ca | <0.5 | <98.5 | — | — | <0.5 | — | — | — | — |
| Zn | — | — | >99.99 | — | <0.001 | — | <0.003 | — | <0.001 |
| Mn | — | — | — | 99.8 | 0.001 | 0.002 | 0.001 | 0.0002 | 0.0003 |

| Material | Zr | Pb | Na | Sn | As | Cd | O |
|---|---|---|---|---|---|---|---|
| Mg | 0.005 | 0.002 | 0.001 | 0.002 | — | — | — |
| Ca | — | — | — | — | — | — | — |
| Zn | — | <0.003 | — | <0.001 | <0.0001 | <0.001 | — |
| Mn | — | 0.0005 | — | — | <0.0001 | — | 0.2 |

| Material | S | N | C | $H_2$ | P | Co | Se | Others |
|---|---|---|---|---|---|---|---|---|
| Mg | — | — | — | — | — | — | — | 0.005 |
| Ca | — | — | — | — | — | — | — | — |
| Zn | — | — | — | — | — | — | — | — |
| Mn | 0.03 | 0.007 | 0.001 | 0.0007 | 0.0005 | 0.0002 | <0.0001 | — |

Alloying Study II—Process Development Run

Three permanent mold 9.5" diameter castings were produced over two casting days utilizing a 450lb electric furnace with direct pour into the mold. The raw material used to produce the castings and melt disks and their compositions are presented in Tables 7A and 7B.

TABLE 7A

Alloying Study II Raw Materials and Suppliers

| Material | Form | Supplier |
|---|---|---|
| Mg | UHP Mg Ingot, Grade 1 | US Mag |
| Ca | Crowns | Titan Int. Inc. |
| Zn | High Grade, 2-14 Mesh Shot | Amalgamet Canada LP |
| Mn | LH Flake | NT Ruddock |

TABLE 7B

Alloying Study II Composition of Raw Materials

| Mg | Ca | Zn | Mn | Al | Si | Fe | Ni | Cu |
|---|---|---|---|---|---|---|---|---|
| REM | 0.001 | 0.001 | 0.005 | 0.006 | 0.005 | 0.007 | 0.001 | 0.001 |
| 0.42 | >99.0 | — | 0.012 | 0.31 | 0.0054 | <0.004 | — | 0.002 |
| — | — | >99.99 | — | <0.001 | — | <0.003 | — | <0.001 |
| — | — | — | 99.8 | 0.001 | 0.002 | 0.001 | — | 0.0003 |

| Material | Zr | Pb | Na | Ti | Sn | As | Cd | O |
|---|---|---|---|---|---|---|---|---|
| Mg | 0.005 | 0.002 | 0.001 | 0.01 | 0.002 | — | — | — |
| Ca | — | — | — | — | — | — | — | — |
| Zn | — | <0.003 | — | — | <0.001 | <0.0001 | <0.001 | — |
| Mn | — | 0.0005 | — | — | — | <0.0001 | — | 0.2 |

TABLE 7B-continued

| | | | Alloying Study II Composition of Raw Materials | | | | |
|---|---|---|---|---|---|---|---|
| Material | S | N | C | H$_2$ | P | Co | Se | Others |
| Mg | — | — | — | — | — | — | — | 0.005 |
| Ca | — | — | — | — | — | — | — | — |
| Zn | — | — | — | — | — | — | — | — |
| Mn | 0.03 | 0.007 | 0.001 | 0.0007 | 0.0005 | 0.0002 | <0.0001 | — |

Alloying Study III—Process Development Run

The raw material used to produce the castings and melt disks and their compositions are presented in Tables 8A and 8B.

TABLE 8A

| Alloying Study III Raw Materials and Suppliers | | |
|---|---|---|
| Material | Form | Supplier |
| Mg | UHP Mg Ingot, Grade 1 | US Mag |
| Ca | Crowns | Titan Int. Inc. |
| Zn | High Grade, 2-14 Mesh Shot | Amalgamet Canada LP |
| Mn | LH Flake | NT Ruddock |

TABLE 8B

| Alloying Study III Composition of Raw Materials | | | | | | | | |
|---|---|---|---|---|---|---|---|---|
| Mg | Ca | Zn | Mn | Al | Si | Fe | Ni | Cu |
| REM | 0.001 | 0.001 | 0.005 | 0.006 | 0.005 | 0.007 | 0.001 | 0.001 |
| 0.42 | >99.0 | — | 0.012 | 0.31 | 0.0054 | <0.004 | — | 0.002 |
| — | — | >99.99 | — | <0.001 | — | <0.003 | — | <0.001 |
| — | — | — | 99.8 | 0.001 | 0.002 | 0.001 | — | 0.0003 |

| Material | Zr | Pb | Na | Ti | Sn | As | Cd | O |
|---|---|---|---|---|---|---|---|---|
| Mg | 0.005 | 0.002 | 0.001 | 0.01 | 0.002 | — | — | — |
| Ca | — | — | — | — | — | — | — | — |
| Zn | — | <0.003 | — | — | <0.001 | <0.0001 | <0.001 | — |
| Mn | — | 0.0005 | — | — | — | <0.0001 | — | 0.2 |

| Material | S | N | C | H$_2$ | P | Co | Se | Others |
|---|---|---|---|---|---|---|---|---|
| Mg | — | — | — | — | — | — | — | 0.005 |
| Ca | — | — | — | — | — | — | — | — |
| Zn | — | — | — | — | — | — | — | — |
| Mn | 0.03 | 0.007 | 0.001 | 0.0007 | 0.0005 | 0.0002 | <0.0001 | — |

Alloying Study I & II Spark OES (Spark Optical Emission Spectrometry)

Spark chemistry was measured utilizing a Mg—Ca alloy standard. During casting, spark chemistry was measured at various mixing steps and prior to pouring the molten metal into the billet to confirm the alloy chemistry met targets. After casting, the top and bottom 0.5" of the casting were sectioned and polished with 120 grit SiC paper prior to spark chemistry measurement. A total of three measurements were performed at each location. For alloying study I, all eight experimental alloys (A1-A8) and the two comparative alloys were tested during melting/alloying (melt discs) and in the as cast condition. For alloying study II, all three experimental alloys were tested during melting/alloying (melt discs) and in the as cast condition.

Compositional Analysis—Spark OES—Alloying Study I

The Spark OES measurements on melt disks and castings are found in Tables 9 and 10, respectively. Data has been refined to include an average of three tests. The ratio of Zn/Ca is presented for each measurement as well as the sum of the trace elements. Castings C1-1, C2-A-2, A1-1, A2-A-2, A3-D-1, A4-A-2, A5-2, A6-A-1, A7-2, and A8-A-1 were down selected for solutionizing, extrusion, and testing (including corrosion and tensile) in SOL+Ext. Trial I. Samples A2-B-2, A4-B-2, and A8-B-1 were utilized for a second test matrix which evaluated the Nie double solutionizing treatment in SOL+Ext. Trial II.

TABLE 9

| | | Composition (wt %) | | | | Trace (wt %) | | | | | SUM |
|---|---|---|---|---|---|---|---|---|---|---|---|
| ID | Crucible | Zn | Ca | Mn | Zn/Ca | Ni | Cu | Fe | Al | Si | Trace |
| C1-1 | 60 lb | 0.56 | 0.547 | 0.002 | 1.01 | 0.001 | 0.001 | 0.017 | 0.017 | 0.011 | 0.047 |
| C2-1 | 10 lb | 1.77 | 0.459 | 0.207 | 3.86 | 0.001 | 0.001 | 0.017 | 0.011 | 0.010 | 0.040 |
| C2-2 | 10 lb | 1.29 | 0.405 | 0.507 | 3.19 | 0.001 | 0.001 | 0.016 | 0.017 | 0.005 | 0.040 |
| A1-1 | 60 lb | 1.93 | 0.819 | 0.513 | 2.36 | 0.001 | 0.001 | 0.026 | 0.015 | 0.008 | 0.051 |
| A2-1 | 60 lb | 1.81 | 0.872 | 0.245 | 2.08 | 0.001 | 0.001 | 0.021 | 0.019 | 0.010 | 0.052 |
| A2-2 | 60 lb | 2.06 | 0.868 | 0.230 | 2.37 | 0.001 | 0.001 | 0.028 | 0.020 | 0.009 | 0.059 |
| A3-1 | 60 lb | 2.37 | 0.898 | 0.572 | 2.64 | 0.001 | 0.001 | 0.028 | 0.017 | 0.009 | 0.056 |
| A4-1 | 10 lb | 2.41 | 0.821 | 0.342 | 2.94 | 0.001 | 0.001 | 0.027 | 0.019 | 0.011 | 0.059 |
| A4-2 | 10 lb | 2.65 | 0.914 | 0.318 | 2.90 | 0.001 | 0.001 | 0.028 | 0.019 | 0.008 | 0.057 |
| A5-1 | 10 lb | 2.42 | 0.859 | 0.187 | 2.82 | 0.001 | 0.001 | 0.023 | 0.018 | 0.010 | 0.053 |
| A5-2 | 10 lb | 2.93 | 0.972 | 0.226 | 3.01 | 0.001 | 0.001 | 0.022 | 0.019 | 0.009 | 0.052 |
| A6-1 | 10 lb | 2.95 | 0.968 | 0.394 | 3.05 | 0.001 | 0.001 | 0.029 | 0.019 | 0.009 | 0.059 |
| A7-2 | 10 lb | 3.30 | 0.917 | 0.241 | 3.60 | 0.001 | 0.001 | 0.022 | 0.019 | 0.009 | 0.052 |
| A8-1 | 10 lb | 3.73 | 0.819 | 0.311 | 4.55 | 0.001 | 0.001 | 0.024 | 0.017 | 0.011 | 0.054 |

Alloying Study I Melt Disc Chemistries

TABLE 10

Alloying Study I Castings Chemistries

| ID | Crucible | $T_{Pour}$ (° C.) | $T_{Mold}$ (° C.) | Position | Composition (wt %) | | | | Trace (wt %) | | | | | SUM |
|---|---|---|---|---|---|---|---|---|---|---|---|---|---|---|
| | | | | | Zn | Ca | Mn | Zn/Ca | Ni | Cu | Fe | Al | Si | Trace |
| C1-1 | 60 lb | 715 | 65 | TOP | 0.5 | 0.45 | 0 | 1.15 | 0 | 0 | 0.02 | 0.01 | 0.01 | 0.04 |
| | | | | BOT | 0.5 | 0.44 | 0 | 1.06 | 0 | 0 | 0.02 | 0.01 | 0.01 | 0.04 |
| C2-A-1 | 10 lb | 695 | 41 | TOP | 1.5 | 0.38 | 0.2 | 4.11 | 0 | 0 | 0.02 | 0.01 | 0.01 | 0.04 |
| | | | | BOT | 1.6 | 0.39 | 0.2 | 4.02 | 0 | 0 | 0.02 | 0.01 | 0.01 | 0.04 |
| C2-B-1 | 10 lb | NR | 61 | TOP | 1.5 | 0.31 | 0.21 | 4.9 | 0 | 0 | 0.02 | 0.01 | 0.01 | 0.04 |
| | | | | BOT | 1.6 | 0.4 | 0.2 | 3.84 | 0 | 0 | 0.02 | 0.01 | 0.01 | 0.04 |
| C2-C-1 | 10 lb | NR | NR | TOP | 1.5 | 0.36 | 0.26 | 4.27 | 0 | 0 | 0.02 | 0.01 | 0.01 | 0.04 |
| | | | | BOT | 1.5 | 0.34 | 0.25 | 4.48 | 0 | 0 | 0.02 | 0.01 | 0.01 | 0.04 |
| C2-A-2 | 10 lb | NR | NR | TOP | 1.2 | 0.3 | 0.55 | 4.07 | 0 | 0 | 0.02 | 0.02 | 0.01 | 0.04 |
| | | | | BOT | 1.2 | 0.32 | 0.55 | 3.85 | 0 | 0 | 0.02 | 0.01 | 0.01 | 0.04 |
| C2-B-2 | 10 lb | NR | NR | TOP | 1.2 | 0.29 | 0.54 | 4.14 | 0 | 0 | 0.02 | 0.01 | 0.01 | 0.04 |
| | | | | BOT | 1.2 | 0.28 | 0.55 | 4.28 | 0 | 0 | 0.02 | 0.01 | 0.01 | 0.04 |
| A1-1 | Haberny | 735 | 108 | TOP | 1.8 | 0.68 | 0.5 | 2.58 | 0 | 0 | 0.03 | 0.02 | 0.01 | 0.05 |
| | | | | BOT | 1.8 | 0.7 | 0.46 | 2.5 | 0 | 0 | 0.03 | 0.02 | 0.01 | 0.06 |
| A2-1 | 60 lb | 727 | 48 | TOP | 1.7 | 0.7 | 0.24 | 2.4 | 0 | 0 | 0.02 | 0.02 | 0.01 | 0.05 |
| | | | | BOT | 1.7 | 0.79 | 0.22 | 2.21 | 0 | 0 | 0.02 | 0.02 | 0.01 | 0.05 |
| A2-A-2 | 60 lb | NR | NR | TOP | 2 | 0.86 | 0.25 | 2.32 | 0 | 0 | 0.03 | 0.02 | 0.01 | 0.06 |
| | | | | BOT | 2 | 0.83 | 0.25 | 2.34 | 0 | 0 | 0.03 | 0.02 | 0.01 | 0.06 |
| A2-B-2 | 60 lb | NR | NR | TOP | 2 | 0.95 | 0.33 | 2.11 | 0 | 0 | 0.03 | 0.02 | 0.01 | 0.07 |
| | | | | BOT | 2 | 0.92 | 0.33 | 2.14 | 0 | 0 | 0.03 | 0.02 | 0.01 | 0.07 |
| A3-A-1 | 60 lb | 740 | 130 | TOP | 2.1 | 0.81 | 0.56 | 2.64 | 0 | 0 | 0.03 | 0.02 | 0.01 | 0.06 |
| | | | | BOT | 2.1 | 0.75 | 0.54 | 2.79 | 0 | 0 | 0.03 | 0.02 | 0.01 | 0.06 |
| A3-B-1 | 60 lb | NR | NR | TOP | 2.3 | 0.96 | 0.51 | 2.39 | 0 | 0 | 0.03 | 0.02 | 0.01 | 0.07 |
| | | | | BOT | 2.1 | 0.95 | 0.52 | 2.24 | 0 | 0 | 0.03 | 0.02 | 0.01 | 0.06 |
| A3-C-1 | 60 lb | NR | NR | TOP | 2.3 | 0.9 | 0.54 | 2.52 | 0 | 0 | 0.03 | 0.02 | 0.01 | 0.06 |
| | | | | BOT | 2.1 | 0.83 | 0.53 | 2.56 | 0 | 0 | 0.03 | 0.02 | 0.01 | 0.06 |
| A3-D-1 | 60 lb | NR | NR | TOP | 2.2 | 0.79 | 0.57 | 2.76 | 0 | 0 | 0.03 | 0.02 | 0.01 | 0.06 |
| | | | | BOT | 2.1 | 0.82 | 0.55 | 2.52 | 0 | 0 | 0.03 | 0.02 | 0.01 | 0.06 |
| A4-1 | 10 lb | 706 | 57 | TOP | 2.3 | 0.74 | 0.3 | 3.05 | 0 | 0 | 0.03 | 0.01 | 0.01 | 0.06 |
| | | | | BOT | 2.2 | 0.6 | 0.32 | 3.59 | 0 | 0 | 0.03 | 0.01 | 0.01 | 0.05 |
| A4-A-2 | 10 lb | NR | NR | TOP | 2.5 | 0.87 | 0.34 | 2.84 | 0 | 0 | 0.03 | 0.02 | 0.01 | 0.06 |
| | | | | BOT | 2.4 | 0.84 | 0.34 | 2.89 | 0 | 0 | 0.03 | 0.02 | 0.01 | 0.06 |
| A4-B-2 | 10 lb | NR | NR | TOP | 2.4 | 0.85 | 0.35 | 2.88 | 0 | 0 | 0.03 | 0.02 | 0.01 | 0.06 |
| | | | | BOT | 2.4 | 0.85 | 0.34 | 2.83 | 0 | 0 | 0.03 | 0.02 | 0.01 | 0.06 |
| A5-1 | 10 lb | 717 | 64 | TOP | 2.2 | 0.67 | 0.2 | 3.29 | 0 | 0 | 0.02 | 0.01 | 0.01 | 0.05 |
| | | | | BOT | 2.2 | 0.68 | 0.19 | 3.27 | 0 | 0 | 0.02 | 0.01 | 0.01 | 0.05 |
| A5-2 | 10 lb | NR | NR | TOP | 2.7 | 0.87 | 0.23 | 3.1 | 0 | 0 | 0.02 | 0.02 | 0.01 | 0.05 |
| | | | | BOT | 2.6 | 0.85 | 0.24 | 3.09 | 0 | 0 | 0.02 | 0.02 | 0.01 | 0.05 |
| A6-A-1 | 10 lb | 693 | 84 | TOP | 2.8 | 0.9 | 0.36 | 3.09 | 0 | 0 | 0.03 | 0.02 | 0.01 | 0.06 |
| | | | | BOT | 2.8 | 1 | 0.34 | 2.77 | 0 | 0 | 0.03 | 0.02 | 0.01 | 0.06 |
| A6-B-1 | 10 lb | NR | NR | TOP | 2.7 | 1.23 | 0.68 | 2.15 | 0 | 0 | 0.04 | 0.05 | 0.01 | 0.1 |
| | | | | BOT | 2.7 | 0.91 | 0.37 | 2.99 | 0 | 0 | 0.03 | 0.03 | 0.01 | 0.07 |
| A7-2 | 10 lb | NR | NR | TOP | 3.1 | 0.8 | 0.26 | 3.79 | 0 | 0 | 0.02 | 0.02 | 0.01 | 0.05 |
| | | | | BOT | 3 | 0.77 | 0.26 | 3.87 | 0 | 0 | 0.02 | 0.02 | 0.01 | 0.05 |
| A8-A-1 | 10 lb | 720 | NR | TOP | 3.3 | 0.61 | 0.3 | 5.37 | 0 | 0 | 0.02 | 0.01 | 0.01 | 0.05 |
| | | | | BOT | 3.8 | 0.99 | 0.24 | 3.81 | 0 | 0 | 0.03 | 0.02 | 0.01 | 0.07 |

TABLE 10-continued

| | | | | | | Alloying Study I Castings Chemistries | | | | | | | |
|---|---|---|---|---|---|---|---|---|---|---|---|---|---|
| | | $T_{Pour}$ | $T_{Mold}$ | | Composition (wt %) | | | | Trace (wt %) | | | | SUM |
| ID | Crucible | (° C.) | (° C.) | Position | Zn | Ca | Mn | Zn/Ca | Ni | Cu | Fe | Al | Si | Trace |
| A8- | 10 lb | NR | NR | TOP | 3.3 | 0.89 | 0.31 | 3.69 | 0 | 0 | 0.03 | 0.03 | 0.01 | 0.08 |
| B-1 | | | | BOT | 3.4 | 0.69 | 0.29 | 4.85 | 0 | 0 | 0.03 | 0.01 | 0.01 | 0.05 |

Compositional Analysis—Spark OS—Alloying Study II

The Spark OES measurements on melt disks and castings are found in Tables 11 and 12, respectively. Data has been refined to include an average of three tests. The ratio of Zn/Ca is presented for each measurement as well as the sum of the trace elements.

TABLE 11

| | | | | | Alloying Study II Melt Disc Chemistries | | | | |
|---|---|---|---|---|---|---|---|---|---|
| Alloy | Composition (wt %) | | | | Trace (wt %) | | | | Sum |
| ID | Zn | Ca | Mn | Zn/Ca | Ni | Cu | Fe | Al | Si | Trace |
| PD A | 2.05 | 1.45 | 0.617 | 1.41 | 0.001 | <0.001 | 0.024 | 0.020 | 0.006 | 0.052 |
| PD B | 2.00 | 1.05 | 0.795 | 1.90 | <0.001 | <0.001 | 0.018 | 0.014 | 0.004 | 0.038 |
| PD C | 2.16 | 1.04 | 0.525 | 2.08 | 0.002 | 0.002 | 0.021 | 0.016 | 0.006 | 0.047 |

TABLE 12

| | | | | | Alloying Study II Casting Chemistries | | | | |
|---|---|---|---|---|---|---|---|---|---|
| Alloy | Composition (wt %) | | | | Trace (wt %) | | | | Sum |
| ID | Zn | Ca | Mn | Zn/Ca | Ni | Cu | Fe | Al | Si | Trace |
| PD A - TOP | 1.92 | 1.480 | 0.736 | 1.30 | 0.001 | 0.001 | 0.025 | 0.022 | 0.005 | 0.054 |
| PD A - BOT | 2.14 | 1.600 | 0.723 | 1.34 | 0.001 | 0.001 | 0.025 | 0.023 | 0.006 | 0.056 |
| PD B - TOP | 1.99 | 1.120 | 0.941 | 1.78 | 0.001 | 0.001 | 0.020 | 0.017 | 0.004 | 0.043 |
| PD B - BOT | 1.91 | 1.090 | 0.933 | 1.75 | 0.001 | 0.001 | 0.019 | 0.017 | 0.004 | 0.042 |
| PD C - TOP | 1.88 | 0.915 | 0.586 | 2.05 | 0.001 | 0.001 | 0.012 | 0.016 | 0.004 | 0.034 |
| PD C - BOT | 1.90 | 0.963 | 0.593 | 1.97 | 0.001 | 0.001 | 0.012 | 0.018 | 0.005 | 0.037 |

Compositional Analysis—Inductively Plasma Optical Emission Spectrometry (ICP-OES)—Alloying Study III Composition data was collected via ICP-OES, which was performed by an external laboratory (e.g., Element Materials Technology). ICP-OES was completed on the final melt discs collected during casting.

The ICP-OES measurements on final melt disks during casting are found in Table 13. The ratio of Zn/Ca is presented for each measurement as well as the sum of the trace elements.

TABLE 13

| | | | | | Alloying Study III Melt Disc Compositions | | | | |
|---|---|---|---|---|---|---|---|---|---|
| | Composition (wt %) | | | | Trace (wt %) | | | | Sum |
| Alloy | Zn | Ca | Mn | Zn/Ca | Ni | Cu | Fe | Al | Si | Trace |
| 165-2 | 2.27 | 0.37 | 0.84 | 6.14 | <0.02 | <0.02 | 0.02 | <0.008 | <0.02 | <0.02 |
| 310-1 | 1.77 | 0.47 | 0.80 | 3.77 | <0.02 | <0.02 | 0.04 | <0.02 | <0.02 | <0.02 |
| 310-2 | 2.09 | 0.46 | 0.85 | 4.54 | <0.02 | <0.02 | 0.05 | <0.02 | <0.02 | <0.02 |
| 029-1 | 3.05 | 0.41 | 0.82 | 7.44 | <0.02 | <0.02 | 0.05 | <0.02 | <0.02 | <0.02 |

Example 2: Extrusion Studies

Alloying Study I Material Processing—Casting, Solution Treatment, Extrusion

Following casting, the materials underwent various processing trials to optimize their properties. A summary of the processing trials is presented in Table 14.

Several studies on solution treatment were carried out to integrate alloying elements into a solid solution state by reducing secondary phases. An effective solution treatment can result in a microstructure characterized by equiaxed grains and minimized secondary phases, which may be refined in size and evenly distributed during subsequent thermomechanical processing. The proper temperature for solution treatment varies based on the alloy's composition and generally requires exploration and optimization for each specific alloy. The samples were solution treated under the conditions specified in Table 14. Solutionizing was performed in a furnace (e.g., manufactured by Across International) under atmospheric conditions. Upon removing from the furnace, samples were cooled via force air cool (FAC) or water quench (WQ). Solution heat treatment was typically conducted before any extrusion for most trials and samples, with the exception of one trial (C2) where the heat treatment, as detailed in Table 14, was applied post-extrusion.

An extrusion limit trial was conducted on samples of castings A3-A-1, A3-B-1, and A3-C-1 (from Table 10) to develop a baseline extrudability diagram for the Mg—Zn—Ca—Mn alloys. The castings were solutionized at 500° C./6.5 h followed by forced air cooling (FAC). The cast material was then extruded at 325° C., 350° C., 375° C., and 400° C. (both container/die and billet temperature). Based on a resulting extrusion diameter of 0.38", the extrusion ratio (ER) is 9.2 for this test matrix. The breakthrough pressure (PBreak) and ram speed (vRAM) were calculated from pressure and displacement sensors attached to the extrusion rig and recorded at 4 Hz through the Omega software package. The extrusion speed (vex) is a product of the ram speed and extrusion ratio, converted into units of m/min for comparison with published literature on extruded magnesium alloys. Each sample was extruded under various pressures and ram speeds to produce an extrusion limit diagram, modeling extrusion speed against container/die temperature. The extruded material from this study underwent metallography.

SOL+Ext. Trial I: Based on initial solutionizing studies with A3, samples of castings A1 through A8 were solutionized either at 450° C./6.5 h with a forced air cool (FAC) or double solutionizing of 500° C./6.5 h/FAC+450° C./6.5 h/FAC. The A1-A8 billets were then extruded with a die/container and billet temperature of 350° C. These samples were compared with comparative alloys C1 and C2, heat treated as shown in Table 14. The C1 and C2 billets were extruded with a die/container and billet temperature of 345° C. and 400° C., respectively. The breakthrough pressure ($P_{Break}$) and ram speed ($v_{RAM}$) were recorded along with the resulting extrusion speed ($v_{ex}$). All billets were extruded into the 0.38" diameter die with an extrusion ratio (ER) of 9.2. The ram speed of the experiment was selected to target an extrusion speed<1 m/min. Two extrusions were performed for each casting. The extruded material from this study underwent metallography, tensile testing, and immersion corrosion testing.

SOL+Ext. Trial II: Samples of castings A2, A4 and A8 were solution heat treated at 320° C./8 h/WQ+430° C./16 h/WQ. See, e.g., Nie et al. as cited above. The billets were then extruded with a die/container and billet temperature of 350° C. The breakthrough pressure (PBreak) and ram speed (vRAM) were recorded along with the resulting extrusion speed (vex). All billets were extruded into the 0.38" diameter die with an extrusion ratio (ER) of 9.2. The ram speed of the experiment was selected to target an extrusion speed<1 m/min. Two extrusions were performed for each casting. The extruded material from this study underwent metallography, tensile testing, and immersion corrosion testing. For immersion corrosion testing samples for comparative alloys C1 and C2, produced in SOL+Ext. Trial I, were included for comparison.

TABLE 14

A summary of the processing trials conducted and the samples, processing conditions, and testing conducted on the RD alloys and comparative alloys.

| Trial | Alloys | Solution Heat Treat | Extrusion | Test Outputs |
|---|---|---|---|---|
| Initial Solution Treat | A3 | 460° C./6.5 h/FAC | No | Metallography |
| | | 500° C./6.5 h/FAC | No | |
| | | 530° C./6.5 h/FAC | No | |
| Extrusion Limit | A3 | 500° C./6.5 h/FAC | Yes | Extrusion Limit Diagram (extrusion settings), Metallography |
| SOL + Ext. Trial I | A1, A6 | 500° C./6.5 h/FAC + 450° C./6.5 h/FAC | Yes | Metallography, Tensile, and Immersion Corrosion |
| | A2-A5, A7, A8 | 450° C./6.5 h/FAC | | |
| | C1 | SOL + AGE SOL: 350° C./12 h + 450° C./8 h/FAC AGE: 250° C./30 min/FAC | | |
| | C2 | *After Ext.: 400° C./4 h/FAC + 200° C./2 h/FAC* | | |
| SOL + Ext. Trial II | A2, A4, A8 | 320° C./8 h/WQ + 430° C./16 h/WQ | Yes | Metallography, Tensile, and Immersion Corrosion |

SOL = Solution heat treat.
Ext. = Extrusion

Extrusion Limit Diagram—Alloying Study I

For alloying study I, the extrusion data collected in executing the extrusion limit test matrix is summarized in Table 15. The billet diameter (DBillet) and length (LBillet) are recorded along with the die/container and billet temperature (all the same). The resulting extrusion breakthrough pressure (PBreak) and ram speed (vRAM) are recorded along with a calculated resulting extrusion speed (vex).

TABLE 15

Extrusion parameters associated with the A3-A-1, A3-B-1, and A3-C-1 castings, solutionized 500° C./6.5 h with a forced air cool.

| Extrusion | Casting | $D_{Billet}$ (in) | $L_{Billet}$ (in) | T (° C.) | $P_{Break}$ (psi) | $V_{RAM}$ (ipm) | $V_{ex}$ (m/min) |
|---|---|---|---|---|---|---|---|
| 220721-1 | A3-A-1 | 1.028 | 1.95 | 350 | 807.0 | 3.22 | 0.75 |
| 220721-2 | A3-A-1 | 1.042 | 1.97 | 350 | 830.8 | 2.86 | 0.66 |
| 220722-1 | A3-A-1 | 1.040 | 1.96 | 400 | 569.1 | 4.64 | 1.08 |
| 220719-2 | A3-B-1 | 1.042 | 1.98 | 350 | 783.6 | 12.98 | 3.02 |
| 220720-1 | A3-B-1 | 1.034 | 1.94 | 350 | 874.5 | 9.07 | 2.11 |
| 220720-2 | A3-B-1 | 1.035 | 2.02 | 325 | 919.9 | 6.68 | 1.55 |
| 220718-1 | A3-C-1 | 1.038 | 1.99 | 325 | 964.3 | 2.50 | 0.58 |
| 220718-2 | A3-C-1 | 1.039 | 1.95 | 350 | 828.3 | 3.05 | 0.71 |
| 220719-1 | A3-C-1 | 1.053 | 2.01 | 375 | 715.8 | 4.12 | 0.96 |

Figure 8:
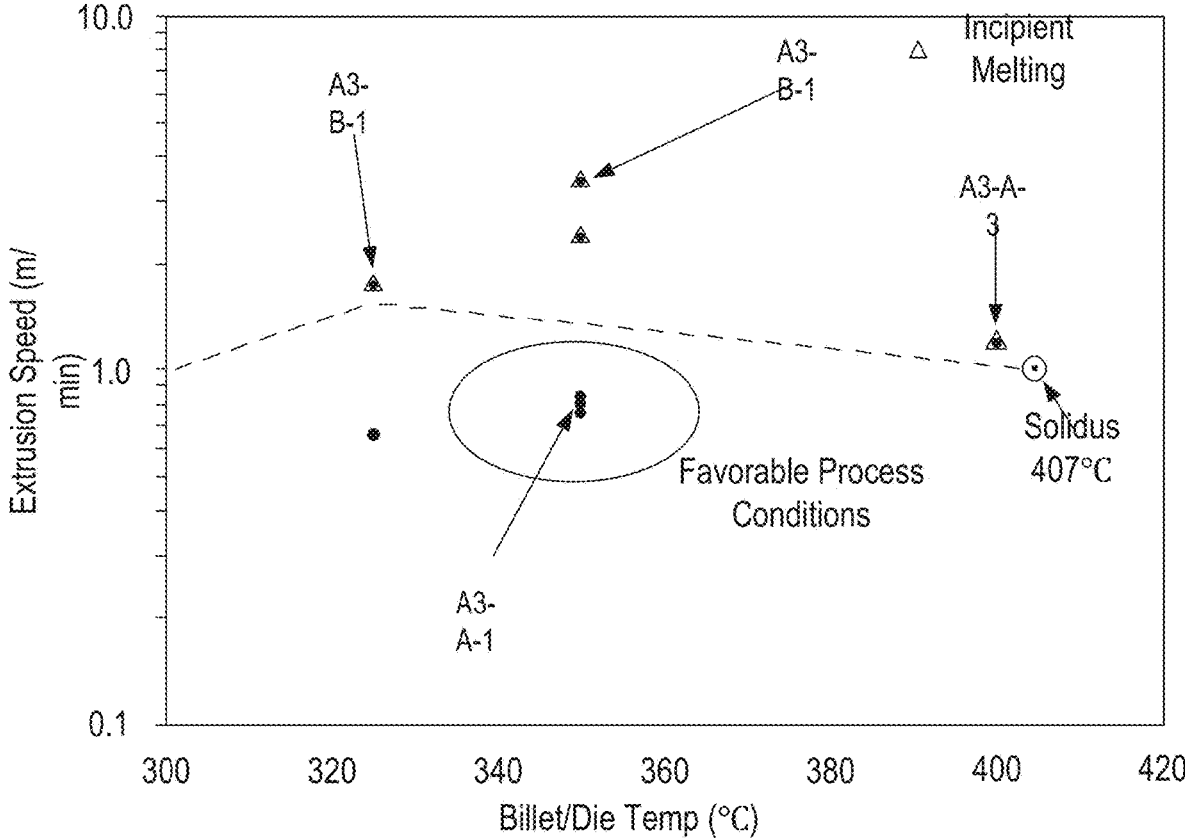
FIG. 8 shows an extrusion speed versus billet/die temperature graph with data points, according to an embodiment.

FIG. 8 shows the extrusion limit diagram associated with alloy A3 castings and estimated boundaries for incipient melting and press limitation. Images of the extrusions (with and without incipient melting) are superimposed on the diagram. The resulting extrusion speed ($v_{ex}$ in Table 16 is plotted against the billet temperature. Incipient melting of extrusions is noted with pictures and triangles. The solidus of alloy A3 is indicated as well as generally favorable processing conditions (i.e., generally, lower extrusion speed and lower breakout pressure to produce an extrusion with a shiny, smooth surface).

Solution Treatment & Extrusion—Trial 1

Figure 9:
FIG. 9 illustrates labeled cylindrical samples arranged with a ruler for scale, according to aspects of the present disclosure.

The extrusion conditions collected in executing Trial 1 are summarized in Table 16. These results fall under the generally favorable extrusion conditions as indicated by casting alloy A3 as shown in FIG. 8. The data summarized in Table 16 is from the samples selected for tensile testing and considered representative of the samples utilized for immersion corrosion testing. FIG. 9 shows representative extrusions for each alloy from SOL+Ext. Trial I.

TABLE 16

SOL + Ext. Trial I extrusion conditions.

| Extrusion | Alloy | Treatment | $D_{Billet}$ (in) | $L_{Billet}$ (in) | T (° C.) | $P_{Break}$ (psi) | $V_{RAM}$ (ipm) | $V_{EX}$ (m/min) |
|---|---|---|---|---|---|---|---|---|
| 220921-2 | C1-1 | SOL + AGE* | 1.056 | 2.00 | 350 | 764.5 | 1.79 | 0.42 |
| 220922-2 | C2-A-2 | As Cast | 1.041 | 2.02 | 400 | 605.9 | 1.57 | 0.36 |
| 220915-1 | A1-1 | 500° C./6.5 h/FAC + 450° C./6.5 h/FAC | 1.048 | 1.96 | 350 | 814.3 | 0.95 | 0.22 |
| 220915-2 | A2-A-2 | 450° C./6.5 h/FAC | 1.046 | 1.95 | 350 | 780.4 | 1.70 | 0.40 |
| 220919-1 | A3-D-1 | 450° C./6.5 h/FAC | 1.057 | 1.73 | 350 | 752.2 | 1.25 | 0.29 |
| 220919-2 | A4-A-2 | 450° C./6.5 h/FAC | 1.050 | 1.98 | 350 | 779.5 | 1.37 | 0.32 |
| 220916-1 | A5-2 | 450° C./6.5 h/FAC | 1.040 | 2.01 | 350 | 729.2 | 0.89 | 0.21 |
| 220920-1 | A6-A-1 | 500° C./6.5 h/FAC + 450 C./6.5 h/FAC | 1.053 | 1.97 | 350 | 796.9 | 1.16 | 0.27 |
| 220920-2 | A7-2 | 450° C./6.5 h/FAC | 1.054 | 2.06 | 350 | 764.9 | 1.55 | 0.37 |
| 220922-1 | A8-A-1-2 | 450° C./6.5 h/FAC | 1.050 | 1.99 | 350 | 778.6 | 1.30 | 0.30 |

*SOL + AGE = SOL: 350° C./12 h + 450° C./8 h/FAC AGE: 250° C./30 min/FAC

Alloying Study II—Process Development Run

The cast material then underwent several processing steps to produce feedstock that could be used to produce hardware for evaluation. A summary of the critical processing steps is presented in Table 17.

TABLE 17

A summary of the processing steps executed and testing conducted on material from Alloying Study II.

| Processing Step | Output | Description | Testing |
|---|---|---|---|
| Casting | PD A, B, & C 9.5" D × 30" Cast Billets | 3 compositions - see Table 11 | Spark OES |
| 1st Extrusion | PD A, B, & C Extrusions | Billet Soak: 350° C. overnight Extrusion Chamber Temp: 350° C. Ram Speed: 0.375 ipm Die: 1-port 3.5" D | N/A |
| Billet Cutting | PD A, B, & C 4" L Billets | Extrusions cut into 4" L billets for solution treatment and 2nd extrusion | N/A |
| Solution Treatment | PD A, B, & C SOL Billets | 430° C./24 hr/FAC | N/A |

TABLE 17-continued

A summary of the processing steps executed and testing
conducted on material from Alloying Study II.

| Processing Step | Output | Description | Testing |
|---|---|---|---|
| 2$^{nd}$ Ext. & Straightening | PD A, B, & C Round Exts & Flat Feedstock | Billet Preheat: 350 C. Extrusion Chamber Temp: 340° C. Ram Speed: 0.3-0.5 ipm Round Die: 4-port 0.27" D Flat Die: 1-port 1.58" W × 0.155" H | Tensile (flats - longitudinal to extrusion direction) |
| Centerless Grinding | PD A, B, C Round Feedstock | Ground to 0.1825" D | N/A |
| Plate Machining | PD A, B, & C Plates | Flat feedstock used to machine 4-hole plates | Immersion Corrosion |

SOL = Solution heat treat.
Ext. = Extrusion

Example 3: Thermal Properties

Alloying Study I Material Processing—Casting, Solution Treatment, Extrusion

Differential Scanning Calorimetry (DSC) testing was performed to determine the solidus temperature for each alloy, which is the temperature at which the alloy starts to melt. Below the solidus temperature, the metal remains completely solid. It is generally advantageous for the solutionizing temperature selected for each alloy to be below the solidus temperature to prevent melting. DSC tests were carried out under flowing argon. The samples were weighed and placed in a graphite-coated aluminum boat. The maximum temperature reached during sampling was typically 540° C., with a heating rate of 5° C./min employed. Experimental alloys A1-A6 & A8 along with comparative alloy C1 were tested in the as-cast condition.

Thermal Properties—DSC

Figure 10:
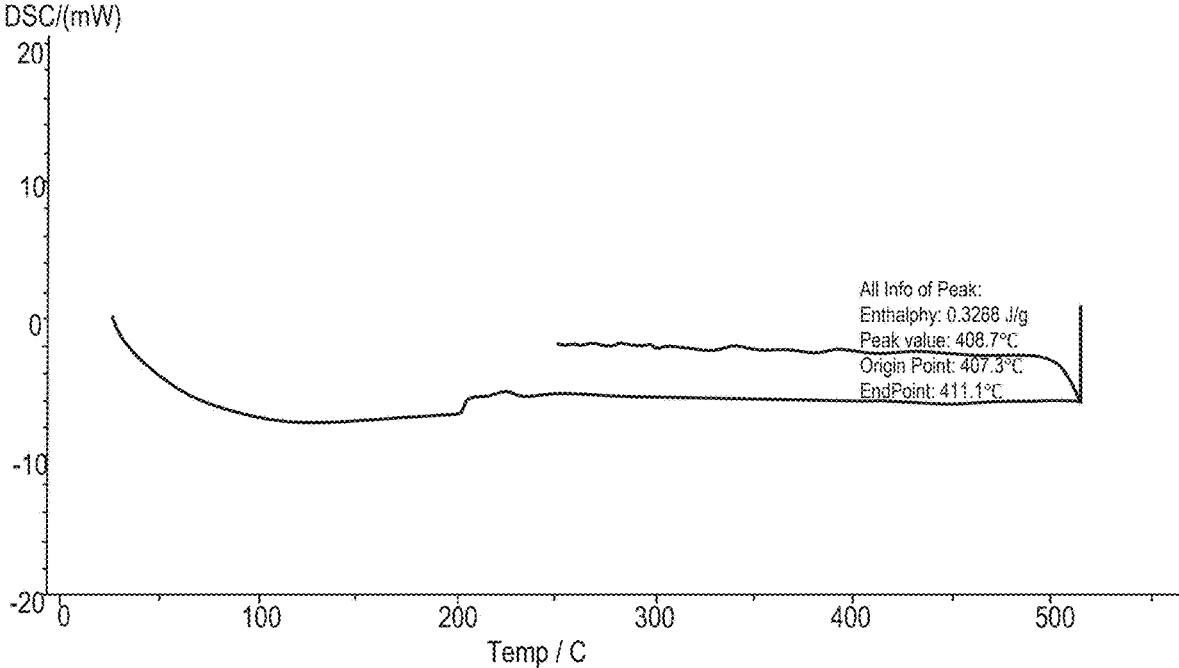
FIG. 10 depicts a Differential Scanning Calorimetry (DSC) graph showing thermal analysis results, according to an embodiment.

An example trace for DSC performed on sample A1-1 with a sample mass of 37.8 mg is shown in FIG. 10. There is a small but measurable peak at 407.3° C. corresponding to the solidus temperature of the alloy. DSC was also performed on other castings with the results summarized in Table 18. All DSC was performed on material extracted from near the top of the casting.

TABLE 18

DSC data for alloys A1-A6, A8, and C1.

| Casting | Crucible | $m_{Sample}$ (mg) | $T_{Max}$ (° C.) | $T_{Solidus}$ (° C.) |
|---|---|---|---|---|
| C1-1 | Coated Al | 38.8 | 560 | — |
| A1-1 | Coated Al | 31.4 | 540 | 407.7 |
| A1-1 | Coated Al | 37.8 | 500 | 407.3 |
| A2-1 | Coated Al | 36.6 | 540 | 407 |
| A3-C-1 | Coated Al | 29.7 | 540 | 406.9 |
| A3-C-1 | Coated Al | 39.4 | 540 | 406.9 |
| A4-1 | Graphite | 14.5 | 665 | 407.9 |
| A5-1 | Coated Al | 39 | 540 | 409 |
| A6-A-1 | Coated Al | 34 | 540 | 405.8 |
| A8-B-1 | Coated Al | 35.2 | 540 | 398.1 |

Example 4: Metallography

Metallography

For both alloying study I and alloying study II, samples were ground, polished, and imaged via light microscopy primarily in an unetched condition. A small number of samples were also etched (5% concentrated $HNO_3$/95% DI $H_2O$). Prepared samples were imaged in etched and unetched conditions to reveal various microstructural features. Metallography samples and their conditions (i.e., as-cast, solution treated, extruded) are summarized in Table 14 for alloying study I and Table 17 for alloying study II.

Metallography—As-Cast and Solution-Treated

Figure 11:
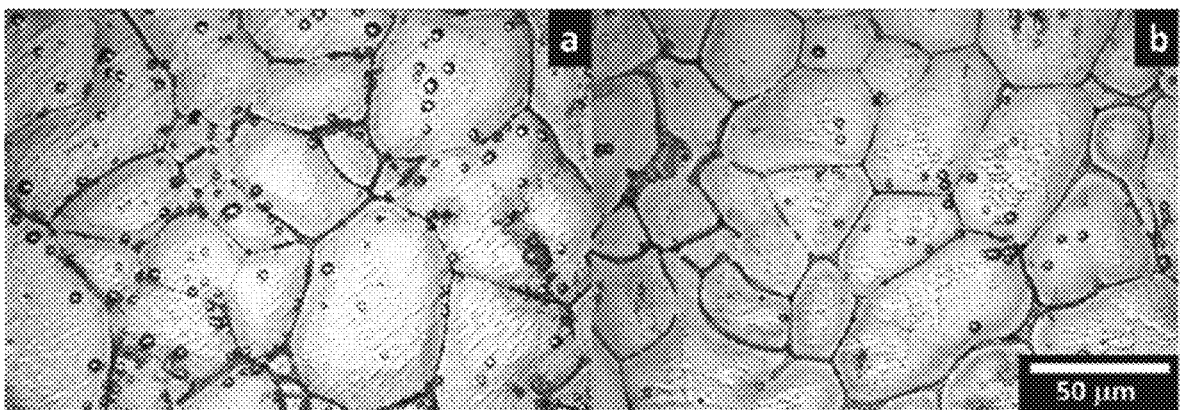
FIG. 11A and FIG. 11B show microscopic views of grain structure analysis, according to aspects of the present disclosure.

As-Cast: Portions from the bottom of the casting for A3-B-1 and A3-D-1 were extracted for microscopy in the as-cast, etched condition. The resulting images after polishing to 1 μm and etching with 5% concentrated HNO3/95% DI H2O by being contacted for 5 seconds with a swab saturated with etching solution are shown FIGS. 11A and 11B. The as-cast microstructure lacks dendritic features, indicative of a fast-cooling rate, and the microstructural features are similar between samples A3-B-1 and A3-D-1.

Figure 12:
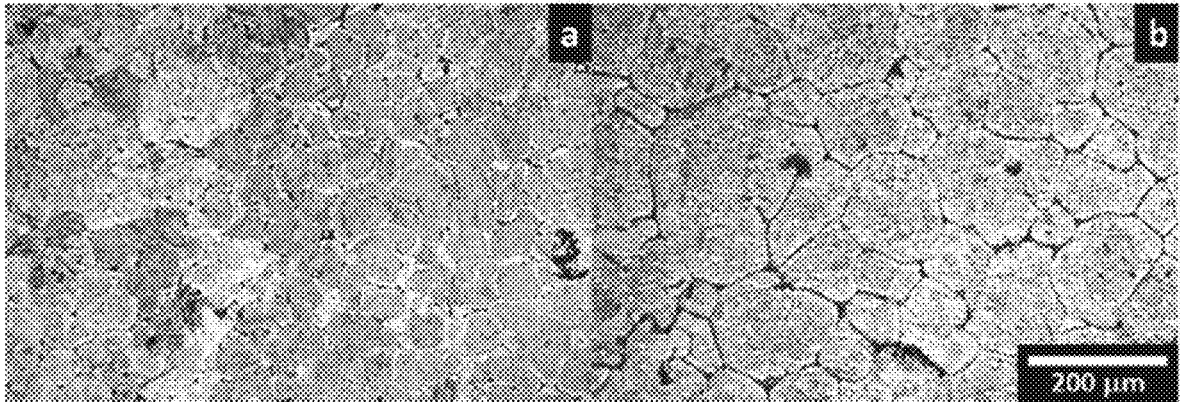
FIG. 12A and FIG. 12B illustrate scanning electron microscope micrographs of microstructural features, according to an embodiment.

Solutionized: Portions from the bottom of the casting for A3-B-1 and A3-D-1 were extracted for microscopy in the solutionized, etched condition. The resulting images after polishing to 1 μm and etching with 5% concentrated HNO3/95% DI H2O (v/v) by being contacted for 5 seconds with a swab saturated with etching solution are shown FIGS. 12A and 12B. Optical microscopy at 100× magnification of sample A3-B-1 solutionized under conditions of 460° C./6.5 h/FAC is shown in FIG. 12A. Optical microscopy at 100× magnification of sample A3-D-1 solutionized under conditions of 500° C./6.5 h/FAC is shown in FIG. 12B. Significant grain growth was observed with solutionizing at 500° C. for 6.5 h as shown in FIG. 12B. With etching, it was difficult to discern the intermetallic phases at the grain boundaries.

Figure 13:
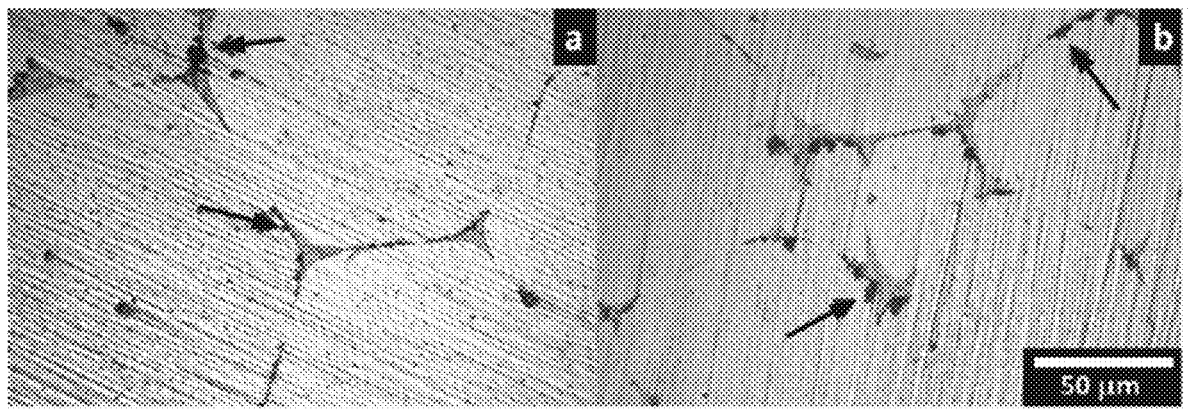
FIG. 13A and FIG. 13B depict metallographic micrographs highlighting intermetallic phases, according to aspects of the present disclosure.

Portions from the bottom of the casting for A3-D-1 were extracted for microscopy in the solutionized, unetched condition. Optical microscopy at 400× magnification of solutionized, unetched sample A3-D-1 under conditions of 500° C./6.5 h/FAC is shown in FIG. 13A. Optical microscopy at 400× magnification of solutionized, unetched sample A3-D-1 under conditions of 530° C./6.5 h/FAC is shown in FIG. 13B. The red arrows indicate porosity accompanying the intermetallic grain boundary phases.

Extrusion Limit Diagram

Figure 14:
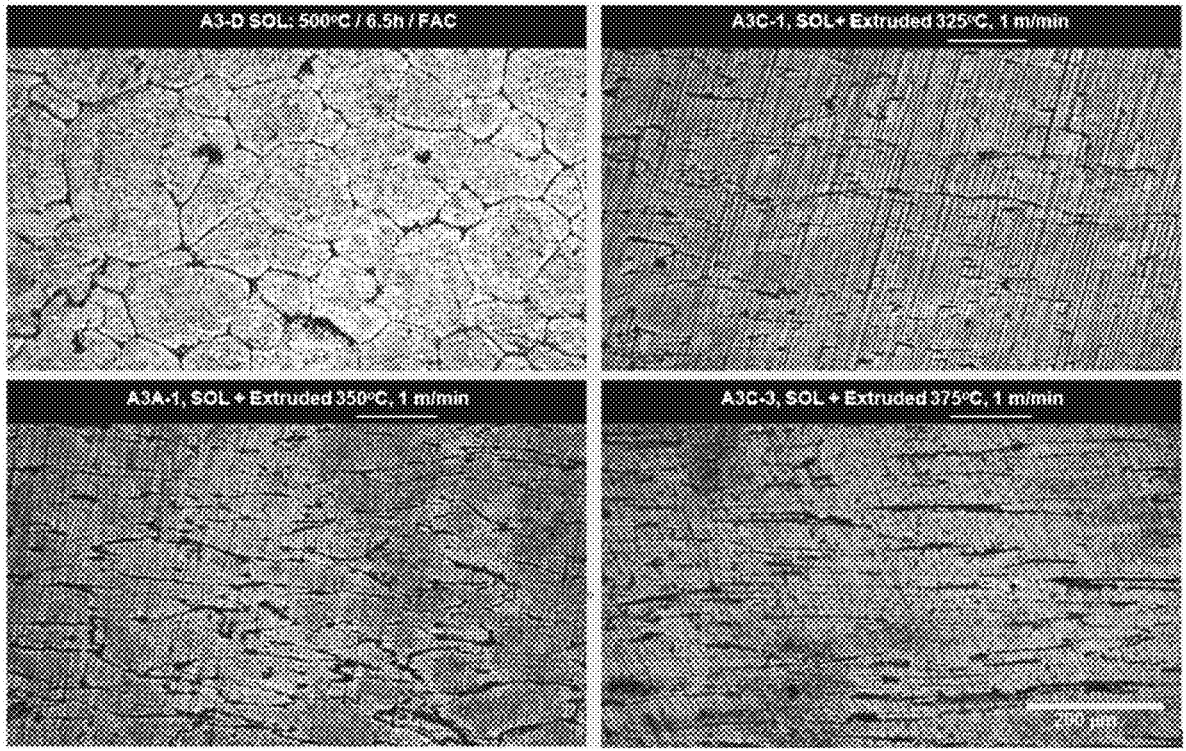
FIG. 14 shows metallographic micrographs comparing microstructures under various processing conditions, according to an embodiment.

Samples of the solutionized A3 extrusions lacking incipient melting were sectioned and polished for optical microscopy. FIG. 14 shows optical microscopy images at 100× Magnification displaying the microstructure of the solution heat-treated samples before and after extrusion across various temperatures. Optical images in FIG. 14 compare the solutionized microstructure with that extruded at three different temperatures (325° C., 350° C., and 375° C.). All three extrusions were processed near an extrusion speed ($v_{ex}$) of 1 m/min. All the images were etched after polish. A significant fraction of intermetallic stringers (elongated intermetallic phases or groups of phases) is observed at grain boundaries both after solutionizing and after extrusion.

6.5. Solution Treatment & Extrusion—Trial 1

Figure 15:
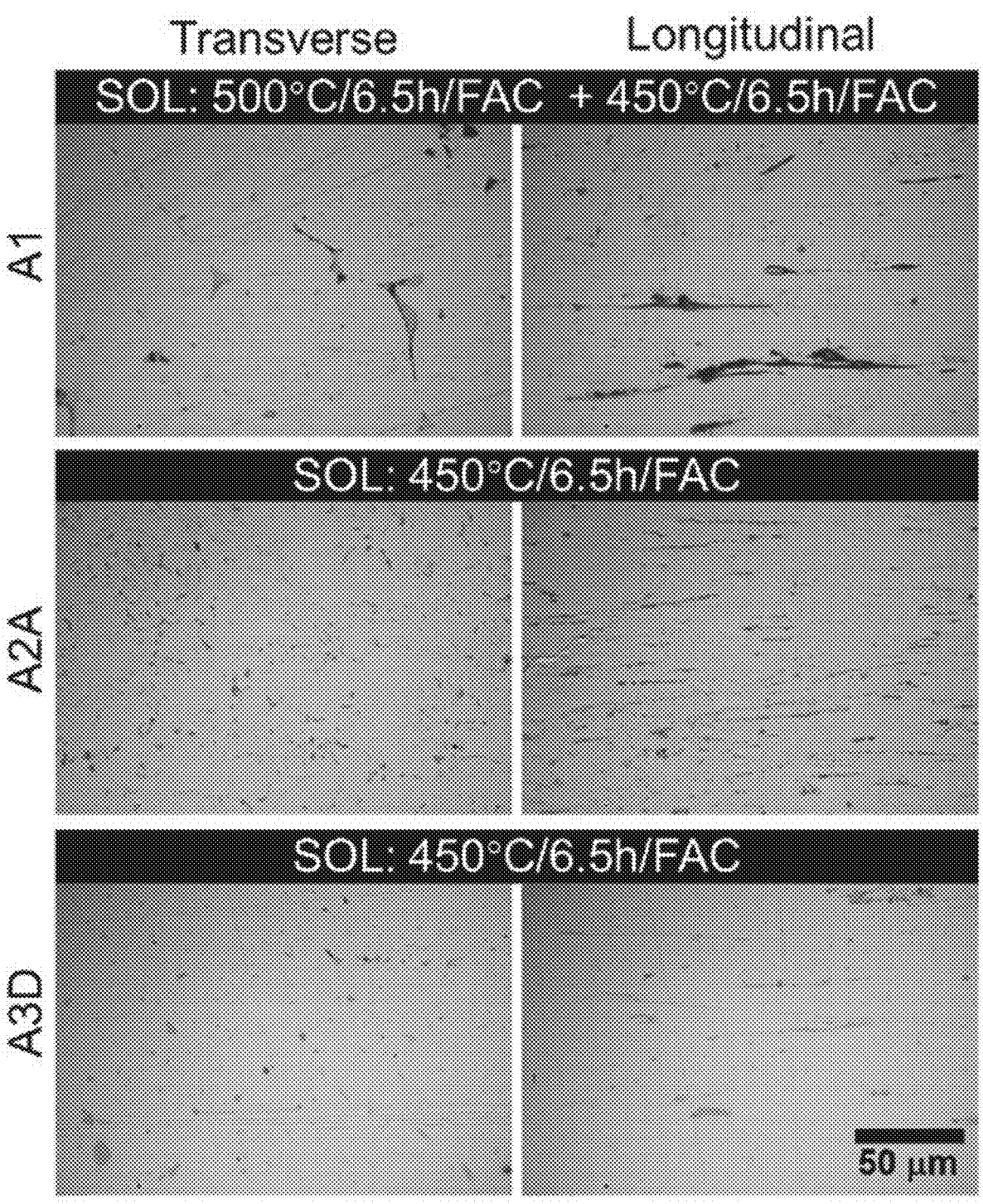
FIG. 15 illustrates metallographic micrographs comparing transverse and longitudinal microstructures of different samples, according to aspects of the present disclosure.

Metallographic preparation and microscopy have been completed on samples A1-A3 in the extruded condition from the solution treatment and extrusion trial I (e.g., SOL+EXT Trial I extrusion). Optical images at 400× magnification in the transverse (left) and longitudinal (right) extrusion directions of trial I samples A1, A2A, and A3D in the solution heat treated+extruded condition are shown in FIG. 15.

Solution Treatment & Extrusion—Trial 2 (Nie)

Figure 16:
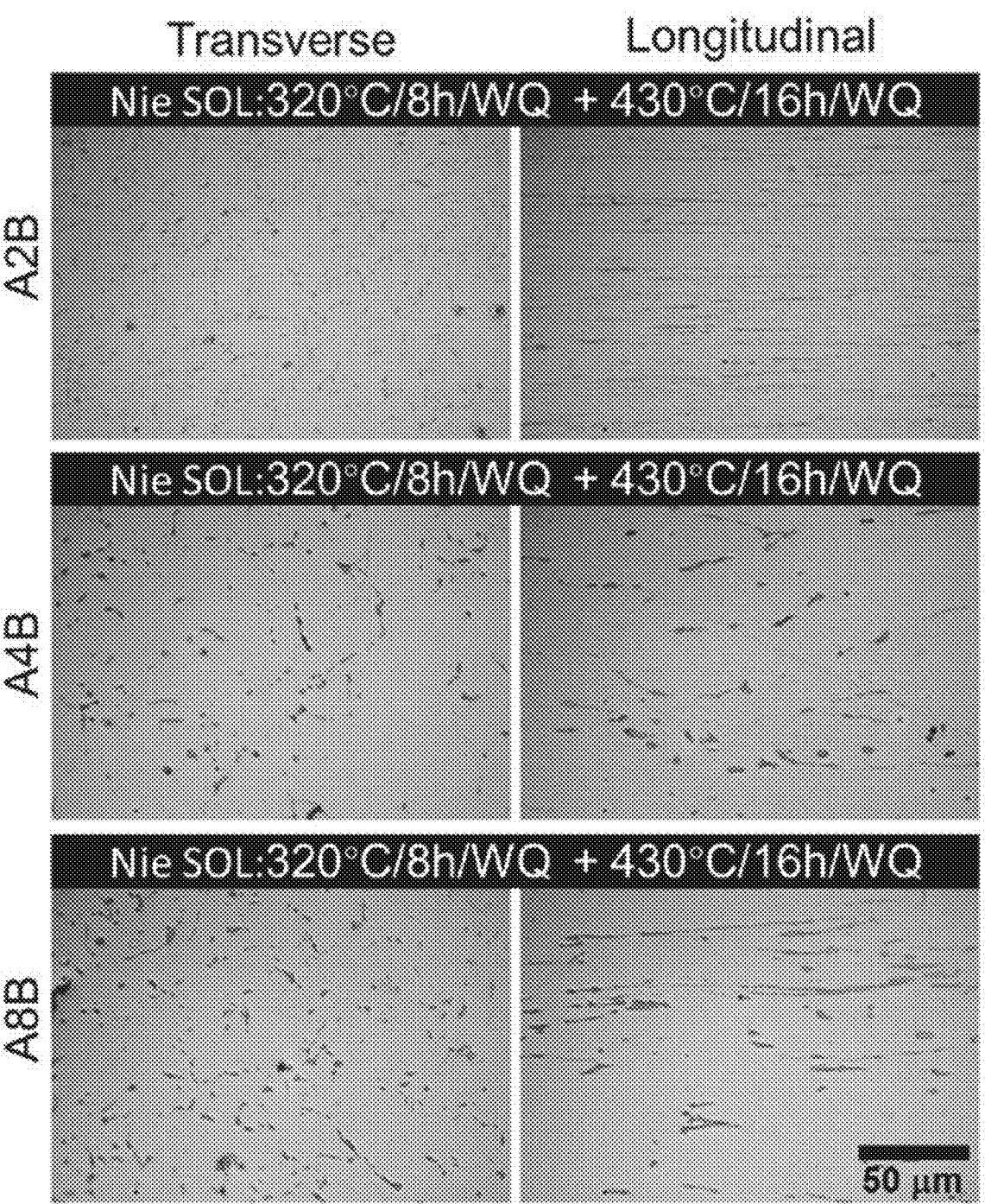
FIG. 16 depicts metallographic micrographs comparing microstructures of different samples after heat treatment, according to an embodiment.
Figure 17:
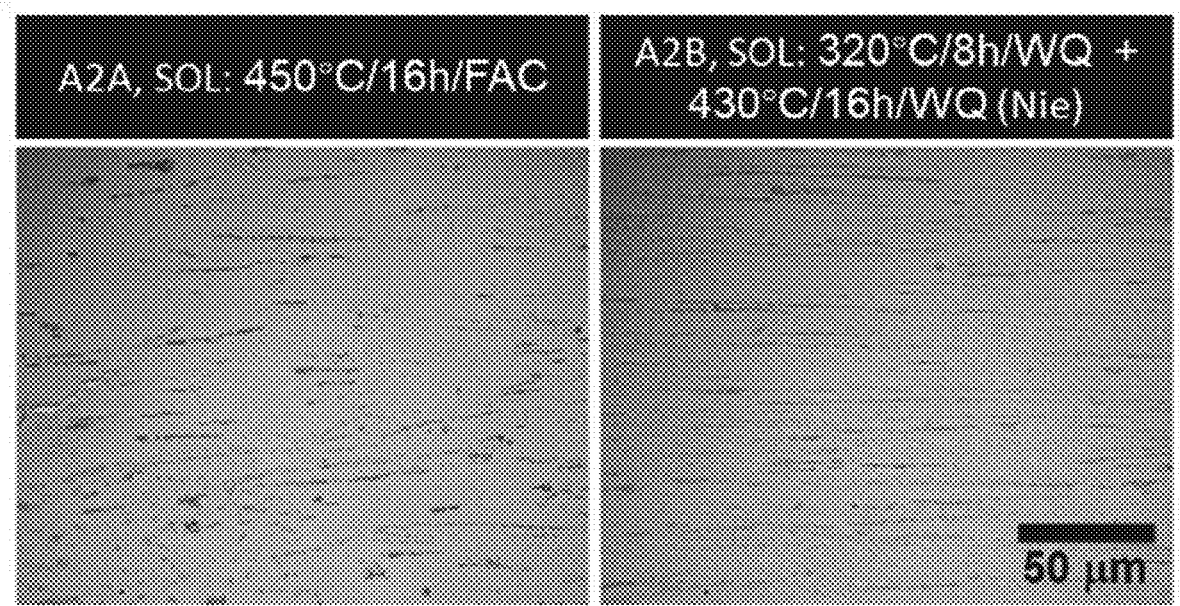
FIG. 17 shows metallographic micrographs comparing microstructures under different solution heat treatment parameters, according to aspects of the present disclosure.

Metallographic preparation and microscopy were completed on the Trial II samples in the solution heat treated then extruded condition. FIG. 16 shows optical images at 400× magnification in the transverse (left) and longitudinal (right) extrusion directions of Alloying Study I Trial II samples A2B, A4B and A8B in the solution heat treated+extruded condition. A comparison of the metallography of alloy A2 for Trial I and Trial II is shown in FIG. 17. FIG. 17 shows optical images at 400× magnification in the longitudinal extrusion directions of Alloying Study I Trial I sample A2A and Alloying Study I Trial II sample A2B in the solution heat treated+extruded condition.

Example 5: Mechanical Properties

Tensile Testing

For each sample that underwent tensile testing as shown in Table 14 for alloying study I, Table 17 for alloying study II, and Table 22 for alloying study III, 3 quasi-static, room temperature tension tests were performed according to ASTM E8. For example, in alloying study I, miniature tensile specimens having geometry 3 were used. For example, in alloying study II, custom sample dimensions of 0.160" gauge diameter were used. For example, in alloying study III, custom sample dimensions of 0.120" by 0.135" rectangular gauge were used. Tensile testing was performed (e.g., by a third-party testing laboratory (TTML)). As the machined tensile samples are approximately 3" in length, the extrusions were straightened (as needed) by tension or tensile pulling at room temperature for small strain prior to machining the tensile samples (e.g., at Terves Inc.). Tensile testing was conducted along the longitudinal direction of extruded feedstock.

Solution Treatment and Extrusion—Trial 1

The tensile properties of alloying study I trial I extrusions are presented in Table 19. Results indicate that properties are very similar to comparative alloy C1, which is known to be suitable for implant applications since it is on the market in Europe, and Grade 2 Titanium (ASTM F67) from which most current craniomaxillofacial hardware is made.

TABLE 19

| | Trial I Tensile Test Results. | | | |
|---|---|---|---|---|
| Alloy | Avg YS-0.2% (MPa) | Avg UTS (MPa) | Avg % Elong. (%) | Max % Elong. (%) |
| A1 | 292 | 310 | 7.2 | 12 |
| A2-A | 265 | 301 | 11.5 | 14 |
| A3-D | 292 | 317 | 9.7 | 14 |
| A4-A | 292 | 319 | 9.0 | 12 |
| A5 | 287 | 313 | 8.5 | 11 |
| A6-A | 286 | 311 | 8.5 | 12 |
| A7 | 261 | 298 | 11.3 | 14 |
| A8-A | 293 | 321 | 8.7 | 13 |
| C1 | 288 | 308 | 7.7 | 12 |

TABLE 19-continued

| | Trial I Tensile Test Results. | | | |
|---|---|---|---|---|
| Alloy | Avg YS-0.2% (MPa) | Avg UTS (MPa) | Avg % Elong. (%) | Max % Elong. (%) |
| C2-A | 132 | 245 | 24.3 | 26 |
| Grade 2 Ti | 275 | 345 | 20 | N/A |

The tensile properties of the Alloying Study I Trial II extrusions along with the tensile properties of Grade 2 Ti (ASTM F67) are presented in Table 20.

TABLE 20

| | Trial II tensile test results. | | | |
|---|---|---|---|---|
| Alloy | Avg YS-0.2% (MPa) | Avg UTS (MPa) | Avg % Elong. (%) | Max % Elong. (%) |
| A2 - Nie | 282 | 305 | 13.8 | 16 |
| A4 - Nie | 279 | 309 | 9.8 | 13 |
| A8 - Nie | 281 | 315 | 13.7 | 16 |
| Grade 2 Ti | 275 | 345 | 20 | N/A |

Alloying Study II—Process Development Run

The tensile properties of the Alloying Study II extrusions (PD C not tested) along with the tensile properties of Grade 2 Ti (ASTM F67) are presented in Table 21.

TABLE 21

| | Alloying Study II Tensile Test Results | | | |
|---|---|---|---|---|
| Alloy | Avg YS-0.2% (MPa) | Avg UTS (MPa) | Avg % Elong. (%) | Max % Elong. (%) |
| PD A | 231 | 272 | 13 | 14 |
| PD B | 259 | 299 | 15.7 | 16 |
| Grade 2 Ti | 275 | 345 | 20 | N/A |

Alloying Study III—Process Development Run

The tensile properties of the Alloying Study III extrusions are presented in Table 22. Only alloys 165-2 and 310-1 underwent tensile testing. Alloys 165-2 and 310-1 were tested in 3 processing conditions as indicated in the second column. Tensile test results for alloying study III indicate improvement in ductility for lower Ca alloys (165-2 and 310-1) compared to PD alloys. YS-0.2% refers to the 0.2% offset Yield Strength, which is a standardized way to determine the yield point of materials that do not have a clear or distinct yield point (like many metals, especially aluminum alloys). When a material doesn't have a sharp yield point on a stress-strain curve, engineers use an offset method to define it. The 0.2% offset yield strength is the stress at which a material shows 0.2% permanent strain (or elongation).

TABLE 22

| | | Alloying Study III Tensile Results | | | |
|---|---|---|---|---|---|
| Alloy | Solution Treatment and Extrusion | Avg YS-0.2% (MPa) | Avg UTS (MPa) | Avg % Elong. (%) | Max % Elong. (%) |
| 165-2 | 410 C./24 hr/AC; 325 C., ER 14 | 161 | 279 | 23 | 24 |
| | 410 C./24 hr/AC; 350 C., ER 14 | 149 | 247 | 28 | 30 |

TABLE 22-continued

| | | Avg | Avg | Avg % | Max % |
|---|---|---|---|---|---|
| Alloy | Solution Treatment and Extrusion | YS-0.2% (MPa) | UTS (MPa) | Elong. (%) | Elong. (%) |
| | | Alloying Study III Tensile Results | | | |
| | No Sol'n Treat; 325 C., ER 14 | 211 | 265 | 22 | 24 |
| 310-1 | 410 C./24 hr/AC; 325 C., ER 14 | 212 | 269 | 26 | 29 |
| | 410 C./24 hr/AC; 350 C., ER 14 | 146 | 249 | 28 | 30 |
| | No Sol'n Treat; 325 C., ER 14 | 210 | 262 | 18 | 20 |

Example 6: Corrosion And Absorption Behavior

Immersion Corrosion Testing

For alloying study I, extruded material was spun on a lathe and machined dry with a Dremel to create 0.25" diameter by 0.5" length corrosion samples for immersion corrosion testing. Prior to testing, samples were cleaned by immersing in a 5% nitric acid solution for 15 seconds, followed by a 5 second rinse in DI water, and a 5 second rinse in 70% alcohol. Once dry, each sample was weighed and measured to collect mass and length. Samples were immersed in DMEM in individual vials and placed in a $CO_2$ incubator (5% $CO_2$; 37° C.). Samples were weighed prior to immersion and at various time points to determine mass loss at each subsequent sample check. For each sample check, samples were removed from vials, rinsed, and dried prior to weighing. This bench-top test is an accelerated test to predict absorption performance by comparing in vitro corrosion rates of the experimental alloys to those of the comparative alloys with published in vivo data. Two immersion corrosion sample sets were tested. The first sample set included the samples from SOL+Ext. Trial I and the second sample set included the samples from SOL+Ext. Trial II (Nie samples), as indicated in Table 14.

Immersion Corrosion Testing

For alloying study II, immersion corrosion testing was completed on small cylindrical samples (0.25" diameter× 0.5" length) and machined plates (both sterilized and unsterilized). A summary of the samples subjected to immersion corrosion testing is included in Table 17. Prior to testing, samples were cleaned via nitric acid solution, 2% sodium hydroxide solution (10 minutes), or 1% Citranox solution (2 minutes).

Figure 85:
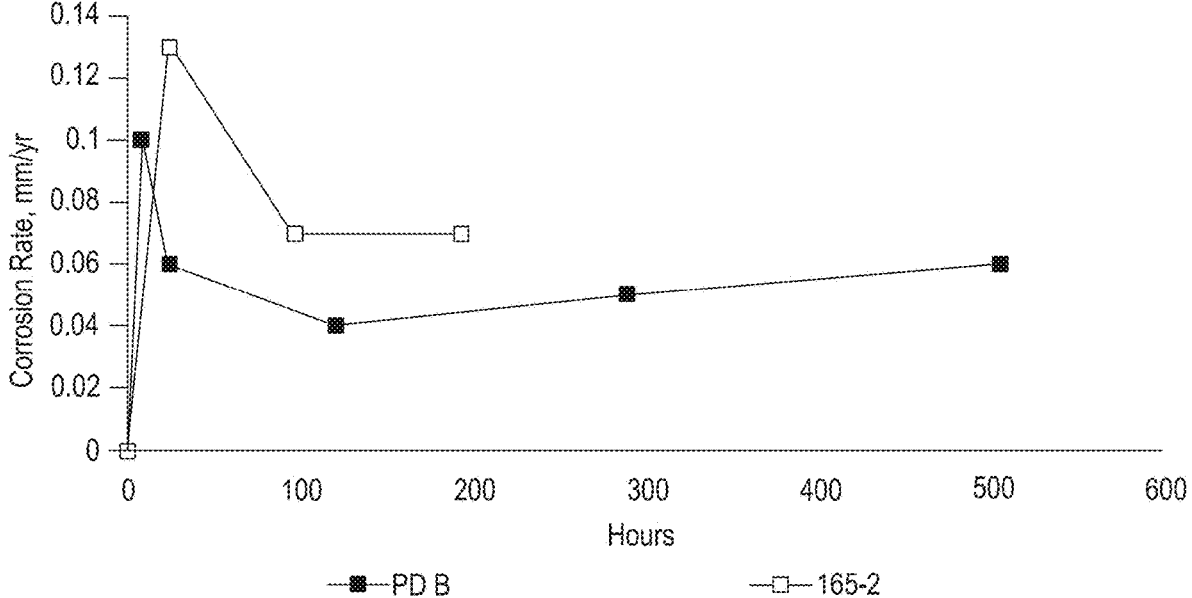
FIGS. 85-87 illustrate a graph of corrosion rate data plotted against time for multiple samples, according to an embodiment.
Figure 86:
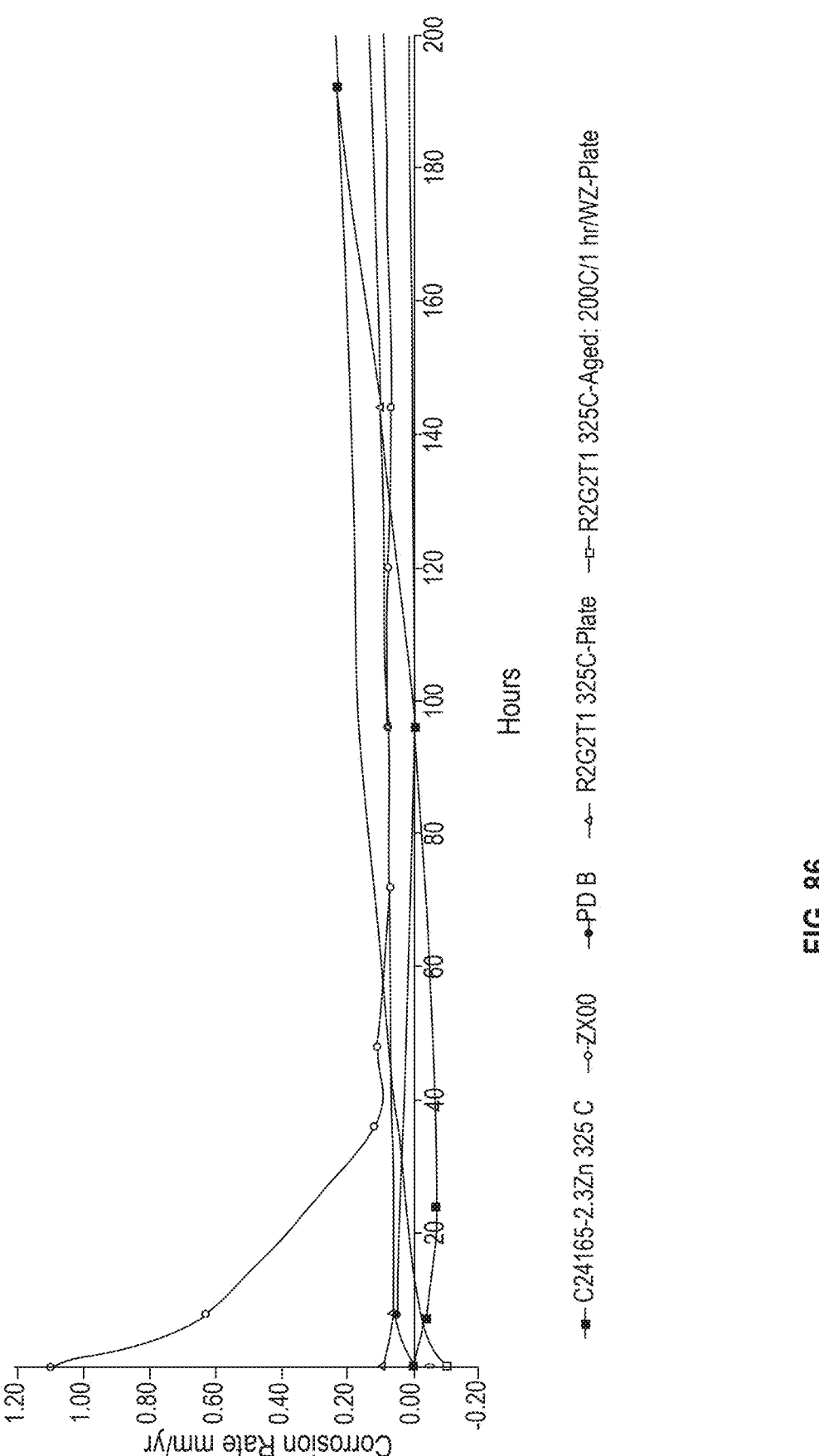
Figure 87:
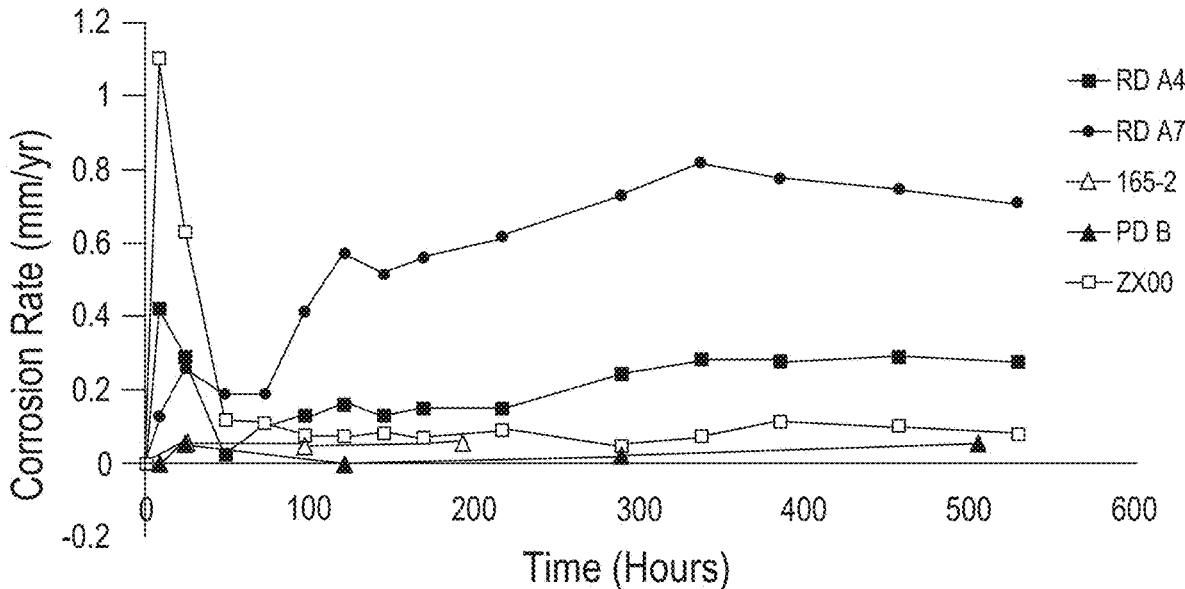

For alloying study III, immersion corrosion testing was completed on machined plates of alloy 165-2. Prior to testing, samples were cleaned via acetone soak for 5 minutes with ultrasonic. Once dry samples were cleaned via immersion in 1% Citranox solution followed by DI H2O rinse and 70% alcohol rinse. In Vitro Corrosion Rate data was not collected at 8 hours for 165-A. Testing of 165-A ended at 1 week. FIGS. 85-87 show corrosion for different samples.

Impact of Precipitate Phase Formation on Corrosion Performance

An in-depth analysis of the precipitate phases (intermetallic phases) in the first prototype (e.g., alpha prototype) alloys was conducted to establish specifications for optimizing the microstructure and controlling absorption performance.

Scanning Electron Microscopy

A subset of samples was imaged in the as-polished condition using a JEOL JSM-5600LV SEM in backscatter mode to visualize precipitate phases. The SEM samples and their conditions (e.g., solution-treatment, extrusion) are summarized in Table 23.

TABLE 23

A summary of the SEM samples and their conditions.

| Alloy | Composition Target | Composition Measured | Processing |
|---|---|---|---|
| RD A4 | Mg—2.5Zn—1Ca—0.4Mn | Mg—2.5Zn—0.9Ca—0.2Mn | ST (450° C./6.5 hr/FAC) |
| RD A7 | Mg—3Zn—1Ca—0.2Mn | Mg—3Zn—0.8Ca—0.3Mn | Extrusion (ER 9, Temp 350° C.) |
| PD B | Mg—2Zn—1Ca—1Mn | Mg—2Zn—1.1Ca—1Mn | 1st Extrusion (ER 7, Temp 350° C.) ST (430° C./24 hr/FAC) 2nd Extrusion (ER 30, Temp ~290° C.) |
| BioMg 250 | Mg—1.2Zn—0.5Ca—0.5Mn | Mg—1.2Zn—0.3Ca—0.6Mn | Extrusion (ER 9, Billet Temp 400° C., Die/Container Temp 350° C.) ST (400° C./4 hr/FAC + 200° C./2 hr/FAC) |

ST = Solution Treatment

Precipitate Phase Analysis

For each sample imaged using SEM (Table 23), precipitate phase analysis was performed utilizing ImageJ software. SEM images underwent thresholding, and phase characterization was performed to determine precipitate phase area fraction and precipitate phase length (microns). The analysis did not differentiate between $Mg_2Ca$ or ternary phase precipitates.

Solution Treatment and Extrusion—Trial 1

Figure 18:
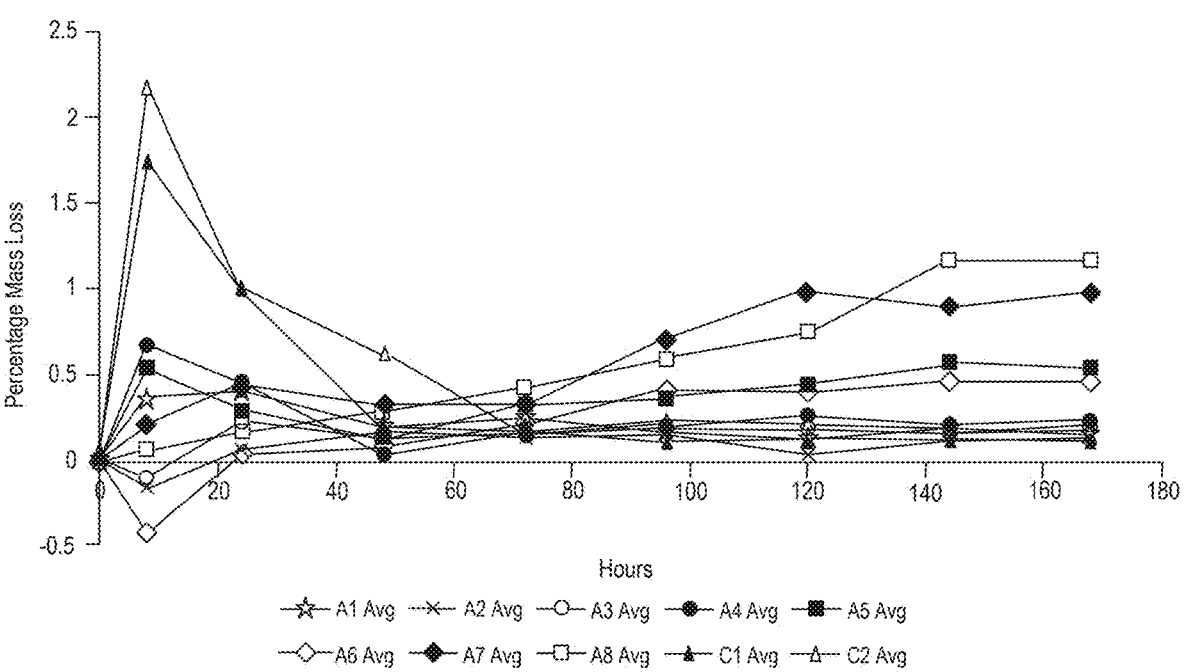
FIG. 18 illustrates a graph of corrosion/mass loss data over time for multiple alloy samples, according to an embodiment.
Figure 19:
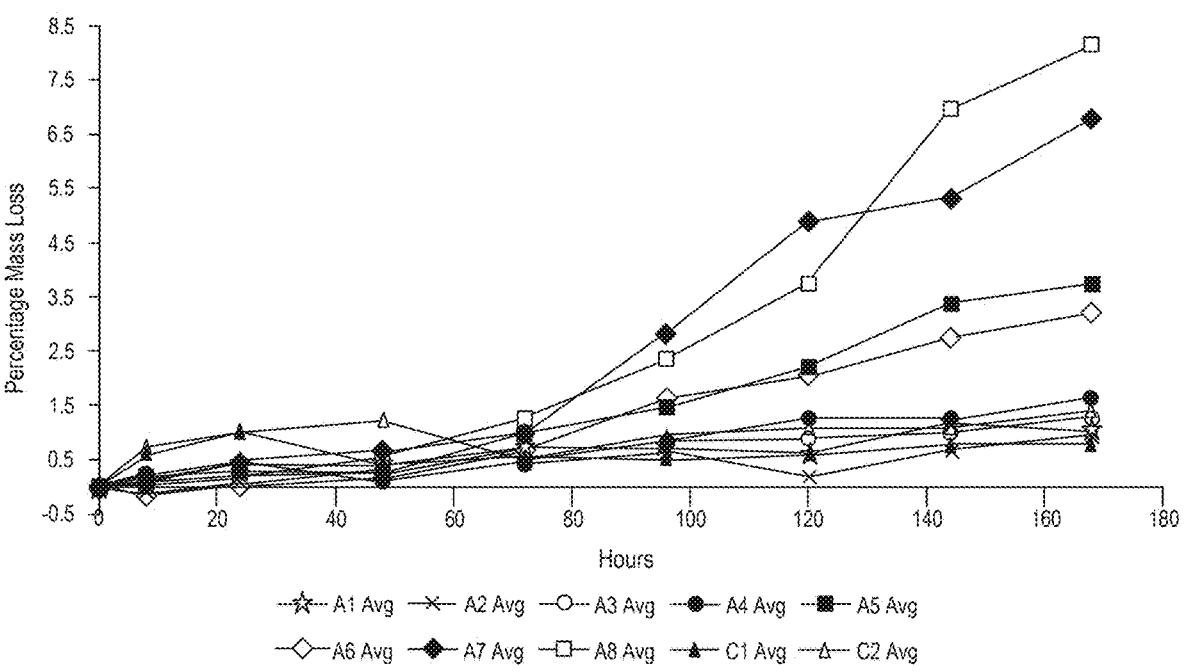
FIG. 19 depicts a graph of absorption/corrosion data over time for multiple alloy samples, according to aspects of the present disclosure.
Figure 20:
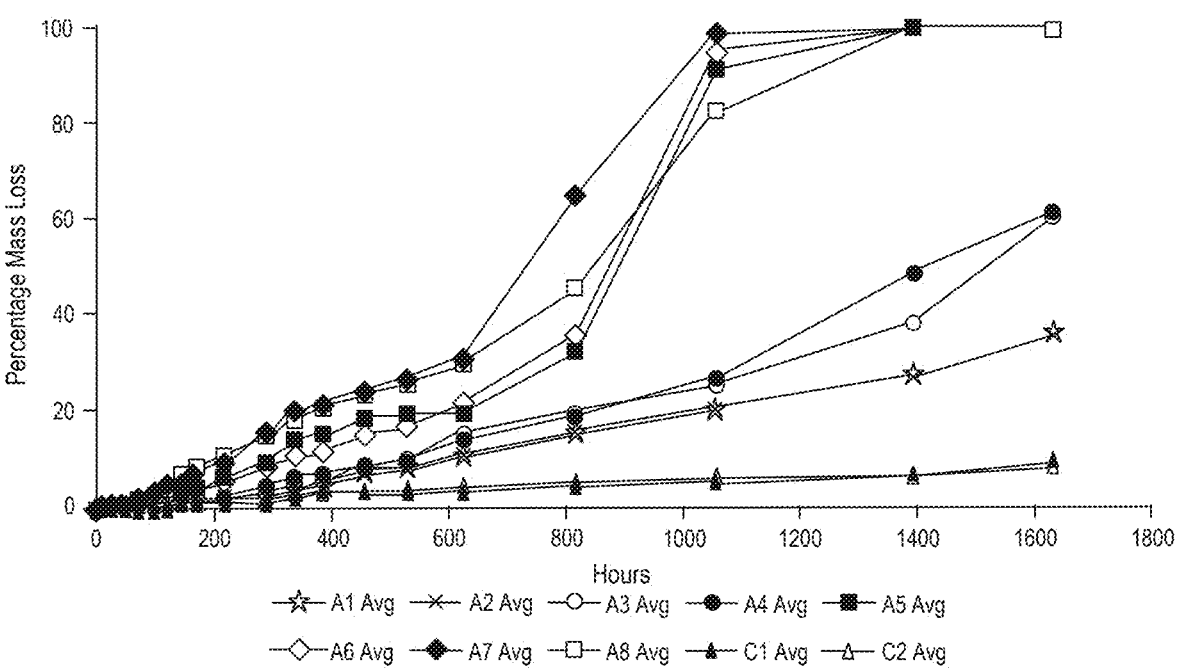
FIG. 20 shows a graph of absorption/mass loss data over time for multiple alloy variants, according to an embodiment.

The immersion corrosion results for the Trial I extrusions are presented as a percentage of mass lost per day (total mass loss divided by total number of days) in FIG. 18, total percentage mass lost in FIG. 19 (first 7 days) and FIG. 20 (full test length).

Figure 21A:
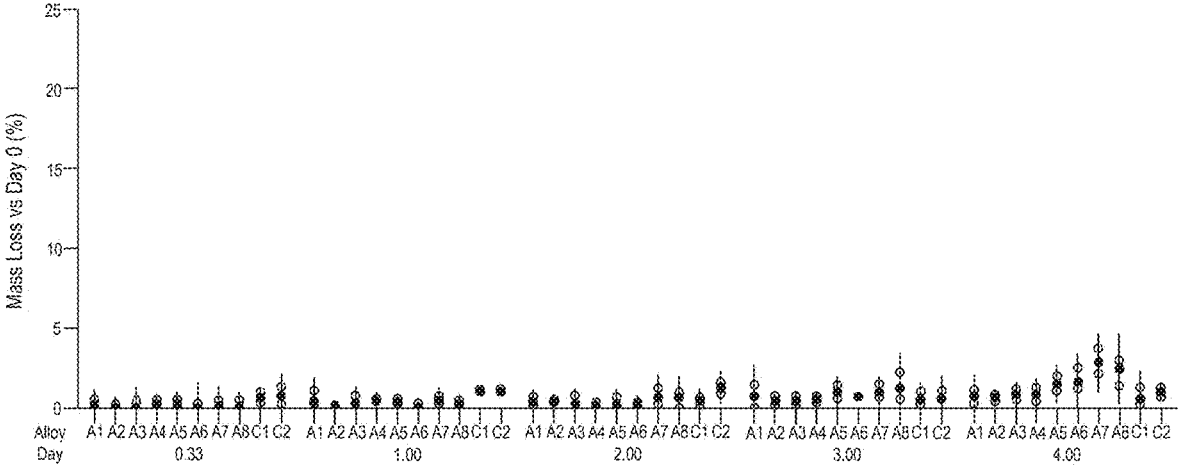
FIGS. 21A and 21B illustrate a time series plot of data points with error bars, according to aspects of the present disclosure.
Figure 21B:
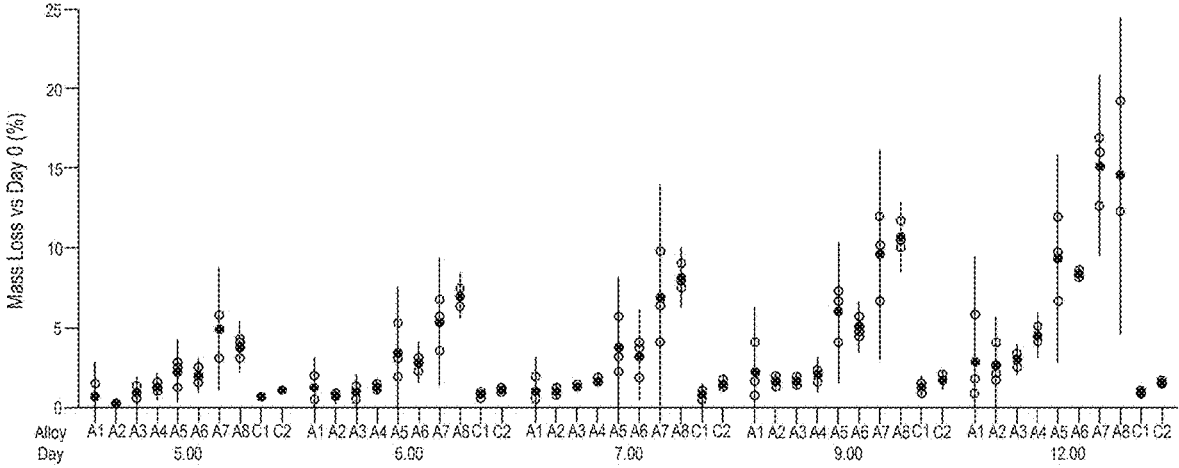
Figure 22A:
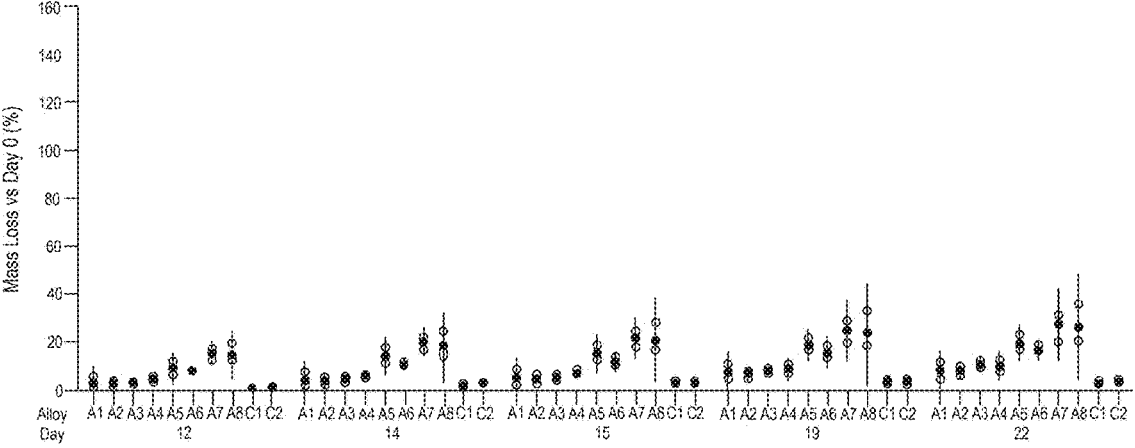
FIGS. 22A and 22B depict a time series plot with data points connected by lines, according to an embodiment.
Figure 22B:
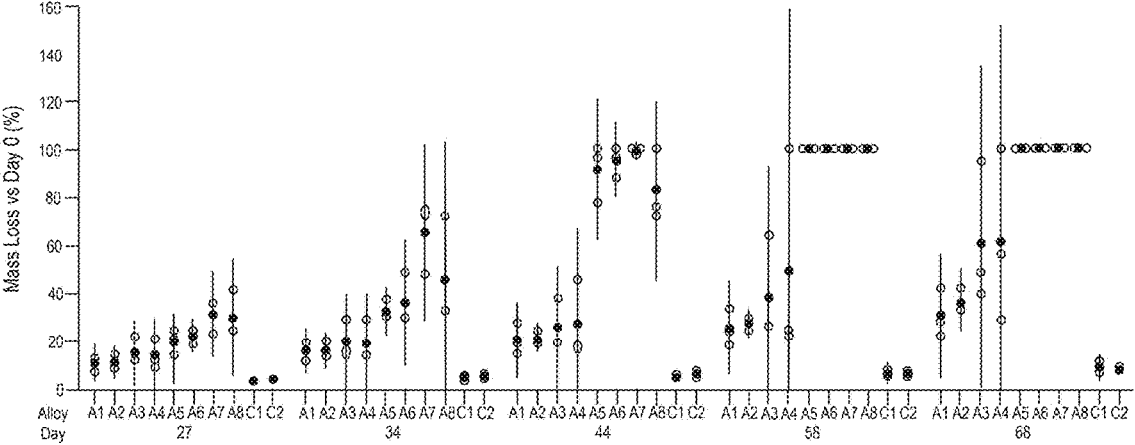
Figure 23A:
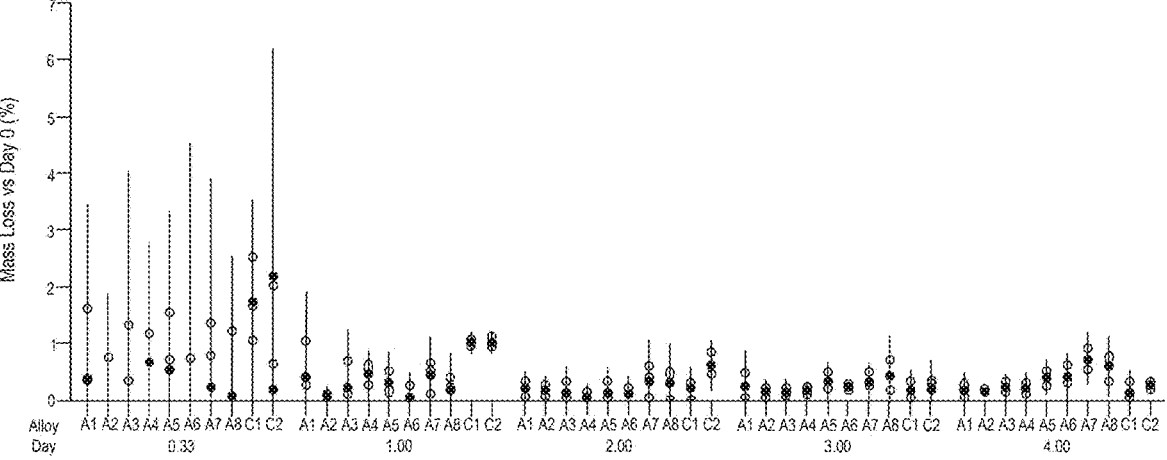
FIGS. 23A and 23B show a scatter plot of corrosion or degradation rate data over time, according to aspects of the present disclosure.
Figure 23B:
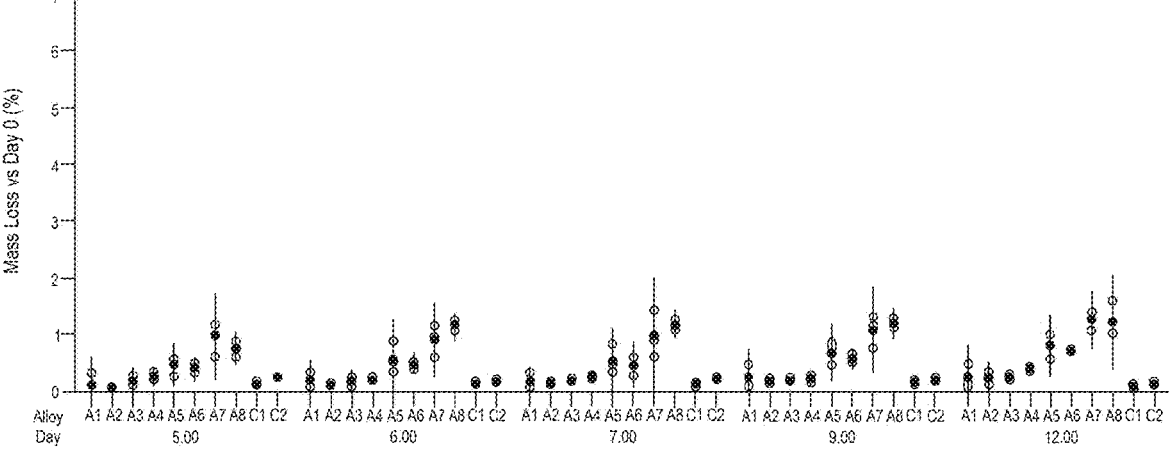
Figure 24A:
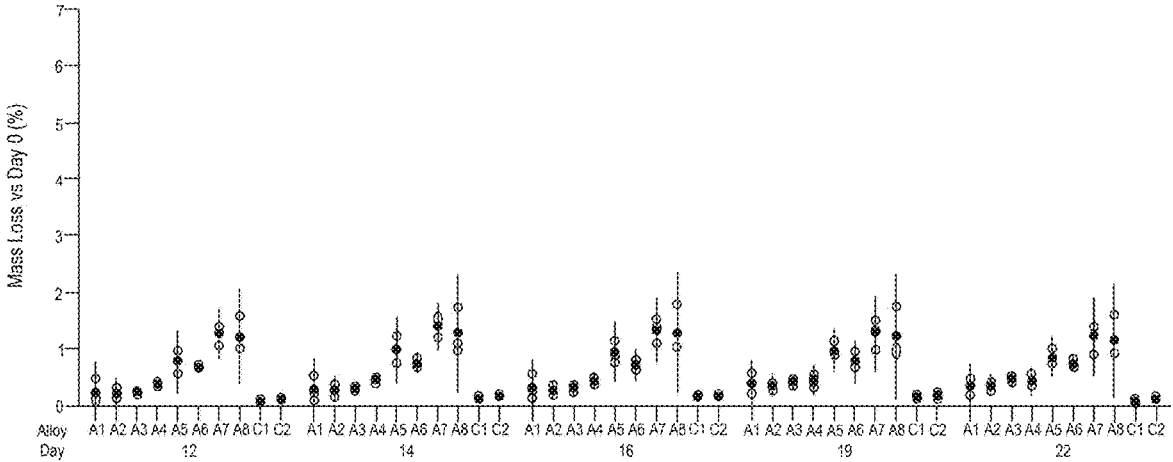
FIGS. 24A and 24B illustrate a graph of corrosion or degradation data plotted over time, according to an embodiment.
Figure 24B:
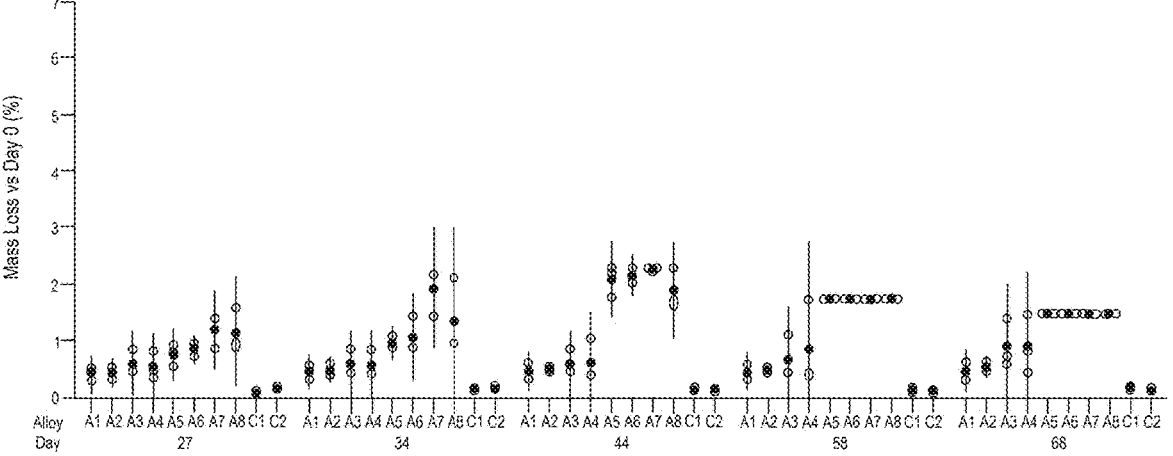
Figure 25A:
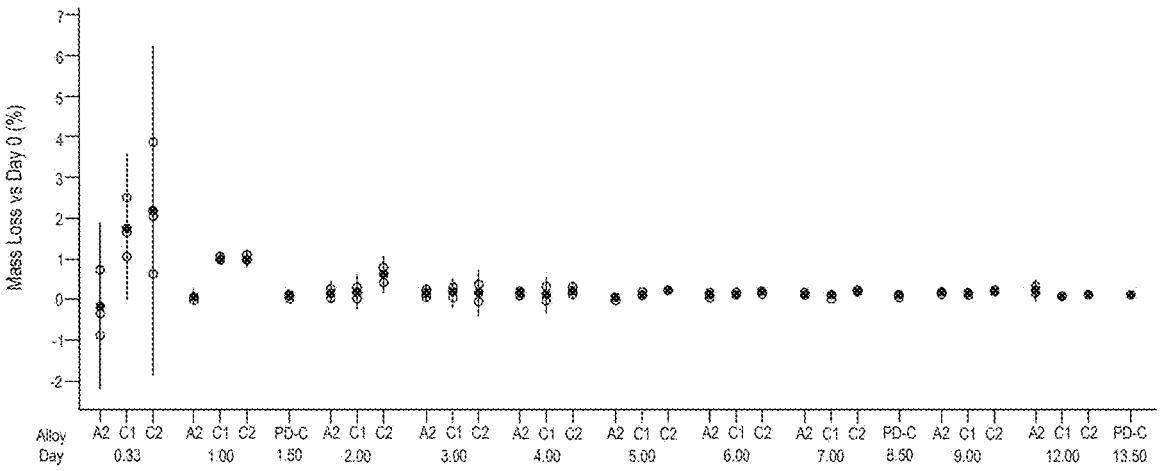
FIGS. 25A and 25B depict a scatter plot of data points over time, according to aspects of the present disclosure.
Figure 25B:
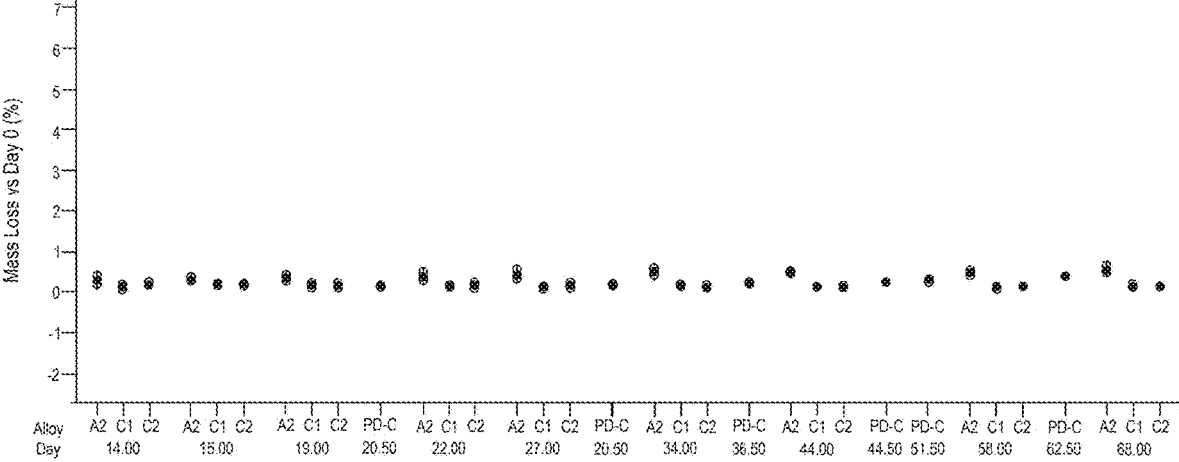

To further analyze the deviation amongst sample groups, the immersion corrosion results for the Alloying Study I Trial I extrusions were plotted in Minitab. The full matrix of alloys (Alloying Study I, Trial I A1-A8, C1, C2) are shown in FIGS. 21-25. FIGS. 21A and 21B show Alloying Study I, Trial I Individual Value Plot of the immersion corrosion results for days 0.33 (8 hours), 1-7, 9, 12 in total percentage mass loss versus test length (days). FIGS. 22A and 22B show Alloying Study I, Trial I Individual Value Plot of the immersion corrosion results for days 12, 14, 16, 19, 22, 27, 34, 44, 58, 68 in total percentage mass loss versus test length (days). FIGS. 23A and 23B show Alloying Study I, Trial I Individual Value Plot of the immersion corrosion results for days 0.33 (8 hours), 1-7, 9, 12 in percentage mass loss per day versus test length (days). FIGS. 24A and 24B show Alloying Study I, Trial I Individual Value Plot of the immersion corrosion results for days 12, 14, 16, 19, 22, 27, 34, 44, 58, 68 in percentage mass loss per day versus test length (days). FIGS. 25A and 25B show Alloying Study I, Impact of Precipitate Phase Formation on Corrosion Performance The precipitate phase data is presented with in vitro corrosion rates through 3 weeks in Table 24.

TABLE 24

| | | | Max | Corrosion Rate | | | |
|---|---|---|---|---|---|---|---|
| Alloy | Composition | % Area Precipitates | Precipitate Length (μm) | 8 hrs | 24 hrs | 168 hrs | 504 hrs |
| RD A4 | Mg—2.5Zn—1Ca—0.4Mn | 2.9 | 140 | 0.42 | 0.29 | 0.15 | 0.28 |
| RD A7 | Mg—3Zn—1Ca—0.2Mn | 4.2 | 172 | 0.13 | 0.26 | 0.56 | 0.71 |
| PD B | Mg—2Zn—1Ca—1Mn | 1.2 | 19 | 0 | 0.05 | 0.03 | 0.05 |
| 165-A | Mg—3.1Zn—0.5Ca—0.8Mn | 5.4 | 2.1 | — | 0.06 | 0.06 | — |
| BioMg 250 | Mg—1.2Zn—0.5Ca—0.5Mn | 0.3 | 14 | 1.39 | 0.63 | 0.13 | 0.09 |

Precipitate phase data for RD A4, RD A7, PD B, 165-A and BioMg 250.

Trial I Individual Value Plot of the immersion corrosion results for A2, C1, and C2 in percentage mass loss per day versus test length (days).

Figure 26:
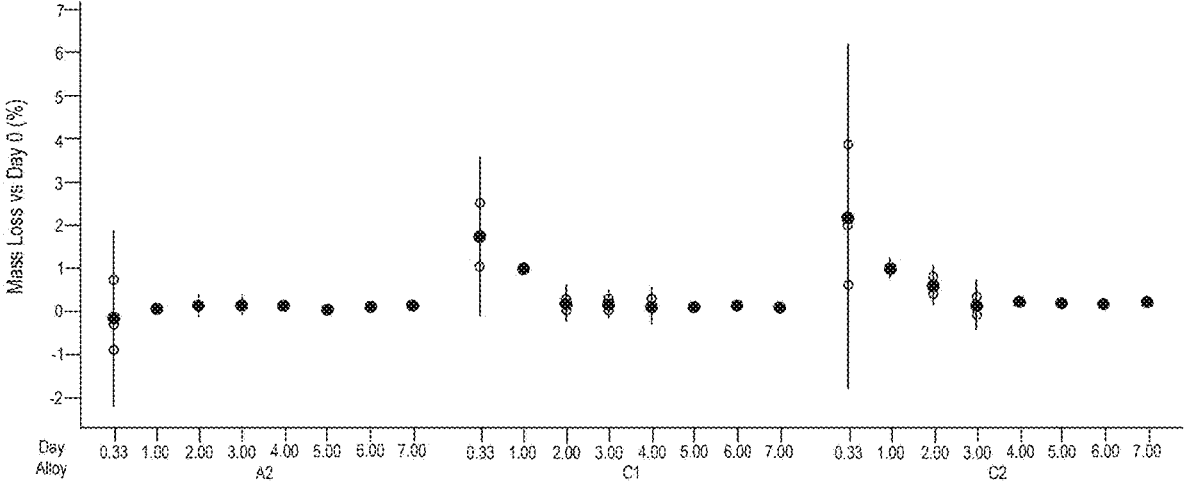
FIG. 26 shows a graph of mass loss data plotted over time for different alloy compositions, according to an embodiment.
Figure 27:
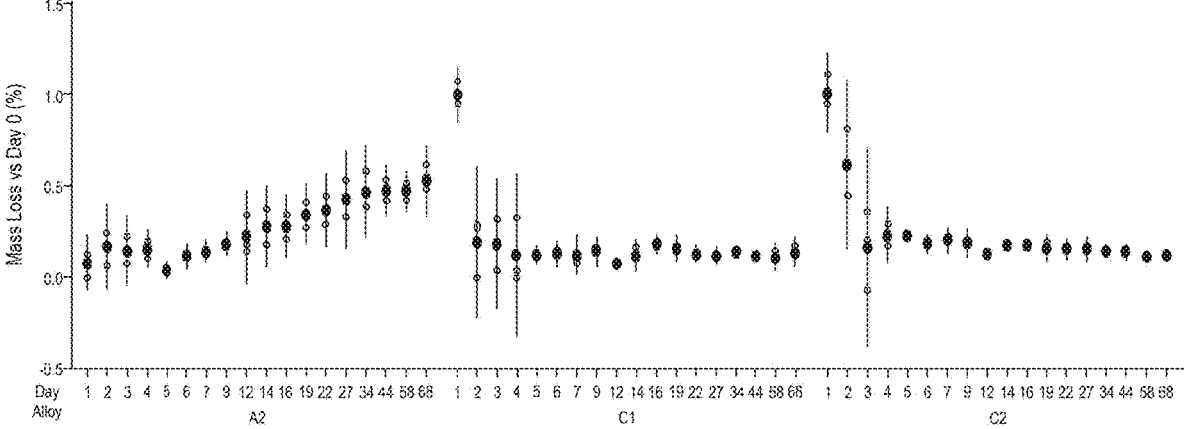
FIG. 27 illustrates a graph of corrosion/absorption data plotted over time with distinct phases, according to aspects of the present disclosure.

A subset of A2 (equivalent composition to PD C), C1, and C2 is presented as a percentage of mass lost per day (total mass loss divided by total number of days) versus test length (days) in FIG. 26 (first 7 days) and FIG. 27 (full test length excluding the 8-hour check).

Figure 28:
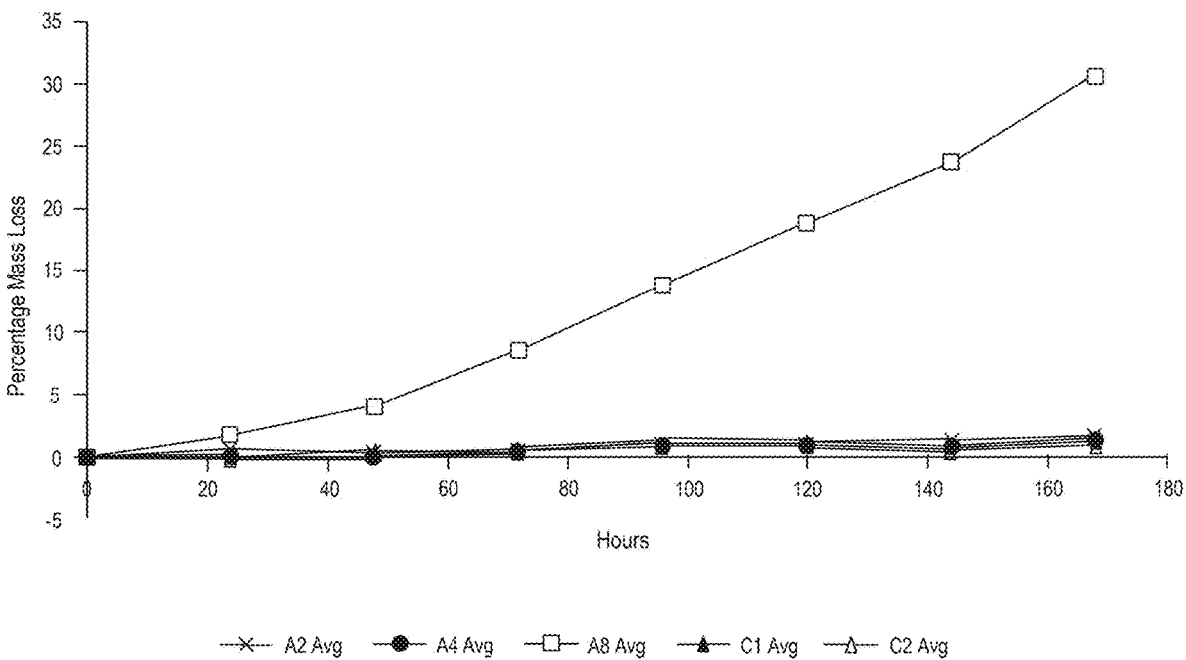
FIG. 28 depicts a graph of corrosion test results comparing different alloy samples over time, according to an embodiment.
Figure 29:
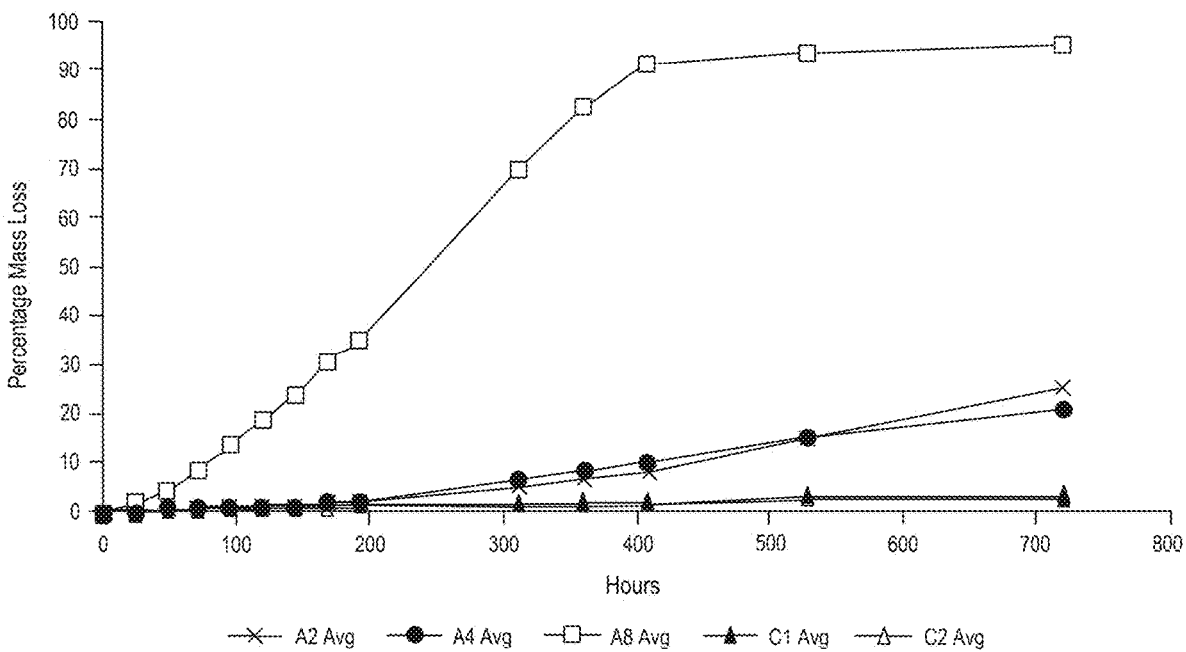
FIG. 29 shows a graph of absorption/mass loss data over time for several alloy compositions, according to aspects of the present disclosure.

The immersion corrosion results for the Allowing Study I Trial II extrusions are presented as a total percentage of mass lost versus test length (hours) in FIGS. 28 (first 7 days) and 29 (full test length).

Figure 30:
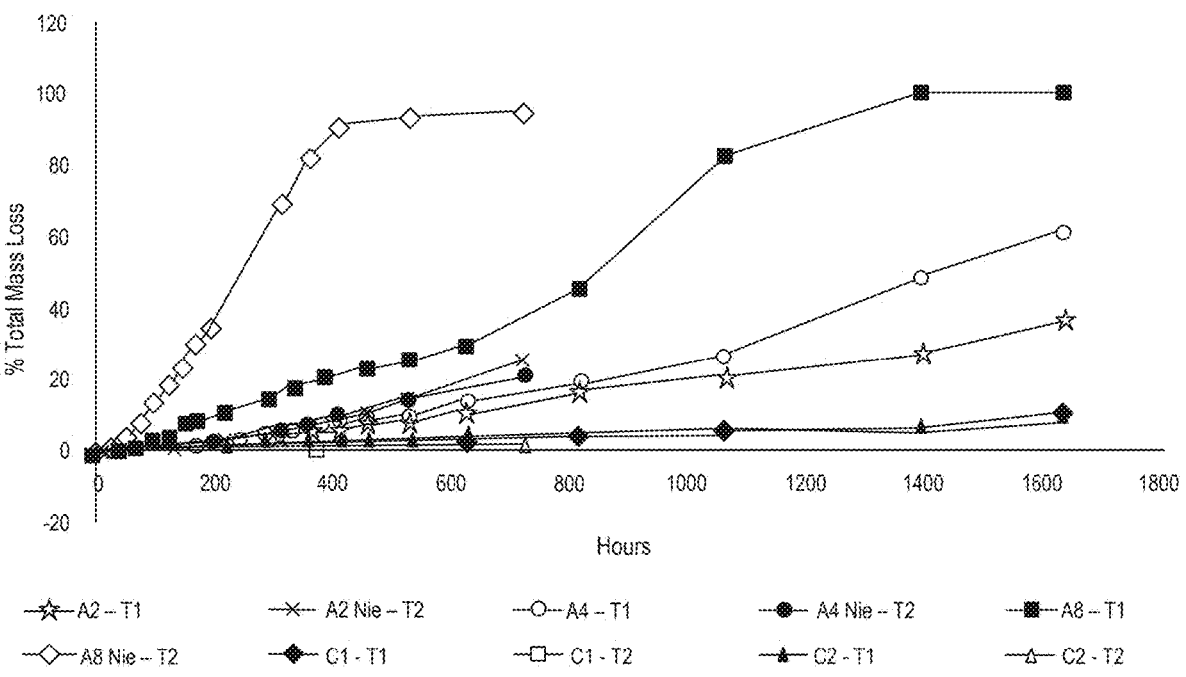
FIG. 30 illustrates a graph of corrosion/mass loss data over time for several alloy samples, according to an embodiment.

An overlay of the immersion corrosion results for the Alloying Study I Trial I (A2, A4, A8, C1, and C2 only) and Alloying Study I Trial II extrusions are presented as a percentage of mass lost per day (total mass loss divided by total number of days) in FIG. 30 (full test length).

Figure 31:
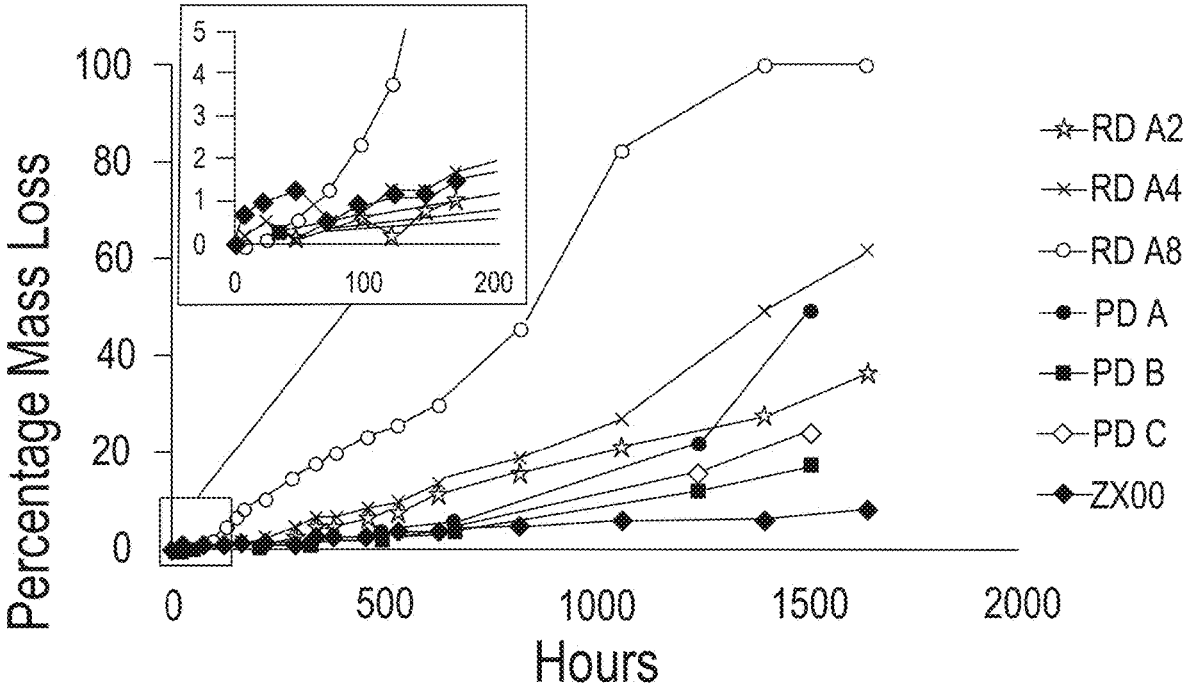
FIG. 31 illustrates a graph of corrosion/mass loss data over time for several alloy samples, according to an embodiment.

The immersion corrosion results for the Alloying Study II PD A-C extrusions are shown as a percentage of total mass lost versus test length (hours) in FIG. 31. This plot also includes an overlay of the results for Alloying Study alloys RD A2, A4, A8 and comparative alloy C1 (ZX00) for comparison. Results show the corrosion rates of the PD alloys were slower than the RD alloys. Looking at the first 200 hours (orange square) shows how the C1 alloy had a burst of corrosion at the start of the test, which was not observed in any of the PD or RD alloys.

Figure 32:
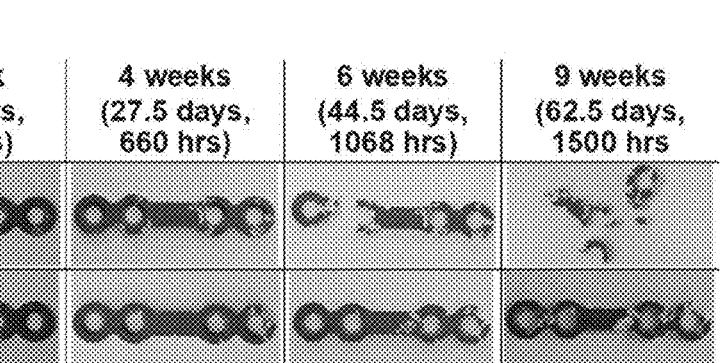
FIG. 32 depicts a photograph of corrosion test results comparing different magnesium alloy samples over time, according to aspects of the present disclosure.

Images of the samples collected at each time point show the progression of the corrosion, highlighting how faster corroding alloys had more pitting. FIG. 32 shows representative images of the Alloying Study II samples prior to immersion and at 1 week (8.5 days, 204 hours), 4 weeks (27.5 days, 660 hours), 6 weeks (44.5 days, 1068 hours), and 9 weeks (62.5 days, 1500 hours). These show the detrimental effects of increased Mg₂Ca by way of chemistry, rather than processing, with the PD-A samples having higher Ca content to produce these detrimental effects. Corrosion rate and localized attack for PD-A are much higher than for PD-B and PD-C.

Figure 33A:
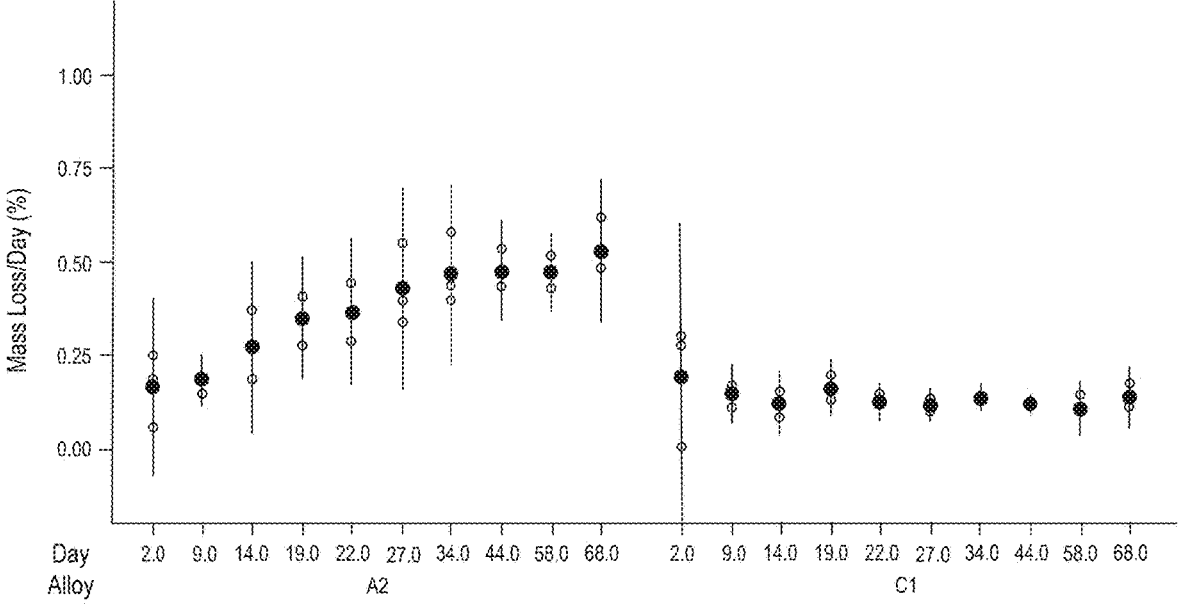
FIGS. 33A and 33B show a graph of corrosion/absorption data plotted over time with multiple data points, according to an embodiment.
Figure 33B:
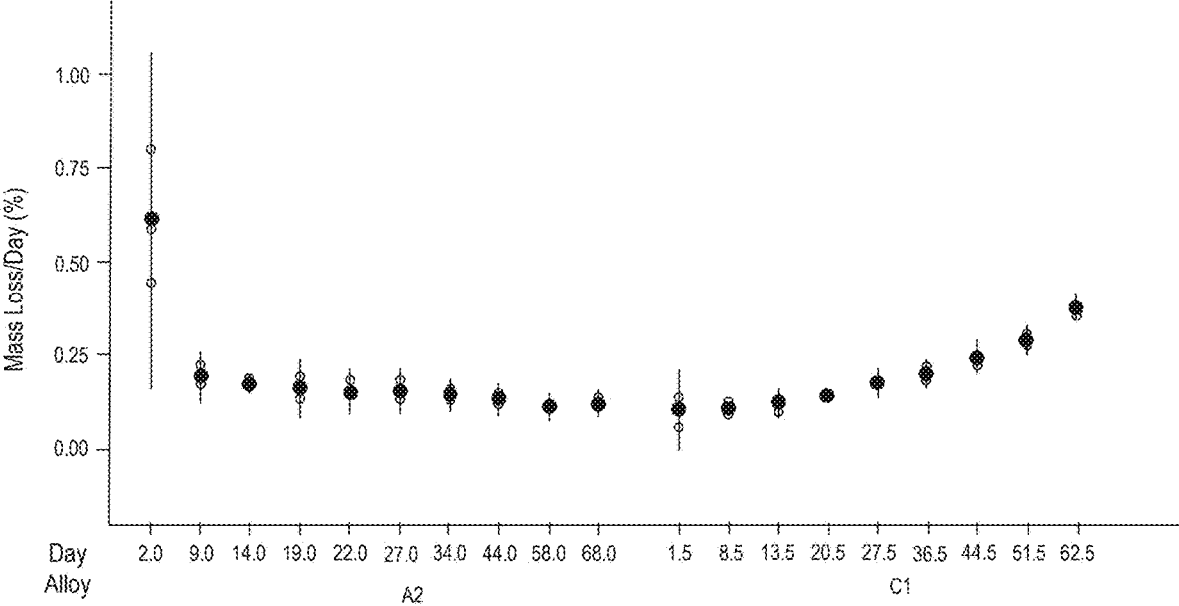

To further analyze the deviation amongst Alloying Study I RD-A2, C1, and C2 and Alloying Study II PD-C (same target composition) samples, the immersion corrosion results for these alloys were plotted in a statistical software package (e.g., Minitab). This data is presented as a percentage of mass lost per day (total mass loss divided by total number of days) versus test length in FIGS. 33A and 33B.

Figure 88A:
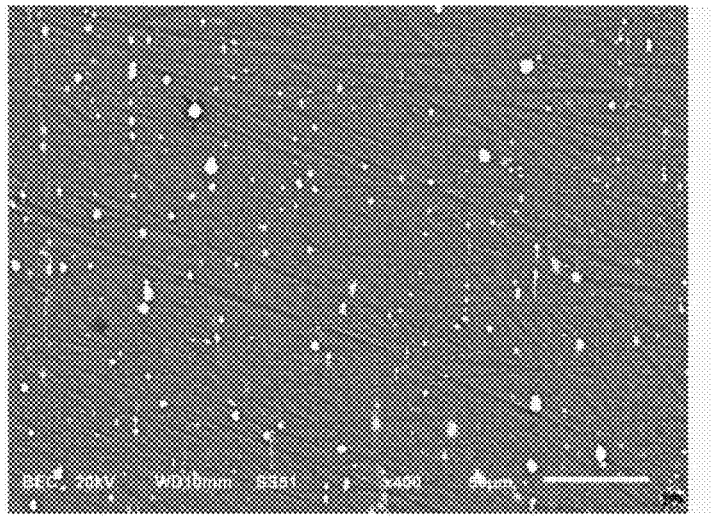
FIGS. 88A and 88B are a SEM micrographs displaying a microstructural view of a magnesium alloy sample.
Figure 88B:
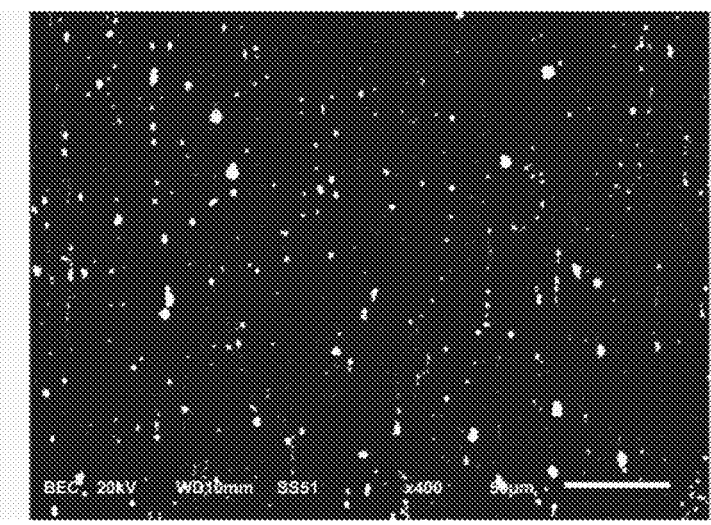

SEM images of 165-2 (410 C/24 hr/AC solution treatment and extrusion at 325 C with extrusion ratio (ER) of 14) were collected in backscatter mode in three locations. See FIGS. 88A and 88B. Thresholding and Analyze Particle features on ImageJ were then used to determine percentage area of precipitate phases and average precipitate size (μm²). The results are presented in Table 24 with the corrosion data. SEM image of 165-2 on left (FIG. 88A) shows precipitate phases. Image on right (FIG. 88B) has undergone thresholding in ImageJ. Excluding the image information bar on the bottom, the Analyze Particles feature on ImageJ was then used to measure the percentage area of precipitate phases and average precipitate size.

Compression Screw Performance

In vitro corrosion testing and torque testing were performed on comparative compression screws (e.g., Syntellix MAGNEZIX) and a first prototype screw (e.g., Curasorb Alpha Prototypes) to evaluate the baseline performance of the bioabsorbable magnesium alloy (e.g., Curasorb Alloy) against a clinically relevant control or comparison. The first prototype or iteration of bioabsorbable magnesium (e.g., Curasorb Alpha Prototype) feedstock material was machined into compression screws matching the geometry of the comparative (e.g., Syntellix) screws. No modifications were made to optimize the mechanical or corrosion performance of the first (e.g., Curasorb Alpha) prototypes.

Torque testing assessed the mechanical strength and failure modes of the screws, measuring the maximum torque each screw could withstand before failure. This evaluation provided critical data on structural integrity and durability, ensuring the screws can endure the mechanical stresses encountered during surgical procedures and throughout the healing process.

Immersion Corrosion Testing

Immersion corrosion testing was conducted on compression screws with a diameter of 3.2 mm and a length of 22 mm. The first prototype (e.g., Curasorb) screws were cleaned with a 1% Citranox solution for 2 minutes before testing, while the comparative (e.g., Syntellix) screws were tested in their as-received condition.

Figure 34:
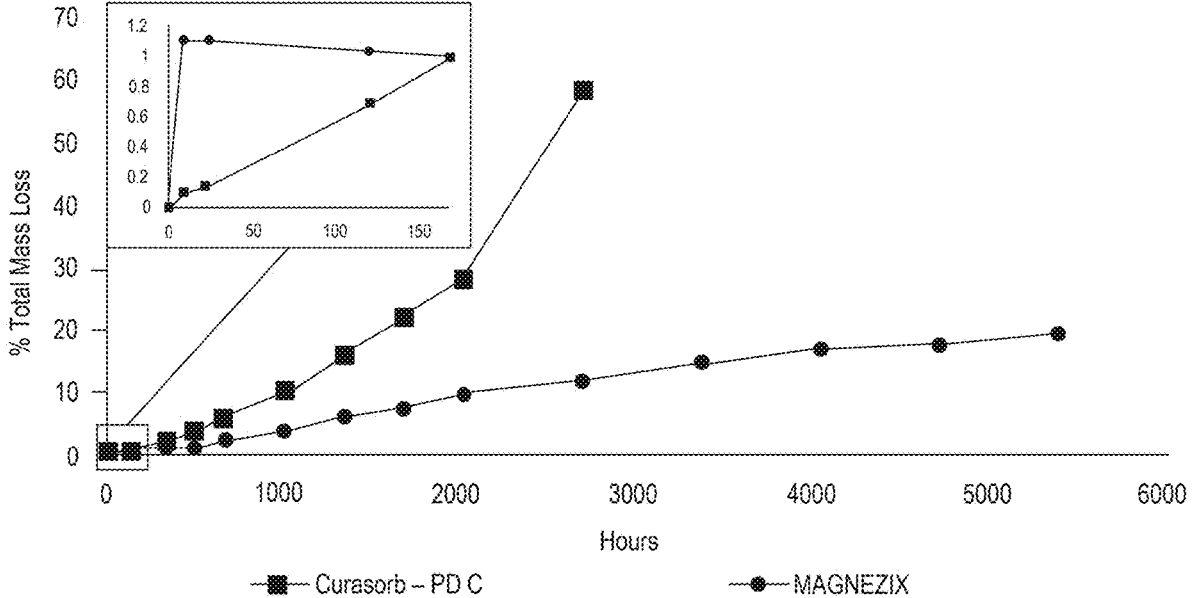
FIG. 34 illustrates a comparison of corrosion/absorption behavior between two materials over time, according to aspects of the present disclosure.

The immersion corrosion results for the compression screws are presented as a percentage of total mass lost versus test length (hours) in FIG. 34. Results show the corrosion rate of the first prototype (e.g., Curasorb) screws started out slower than the comparative (e.g., MAGNEZIX) screws, avoiding the burst of absorption exhibited by the comparative (e.g., MAGNEZIX) screws in the first 24 hours of the test. The corrosion rate of the first prototype (e.g., Curasorb)

screws then sped up in the later stages to be faster than the comparative (e.g., MAGNEZIX) screws at approximately 1 week in vitro.

Torque Testing

Torque testing was performed on compression screws with a diameter of 3.2 mm and a length of 30 mm. Testing was conducted at room temperature by securing each screw in separate collets. The top collet was rotated to apply torque until the screw failed. The maximum torque achieved prior to failure was recorded as a measure of mechanical strength. Additionally, the location of the fracture was documented to provide insights into the failure modes of the screws.

Torque Testing

Figure 35A:
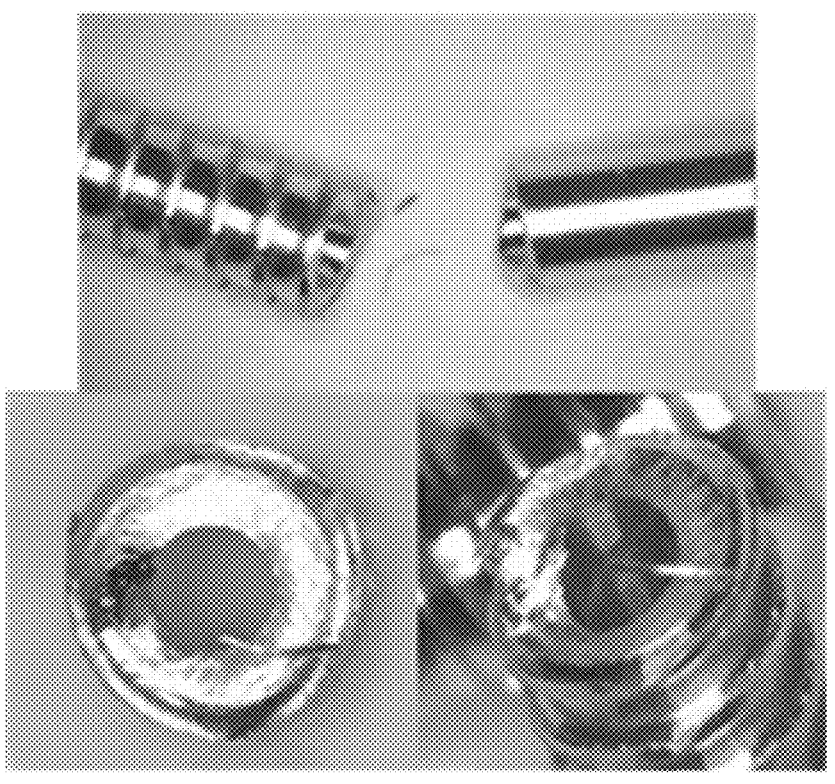
FIG. 35A and FIG. 35B show detailed microscopic views of metallic screws and components, according to aspects of the present disclosure.
Figure 35B:
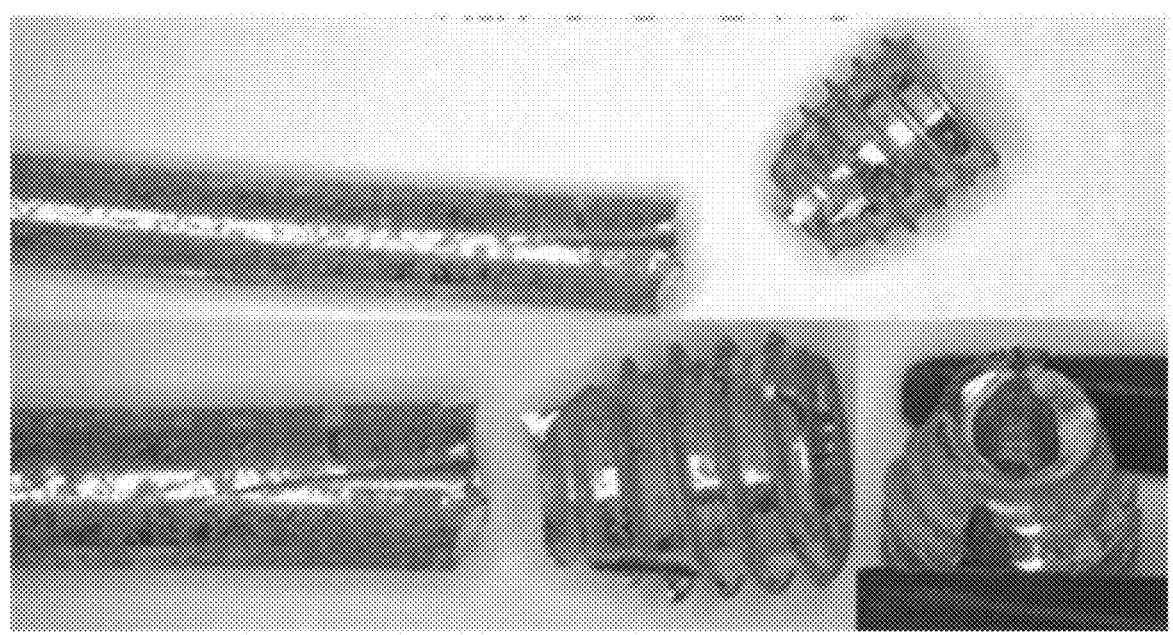

The first prototype (e.g., Curasorb) compression screws had similar torque performance to the comparative (e.g., MAGNEZIX) screws, as summarized in Table 25. The first prototype (e.g., Curasorb) screws all failed at the transition between the screw shaft and bottom threads. The comparative (e.g., MAGNEZIX) screws mainly failed at the transition between the screw shaft and top threads; however, the first sample failed due to slipping in the grips. Representative images of the fractures are shown in FIGS. 35A and 35B.

this burst. These same characteristics cause the absorption rate to remain slow after healing when the Mg2Ca phases exposed at the implant surface have degraded. Alternatively, the experimental alloys A5-A8 (e.g., Curasorb alloys A5-A8) clearly show three distinct stages of corrosion—an initial state of steady corrosion, a middle stage of slow-to-no corrosion as the protective oxide layer builds, and a final stage of increasing corrosion as the oxide layer breaks down and the material fully dissolves. The test concluded before alloys A1-A4 exhibited all three stages.

Analysis of precipitate phases (intermetallic phases) in the first prototype (e.g., Curasorb Alpha Prototype) alloys provided valuable insights into how microstructural features influence corrosion performance and the ability to tailor absorption profiles for various applications. SEM imaging and ImageJ (e.g., Java-based image processing program) analysis revealed the distribution, size, and morphology of precipitates, which are critical factors in determining corrosion behavior, although these are somewhat generalized since this analysis does not account for precipitate species (ternary vs Mg2Ca). The precipitate phase area fraction and length were quantified for each sample, highlighting variations across processing conditions and compositions. In

TABLE 25

Compression Screw torque testing results.

| Alloy | Max Torque (in-lbs) | Avg Torque (in-lbs) | Std Dev Torque (in-lbs) | Failure Mode |
|---|---|---|---|---|
| PD C (Curasorb) | 5.44 5.42 5.44 | 5.43 | 0.0094 | Fracture at the transition between the screw shaft and bottom threads |
| Comparative (MAGNEZIX) | 5.78 5.60 5.92 | 5.77 | 0.1310 | Stripped out of lower threads Fractured at upper threads Fractured at upper threads |

Discussion of Examples 1-7

Immersion Corrosion Results

The immersion corrosion results demonstrate the ability to adjust the composition of the alloys to produce a matrix of alloys with different corrosion rates, thus demonstrating that the corrosion rate of its alloy can be tailored to meet the needs of an application. It appeared that, though the corrosion profile of the alloys changed, the tensile properties were consistent across the group of experimental alloys. Further, the immersion corrosion results of the SOL+Ext. Trial I samples show how the comparative alloys have a burst of corrosion at the start and then flatten out to a slow corrosion rate as time progresses (FIG. 18). Such a profile can be problematic in vivo by causing bone density loss adjacent to the implant resulting from the fast initial release rate of alloy absorption products (e.g., published preclinical studies, EU-based surgeon interviews). Initial burst of absorption can result in high osteoblast activity, followed by high osteoclastic activity as the absorption induced osteoblastic activity decreases, causing the poor osseointegration of the implant and the resulting instability. The slow rate of absorption after the burst results in implants that remain far beyond the target of 1-2 years to reach full absorption. The comparative alloys included in this feasibility study were engineered to have a minimal fraction of secondary phases to minimize absorption; however, they lack the protective oxide layer (produced by high Mn content) to prevent the initial burst, while also containing Mg2Ca which promotes general, a higher precipitate phase fraction was associated with increased corrosion rates, although this relationship was not observed in BioMg250 due to its rapid absorption within the first 24 hours. This complexity may arise from the interplay between ternary/Mg2Ca precipitate phase mix and lower surface oxide stability of this alloy due to low Mn content, which can fundamentally change its performance.

Figure 36A:
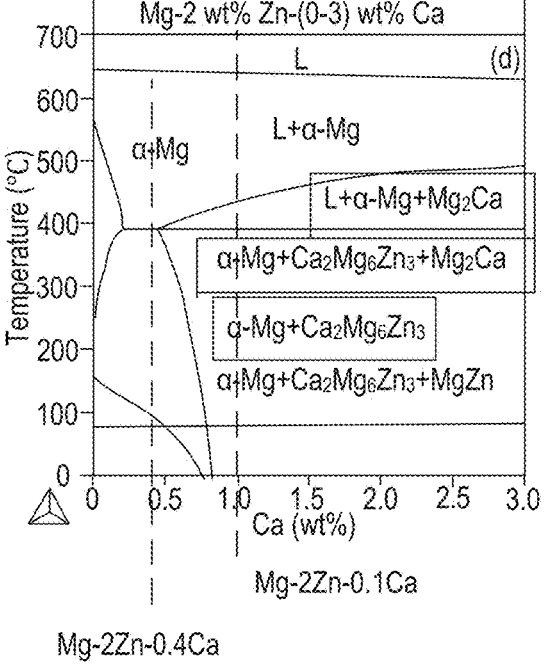
FIGS. 36A and 36B illustrate phase diagrams for magnesium alloy compositions, according to an embodiment.
Figure 36B:
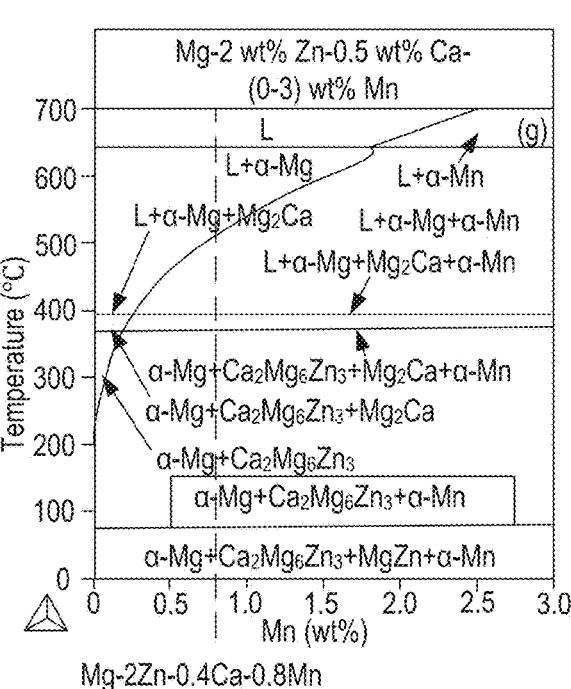

Experimental findings of the importance of optimizing precipitate size and distribution to achieve the desired absorption profile were supplemented by additional studies demonstrating the importance of controlling the phase species type (ternary vs. $Mg_2Ca$). Ultimately, it was demonstrated that a lower amount of $Mg_2Ca$ would reduce the overall corrosion rate and the occurrence of localized corrosion, which can be achieved by lowering the amount of Ca in the alloy and/or maintaining thermo-mechanical processing conditions below the $Mg_2Ca$ region of the phase diagram as shown in FIGS. 36A and 36B. See, e.g., Bahzenov et al. as cited above. FIGS. 36A and 36B show phase diagrams indicate the formation of Mg2Ca and ternary precipitate phases. In FIG. 36A, the Mg-2Zn-(0-3)Ca diagram indicates the formation of Mg2Ca can be avoided by staying in the area $\alpha$-Mg+$Ca_2Mg_6Zn_3$. In FIG. 36B, the addition of low amounts Mn to Mg-2Zn-0.5Ca indicates that the formation of $Mg_2Ca$ can be reduced through thermomechanical processing below 375° C. Experimentally, this principle was demonstrated in the immersion corrosion results of the PD A and PD C alloys, with the corrosion rate of PD A being higher and accelerating much faster as the test progressed (FIG. 31). A larger amount of Ca was present in PD A than PD C, while Zn and Mn content was the same, probably causing the formation of more $Mg_2Ca$ phases in the PD A alloy. Fundamental principles of corrosion explain how the small phase/area fraction of $Mg_2Ca$ anodes can rapidly be sacrificed to the much larger surrounding cathodic matrix and ternary phases, resulting in fast localized corrosion of the $Mg_2Ca$ phases. Comparative alloys (e.g., Bioretec and NanoMag alloys) contain $Mg_2Ca$ which may explain their absorption burst effects that lead to poor osseointegration. In the case of the first and second prototypes (e.g., Curasorb), the robust surface oxide layer formed by the high Mn content was able to counteract these bursts caused by the $Mg_2Ca$, however rapidly accelerating non-uniform absorption occurred earlier over the test duration for samples with increasing $Mg_2Ca$. By eliminating the $Mg_2Ca$, the anode to cathode ratio can be made very large (anodic matrix to cathodic ternary phase) to practically nullify any microgalvanic effects, thus decreasing absorption rate and eliminating non-uniform corrosion as the implant absorbs. This elimination of $Mg_2Ca$ is the basis for improved performance of the second prototypes (e.g., Curasorb Beta prototypes).

A very large anodic to cathodic ratio may be considered as greater than 20:1, and in some cases, greater than 50:1.

In some cases, the anodic phase (magnesium-rich matrix) may comprise 95% to 99.5% of the alloy's volume or surface area. In some cases, the cathodic phases (ternary intermetallic phases and any residual $Mg_2Ca$) may comprise 0.5% to 5% of the alloy's volume or surface area. In some cases, the cathodic phase is substantially free of $Mg_2Ca$. In some cases, the cathodic phase is completely free of $Mg_2Ca$. In some cases, the anodic to cathodic ratios may range from a minimum ratio of 95:5 or 19:1. In some cases, the anodic to cathodic ratio may range from a maximum ratio: 99.5:0.5 or 199:1

In some embodiments, the anodic to cathodic ratio may be greater than 20:1. In some embodiments, the anodic to cathodic ratio may be greater than 50:1. In some embodiments, the anodic to cathodic ratio may be between 30:1 and 150:1. In some embodiments, the anodic to cathodic ratio may be between 40:1 and 100:1

The anode to cathode ratio can help control the corrosion and absorption behavior of the magnesium alloy. A large anode to cathode ratio can help reduce localized corrosion by distributing the anodic reactions over a larger area relative to the cathodic sites (i.e., corrosion control). By making the matrix (bulk material) anodic relative to small cathodic ternary phases, the corrosion process can become more uniform across the entire surface of the implant (i.e., uniform degradation). Microgalvanic corrosion can occur when there is a significant electrochemical potential difference between different phases in the alloy. A large anode to cathode ratio can minimize these microgalvanic effects. The large ratio can help slow down the overall corrosion rate, which translates to a slower absorption rate of the implant. By eliminating non-uniform corrosion, the mechanical integrity of the implant can be maintained for a longer period during the absorption process. Creating a microstructure where the magnesium matrix acts as a large anode, with small, well-distributed cathodic ternary phases can help achieve the controlled, multi-phase absorption profile.

The comparative MAGNEZIX alloy is vastly different from the other alloys tested metallurgically, however the absorption profile learnings are still critical. Like the comparative Bioretec and NanoMag alloys, the MAGNEZIX alloy demonstrates a big burst of absorption that produces poor osseointegration. Unlike those alloys, MAGNEZIX does demonstrate an acceptable time to full absorption, typically around 9 months for full absorption of the compression screw. Thus, the bench test results of the comparative MAGNEZIX provide realistic targets for benchtop absorption testing to down select bioabsorbable magnesium (e.g., Curasorb prototypes) for future preclinical studies.

Processing

In general, casting with the laboratory scale billets (solidification within 30 s would correspond to a cooling rate of 1-3° C./s) results in somewhat fine (50 μm) grain size. Solutionizing at 500° C. and 530° C. results in significant grain growth (not as significant with solutionizing at 460° C.). This seems to indicate a lower temperature solutionizing treatment.

DSC testing provided solidus data upon heating. In general, the solidus is very similar to the CALPHAD results presented by Bazehenov for all the alloys in the test matrix.

The solution treatment (SOL+Ext. Trial II) had varying effects on the tensile properties of the A2, A4, and A8 alloys as compared to the original solution treatment recipe (Trial I); however, differences were observed for corrosion properties and the size of the secondary phases for A2. As composition does not change for each respective alloy, the solution treatment's effect on the size and shape of the secondary phases may be the primary driver on the tensile and corrosion properties of the material. The solutionizing treatment (SOL+Ext. Trial II) appears to produce smaller secondary phases (as compared to Trial I); however, the secondary phases are more elongated. Producing smaller and more spherical secondary phases is generally expected to produce a material with a better controlled corrosion rate. It appears even though they are smaller; these elongated secondary phases had a negative effect in slowing the corrosion rate. Alloying Study II explored further refinement of secondary phases by altering the processing steps. As-cast material was homogenized (equiaxed grains) and extruded (break-up grains and secondary phases to reduce size), followed by solution treatment (produce more spherical secondary phases) and a second extrusion (reduce size of grains and secondary phases). Breaking down the microstructure via extrusion prior to heat treatment can have profound effects on microstructural evolution. This is observed by comparing the immersion corrosion results of Alloying Study I alloy A2 and Alloying Study II alloy PD C (FIG. 31), as the corrosion rate was successfully reduced for this composition by lowering the solution treat temperature and adding in a second extrusion step. Even with these reductions, there is an opportunity to further improve secondary phase uniformity and produce a material with a more uniform and slower corrosion rate.

It is important to note that all heat treatments in Alloying Study I were performed before extrusion in the as-cast state, without a second processing step to further manipulate the alloys, which is a limitation of pilot scale production. Commercial scale production was therefore important for the ability to perform additional processing and further modify microstructure and performance, along with reduction of variation, specifically on the absorption of the alloys so they are more uniform and predictable to aid in implant design. Alloying Study II presents an initial study in using commercial-grade equipment to process material. Alloying Study II found that using a low solution treat temperature (under 430° C.) and fragmenting precipitate phases with a high extrusion ratio (~30) produced an alloy with a more consistent and slower corrosion rate. However, further process optimization will be explored to further break down intermetallic phases without compromising material strength, given the tensile results indicate the alloys' strength is relatively low.

Example 8: In Vivo Performance

Preclinical Evaluation of a Akesorb Maxillofacial System for repair of frontal bone fractures in an ovine model A pilot preclinical study was conducted to evaluate the first prototypes (e.g., Alpha prototypes) of its Maxillofacial Fixation System in an ovine frontal bone ostectomy model. The study aimed to assess the system's efficacy, safety, and absorption profile in support of further implant system development. Results, including digital images, radiographs, and micro-CT images, demonstrated strong bone-to-implant contact through the first six weeks, confirming the bioabsorbable magnesium alloy's (e.g., Curasorb alloy's) ability to integrate well with surrounding bone tissue using controlled absorption without a coating. Notably, the study confirmed the avoidance of an initial burst of absorption, maintaining bone density adjacent to the implants, a key challenge in bioabsorbable magnesium alloys.

Early signs of bone bridging were observed at 12 weeks, indicating successful localized healing at the implant sites. Histopathological findings revealed only slight inflammation and mild reactivity, further confirming the biocompatibility of the Curasorb alloy. Importantly, no osteolysis or adverse effects on bone or surrounding tissue were observed. Additionally, the study demonstrated the efficacy of Curasorb plates and screws in achieving ostectomy healing and safely supporting bone repair.

MicroCT data revealed a 32% volume loss at 6 weeks and 55% volume loss at 12 weeks, indicating the in vivo absorption rate in frontal bone applications is approximately six times faster than the in vitro corrosion rate. There is an opportunity to optimize the absorption profile of the alloy further by reducing anodic phases (Mg2Ca), which contributed to nonuniform absorption, enhancing the implant's overall performance.

In summary, this study successfully demonstrated the alloy's ability to maintain bone density, promote bone healing, ensure implant safety, and deliver a manageable absorption profile in a fast-absorbing (low bone density with high blood flow) preclinical model. In vitro and in vivo comparisons to comparative alloys demonstrate superior short-term and comparable long-term absorption performance with a clear development path toward optimization and commercialization.

A bioabsorbable magnesium alloy (e.g., Curasorb Alloy) with superior absorption characteristics over existing bioabsorbable magnesium technology for use in maxillofacial fixation is being developed. One goal in alloy development was to demonstrate that absorption can be made to begin slower than comparative alloys, avoiding the initial burst of absorption that can cause bone density loss that does not recover until full absorption of the implant. The main objectives of the pilot preclinical study were: confirm avoidance of an initial burst of absorption maintains bone density adjacent to the implants made from the alloy, demonstrate efficacy of plates and screws made from the alloy to achieve ostectomy healing, assess the safety of the plates and screws for repair of bone fractures, and determine in vivo absorption profile to correlate to in vitro corrosion profile.

The bioabsorbable magnesium alloy may be used in biodegradable orthopedic implants. The alloy is designed to have a multi-stage absorption profile that allows the material to fit the needs of bioabsorbable implants, surpassing existing technologies. As the alloy absorbs, the magnesium metal is oxidized to ionic magnesium, which is an essential nutrient to the body and cellular function, then absorbed into the body.

The first iteration of the alloy is being developed for the Akesorb Maxillofacial System, designed for use in maxillofacial trauma and reconstruction. The system includes a variety of screw sizes (in both diameter and length) as well as plates in different shapes and sizes. To ensure the performance of these implants through the healing process, a preclinical study was conducted. The success of this system can be measured by its absorption profile, particularly in relation to bone response and healing in the preclinical model. In bioabsorbable magnesium systems used in orthopedic applications, magnesium alloys, when engineered with an appropriate absorption profile, can demonstrate safety and efficacy.

Extensive bench testing, which demonstrated the system's superior performance compared to existing bioabsorbable magnesium alloys, was conducted. The alloying studies highlighted the ability to produce a range of materials, each exhibiting a controlled absorption profile with intentional variations in overall absorption rates. Notably, these studies showed that the alloy's initial absorption rate is slower than that of comparative alloys, as designed. Based on the bench testing results, Alloy PD B was selected to manufacture implants for the pilot preclinical study. Alloy PD B was chosen as it had the slowest in vitro corrosion rate of the alloys studied—0.03 mm/yr at 24 hours and 0.04 mm/yr at 504 hours.

To assess the potential clinical success of utilizing the bioabsorbable magnesium alloy (e.g., Curasorb) in maxillofacial applications, a pilot preclinical study was executed to assess the safety and efficacy of the Akesorb Maxillofacial system. Two animals (ovine) were implanted. A cranioosteoplasty of the frontal bone was performed bilaterally, and plate and screw prototypes (e.g., Curasorb) were utilized to stabilize the ostectomy. After implantation, a single animal survived until 6-weeks, and the remaining animal survived until 12-weeks. Ex vivo analysis included radiographic and microCT analysis, histology, histomorphometry, and histopathologic evaluation.

An ovine model was selected for this study because of comparable anatomy and physiology of the ovine frontal bone to that of the human. See, e.g., Herzog P, Rendenbach C Turostowski M, Ellinghaus A, Soares A P, Heiland M, Duda G N, Schmidt-Bleek K, Fischer H (2024) Titanium versus plasma electrolytic oxidation surface-modified magnesium miniplates in a forehead secondary fracture healing model in sheep. Acta Biomaterialia 185:98-110, which is hereby incorporated by reference in its entirety herein. This literature can also be found in https://doi.org/10.1016/j.actbio.2024.07.005. See, e.g., Suuronen R, Pohjonen T, Vasenius J, Vainionpaa S (1992) Comparison of absorbable self-reinforced multilayer poly-1-lactide and metallic plates for the fixation of mandibular body osteotomies: an experimental study in sheep. J Oral Maxillofac Surg. 50(3):255-62, which is hereby incorporated by reference in its entirety herein. This literature can also be found in https://doi.org/10.1016/0278-2391(92)90322-q. See, e.g., Turostowski M, Rendenbach C, Herzog P, Ellinghaus A, Soares A P, Heiland M, Duda G N, Schmidt-Bleek K, Fischer H (2024) Titanium vs PEO Surface-Modified Magnesium Plate Fixation in a Mandible Bone Healing Model in Sheep. ACS Biomaterials Science & Engineering 10(8):4901-4915, which is hereby incorporated by reference in its entirety herein. This literature can also be found in https://doi.org/10.1021/acsbiomaterials.4c00602.

The ovine model is an accepted translational model of cranio-osteoplasty. The implants used in this study are being designed for fixation in fracture repair and reconstructive procedures for trauma and orthognathic procedures involving the maxilla, zygoma, orbital rim, and frontal bone in adult patients. Since this is the first preclinical study using the bioabsorbable magnesium alloy (e.g., Curasorb), a frontal bone model was used for this study for the simplicity of the model and the low-risk nature for the animal. Frontal bone is also a lower density bone than other maxillofacial anatomies, which may result in faster absorption. See, e.g., Marek R, Cwieka H, Donohue N, Holweg P, Moosmann J, Beckmann F, Brcic I, Schwarze U Y, Iskhakova K, Chaabane M, Sefa S, Zeller-Plumhoff B, Weinberg A M, Willumeit-Römer R, Sommer N G (2022) Degradation behavior and osseointegration of Mg—Zn—Ca screws in different bone regions of growing sheep: a pilot study. Regenerative biomaterials, 10, rbac077, which is hereby incorporated by reference in its entirety herein. This literature can also be found at https://doi.org/10.1093/rb/rbac077. Pairing a fast absorption environment with the small dimensional profile of the implants makes this a challenging test to achieve implant functional survival through bone fusion, albeit at low risk for the animal. Future studies will assess the safety and efficacy of using these devices in higher risk anatomies and of those with load-bearing functions, such as the zygoma, maxilla, and mandible.

Micro-computed tomography (micro-CT) is commonly used to assess osteotomy healing and evaluate bone loss in the context of bioabsorbable magnesium implants. See, e.g., Herzog, Holweg, Turostowski, and Marek as previously cited. See, e.g., Imwinkelried T, Beck S, Schaller B (2020) Pre-clinical testing of human size magnesium implants in miniature pigs: Implant degradation and bone fracture healing at multiple implantation sites. Materials Science & Engineering C 108:110389, which is hereby incorporated by reference in its entirety herein. This literature can also be found at https://doi.org/10.1016/j.msec.2019.110389. See, e.g., Kopp A, Fischer H, Soares A P, Schmidt-Bleek K, Leber, C, Kreiker H, Duda G, Kroger N, van Gaalen K, Hanken H, Jung O, Smeets R, Heiland M, Rendenbach C (2023) Long-term in vivo observations show biocompatibility and performance of ZX00 magnesium screws surface-modified by plasma-electrolytic oxidation in Göttingen miniature pigs. Acta Biomaterialia 157: 720-733, which is hereby incorporated by reference in its entirety herein. This literature can also be found at https://doi.org/10.1016/j.actbio.2022.11.052. See, e.g., Naujokat H, Seitz J M, Agil Y, Damm T, Möller I, Güilses A, Wiltfang J (2017) Osteosynthesis of a cranio-osteoplasty with a biodegradable magnesium plate system in miniature pigs. Acta Biomaterialia 62:434-445, which is hereby incorporated by reference in its entirety herein. This literature can also be found at https://doi.org/10.1016/j.actbio.2017.08.031. See, e.g., Naujokat H, Ruff C B, Klüter T, Seitz J M, Agil Y, Wiltfang J (2020) Influence of surface modifications on the degradation of standard-sized magnesium plates and healing of mandibular osteotomies in miniature pigs. International Journal of Oral and Maxillofacial Surgery 49(2):272-283, which is hereby incorporated by reference in its entirety herein. This literature can also be found at https://doi.org/10.1016/j.ijom.2019.03.966. See, e.g., Schaller B, Burkhard J P M, Chagnon, M, Beck S, Imwinkelried T, Assad M (2018) Fracture healing and bone remodeling with human standard-sized magnesium versus polylactide-co-glycolide plate and screw systems using a mini-swine craniomaxillofacial osteotomy fixation model. Journal of Craniomaxillofacial Trauma 76:2138-2150, which is hereby incorporated by reference in its entirety herein. This literature can also be found at https://doi.org/10.1016/j.joms.2018.03.039.

By performing longitudinal scans at different time points, the progression of bone response around implants can be quantitatively assessed, enabling the identification of potential complications such as peri-implantitis or implant-associated bone resorption. These assessments aid in determining the biocompatibility and long-term performance of implants, providing essential data for the development and refinement of implant materials and designs, ultimately ensuring their safety and efficacy for clinical applications. Further, micro-CT images can demonstrate the overall morphology of the healing bone, bone/tissue health, and absorption of the implant.

Further quantitative and qualitative assessment of bone healing, bone/tissue health and implant absorption in studies on bioabsorbable magnesium are conducted through histomorphometry and histopathological assessment. See, e.g., Holweg, Imwinkelried (2020), Marek, Naujokat (2017), Naujokat (2020), and Schaller as previously cited. See, e.g., Grin N G, Holweg P, Tangl S, Eichler J, Berger L, van den Beucken JJJP, Löffler J F, Klestil T, Weinberg A M (2018) Comparison of a resorbable magnesium implant in small and large growing-animal models. Acta Biomaterialia 78:378-386, which is hereby incorporated by reference in its entirety herein. This literature can also be found at https://doi.org/10.1016/j.actbio.2018.07.044. See, e.g., Torroni A, Xiang C, Witek L, Rodriguez E D, Flores R L, Gupta N, Coelho P G (2018) Histo-morphologic characteristics of intra-osseous implants of WE43 Mg alloys with and without heat treatment in an in vivo cranial bone sheep model. Journal of cranio-maxillo-facial surgery: official publication of the European Association for Cranio-Maxillo-Facial Surgery 46(3):473-478, which is hereby incorporated by reference in its entirety herein. This literature can also be found at https://doi.org/10.1016/j.jcms.2017.12.028.

Histomorphometry allows for the quantitative assessment of bone and tissue health by measuring parameters like bone volume, trabecular thickness, and the extent of bone loss surrounding the implants over time. It also allows for quantitative assessment of implant absorption by measuring the amount of implant material area remaining. It provides critical insights into the implant's biocompatibility and its effects on the local bone environment. Concurrently, histopathological analysis offers a qualitative assessment of tissue responses, highlighting any inflammatory reactions, foreign body responses, or other pathological changes induced by the implants. Together, these techniques enable researchers to gauge the overall biocompatibility, degradation kinetics, and impact on bone health of bioabsorbable magnesium implants, informing their safety and efficacy for potential clinical use while shedding light on necessary design improvements.

Materials and Methods

Device Description

Figure 37:
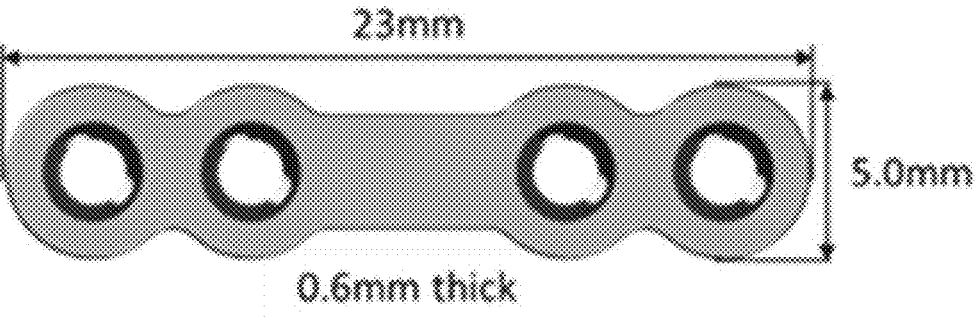
FIG. 37 and FIG. 38 depict orthogonal views of a plate and screw design, according to aspects of the present disclosure.
Figure 38:
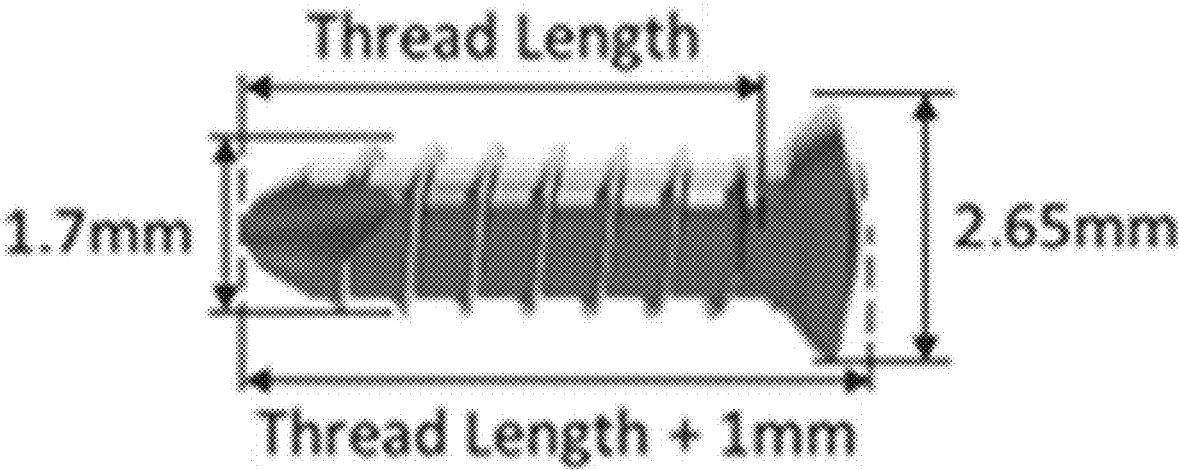

The magnesium implants used in benchtop testing and the pilot preclinical study were prototypes of a 4-hole plate with bar (0.6 mm thick, 5 mm wide, 23 mm long) and 1.7 mm self-tapping screws (1.7 mm diameter, 5 mm thread length). Table 26 shows the Test Article Identifiers. Schematics of the plate and screw prototypes are provided in FIGS. 37 and 38.

The implants were manufactured from a bioabsorbable magnesium alloy (e.g., Curasorb Alloy) composed of Mg-2.0Zn-1.0Ca-1.0Mn (Alloy PD-B, Lot 1353DX-2, X22341-02). The composition ranges of Alloy PD-B are provided in Table 27.

TABLE 26

Test Article Identifiers

| Part Number | Rev | Description | Lot Number | Quantity |
|---|---|---|---|---|
| 21028 | P2 | Akesorb four-hole plate with bar | 21028 2023 Jul. 24 | 4 plates/animal |
| 21029 | P1 | 1.70 mm Akesorb screw, 5 mm (thread length) | 21029 2023 Jul. 20 | 4 screws/plate 16 screws/animal |

TABLE 27

Composition ranges for the preclinical alloy (PD B)

| | | Composition Ranges | | | | | | | |
|---|---|---|---|---|---|---|---|---|---|
| | | Alloying Elements | | | Trace Elements | | | | |
| Alloy | Mg | Zn | Ca | Mn | Fe | Ni | Cu | Al | Si |
| PD-B | balance | 2.0 ± 0.2 | 1.0 ± 0.2 | 1.0 ± 0.2 | <0.010 | <0.010 | <0.010 | <0.010 | <0.010 |

Benchtop Testing—Immersion Corrosion Testing

Benchtop immersion corrosion testing was conducted to determine the in vitro corrosion rate of Alloy PD-B. Three sets of plate samples (1 plate/sample) and three sets of screw samples (4 screws/sample) were analyzed. Cleaned and sterilized samples were weighed and imaged in the as-received condition prior to testing to get the initial sample weight. Samples were then placed in separate beakers of DMEM (Gibco Dulbecco's Modified Eagle Medium, ThermoFisher Scientific catalog number 11965118) with 0.2% sodium azide. A volume of 50 mL DMEM solution per cm² of sample surface area was used for each sample. Each beaker was covered with parafilm to allow gas transfer without allowing solution evaporation and then placed in a $CO_2$ incubator set at 37° C. and 5% $CO_2$. At each time point (8 hours, 1 day, 5 days, 12 days, 21 days), the beakers were removed from the incubator, and the samples were removed from their beakers. The samples were rinsed in DI $H_2O$, rinsed in 70% alcohol, and then placed on a paper towel to dry. Once dry, the samples were weighed and imaged. After the sample check was complete, samples were placed back into their respective beakers, and the beakers were placed back into the CO2 incubator. Weight loss at each time point was used to determine the corrosion rate per Equation 1:

$$CR = (87.6 * W)/(SA * T * D),$$ (Equation 1)

where 87.6 is a constant that gives the corrosion rate in the units of mm/year, W is the weight loss of the implant in mg, SA is the initial surface area of the implant in mm², T is the total time of implantation in hours, and D is the density of the alloy (e.g., Curasorb Alloy PD-B) in gm/cm³.

Benchtop Testing—In Vitro Corrosion Rate

Figure 39:
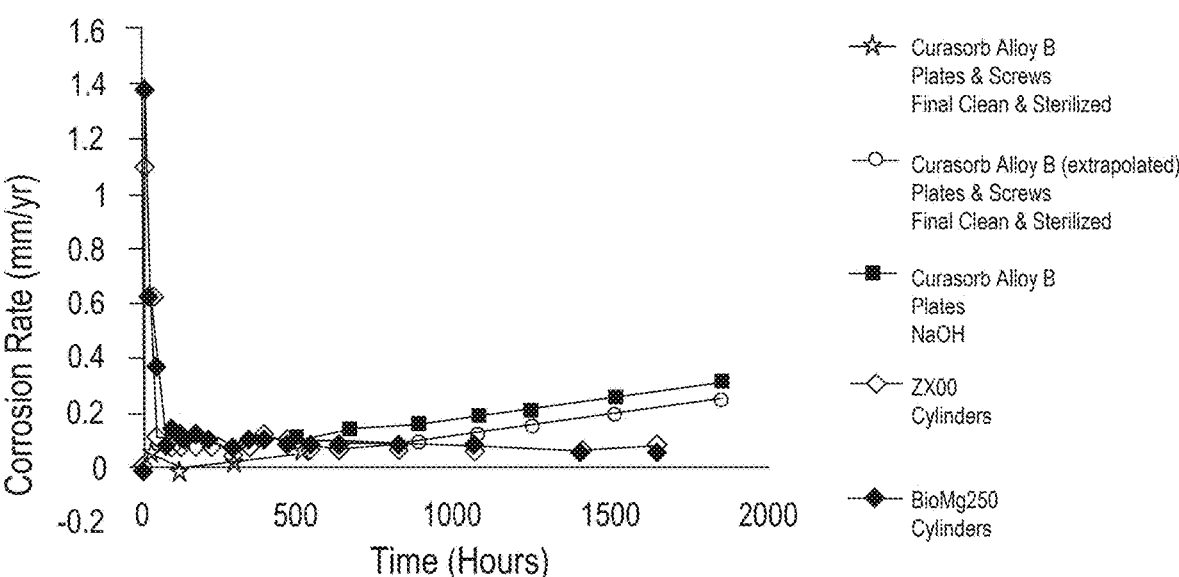
FIG. 39 illustrates a comparison of corrosion/absorption behavior between materials over time, according to aspects of the present disclosure.

Cleaned and sterilized plates and screws were tested to determine the in vitro corrosion rate (CR) of Curasorb Alloy PD-B. Alloy PD-B had an average CR of 0.00 mm/yr at 8 hours (no mass loss), 0.05 mm/year at 1 day, 0.05 mm/year at 3 weeks, and 0.11 mm/year at 6 weeks. It is important to note that the 6-week CR data for Alloy PD-B is an extrapolation based on the trend observed through the 3-week timepoint and of Alloy PD-B samples cleaned using a different method (NaOH). FIG. 39 provides a comparison of the CRs over time for Alloy PD-B, ZX00, and BioMg250. The comparative alloys, ZX00 and BioMg250, show a burst of corrosion at the onset of immersion corrosion testing in vitro, a behavior not observed with the bioabsorbable magnesium alloy PD-B (e.g., Curasorb). The burst of absorption observed in the lean magnesium alloys (ZX00 and BioMg250) is attributed to the excessive $Mg_2Ca$ phases present in these alloys.

5.3. Ovine Frontal Bone Ostectomy Pilot Preclinical Study Design

Alloy PD B was used to manufacture plates and screws for a pilot preclinical study in an ovine model. The study aimed to demonstrate the prototype's efficacy in promoting osteotomy healing and to ensure alloy elements in the blood remain at normal physiological levels. Alloy PD B was chosen for this study as it had the slowest corrosion rate of the alloys studied. Achieving an absorption rate that is slow enough for the application is the greatest challenge when designing a bioabsorbable alloy.

This small study had two time points (6 weeks and 12 weeks) and one animal per time point. The test article was a four-hole plate with bar (0.6 mm thick×5 mm width×23 mm length) and 1.7 mm self-tapping screws (1.7 mm thread diameter×6 mm length). A brief overview of the surgical procedure is illustrated in FIGS. 40A-40E. An unstable osteotomy was formed by making a 2 cm×2 cm incision on the animal's frontal bone. As shown in FIG. 40A, the implantation was performed at the frontal bone with a single midline sagittal incision. A 2 cm×2 cm square was outlined to show the right and left osteotomies. As shown in FIG. 40B, a 1.1 mm drill bit and 1.5 mm tap were used to create and prepare pilot holes. As shown in FIG. 40C, screws were driven into frontal bone to secure the plate to the frontal bone osteotomy, with only 1 screw visible in FIG. 40C. Two plates, each secured by screws, were placed on either side of the osteotomy, as shown in FIG. 40D. FIG. 40D is a cadaveric photograph showing a 2 cm×2 cm square frontal bone ostectomy secured with two four-hole plates with four screws in each plate. As shown in FIG. 40E, screws were placed through all four holes on all four plates to secure the plates to the native frontal bones.

Histopathology

Four sections at each time point (6-weeks and 12-weeks) from the right anterior, right posterior, left anterior, and left posterior bone through the plate and screws were examined.

In all sections, the plate and screws were present, and histologic changes were similar in all sections at both time points. Overall histologic changes consisted of bone surrounding the screws (more bone appeared to be in direct contact with the screws at the 6-week time point compared to the 12-week time point), mild to moderate degeneration of the screws and plates, moderate fibrosis surrounding the screws where not in contact with the bone, mild infiltration of lymphocytes, macrophages, and giant cells in the fibrosis and surrounding areas of screw degeneration, mild new bone formation, and active bone resorption with osteoclasts within resorption lacunae.

The average inflammatory and total reactivity scores for the groups were:

6-weeks: Average total reactivity score: 13.5 Average inflammation score: 6

12-weeks: Average total reactivity score: 14.5 Average inflammation score: 5.25

The inflammation between all groups was similar. Using an inflammation reactivity grading profile of Minimal Reaction: 0.0-2.9, Sight Reaction: 3.0-8.9, Moderate Reaction: 9.0-15.0, and Severe Reaction: >15.1, all groups were assessed as having a slight inflammatory reaction. The total average reactivity score was lower at 6 weeks compared to 12 weeks (13.5 versus 14.5). The 12-week time points had minimally higher implant degradation and fibrosis than the 6-week time point which accounts for the score difference.

Evaluation of the Akesorb MaxilloFacial System biocompatibility and reactivity ranking scores demonstrated slight inflammation and mild total reactivity across both time groups. Overall, degradation of the bioabsorbable plates and screws was increased at 12-weeks compared to 6-weeks and the material only resulted in a slight inflammation reactive.

FIGS. 77-80 illustrate representative photomicrographs obtained from an animal model at six weeks post-implantation.

Figure 77:
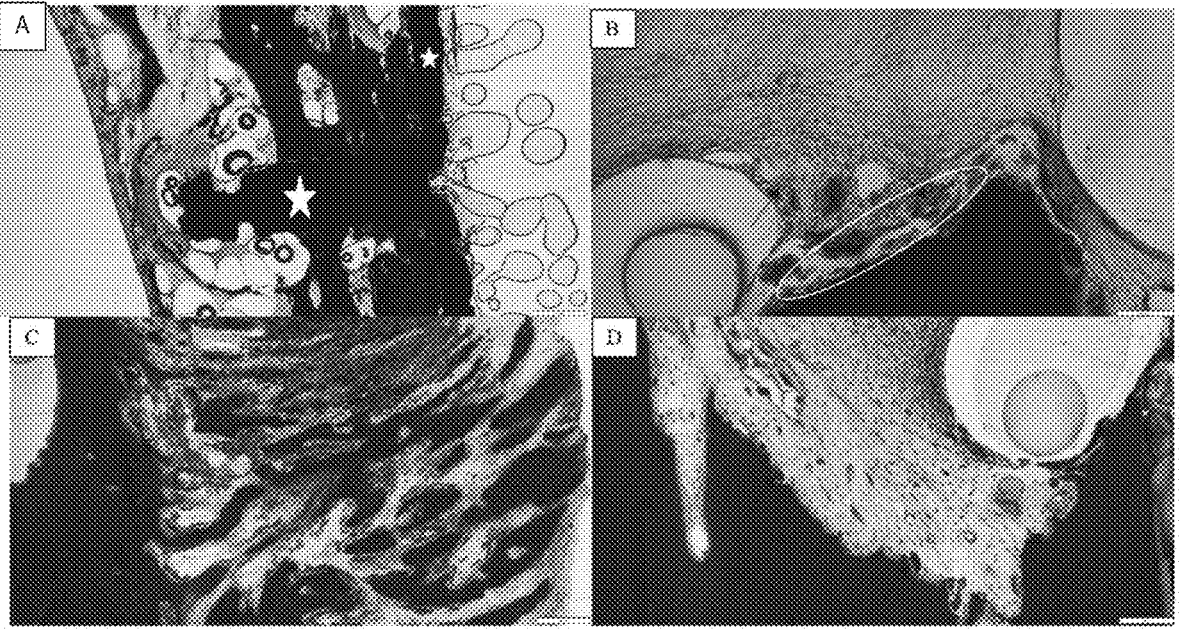

FIG. 77. Six-week time point, MTG01, right anterior region.

A (2×): Bone plate and screws (indicated by stars).

B (20×): Degeneration of screw (circled), surrounded by fibrous tissue and infiltrating lymphocytes, macrophages, and multinucleated giant cells (arrows).

C (10×): Evidence of periosteal new bone formation.

D (20×): Mature bone remodeling with visible osteoclasts (arrows).

One section of frontal bone with respiratory mucosa is examined. Along one edge, there is silver (subgross) to black/brown (microscopic) material that is consistent with the plate/screws. The main body of the screws are surrounded by dense bone. There is mild degradation of the material and over and under the screws there is moderate dense fibrosis with mild infiltration by lymphocytes, macrophages, and rare giant cells that surround the screws. There is mild periosteal new bone formation with increased osteoblasts and osteocytes. There are areas with mild osteoclast activity of mature trabecular bone.

FIG. 78. Six-week time point, MTG01, right posterior region.

A (2×): Bone plate and screws (indicated by stars).

B (10×): Degenerating screw (arrows) surrounded by fibrous tissue and infiltrating lymphocytes, macrophages, and multinucleated giant cells.

C (4×): New bone formation (circled).

D (10×): Mature bone remodeling with visible osteoclasts (arrows).

E (10×): Particulate debris (star) present within the fibrous tissue surrounding the screw.

One section of frontal bone with respiratory mucosa is examined. Along one edge, there is silver (subgross) to black/brown (microscopic) material that is consistent with the plate/screws. The main body of the screws are surrounded by dense bone. There is mild degradation of the material (mainly where it is not in contact with bone) and over and under the screws there is moderate dense fibrosis with mild infiltration by lymphocytes, macrophages, and rare giant cells that surround the screws and particulate material. There is mild new bone formation with increased osteoblasts and osteocytes. There are areas with mild osteoclast activity of mature trabecular bone.

Figure 79:
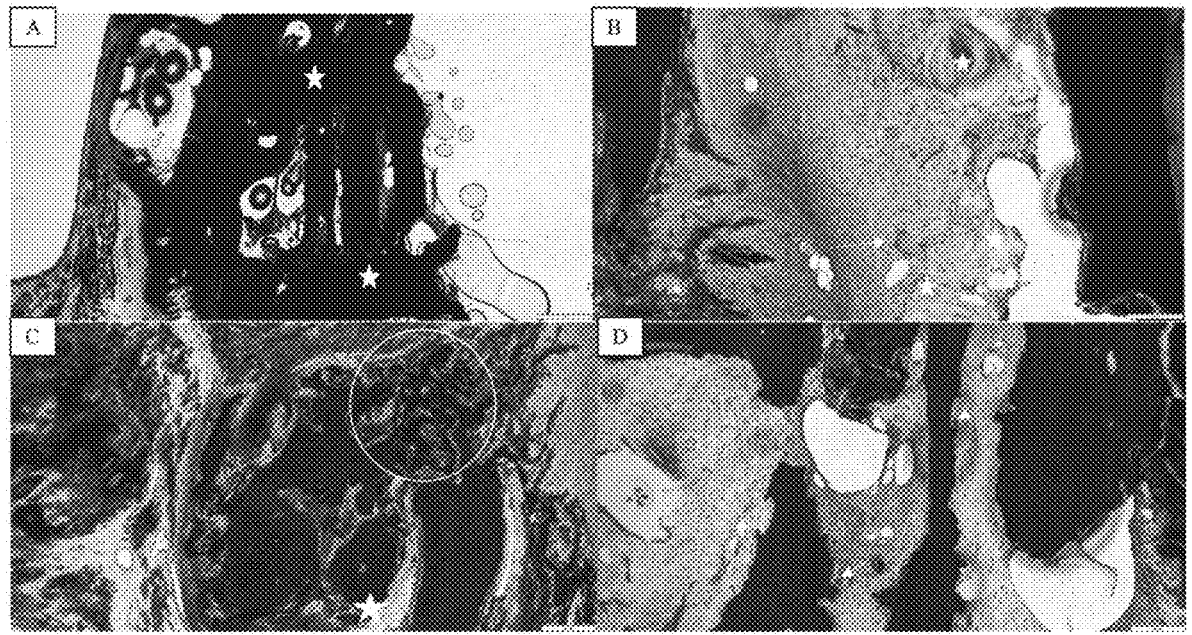

FIG. 79. Six-week time point, MTG01, left anterior region.

A (2×): Bone plate and screws (indicated by stars).

B (10×): Degenerating screw surrounded by fibrous tissue and infiltrating lymphocytes, macrophages, and multinucleated giant cells (arrow), with associated particulate debris (stars).

C (10×): New bone formation (circled).

D (10×): Mature bone remodeling with visible osteoclasts (arrows).

One section of frontal bone with respiratory mucosa is examined. Along one edge, there is silver (subgross) to black/brown (microscopic) material that is consistent with the plate/screws. The main body of the screws are surrounded by dense bone. There is mild degradation of the material (mainly where it is not in contact with bone) and over and under the screws there is moderate dense fibrosis with mild to moderate infiltration by lymphocytes, macrophages, and rare giant cells that surround the screws and particulate material. There is mild new bone formation with increased osteoblasts and osteocytes. There are areas with mild osteoclast activity of mature trabecular bone.

Figure 80:
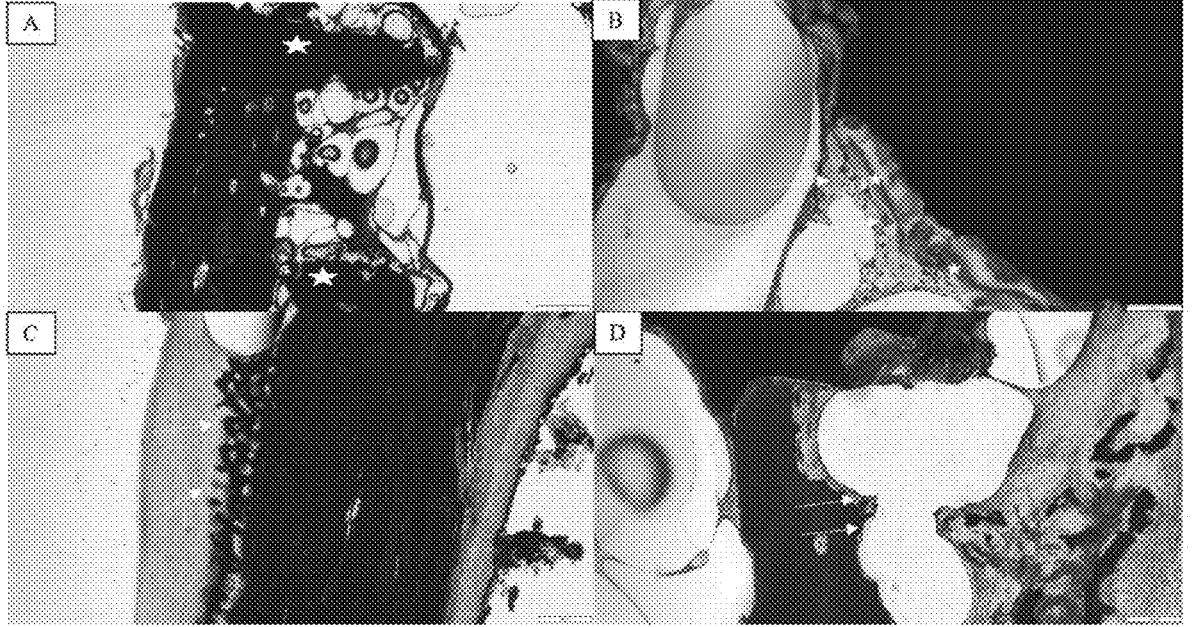

FIG. 80. 6-weeks, MTG01, Left posterior.

A (2×): Bone plate and screws (stars).

B (20×): Screw degeneration (stars) surrounded by fibrosis and lymphocytes, macrophages, and giant cells (arrows).

C (20×): Periosteal new bone formation (arrows).

D (10×): Mature bone remodeling with osteoclasts (arrows) with surrounding fibrosis.

One section of frontal bone with respiratory mucosa is examined. Along one edge, there is silver (subgross) to black/brown (microscopic) material that is consistent with the plate/screws. The main body of the screws are surrounded by dense bone. There is mild degradation of the material (mainly where it is not in contact with bone) and over and under the screws there is moderate dense fibrosis with mild to moderate infiltration by lymphocytes, macrophages, and rare giant cells that surround the screws and particulate material. There is mild periosteal new bone formation with increased osteoblasts and osteocytes. There are areas where mild osteoclast activity of mature trabecular bone.

Figure 81:
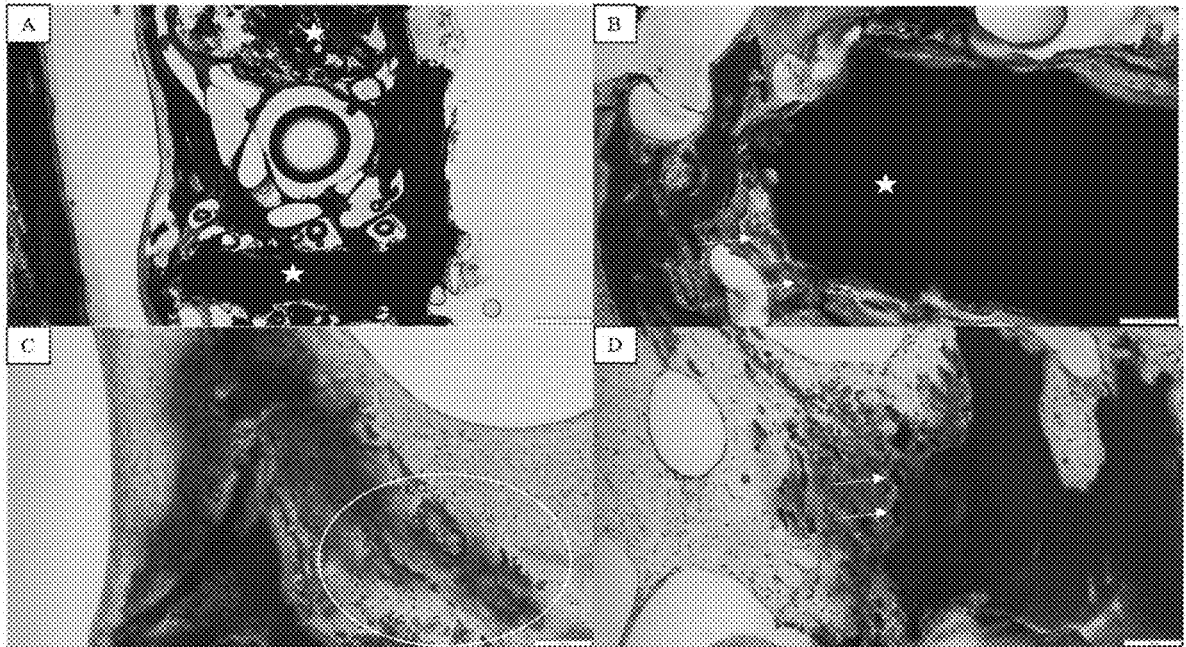

FIG. 81. 12-weeks, MTG02, Right anterior.

A (2×): Bone screws (stars).

B (10×): Mild fibrosis with lymphocytes, macrophages, and giant cells surrounding screw (star) and screw degeneration (arrows).

C (20×): New bone formation (circle).

D (10×): Mature bone remodeling with osteoclasts (arrows) with surrounding fibrosis.

Two sections of frontal bone with respiratory mucosa are examined. Along one edge, there is silver (subgross) to black/brown (microscopic) material that is consistent with the plate/screws.

There is moderate degradation of the material and it is surrounded by moderate dense fibrosis with mild infiltration by lymphocytes, macrophages, and rare giant cells. There are areas surrounding the material and within the fibrosis where there is mild new bone formation with increased osteoblasts and osteocytes. There are areas of fragmented bone with mild osteoclast activity.

Figure 82:
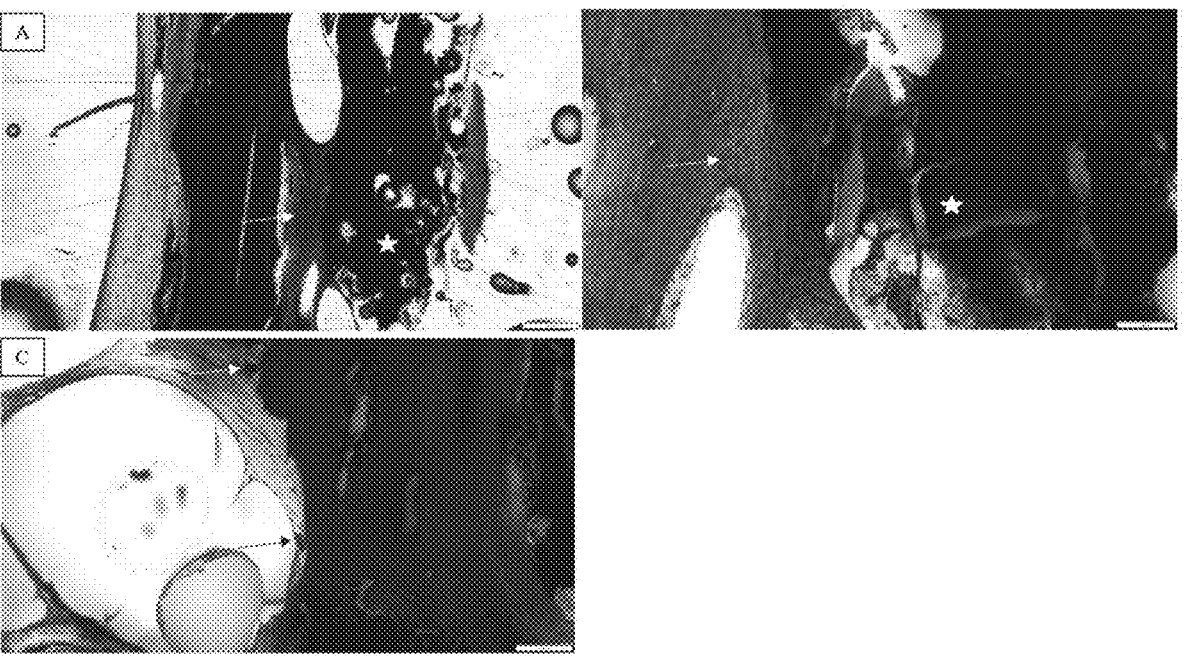

FIG. 82. 12-weeks, MTG02, Right posterior.

A (4×): Bone screw (star) with degeneration and surrounding fibrosis (arrows).

B (20×): Mild fibrosis with lymphocytes, macrophages, and giant cells (arrows) and screw degeneration (star).

C (20×): Mature bone remodeling with osteoclasts (arrows).

One section of frontal bone with respiratory mucosa is examined. Along one edge, there is silver (subgross) to black/brown (microscopic) material that is consistent with the plate/screws. There is moderate degradation of the material and it is surrounded by moderate dense fibrosis with mild infiltration by lymphocytes, macrophages, and giant cells. In some areas with degradation of the material there is in filtration by lymphocytes and macrophages. There are areas surrounding the material and within the fibrosis where there is mild new bone formation with increased osteoblasts and osteocytes. There are areas of mature bone with osteoclast activity.

Figure 83:
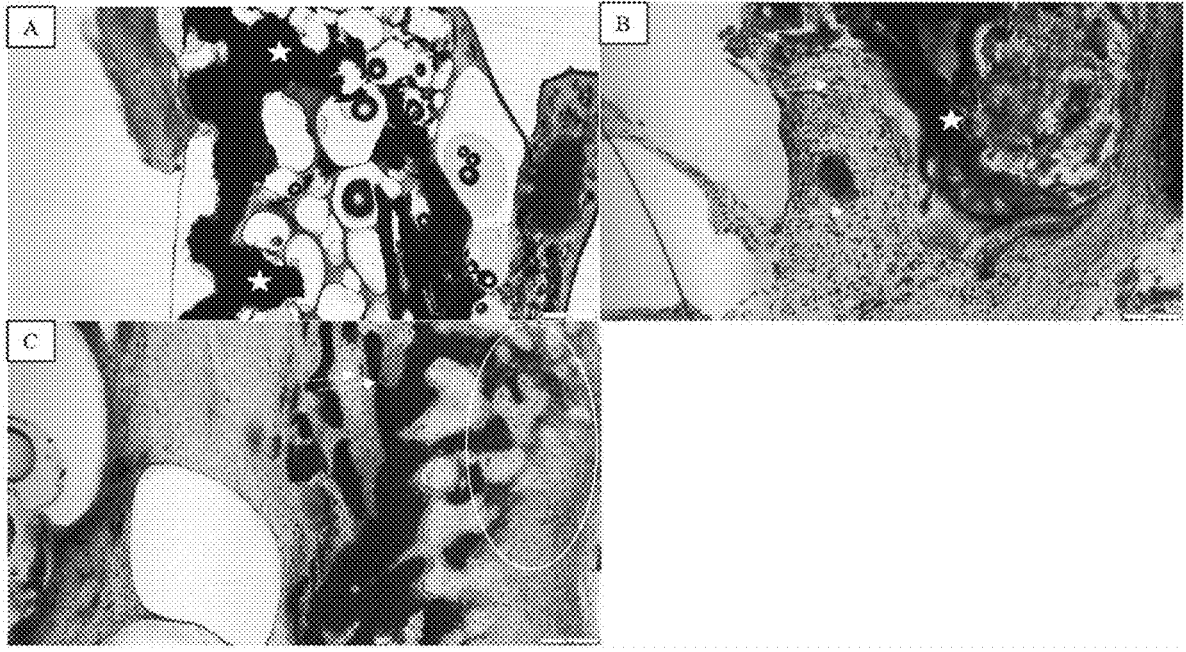

FIG. 83. 12-weeks, MTG02, Left anterior.

A (2×): Bone screw (stars).

B (10×): Fibrosis with lymphocytes, macrophages, and giant cells (arrows) surrounding screw degeneration (star).

C (20×): Mature bone remodeling with osteoclasts (arrows) and new bone formation (circle).

Two sections of frontal bone with respiratory mucosa are examined. Along one edge, there is silver (subgross) to black/brown (microscopic) material that is consistent with the plate/screws. There is moderate degradation of the material and it is surrounded by moderate dense fibrosis with rare neovascularization and mild infiltration by lymphocytes, macrophages, and giant cells. There are areas surrounding the material and within the fibrosis where there is mild new bone formation with increased osteoblasts and osteocytes. There are areas of fragmented bone with mild osteoclast activity.

Figure 84:
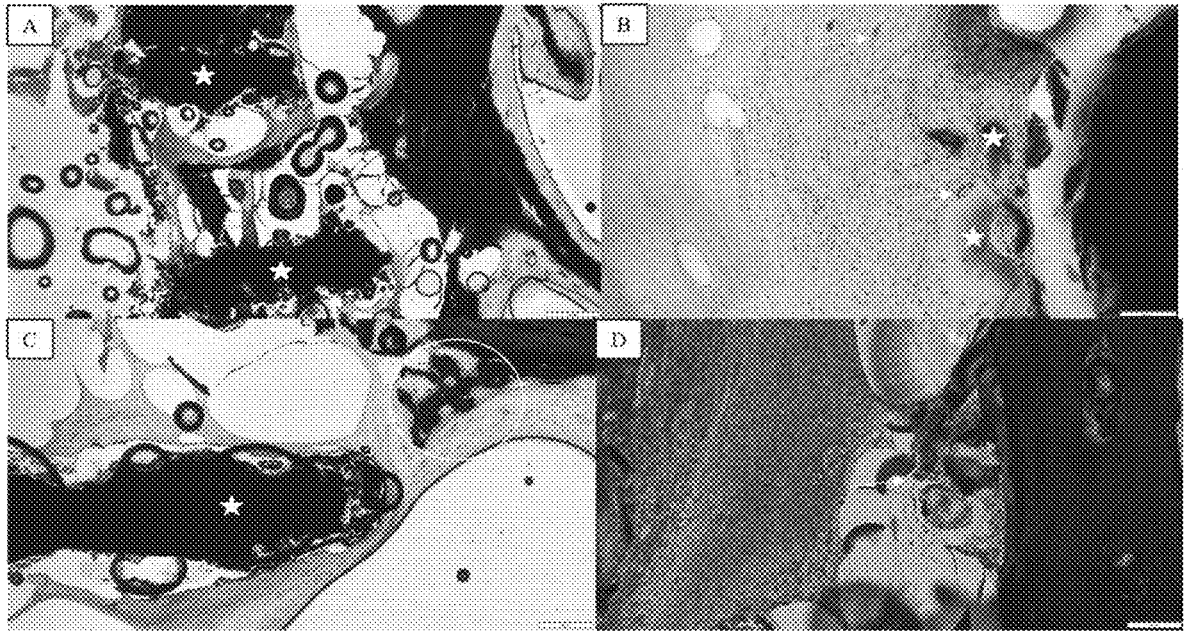

FIG. 84. 12-weeks, MTG02, Left posterior.

A (2×): Bone screw (stars).

B (20×): Fibrosis with lymphocytes, macrophages, and giant cells (arrows) surrounding screw degeneration (star).

C (4×): Bone screw (star) surrounding by fibrosis with new bone (circle).

D (20×): Mature bone remodeling with osteoclasts (arrows). Two sections of frontal bone with respiratory mucosa are examined. Along one edge, there is silver (subgross) to black/brown (microscopic) material that is consistent with the plate/screws. There is moderate degradation of the material and it is surrounded by moderate dense fibrosis with rare neovascularization and mild infiltration by lymphocytes, macrophages, and giant cells. There are areas surrounding the material and within the fibrosis where there is mild new bone formation with increased osteoblasts and osteocytes. There are areas of fragmented bone with mild osteoclast activity.

SEM/EDS of Histology Blocks

One of the 6-week tissue blocks was evaluated using Scanning Electron Microscopy and Electron-Dispersive Spectroscopy (SEM/EDS) to capture images and analyze the corrosion products formed during implantation. EDS scans of the surface layers were used to identify changes in corrosion products. See, e.g., Klima, K., Ulmann, D., Bartoš, M., Španko, M., Dušková, J., Vrbová, R., Pinc, J., Kubásek, J., Vlk, M., Ulmannová, T., Foltán, R., Brizman, E., Drahoš, M., Beňo, M., Machoň, V., & Čapek, J. (2021). A Complex Evaluation of the In-Vivo Biocompatibility and Degradation of an Extruded ZnMgSr Absorbable Alloy Implanted into Rabbit Bones for 360 Days. International *journal of molecular sciences*, 22(24), 13444, which is hereby incorporated by reference in its entirety herein. The literature can also be found at https://doi.org/10.3390/ijms222413444. SEM imaging, combined with ImageJ analysis, was also used to determine the thickness of the corrosion layer.

Sample Preparation

Histology block samples were polished using 1200 grit SiC grinding paper, followed by polishing with 1 μm MetaDi Supreme Diamond Suspension (Buehler 40-6730) and TexMet C cloth (Buehler 40-1108). The polished samples were then imaged and analyzed using a JEOL 6610 LV SEM with EDS (Michigan State University's Plant Sciences Building).

Figure 42:
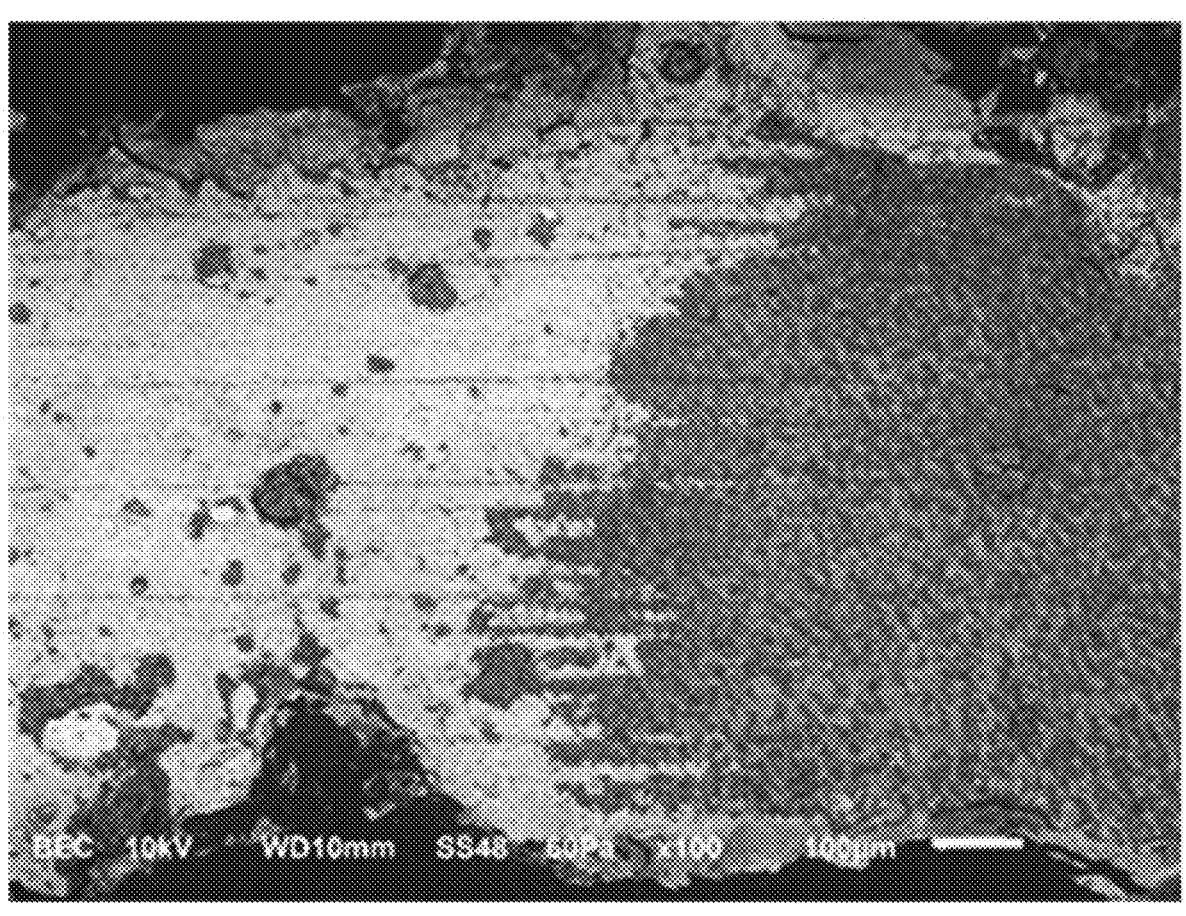
FIG. 42 illustrates a scanning electron microscope micrograph of a microstructure sample, according to an embodiment.

Analysis of the 6-week and 12-week histology samples using scanning electron microscopy (SEM) revealed evidence of localized pitting at $Mg_2Ca$ precipitate phases at the edge of the implant, as shown in FIGS. 41A and 41B, and preferentially attacking the $Mg_2Ca$ phases with rapid progression along the screw length in FIG. 42. FIGS. 41A and 41B show SEM images of 6-week histology samples. FIG. 41A shows the center of the screw. In FIG. 41B, screw thread shows localized pitting at precipitate phase locations along the edge of the implant. A large pit at the screw surface is indicated by a white arrow. Comparing the size of the $Mg_2Ca$ precipitate phases near the edge of the implant to those at its center, the size and fraction are larger at the surface, further promoting localized attack and breakdown of the protective oxide layer. FIG. 42 shows SEM image of a 12-week histology sample showing localized pitting at precipitate phase locations occurring rapidly along the screw length. Table 28 shows that the amount and size of precipitates were larger near the corrosion layer along with a comparison to the feedstock material (machined PD B plates). This finding further demonstrates the pitting potential of $Mg_2Ca$ and its impact on corrosion uniformity.

TABLE 28

Comparison of precipitate phase size and amount at the center and edge of 6-week screw explant, with reference to implant feedstock material (PD B).

| Sample | Time Point (weeks) | % Area Precipitates | Avg Precipitate Size (micron$^2$) | Std Dev Precipitate Size (micron$^2$) |
|---|---|---|---|---|
| PD B - Feedstock | 0 | 1.2 | 6.8 | 12.6 |
| Center of Screw | 6 | 0.9 | 5.9 | 8.14 |
| Edge of Screw Threads | 6 | 3.0 | 10.7 | 20.4 |

Figure 43:
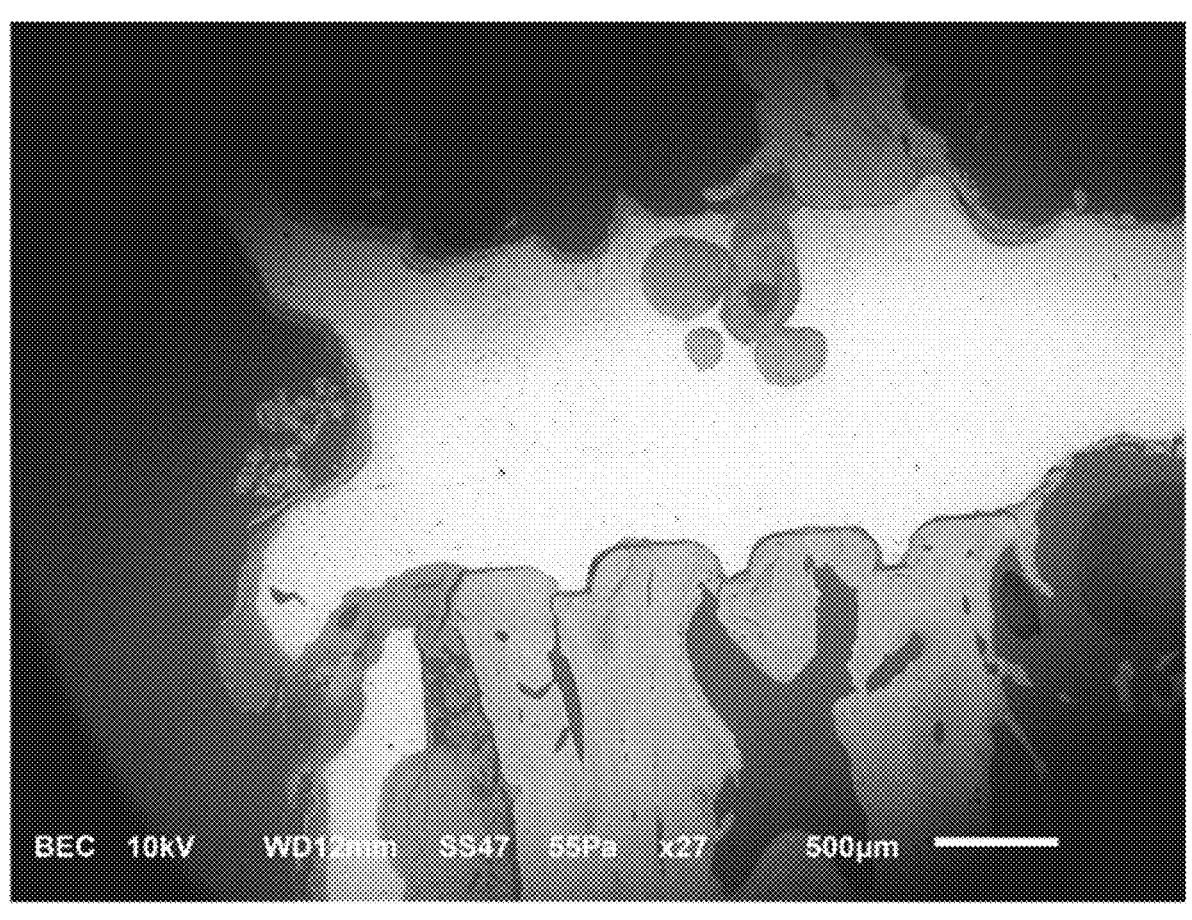
FIG. 43 depicts a scanning electron microscope image showing the interface between a plate and screw component, according to aspects of the present disclosure.

SEM/EDS of Histology Blocks: A representative backscatter SEM image of an explanted left anterior screw and plate at 6 weeks is shown in FIG. 43. The thickness of implant corrosion layer was measured at various locations around the perimeter of the plate and screw and the averages of these measurements are presented in Table 29.

TABLE 29

Thickness of the implant corrosion layer at various locations around the perimeter of the plate and screw.

| Tissue Block Sample | Location | Average Thickness of Corrosion Layer (microns) |
|---|---|---|
| MTG01 - 6 week Left Ant. Tissue Block | Top of Plate | 94 |
| | Bottom of Plate (along bone) | 340 |
| | Screw Head | 118 |
| | Screw threads (in bone) | 42 |

Figure 44:
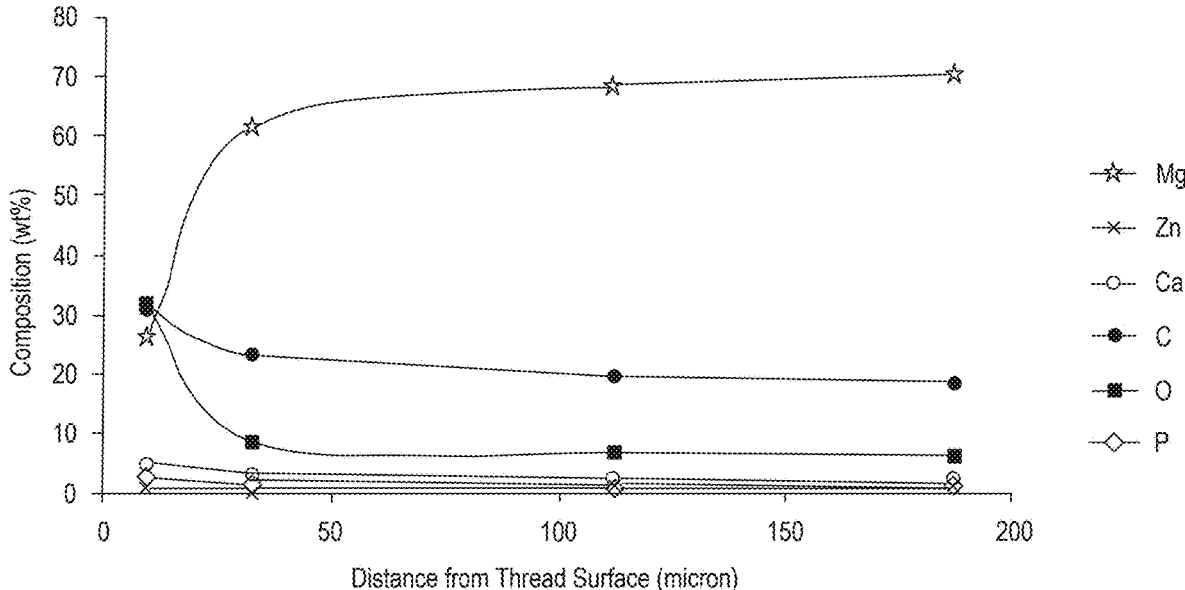
FIG. 44 shows a graph of elemental composition analysis measured from a thread surface inward, according to an embodiment.
Figure 45:
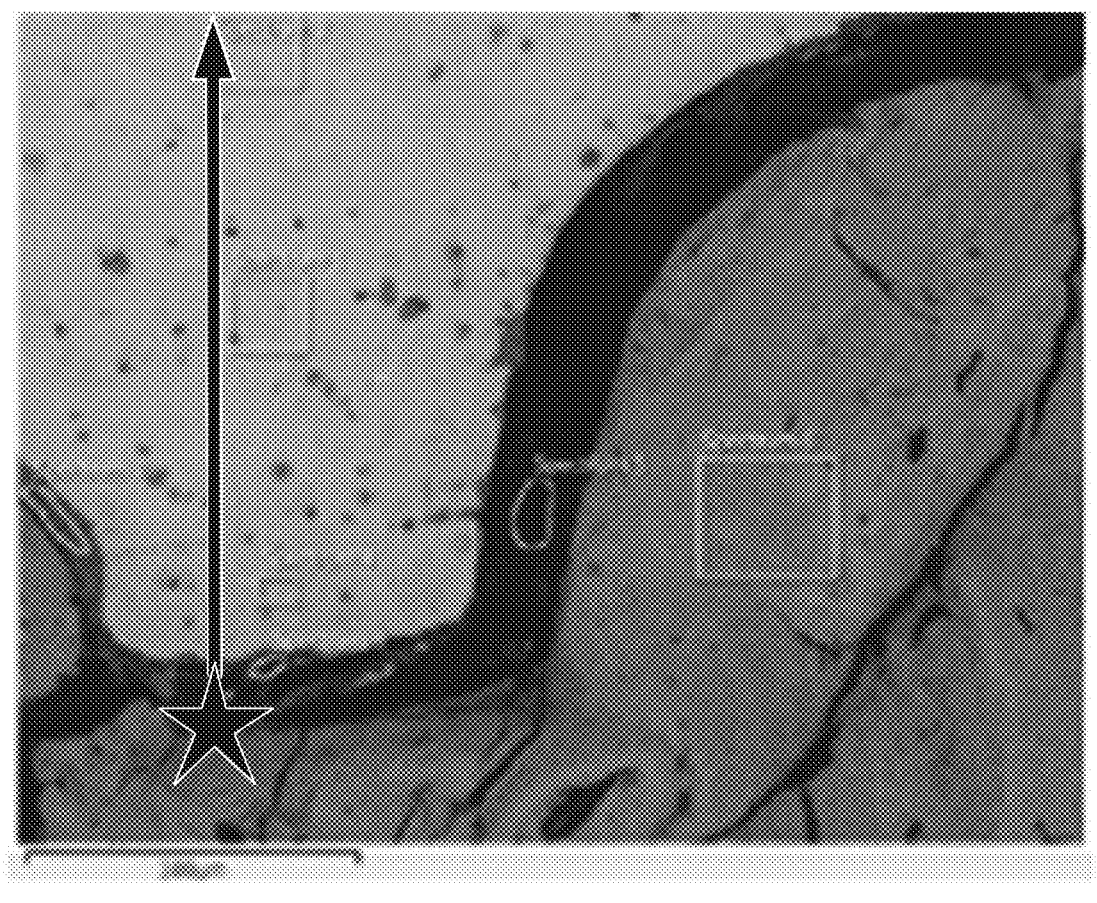
FIG. 45 illustrates a scanning electron microscope micrograph displaying an elemental analysis location on a thread surface, according to aspects of the present disclosure.

The threads of the screws at 6 weeks were analyzed using EDS to evaluate how the composition of the corrosion product and implant changes from the edge of the corrosion layer toward the center of the implant. The results demonstrated Ca, C, O, and P content in the corrosion layer was higher than that of the implant itself. The Mg content was lower in the corrosion layer than in the screw itself while the Zn content remained relatively unchanged. The results are presented in FIGS. 44 and 45. FIG. 44 is a plot showing the composition of the corrosion product and implant from the edge of the corrosion layer to the center of the implant. FIG. 45 is a corresponding SEM image indicating the locations where the EDS spectra were collected. In the SEM image, the star marks the edge of the corrosion product layer, and the arrow points toward the center of the implant.

Discussion

Maxillofacial Frontal Bone Ostectomy Pilot Preclinical Study

The PD-B alloy (e.g., Curasorb Alloy) demonstrated promising outcomes in this pilot preclinical study, with notable successes in early bone-to-implant integration and localized healing. Both the 6-week and 12-week timepoints revealed important insights into the in vivo absorption profile and bone regeneration potential of Curasorb Alloy.

The digital images show that new tissue has formed over most of the bilateral osteotomies and some tissue overgrowth has formed on the implants. The digital images also present evidence of absorption of the implants, as the devices have darkened since implantation. The radiographs demonstrate bone healing has begun along the osteotomy lines.

Figure 46A:
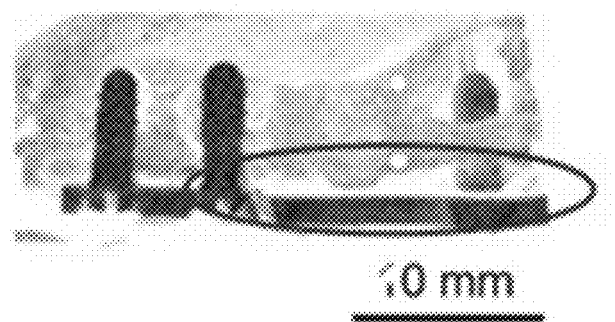
FIGS. 46A, 46B, 47A, and 47B depict microscopic images of bone samples with implanted devices, according to an embodiment.
Figure 47A:
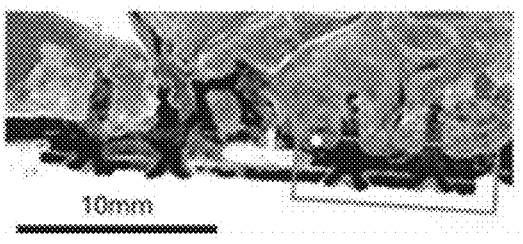
Figure 46B:
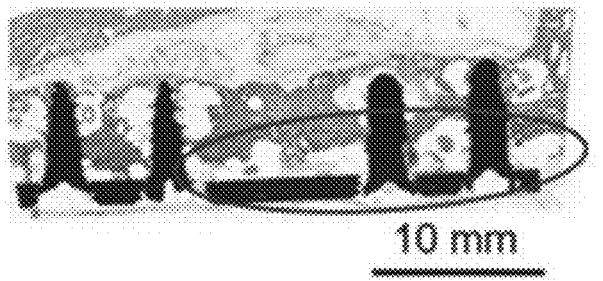
Figure 47B:
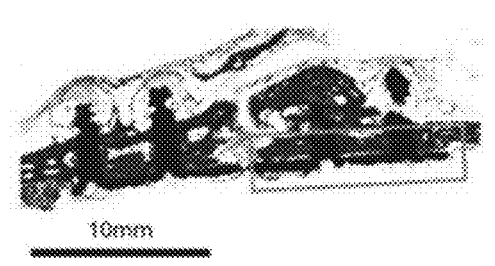

2D and 3D micro-CT images and radiographs demonstrate the progression of bone fusion of the ostectomies, with a strong bone-to-implant interface for all 8 alloy plate systems of differing compositions as shown in Table 3. Compared to similar preclinical studies utilizing MgYREZr magnesium alloys by Schaller et al, Imwinkelried et al (2020), and Naujokat et al (2017), the Curasorb-based Akesorb Maxillofacial System prototypes demonstrate a slower initial absorption rate resulting in the strong bone-implant interface, as predicted by in-vitro testing and published literature. Comparison of 2D micro-CT images and histology images from Imwinkelried et al (2020) (FIG. 46) revealed that both methods show bone density loss due to fast-absorbing magnesium-based implants. In contrast, the Curasorb-based system maintained bone density, confirming the first objective of this Akesorb pilot preclinical study has been achieved. FIGS. 46A and 46B show a 2D micro-CT (top) and histology (bottom) of 6-week MgYREZr explants in a porcine mandible osteotomy [Imwinkelried et al (2020)], and FIGS. 47A and 47B show a 2D micro-CT (top)

and histology (bottom) of 6-week Curasorb Alloy (right) explants in the ovine frontal bone ostectomy preclinical study.

At 6-weeks, micro-CT reconstructions demonstrated strong bone-to-implant contact and evidence of immature bone remodeling, indicating successful early integration of the Curasorb implants. By the 12-week timepoint, a substantial amount of implant resorption was evident, and the micro-CT reconstructions revealed partial bone bridging across the defect. The quantitative micro-CT analysis of bone volume fraction and bone mineral density evaluated a ROI that included bone adjacent to the implant, however this analysis does not inform on the efficacy of the repair or on the resorption of the implant. Due to the implant and screw material residing in a similar density range of the surrounding bone, a shortcoming of using microCT to evaluate the implant regions does not allow the differentiation of implant material to surrounding bone. When evaluating microCT, ROI2 regions may include the native bone as well.

Similarly, histomorphometry did not provide conclusive insights into the repair's efficacy due to the heterogeneous structure of the underlying bone. When sectioning for histology, exact centerline cuts were not achievable which caused the plane of histology slides to be slightly off. This posed a potential limitation when evaluating the implant constructs using histomorphometry analysis due to each slide cut in a different plane sometimes reducing the amount of implant in a section. Alternative analyses such as semi-quantitative assessments of bone repair and bridging may improve future studies. A more detailed study with larger sample size needs to be conducted to determine the appropriateness of the technique.

MicroCT and histomorphometry results demonstrated a slight decrease in absorption rate from 6-weeks to 12-weeks. MicroCT data revealed 32% absorption (absorption rate of 0.62 mm/yr) at 6 weeks and 55% absorption at 12 weeks (absorption rate of 0.54 mm/yr). Histomorphometry analysis revealed similar results, demonstrating a 35% absorption (absorption rate of 0.69 mm/yr) at 6 weeks and 65% absorption (absorption rate of 0.64 mm/yr) at 12-weeks. Meanwhile, the in vitro corrosion results demonstrated a corrosion rate of 0.05 mm/yr at 3 weeks (measured) and 0.11 mm/yr at 6 weeks (extrapolated), indicating the in vivo absorption rate in frontal bone applications is approximately six times faster than the in vitro corrosion rate.

Histopathology results showed slight inflammation and mild reactivity at both time points, indicating good biocompatibility. Further, neither time point showed evidence of necrosis. A study on WE43 (MgYREZr) plate and screw systems with a PEO coating versus polylactide-co-glycolide (PLGA) plate and screw systems in a porcine supraorbital rim osteotomy and zygomatic arch osteotomy model by Schaller et al demonstrated similar results, with slight inflammation at 1 month and minimal inflammation at 9 months for both treatment groups. Similar findings of no to slight inflammation with WE43 were also reported by Naujokat et al (2017) and Torroni et al. A study on ZX00 and Ti compression screws inserted into ovine tibiae by Marek et al reported no to slight inflammation for the ZX00-screws and no inflammation for the Ti-screws, with comparable results for ZX00 implants observed in studies by Holweg et al. and GrUn et al. Overall, Curasorb demonstrates comparable biocompatibility to WE43 and ZX00, showing a consistent lack of necrosis and only mild inflammatory responses.

SEM/EDS results revealed significant differences in elemental composition between the corrosion layer and the uncorroded implant core, which are indicative of the mechanisms driving the degradation process. The elevated levels of calcium, carbon, oxygen, and phosphorus in the corrosion layer suggest the formation of calcium and phosphorus-rich corrosion products, likely hydroxyapatite or similar compounds. These products are commonly associated with the biological environment and indicate potential interaction between the implant material and surrounding tissue fluids. Such interactions may play a critical role in promoting osseointegration, as these compounds are biologically compatible and can support bone regeneration. The reduced magnesium content in the corrosion layer relative to the implant core aligns with the expected dissolution of magnesium during the corrosion process. This dissolution is a key feature of bioabsorbable magnesium alloys, where magnesium degrades and is replaced by corrosion products. In contrast, the relatively unchanged zinc content suggests that zinc plays a more stable role within the alloy, potentially contributing to the mechanical integrity of the implant during the degradation process. The presence of biologically favorable elements in the corrosion layer supports the potential of the material to facilitate osseointegration. However, the balance between corrosion rate and mechanical integrity remains critical and warrants further optimization.

Comparing the Corrosion Rates of Comparative Bioabsorbable Magnesium Alloys

Figure 48:
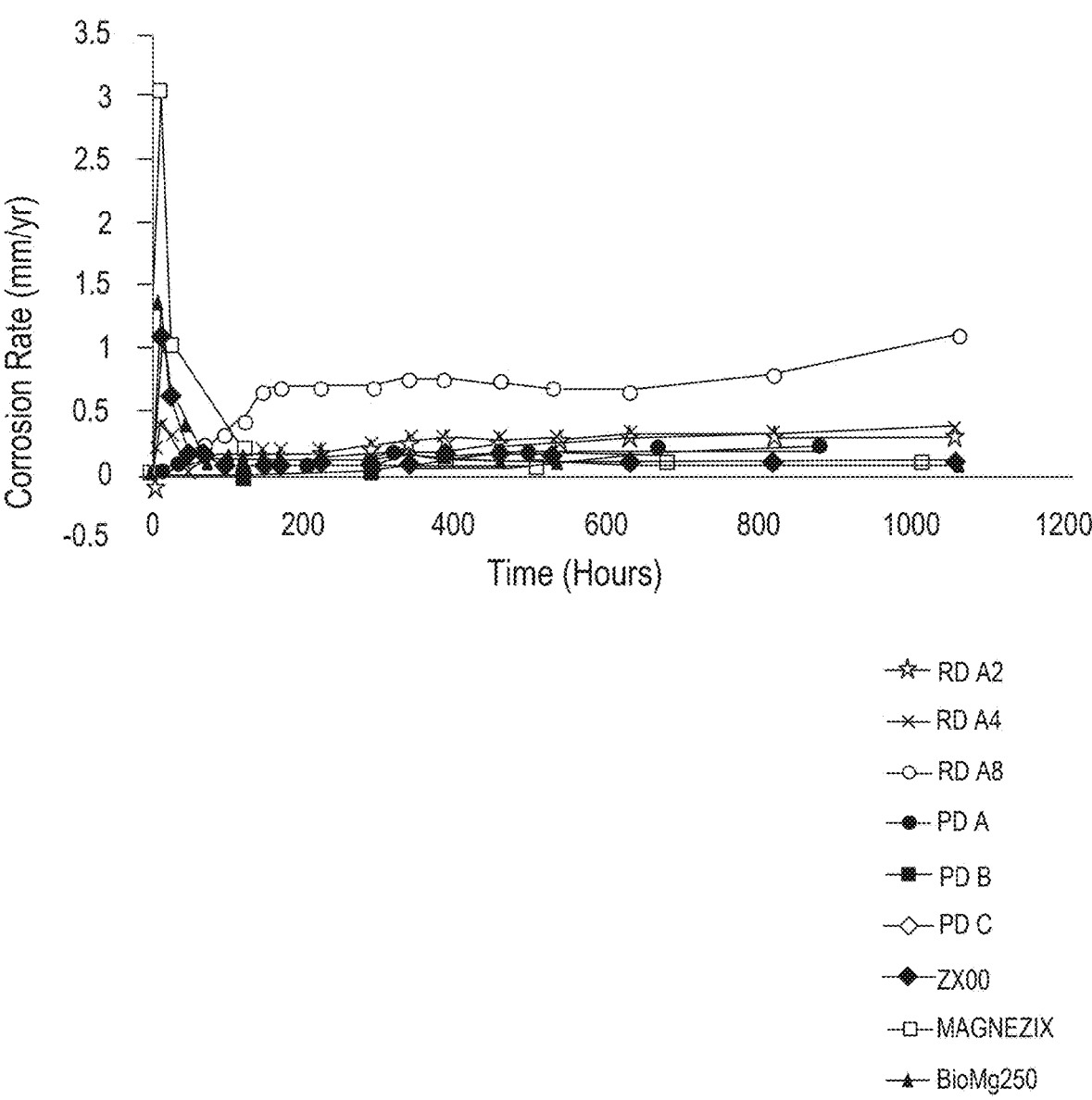
FIG. 48 shows a graph comparing corrosion rates over time for several different materials, according to aspects of the present disclosure.

The in vitro immersion corrosion results for multiple iterations of Curasorb Alloy along with a comparison to comparative alloys ZX00, BioMg250, and MAGNEZIX (a MgYREZr alloy) is presented in FIG. 48. The immersion corrosion results show how the comparative alloys have a burst of corrosion at the start, and then flatten out to a slow corrosion rate as time progresses. Such a profile can be problematic in vivo since published preclinical studies, confirmed by EU-based surgeon interviews, have widely documented bone density loss adjacent to the implant resulting from the fast initial release rate of alloy absorption products. Initial burst of absorption can result in a loss of the overall strength of the implant prior to healing, confirmed by reports of clinical failures, of the fracture/osteotomy and the overall, relatively, slow rate of absorption after the burst results in implants that remain far beyond the target of 1-2 years to reach full absorption.

Figure 49:
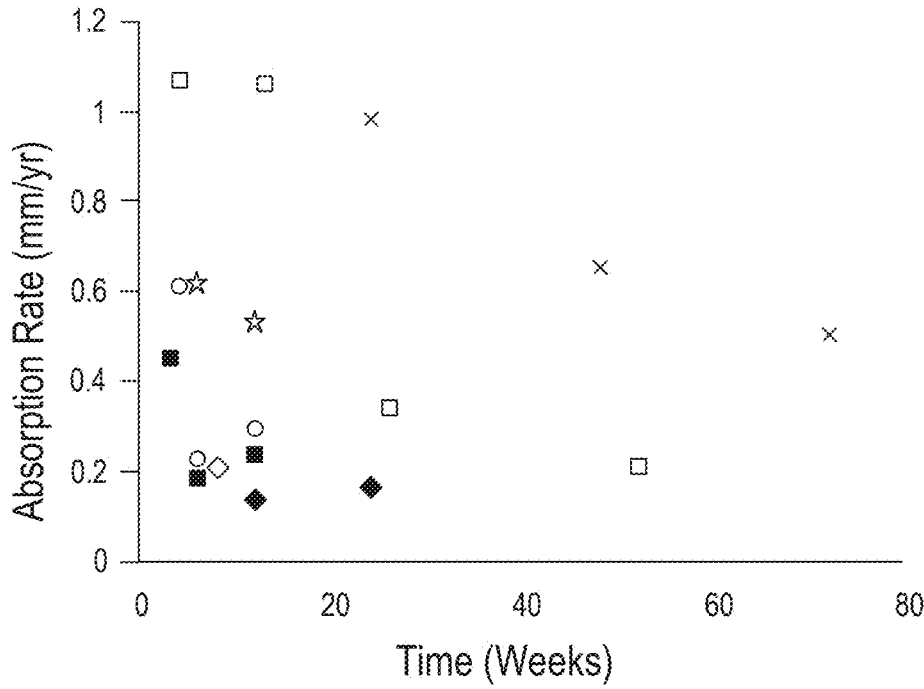
FIG. 49 illustrates a scatter plot comparing absorption rates over time for different materials, according to an embodiment.

Multiple preclinical studies of competing bioabsorbable magnesium alloys have been published for comparison to the ovine frontal bone pilot preclinical study. Edick et al studied BioMg250 plates and screws in a canine mandible fracture model, determining absorption rate at 4-weeks, 13-weeks, 26-weeks, and 52-weeks via micro-CT and mass loss. Kopp et al studied ZX00MEO screws with and without a PEO coating in a porcine frontal bone model (no osteotomy), determining absorption rate at 6 months, 12 months, and 18 months via micro-CT. See, e.g., Edick J, Woldring C, Decker R, Woods S, Petticoffer A, Wilson T, Sfeir C, Lukashova L, Stanley J, LeBeau S (2021) Performance of BioMg 250 Hardware Demonstrated by Biomechanical Testing, Histology and Absorption Characterization in a Canine Mandible Osteotomy Model Through 52 Weeks. Marek et al studied ZX00 screws in an ovine tibial model (no osteotomy), inserting screws in the epiphysis and metaphysis of the bone and determining absorption rate at 4-weeks, 6-weeks and 12-weeks via microCT. Holweg et al studied ZX00 screws in an ovine tibial model (with and without osteotomy), inserting screws in the epiphysis and tibial shaft of the bone and determining absorption rate at 3-weeks, 6-weeks and 12-weeks via microCT Naujokat et al (2020) studied MgYREZr alloy plates and screws with and without surface conditioning (hydrogenation or fluoridation) in a porcine mandibular osteotomy model, determining absorption rate at 8 weeks via microCT and histological analysis. Imwinkelried et al (2013) studied MgYREZr alloy plates and screws with and without surface modification in a porcine nasal bone model (no osteotomy), determining absorption rate at 12 weeks and 24-weeks via weight loss. See, e.g., Imwinkelried T, Beck S, Iizuka T, Schaller B (2013) Effect of a plasmaelectrolytic coating on the strength retention of in vivo and in vitro degraded magnesium implants. Acta Biomaterialia 9(10):8643-8649, which is hereby incorporated by reference in its entirety herein. The literature can also be found at https://doi.org/10.1016/J.actbio.2012.08.047. The internal pilot preclinical testing of Curasorb Alloy in an ovine frontal bone ostectomy model determined absorption rate at 6 weeks and 12 weeks via microCT and histological analysis. A summary of these results (non-coated implants only) is presented in FIG. 49. FIG. 49 shows the in vivo absorption rates of Curasorb Alloy and comparative alloys ZX00, BioMg250, and MgYREZr in various preclinical models. The internal in vitro immersion corrosion results of Curasorb Alloy PD-B, ZX00, BioMg250, and MAGNEZIX Alloy (MgYREZr, Syntellix) and the in vivo absorption rates are presented in Table 30. Table 30 also includes a comparison of the in vitro results to their respective material in vivo absorption rates.

TABLE 30

Comparison of in vitro corrosion rates and in vivo absorption rates
of Curasorb Alloy and comparative alloys ZX00, BioMg250, and MgYREZr.

| Alloy | In Vitro Corrosion Rate (mm/yr) | | In Vivo Model | Osteotomy? | In Vivo Absorption Rate (mm/yr) | | In Vivo to In Vitro |
|---|---|---|---|---|---|---|---|
| | 24 hrs | 6 wks | | | | | |
| Curasorb PD-B | 0.05 | 0.11 | Ovine Frontal Bone | Yes | 6 weeks: 0.62 | 12 weeks: 0.54 | 6x |
| ZX00 | 0.63 | 0.08 | Porcine Frontal Bone | No | 24 weeks: 0.73 | | 9x |
| | | | Ovine Tibia | Yes | 6 weeks: 0.18 | 12 weeks: 0.24 | 2x |
| | | | Ovine Tibia | No | 6 weeks: 0.23 | 12 weeks: 0.30 | 3x |

TABLE 30-continued

Comparison of in vitro corrosion rates and in vivo absorption rates
of Curasorb Alloy and comparative alloys ZX00, BioMg250, and MgYREZr.

| Alloy | In Vitro Corrosion Rate (mm/yr) | | In Vivo | | In Vivo Absorption | | In Vivo to In |
|---|---|---|---|---|---|---|---|
| | 24 hrs | 6 wks | Model | Osteotomy? | Rate (mm/yr) | | Vitro |
| MAGNEZIX (MgYREZr) | 1.02 | 0.08 | Porcine Mandible | Yes | 8 weeks: 0.21 | | 3x |
| | | | Porcine Nasal Bone | No | 12 weeks: 0.14 | 24 weeks: 0.16 | 2x |
| BioMg250 | 0.63 | 0.09 | Canine Mandible | Yes | 4 weeks: 1.1 | 13 weeks: 1.1 | 12X |

A large discrepancy in the correlation from in vivo to in vitro data for frontal bone indications is observed between Curasorb Alloy and ZX00. Several factors may be influencing this difference, including implant type, osteotomy vs no osteotomy, and the time point used to compare the ZX00 in vivo data (24 weeks) to the in vitro data (6 weeks). The culprits of this discrepancy may be due to the implant type and difference in timepoints. Kopp et al presented the degradation rate of ZX00 screws inserted in frontal bone, whereas this study studied the degradation rate of Curasorb Alloy plates and screws used to fixate an ostectomy in frontal bone, presenting the degradation rate of the entire construct (plate and screws). The degradation rate of screws inserted directly into bone is expected to be higher than a plate and screw construct due to exposure to cancellous bone tissue and the internal environment within the bone being more acidic and having more metabolic activity. In fact, Marek et al demonstrated higher absorption rates for screws inserted in the epiphysis than in the metaphysis of the distal tibia, due to differences in blood supply and bone density. Both the ovine tibia data and the frontal bone data sets indicate that the absorption rate is lower in the presence of an osteotomy; however, Holweg et al reported that ZX00 screws did not show a significant difference in volume loss between the fractured and non-fractured sides. This trend goes against conventional wisdom, as the presence of a fracture or osteotomy would increase the mechanical load on the implant and increased osteoclast activity due to bone remodeling, both of which can cause the absorption rate to increase; however, Holweg's observation may be due to the already lower absorption rates observed in extremities as opposed to maxillofacial indications.

A large discrepancy in the correlation from in vivo to in vitro data for mandible indications is also observed between the MgYREZr and BioMg250 study. This discrepancy may be due to how the MgYREZr in vitro and in vivo data was collected and due differences in processing between the material used in the BioMg250 study and the material used in internal immersion corrosion testing. Due to the oxide layer that forms on RE-based bioabsorbable magnesium samples, differences in both absorption and corrosion rates can be observed whether or not that oxide layer is included, the thickness of the oxide layer itself, and the method of determining absorption/corrosion rate (i.e., by mass or by volume).

Reducing the amount of $Mg_2Ca$ phases may help control corrosion rate and uniformity by controlling precipitate phase size and volume fraction. Eliminating anodic phases can help reduce $Mg_2Ca$.

Example 9: Process Optimization

This example demonstrates the process optimization for second extrusions of a magnesium alloy with composition Mg-2% Zn-1% Ca-1% Mn. Various extrusion conditions and heat treatments were explored to optimize the alloy's microstructure, mechanical properties, and corrosion resistance.

Samples were prepared under different processing conditions, including solution treatment temperatures of 410° C. and 430° C., followed by extrusion at different temperatures (350° C. and 400° C.) and extrusion ratios (ER 25 and ER 39). See Table 31.

TABLE 31

| Sample ID | Ext. ID - Billet # | Target Comp. (wt %) | Sample Condition | Testing |
|---|---|---|---|---|
| PD 26-1 | B-21 | Mg—2%Zn—1%Ca—1%Mn | ST: 410° C./24 hrs/FAC | Tensile, |
| PD 26-2 | (vertical ST) | | ST: 410° C./24 hrs/FAC + Ext.: ER 25, 350° C. | Metallography, Immersion |
| PD 26-3 | | | ST: 410° C./24 hrs/FAC + Ext.: ER 39, 400° C. | Corrosion |
| PD 26-4 | B-24 | | ST: 430° C./24 hrs/FAC | Metallography, |
| PD 26-5 | (vertical ST) | | ST: 430° C./24 hrs/FAC + Ext.: ER 25, 350° C. | Immersion Corrosion |
| PD 26-6 | | | ST: 430° C./24 hrs/FAC + Ext.: ER 39, 400° C. | |

Figure 50:
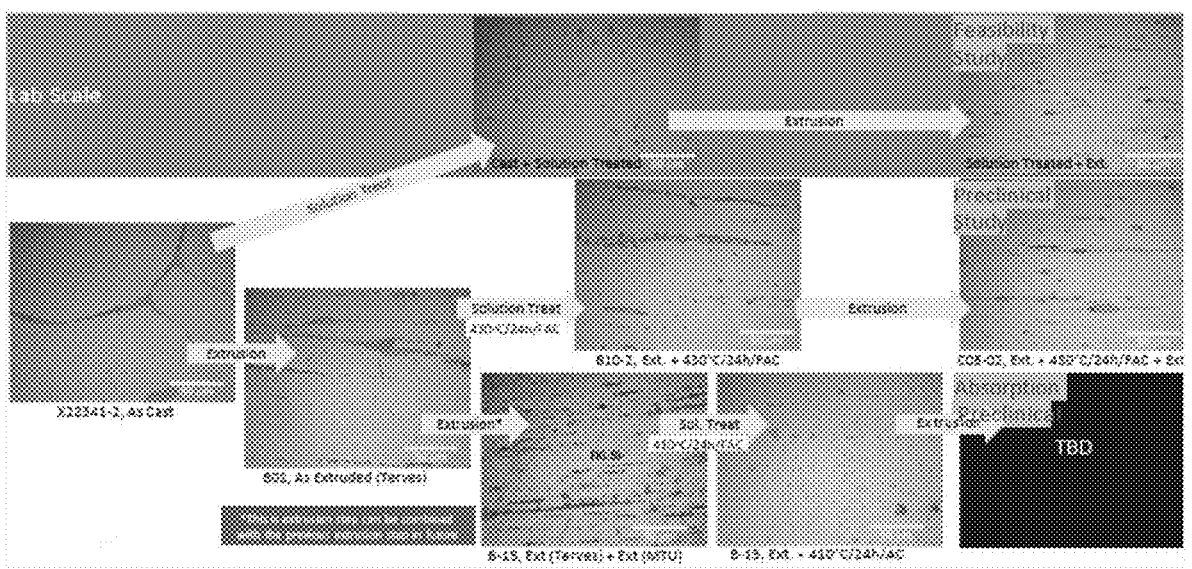
FIG. 50 depicts a series of microscopic metallographic images arranged in a process sequence format, according to aspects of the present disclosure.

Several sets of metallographic images are presented, showing the microstructure of different samples in the longitudinal direction relative to extrusion. FIG. 50 shows metallographic images of a sample undergoing different processes.

FIG. 51 shows metallographic images of group I samples (Ext. ID—Billet B-21). These include comparisons between different extrusion ratios and temperatures. Scanning Electron Microscopy images of group I samples shown in FIG. 52, highlighting the presence of bright intermetallic phases (identified as ternary phase) and dark intermetallic phases (identified as $Mg_2Ca$).

FIG. 53 shows metallographic images of group I samples (Ext. ID—Billet B-21). These include comparisons between different extrusion ratios and temperatures.

Metallography results suggest large IMs present in billets may have been reduced in size; however, higher temperatures (350 C and 375 C), did not show a reduction in size of the average billet IM.

Tensile testing results showed a significant decrease in strength for material extruded at higher temperatures. See Table 32. For instance, samples extruded at 400° C. (ER 39) exhibited a yield strength of 97 MPa, compared to 159 MPa for samples extruded at 350° C. (ER 25). This suggests that higher extrusion temperatures negatively impact the alloy's mechanical properties.

temperature to 325° C. or lower. This can be achieved by modifying the extrusion container geometry or billet length. The next phase of experiments will include extrusions using a 6.5×2 mm die, with one extrusion performed at the lowest possible temperature and another at 350° C. using a new process.

This example illustrates the iterative nature of alloy development and processing optimization, highlighting the complex interplay between processing parameters, microstructure, and material properties in bioabsorbable magnesium alloys.

TABLE 32

| Sample ID | Extrusion Parameters | Yield Strength, MPa | Tensile Strength, MPa | % elongation |
|---|---|---|---|---|
| Preclinical Plate | Temp: ~290° C.*; ER: 30 | 259 | 299 | 15.7 |
| PD-26-1 | Extrusion Billet | 130 | 238 | 23.0 |
| PD-26-2 | Temp: 350° C.; ER 25 | 159 | 262 | 12.0 |
| PD-26-3 | Temp: 400° C.; ER 39 | 97 | 240 | 19.7 |

*Extrusion temperature for preclinical plate material is an estimate. Extrusion temperature was measured by measuring the die temperature prior to extrusion.

Figure 54:
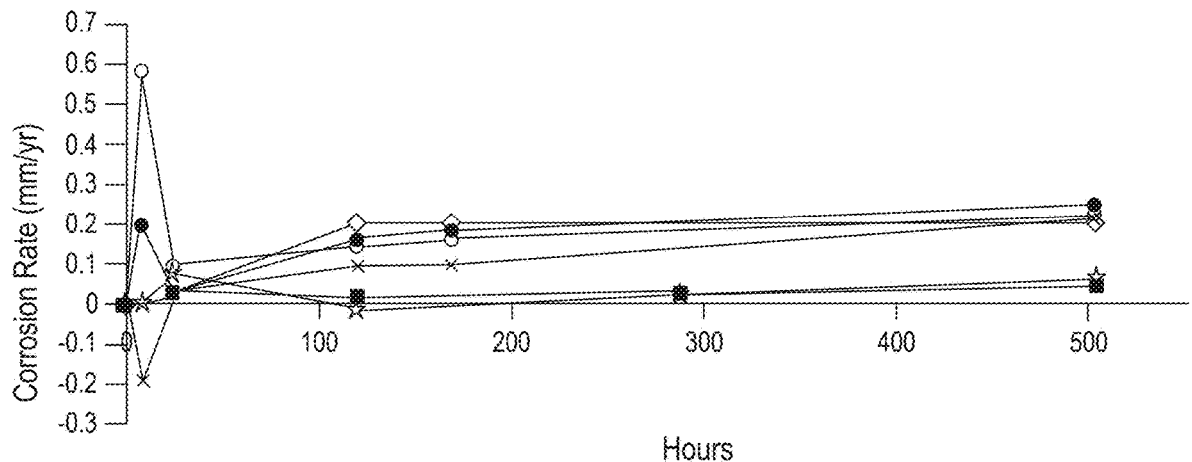
FIG. 54 illustrates a graph of corrosion rate data plotted against time for multiple samples, according to an embodiment.

Immersion corrosion tests indicated that higher extrusion ratios may have a positive impact on corrosion properties. However, the higher extrusion ratio was not sufficient to compensate for the negative effects of high extrusion temperatures on mechanical properties. See FIG. 54.

FIG. 55 shows samples of preclinical, group 1, and group 2 materials.

Large dip in strength was observed in material extruded at higher temperature (PD-26-3). Higher extrusion ratio was not enough to compensate for high extrusion temperature, suggesting that extrusion temperature should be reduced to 325 C or lower. Immersion corrosion results suggest that higher extrusion ratios did have a positive impact on corrosion properties.

Based on these findings, it was determined that future optimization efforts should focus on reducing the extrusion Example 10: Annealing and Aging of Alloy B Plates The purposed of these tests is to discern the effects of annealing and subsequent aging of Alloy B plates and to find the ideal temperature for reducing the formation of $Mg_2Ca$ precipitates.

Table 33 shows different samples and their extrusion-anneal-aging conditions. The following heat treat regime was executed: One specimen from each extrusion-anneal-aging setup was put aside to be imaged via SEM. Three specimens from each extrusion-anneal-aging group were later subjected to immersion corrosion in DMEM+0.2% Sodium-Azide solution to determine the effects of the heat treatment on corrosion properties.

TABLE 33

| Sample ID | Traceability Info | Sample Condition | Sample Description | Comments |
|---|---|---|---|---|
| PD-31-1 | Heat #1353DX, Charge #2 | CM R1G1T1 ST: 410° C./24 | 4-hole plate w/bar | n = 4 400° C./4 hr/AC |
| PD-31-2 | Billet ID: X22341-02 Ext.ID-Billet#: | hrs/FAC + Ext.: ER 25, 350° C. | (21028 Ver P2) | n = 4 400° C./4 hr/AC + 200° C./2 hr/AC |
| PD-31-3 | B-12 Mg—2%Zn—1%Ca—1%Mn | | | n = 4 400° C./4 hr/AC + 250° C./2 hr/AC |
| PD-31-4 | | | | n = 4 400° C./4 hr/AC + 300° C./2 hr/AC |
| PD-31-5 | | CM R1G1T2 ST: 410° C./24 | | n = 4 400° C./4 hr/AC |
| PD-31-6 | | hrs/FAC + Ext.: ER 39, 400° C. | | n = 4 400° C./4 hr/AC + 200° C./2 hr/AC |
| PD-31-7 | | | | n = 4 400° C./4 hr/AC + 250° C./2 hr/AC |
| PD-31-8 | | | | n = 4 400° C./4 hr/AC + 300° C./2 hr/AC |

FIGS. 59-64 depict a graph showing total percentage mass loss over time for multiple magnesium alloy samples under different heat treatment conditions.

FIGS. 65-68 show a series of images documenting the progressive degradation of magnesium alloy plate samples over time.

FIGS. 69-76 shows a SEM micrograph displaying a microstructural view of a magnesium alloy sample.

This experiment shows that high temperature heat treatment can be used to dissolve the ternary phase, then age at increasing temperatures to gradually re-introduce ternary phases in varying amounts to vary the corrosion rate.

The just-annealed group showed the lowest corrosion rate in both cases. Intuitively, this makes sense since there would be less time to grow precipitates without the subsequent aging.

Subsequent aging following a homogenizing anneal increases corrosion rate with increasing temperature. Intuitively, this makes sense, since higher temps provide more energy for precipitates to grow and become coarser. The SEM images show this trend with the precipitates becoming more agglomerated with greater temperature.

Example 10: Microstructure Data for In Vitro and In Vivo Samples

Tables 34-40 depict tables including microstructure data quantifying the IM % area (volume fraction as measured by area percent in a cross-sectional image or similar technique) and IM particle size for a plurality of materials, including preclinical materials. FIG. 10A-10C depict data used to set maximums for IM % area and max IM particle size (particle length). In FIG. 10A-10C, the heat treatment, extrusion ratio (ER), and extrusion temperature vary for these samples, showing how processing affects IM area fraction and IM size. Particle Size (Area) and Particle Length are presented as an average, standard deviation and maximum for each micrograph analyzed. Aspect Ratio (AR) is the ratio of the major to minor axis of an elliptical fit for each IM and is presented as an average and standard deviation. Corrosion Rate was collected via immersion corrosion (corrosion rate determined via mass loss) in a simulated body fluid to determine how IM % area and size affect corrosion rate. A larger IM Area and Particle length (average and maximum) has been found to relate to higher immersion corrosion rates. Larger Particle length correlates with a higher aspect ratio. Larger I M Particles (length and area) with high AR are referred to as stringers and cause nonuniform corrosion, as corrosion localizes at the TIs.

TABLE 34

| Material | Image | Composition | Processing Info |
|---|---|---|---|
| Preclinical | S2_01_400x BEC<br>S2_02_400x BEC<br>S2_03_400x BEC | Mg—2%Zn—1%Ca—1%Mn<br>2Zn—1.11Ca—0.94Mn | Cast<br>1st Extrusion (ER 7, Temp 350° C.) Solution Treat (430° C./24 hr/FAC) 2nd Extrusion (ER 30, Temp ~290° C.) |
| C2 | C2_01_400x<br>C2_02_400x<br>C2_03_400x<br>C2_04_400x<br>C2_05_400x | Mg—1.2%Zn—0.5%Ca—0.5%Mn<br>1.23Zn—0.31Ca—0.55Mn | Cast<br>Extrusion (ER 9, Billet Temp 400° C., Die/Container Temp 350° C.)<br>ST (400° C./4 hr/FAC + 200° C./2 hr/FAC) |
| Pilot A4 | PilotA4_01_400x<br>PilotA4_02_400x<br>PilotA4_03_400x<br>PilotA4_04_400x<br>PilotA4_05_400x | Mg—2.5%Zn—1%Ca—0.4%Mn<br>2.46Zn—0.859Ca—0.242Mn | Cast<br>ST (450° C./6.5 hr/FAC)<br>Extrusion (ER 9, Temp 350° C.) |
| Pilot A5 | PilotA5_01_400x<br>PilotA5_02_400x<br>PilotA5_03_400x<br>PilotA5_04_400x<br>PilotA5_05_400x | Mg—2.5%Zn—1%Ca—0.2%Mn<br>2.66Zn—0.858Ca—0.234Mn | Cast<br>ST (450° C./6.5 hr/FAC)<br>Extrusion (ER 9, Temp 350° C.) |
| Pilot A7 | PilotA7_01_400x<br>PilotA7_02_400x<br>PilotA7_03_400x<br>PilotA7_04_400x<br>PilotA7_05_400x | Mg—3%Zn—1%Ca—0.2%Mn<br>3Zn—0.788Ca—0.258Mn | Cast<br>ST (450° C./6.5 hr/FAC)<br>Extrusion (ER 9, Temp 350° C.) |
| A2 | A2_Nie_Long_400x_b<br>A2_Nie_Transverse_400x_a | Mg—2%Zn—1%Ca—0.2%Mn<br>2Zn—0.85Ca—0.25Mn | Cast<br>ST (320° C./8 hr/FAC + 430° C./16 hr/FAC)<br>Extrusion (ER 9, Temp 350° C.) |

TABLE 35

| Material | Image | Composition | Processing Info |
|---|---|---|---|
| A4 | A4_Nie_Long_400x_a<br>A4_Nie_Transverse_400x_a | Mg—2.5%Zn—1%Ca—0.4%Mn<br>2.46Zn—0.859Ca—0.242Mn | Cast<br>ST (320° C./8 hr/FAC +<br>430° C./16 hr/FAC)<br>Extrusion (ER 9,<br>Temp 350° C.) |
| A8 | A8_Nie_Long_400x_a<br>A8_Nie_Transverse_400x_b | Mg—3.5%Zn—0.8%Ca—0.3%Mn<br>3.54Zn—0.80Ca—0.299Mn | Cast<br>ST (320° C./8 hr/FAC +<br>430° C./16 hr/FAC)<br>Extrusion (ER 9,<br>Temp 350° C.) |
| R1<br>G1T1<br>350 | S4_01_400x BEC<br>S4_02_400x BEC<br>S4_03_400x BEC | Mg—2%Zn—1%Ca—1%Mn<br>2Zn—1.11Ca—0.94Mn | Cast<br>1st Extrusion (ER 7,<br>Temp 350° C.) 2nd<br>Extrusion (ER 14,<br>Temp ~350° C.) Solution<br>Treat (410° C./24 hr/FAC)<br>3rd Extrusion (ER 25,<br>Temp 350° C.) |
| R2<br>G1T1<br>325 | S1_01_400x<br>S1_02_400x<br>S1_03_400x<br>S1_04_400x<br>S1_05_400x | Mg—2%Zn—1%Ca—1%Mn<br>2Zn—1.11Ca—0.94Mn | Cast<br>1st Extrusion (ER 7,<br>Temp 350° C.) 2nd<br>Extrusion (ER 14,<br>Temp ~350° C.) Solution<br>Treat (410° C./24 hr/FAC)<br>3rd Extrusion (ER 39,<br>Temp 325° C.) |
| R2<br>G1T2<br>350 | S2_01_400x<br>S2_02_400x<br>S2_03_400x<br>S2_04_400x<br>S2_05_400x | Mg—2%Zn—1%Ca—1%Mn<br>2Zn—1.11Ca—0.94Mn | Cast<br>1st Extrusion (ER 7,<br>Temp 350° C.) 2nd<br>Extrusion (ER 14,<br>Temp ~350° C.) Solution<br>Treat (410° C./24 hr/FAC)<br>3rd Extrusion (ER 39,<br>Temp 350° C.) |
| R2<br>G2T1<br>325 | S3_01_400x<br>S3_02_400x<br>S3_03_400x<br>S3_04_400x<br>S3_05_400x | Mg—2%Zn—1%Ca—1%Mn<br>2Zn—1.11Ca—0.94Mn | Cast<br>1st Extrusion (ER 7,<br>Temp 350° C.) 2nd<br>Extrusion (ER 14,<br>Temp ~350° C.) Solution<br>Treat (430° C./24 hr/FAC)<br>3rd Extrusion (ER 39,<br>Temp 325° C.) |

TABLE 36

| Material | % Area IM (Total) | | | IM Area (Particle Size, micron$^2$) Particles larger than 1 micron$^2$ | | | | |
|---|---|---|---|---|---|---|---|---|
| | % Area IM | Avg Avg | Std Dev | Average | Avg Avg | Std Dev | Max | Avg Max |
| Preclinical | 1.4 | 1.7 | 0.5 | 12.1 | 12.9 | 30.8 | 147.6 | 322.0 |
| | 1.4 | | | 9.7 | | 24.8 | 153.6 | |
| | 2.4 | | | 16.8 | | 77.4 | 664.7 | |
| C2 | 0.3 | 0.3 | 0.2 | 2.2 | 3.0 | 2.3 | 15.4 | 17.7 |
| | 0.5 | | | 2.3 | | 2.2 | 15.7 | |
| | 0.5 | | | 5.9 | | 6.2 | 32.1 | |
| | 0.1 | | | 2.1 | | 1.8 | 9.6 | |
| | 0.1 | | | 2.5 | | 3.1 | 15.9 | |
| Pilot A4 | 2.8 | 2.9 | 0.2 | 9.9 | 9.6 | 16.8 | 93.4 | 170.5 |
| | 2.6 | | | 9.5 | | 23.8 | 206.9 | |
| | 3.2 | | | 9.6 | | 20.3 | 220.7 | |
| | 2.8 | | | 8.3 | | 16.3 | 138.4 | |
| | 3.1 | | | 10.8 | | 23.5 | 193.0 | |
| Pilot A5 | 2.8 | 2.8 | 0.2 | 7.9 | 7.8 | 8.5 | 56.5 | 71.3 |
| | 2.7 | | | 6.9 | | 8.1 | 63.8 | |
| | 3.2 | | | 7.6 | | 10.6 | 77.5 | |
| | 2.6 | | | 7.0 | | 8.6 | 66.0 | |
| | 2.6 | | | 9.4 | | 12.8 | 92.7 | |
| Pilot A7 | 3.6 | 4.2 | 0.6 | 10.7 | 12.0 | 23.6 | 193.8 | 333.5 |
| | 4.7 | | | 10.7 | | 30.2 | 378.2 | |
| | 4.6 | | | 16.4 | | 50.2 | 499.3 | |
| | 3.4 | | | 12.4 | | 30.8 | 278.8 | |
| | 4.9 | | | 9.9 | | 28.8 | 317.6 | |

TABLE 36-continued

| Material | % Area IM (Total) | | | IM Area (Particle Size, micron$^2$) Particles larger than 1 micron$^2$ | | | | |
|---|---|---|---|---|---|---|---|---|
| | % Area IM | Avg Avg | Std Dev | Average | Avg Avg | Std Dev | Max | Avg Max |
| A2 | 9.7 | NA | NA | 2.6 | NA | 2.9 | 24.1 | NA |
| | 10.2 | | | 2.5 | | 2.2 | 20.6 | |

TABLE 37

| Material | % Area IM (Total) | | | IM Area (Particle Size, micron$^2$) Particles larger than 1 micron$^2$ | | | | |
|---|---|---|---|---|---|---|---|---|
| | % Area IM | Avg Avg | Std Dev | Average | Avg Avg | Std Dev | Max | Avg Max |
| Preclinical | 1.4 | 1.7 | 0.5 | 12.1 | 12.9 | 30.8 | 147.6 | 322.0 |
| | 1.4 | | | 9.7 | | 24.8 | 153.6 | |
| | 2.4 | | | 16.8 | | 77.4 | 664.7 | |
| C2 | 0.3 | 0.3 | 0.2 | 2.2 | 3.0 | 2.3 | 15.4 | 17.7 |
| | 0.5 | | | 2.3 | | 2.2 | 15.7 | |
| | 0.5 | | | 5.9 | | 6.2 | 32.1 | |
| | 0.1 | | | 2.1 | | 1.8 | 9.6 | |
| | 0.1 | | | 2.5 | | 3.1 | 15.9 | |

TABLE 37-continued

| Material | % Area IM (Total) | | | IM Area (Particle Size, micron²) Particles larger than 1 micron² | | | | |
|---|---|---|---|---|---|---|---|---|
| | % Area IM | Avg Avg | Std Dev | Average | Avg Avg | Std Dev | Max | Avg Max |
| Pilot A4 | 2.8 | 2.9 | 0.2 | 9.9 | 9.6 | 16.8 | 93.4 | 170.5 |
| | 2.6 | | | 9.5 | | 23.8 | 206.9 | |
| | 3.2 | | | 9.6 | | 20.3 | 220.7 | |
| | 2.8 | | | 8.3 | | 16.3 | 138.4 | |
| | 3.1 | | | 10.8 | | 23.5 | 193.0 | |
| Pilot A5 | 2.8 | 2.8 | 0.2 | 7.9 | 7.8 | 8.5 | 56.5 | 71.3 |
| | 2.7 | | | 6.9 | | 8.1 | 63.8 | |
| | 3.2 | | | 7.6 | | 10.6 | 77.5 | |
| | 2.6 | | | 7.0 | | 8.6 | 66.0 | |
| | 2.6 | | | 9.4 | | 12.8 | 92.7 | |
| Pilot A7 | 3.6 | 4.2 | 0.6 | 10.7 | 12.0 | 23.6 | 193.8 | 333.5 |
| | 4.7 | | | 10.7 | | 30.2 | 378.2 | |
| | 4.6 | | | 16.4 | | 50.2 | 499.3 | |
| | 3.4 | | | 12.4 | | 30.8 | 278.8 | |
| | 4.9 | | | 9.9 | | 28.8 | 317.6 | |
| A2 | 9.7 | NA | NA | 2.6 | NA | 2.9 | 24.1 | NA |
| | 10.2 | | | 2.5 | | 2.2 | 20.6 | |

TABLE 38

| Material | % Area IM (Total) | | | IM Area (Particle Size, micron²) Particles larger than 1 micron² | | | | |
|---|---|---|---|---|---|---|---|---|
| | % Area IM | Avg Avg | Std Dev | Average | Avg Avg | Std Dev | Max | Avg Max |
| A4 | 11.6 | NA | NA | 3.5 | NA | 4.0 | 28.5 | NA |
| | 6.0 | | | 3.3 | | 2.7 | 23.4 | |
| A8 | 6.0 | NA | NA | 7.9 | NA | 10.4 | 77.1 | NA |
| | 12.3 | | | 2.3 | | 1.9 | 13.9 | |
| R1 G1T1 350 | 2.9 | 2.5 | 0.3 | 7.4 | 6.3 | 34.7 | 518.5 | 315.4 |
| | 2.2 | | | 6.0 | | 26.2 | 382.0 | |
| | 2.5 | | | 5.4 | | 6.6 | 45.9 | |
| R2 G1T1 325 | 2.0 | 1.9 | 0.3 | 8.2 | 7.1 | 19.0 | 190.3 | 163.4 |
| | 1.5 | | | 5.2 | | 5.4 | 32.8 | |
| | 1.7 | | | 6.1 | | 8.5 | 70.6 | |
| | 2.1 | | | 8.0 | | 26.0 | 345.6 | |
| | 2.3 | | | 7.8 | | 15.0 | 177.8 | |
| R2 G1T2 350 | 1.6 | 1.8 | 0.1 | 5.6 | 5.5 | 6.4 | 48.7 | 80.1 |
| | 2.0 | | | 7.0 | | 14.7 | 161.0 | |
| | 1.8 | | | 5.5 | | 6.3 | 55.5 | |
| | 1.8 | | | 4.5 | | 4.6 | 31.4 | |
| | 2.0 | | | 5.0 | | 8.3 | 104.0 | |
| R2 G2T1 325 | 2.1 | 2.2 | 0.1 | 7.3 | 8.0 | 9.4 | 66.9 | 114.4 |

TABLE 39

| Material | IM AR Particles larger than 1 micron2 | | | | IM Particle Length (micron) Particles larger than 1 micron² | | | | | Corrosion Rate (mm/year) | | |
|---|---|---|---|---|---|---|---|---|---|---|---|---|
| | Average | Avg Avg | Std Dev | Avg Std Dev | Average | Avg Avg | Std Dev | Max | Avg Max | 8 hours | 1 Day | 3 Weeks |
| Preclinical | 2.0 | 2.1 | 0.7 | 0.8 | 4.4 | 4.4 | 5.7 | 29 | 26.3 | 0 | 0.03 | 0.04 |
| | 2.0 | | 0.9 | | 4.3 | | 4.3 | 24.7 | | | | |
| | 2.1 | | 0.9 | | 4.6 | | 5.8 | 24.7 | | | | |
| C2 | 1.9 | 2.4 | 0.9 | 1.4 | 2.5 | 3.0 | 1.7 | 11.9 | 11.9 | 1.39 | 0.63 | 0.09 |
| | 2.1 | | 1.1 | | 2.7 | | 1.6 | 12.9 | | | | |
| | 1.9 | | 0.6 | | 3.9 | | 2.2 | 11.6 | | | | |
| | 2.5 | | 1.9 | | 2.7 | | 1.9 | 9.4 | | | | |
| | 3.4 | | 2.4 | | 3.3 | | 2.8 | 13.6 | | | | |
| Pilot A4 | 5.0 | 4.9 | 4.1 | 4.4 | 7.7 | 7.5 | 8.8 | 47.4 | 81.9 | 0.42 | 0.29 | 0.28 |
| | 4.9 | | 4.3 | | 7.7 | | 12.8 | 140.1 | | | | |
| | 4.9 | | 4.2 | | 7.4 | | 9.1 | 78.9 | | | | |
| | 4.9 | | 4.4 | | 7.0 | | 9.1 | 63.7 | | | | |
| | 4.6 | | 4.7 | | 8.0 | | 11.1 | 79.4 | | | | |
| Pilot A5 | 4.5 | 4.4 | 3.4 | 3.4 | 6.9 | 6.7 | 5.7 | 30.9 | 38.0 | 0.3 | 0.17 | 0.52 |
| | 4.0 | | 2.9 | | 6.0 | | 5.0 | 32.7 | | | | |
| | 4.6 | | 3.5 | | 6.6 | | 6.1 | 36.1 | | | | |
| | 4.7 | | 3.9 | | 6.6 | | 6.3 | 46.6 | | | | |
| | 4.2 | | 3.3 | | 7.3 | | 7.1 | 43.8 | | | | |
| Pilot A7 | 6.0 | 6.3 | 3.8 | 5.9 | 8.6 | 9.2 | 11.6 | 71.9 | 97.9 | 0.13 | 0.26 | 0.71 |
| | 6.1 | | 6.0 | | 8.6 | | 12.2 | 82.6 | | | | |
| | 7.7 | | 6.9 | | 11.9 | | 18.7 | 171.8 | | | | |
| | 6.7 | | 6.4 | | 9.5 | | 12.4 | 78.7 | | | | |
| | 4.9 | | 4.5 | | 7.1 | | 9.4 | 84.4 | | | | |
| A2 | 3.2 | NA | 2.4 | NA | 3.5 | NA | 2.8 | 27.8 | NA | NR | 0.28 | 0.4 |
| | 2.9 | | 1.5 | | 3.2 | | 1.4 | 10.6 | | | | |

TABLE 40

| Material | IM AR Particles larger than 1 micron2 | | | | IM Particle Length (micron) Particles larger than 1 micron 2 | | | | | Corrosion Rate (mm/year) | | |
|---|---|---|---|---|---|---|---|---|---|---|---|---|
| | Average | Avg Avg | Std Dev | Avg Std Dev | Average | Avg Avg | Std Dev | Max | Avg Max | 8 hours | 1 Day | 3 Weeks |
| A4 | 4.0 | NA | 2.5 | NA | 4.3 | NA | 2.9 | 21.2 | NA | NR | 0.11 | 0.42 |
| | 2.7 | | 1.5 | | 3.4 | | 1.7 | 12.6 | | | | |
| A8 | 4.5 | NA | 3.6 | NA | 6.9 | NA | 6.4 | 42.4 | NA | NR | 1.07 | 2.61 |
| | 3.1 | | 1.7 | | 3.1 | | 1.4 | 14.7 | | | | |
| R1 | 1.7 | 1.6 | 0.5 | 0.5 | 3.6 | 3.4 | 2.8 | 34.8 | 25.1 | 0.19 | 0.03 | 0.2 |
| G1T1 | 1.7 | | 0.5 | | 3.3 | | 2.2 | 29.5 | | | | |
| 350 | 1.6 | | 0.4 | | 3.4 | | 1.7 | 11.1 | | | | |
| R2 | 1.5 | 1.6 | 0.6 | 0.6 | 3.7 | 3.6 | 2.7 | 24.3 | 23.8 | | TBD | |
| G1T1 | 1.6 | | 0.6 | | 3.3 | | 1.7 | 13.1 | | | | |
| 325 | 1.5 | | 0.6 | | 3.5 | | 1.8 | 14.5 | | | | |
| | 1.6 | | 0.6 | | 3.6 | | 2.6 | 26.1 | | | | |
| | 1.6 | | 0.9 | | 4.0 | | 3.8 | 41.2 | | | | |
| R2 | 1.4 | 1.6 | 0.3 | 0.7 | 3.3 | 3.4 | 1.5 | 10.6 | 14.2 | | TBD | |
| G1T2 | 1.5 | | 0.5 | | 3.4 | | 2.2 | 19.8 | | | | |
| 350 | 1.8 | | 0.9 | | 3.6 | | 2.0 | 16.6 | | | | |
| | 1.8 | | 0.8 | | 3.2 | | 1.5 | 10.9 | | | | |
| | 1.7 | | 0.8 | | 3.2 | | 1.9 | 13.4 | | | | |
| R2 | 1.6 | 1.7 | 0.7 | 0.7 | 3.8 | 3.9 | 2.3 | 16.6 | 19.4 | | TBD | |
| G2T1 | 1.6 | | 0.8 | | 4.2 | | 2.5 | 17.4 | | | | |
| 325 | 1.7 | | 0.8 | | 3.8 | | 2.5 | 19.7 | | | | |
| | 1.8 | | 0.8 | | 4.1 | | 2.7 | 20.5 | | | | |
| | 1.6 | | 0.6 | | 3.5 | | 2.4 | 22.7 | | | | |

While the disclosure has been described in connection with what is presently considered to be the most practical and preferred embodiments, it is to be understood that the disclosure is not to be limited to the disclosed embodiments, but on the contrary, is intended to cover various modifications and equivalent arrangements included within the spirit and scope of the appended claims, which scope is to be accorded the broadest interpretation so as to encompass all such modifications and equivalent structures as permitted under the law. Furthermore, it should be understood that while the use of the word preferable, preferably, or preferred in the description above indicates that feature so described may be more desirable, it nonetheless may not be necessary and any embodiment lacking the same may be contemplated as within the scope of the disclosure, that scope being defined by the claims that follow. For specific numerical values provided, it is to be understood that a numerical value within plus or minus 10%, within plus or minus 5%, within plus or minus 3%, within plus or minus 1%, and/or within plus or minus 0.5% of the specified value could be used. For specific numerical values of a property provided, it is to be understood that a range encompassing the specific numerical values of the property within plus or minus 20%, within plus or minus 15%, within plus or minus 10%, within plus or minus 5%, within plus or minus 3%, within plus or minus 1%, and/or within plus or minus 0.5% of the lowest specified value and the highest specified value could be used. In reading the claims it is intended that when words such as "a," "an," "at least one" and "at least a portion" are used, there is no intention to limit the claim to only one item unless specifically stated to the contrary in the claim. Further, when the language "at least a portion" and/or "a portion" is used the item may include a portion and/or the entire item unless specifically stated to the contrary.

What is claimed is:

1. A bioabsorbable magnesium alloy for use in an orthopedic implant, comprising:
magnesium;
zinc in an amount of 0.5-4 weight percent;
calcium in an amount of 0.2-10 weight percent; and
manganese in an amount of 0.5-1.0 weight percent;
wherein the alloy comprises a microstructure having a $Mg_2Ca$ phase and ternary intermetallic phases;
wherein the $Mg_2Ca$ phase comprises less than 1.0 wt % of the alloy;
wherein an average diameter of $Mg_2Ca$ phase precipitates is less than 200 nanometers (nm);
wherein the alloy forms a protective oxide layer when exposed to physiological conditions; and
wherein the alloy exhibits a controlled, multi-phase absorption profile when exposed to physiological conditions, the profile comprising an initial period of minimal degradation, followed by a steady-state phase, and concluding with an accelerated absorption phase.

2. The bioabsorbable magnesium alloy of claim 1, wherein the zinc is present in an amount of greater than 2 weight percent and less than or equal to 4 weight percent.

3. The bioabsorbable magnesium alloy of claim 1, wherein the calcium is present in an amount of 0.3-0.8 weight percent.

4. The bioabsorbable magnesium alloy of claim 1, wherein the manganese is present in an amount of 0.6-1.0 weight percent.

5. The bioabsorbable magnesium alloy of claim 1, wherein the initial period of minimal degradation lasts for 7-14 days, the steady-state phase extends from approximately 2 to 8 weeks post-implantation, and the accelerated absorption phase begins after 8-12 weeks.

6. The bioabsorbable magnesium alloy of claim 1, magnesium acts as an anodic phase and the ternary intermetallic phases acts as cathodic phases, and the alloy has an anode-to-cathode ratio of at least 20:1.

7. A bioabsorbable magnesium alloy for use in an orthopedic implant, comprising:

magnesium;

zinc in an amount of 0.5-4 weight percent;

calcium in an amount of 0.2-1.0 weight percent; and a third alloying element in an amount of 0.1-1.0 weight percent;

wherein the alloy comprises a microstructure having:

a ternary intermetallic phase with a volume fraction between 0.5% and 5%;

the ternary intermetallic phase having an average particle size between 50 nm and 500 nm; and $Mg_2Ca$ phase present in a volume fraction of less than 1% with an average particle diameter of less than 200 nm;

wherein the alloy exhibits a controlled, multi-phase absorption profile when exposed to physiological conditions, the profile comprising an initial period of minimal degradation, followed by a steady-state phase, and concluding with an accelerated absorption phase.

8. The bioabsorbable magnesium alloy of claim 7, wherein the ternary intermetallic phase comprises $Ca_2Mg_6Zn_3$.

9. The bioabsorbable magnesium alloy of claim 7, wherein the ternary intermetallic phase has a volume fraction between 1% and 3%.

10. The bioabsorbable magnesium alloy of claim 7, wherein the ternary intermetallic phase has an average particle size between 100 nm and 300 nm.

11. The bioabsorbable magnesium alloy of claim 7, wherein the $Mg_2Ca$ phase is present in a volume fraction of less than 0.5%.

12. The bioabsorbable magnesium alloy of claim 7, wherein the $Mg_2Ca$ phase has an average particle diameter of less than 100 nm.

13. The bioabsorbable magnesium alloy of claim 7, wherein the alloy forms a protective oxide layer when exposed to physiological conditions, the protective oxide layer having a thickness between 10 nm and 500 nm.

14. An orthopedic implant device, comprising:

a body formed from a bioabsorbable magnesium alloy, the alloy comprising magnesium, 1-4 weight percent zinc, 0.2-1.0 weight percent calcium, and 0.3-1.0 weight percent manganese;

wherein the alloy comprises a microstructure having a lower amount of $Mg_2Ca$ phase relative to ternary intermetallic phases;

wherein the ternary intermetallic phases comprise $Ca_2Mg_6Zn_3$ and have a volume fraction between 0.5% and 5%, wherein the alloy forms a protective oxide layer when exposed to physiological conditions, the protective oxide layer having a thickness between 10 nm and 500 nm; and wherein the alloy exhibits a controlled, multi-phase absorption profile when exposed to physiological conditions, the profile comprising an initial period of minimal degradation, followed by a steady-state phase, and concluding with an accelerated absorption phase.

15. The orthopedic implant device of claim 14, wherein the zinc is present in an amount of 2-2.5 weight percent, the calcium is present in an amount of 0.8-1.0 weight percent, and the manganese is present in an amount of 0.6-1.0 weight percent.

16. The orthopedic implant device of claim 14, wherein the ternary intermetallic phases has an average particle size between 50 nm and 500 nm.

17. The orthopedic implant device of claim 14, wherein the $Mg_2Ca$ phase is present in a volume fraction of less than 0.5% with an average particle diameter of less than 100 nm.

18. The orthopedic implant device of claim 17, wherein the device is configured for use in maxillofacial trauma and reconstruction applications.

* * * * *